US012571794B2

(12) United States Patent (10) Patent No.: US 12,571,794 B2

Mercati et al. (45) Date of Patent: Mar. 10, 2026

(54) EPIGEN AU/11: A NATURAL MATRIX FOR RESTORING HOMEOSTASIS IN CANCER CELL-INFILTRATED TISSUE

(71) Applicant: Bios-Therapy, Physiological Systems for Health S.p.A., Sansepolcro (IT)

(72) Inventors: Valentino Mercati, Sansepolcro (IT); Jacopo Lucci, Sansepolcro (IT)

(73) Assignee: Bios-Therapy, Physiological Systems for Health S.p.A., Sansepolcro (IT)

( * ) Notice: Subject to any disclaimer, the term of this patent is extended or adjusted under 35 U.S.C. 154(b) by 0 days.

(21) Appl. No.: 19/044,249

(22) Filed: Feb. 3, 2025

(65) Prior Publication Data

US 2025/0383342 A1 Dec. 18, 2025

Related U.S. Application Data

(60) Continuation-in-part of application No. 18/970,350, filed on Dec. 5, 2024, which is a division of application No. 18/744,862, filed on Jun. 17, 2024.

(30) Foreign Application Priority Data

Jun. 17, 2024 (WO) .................. PCT/IB2024/055892
Dec. 23, 2024 (WO) .................. PCT/IB2024/063120

(51) Int. Cl.
*A61K 36/00* (2006.01)
*G01N 33/50* (2006.01)

(52) U.S. Cl.
CPC ..... *G01N 33/5088* (2013.01); *G01N 33/5023* (2013.01)

(58) Field of Classification Search
CPC .................................................... A61K 36/00
See application file for complete search history.

(56) References Cited

FOREIGN PATENT DOCUMENTS

JP          7616724  B1      1/2025
WO      WO-2006039807  A1 *   4/2006   ......... A61K 36/9068
WO      WO-2018138678  A1      8/2018

OTHER PUBLICATIONS

Abatangelo, L., et al., "Comparative Study of Gene Set Enrichment Methods," BMC Bioinformatics 10:275, 12 Pages, BioMed Central, United Kingdom (Sep. 2009).

(Continued)

*Primary Examiner* — Rosanne Kosson

(74) *Attorney, Agent, or Firm* — STERNE, KESSLER, GOLDSTEIN & FOX P.L.L.C.

(57) ABSTRACT

The present invention relates to a 100% natural product consisting of natural matrices showing emerging properties, which allows to re-establish a correct metabolism in tissues infiltrated by cancer cells, adjuvating cancer treatment and tissue homeostasis. The product of the invention, as demonstrated by the inventors, is itself a natural matrix, representing native natural intelligence, said natural intelligence being the only capable to allow a physiological endogenous interconnection with other entities which are self-assembled in nature, such as the human species. By modulating tumor microenvironment and thus selectively inducing cancer cells mortality, the product achieves reconstitution of conditions favourable to tissue homeostasis in tissues infiltrated by cancer cells. Factually, the invention allows for a shift of paradigm based on the passage from a deterministic validation of properties to a probabilistic one based on functional redundancy logics, that will grant an industrially viable source of innovation for manufacturers in the field of 100% natural therapeutic or beneficial products.

22 Claims, 57 Drawing Sheets

NUCLEI OF VIABLE CELLS (%), 72h

(56) References Cited

OTHER PUBLICATIONS

Figure 1:
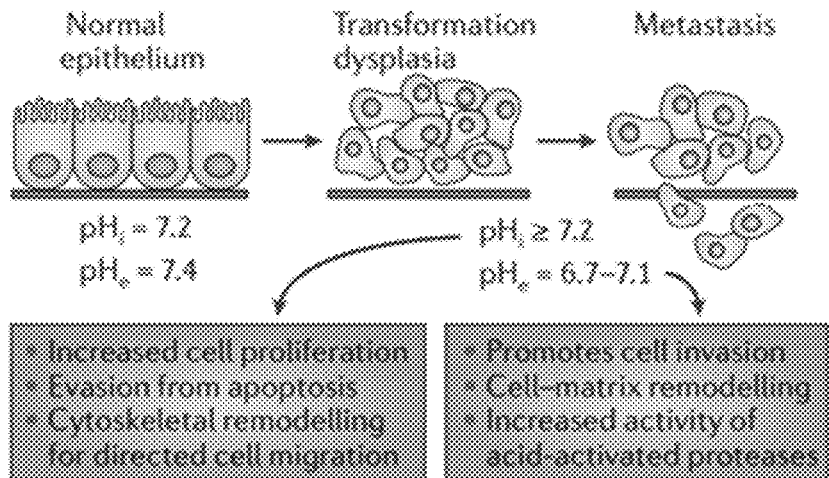

Amodio, P., et al., "Variability of Trail Making Test, Symbol Digit Test and Line Trait Test in Normal People. A Normative Study Taking Into Account Age-dependent Decline and Sociobiological Variables," Aging Clinical and Experimental Research 14(2):117-131, Springer, Germany (Apr. 2002).

Barbosa, D.J., et al., "In Vitro Models for Neurotoxicology Research," Toxicology Research 4(4):801-842, Oxford Academic, United Kingdom (Mar. 2015).

Bartsch, R.P., et al., "Network Physiology: How Organ Systems Dynamically Interact," PLoS One 10(11):e0142143, 36 Pages, Public Library of Science, United States (Nov. 2015).

Benedetto, S.D., et al., "Contribution of Neuroinflammation and Immunity to Brain Aging and the Mitigating Effects of Physical and Cognitive Interventions," Neuroscience and Biobehavioral Reviews 75:114-128, Pergamon Press, United States (Apr. 2017).

Boxall, A.B.A., et al., "Pharmaceuticals and Personal Care Products in the Environment: What Are the Big Questions?" Environmental Health Perspectives 120(9):1221-1229, National Institute of Environmental Health Sciences, United States (Sep. 2012).

Calabrese, E.J., and Baldwin, L.A., "Toxicology Rethinks Its Central Belief," Nature 421(6924):691-692, Nature Publishing Group, United Kingdom (Feb. 2003).

Carlesimo, G.A., et al., "Explicit Memory and Repetition Priming in Dementia: Evidence for a Common Basic Mechanism Underlying Conscious and Unconscious Retrieval Deficits," Journal of Clinical and Experimental Neuropsychology 17(1):44-57, Routledge, United Kingdom (Feb. 1995).

Carlesimo, G.A., et al., "The Mental Deterioration Battery: Normative Data, Diagnostic Reliability and Qualitative Analyses of Cognitive Impairment. The Group for the Standardization of the Mental Deterioration Battery," European Neurology 36(6):378-384, Karger, Switzerland (1996).

Chang, J., et al., "Systemic and local adipose tissue in knee osteoarthritis," Osteoarthritis Cartilage 26(7):864-871, Elsevier, Netherlands (Jul. 2018).

Chindelevitch, L., et al., "Causal reasoning on biological networks: interpreting transcriptional changes," Bioinformatics 28(8):1114-1121, Oxford University Press, United Kingdom (Apr. 2012).

NCT03581929, "Efficacy of Memormax in Subjects With MCI (ABO-Memo)," CliniclTrials.gov, accessed at https://clinicaltrials.gov/study/NCT03581929?term=NCT03581929&rank=1, accessed on Jul. 29, 2020, 16 pages.

Dolan, R.D., and Mcmillan, D.C., "The Prevalence of Cancer Associated Systemic Inflammation: Implications of Prognostic Studies Using the Glasgow Prognostic Score," Critical Reviews in Oncology Hematology 150:102962, Elsevier Scientific Publishers, Netherlands (Jun. 2020).

Dolan, R.D., et al., "The Role of the Systemic Inflammatory Response in Predicting Outcomes in Patients With Operable Cancer: Systematic Review and Meta-analysis," Scientific Reports 7(1):16717, Nature Publishing Group, United Kingdom (Dec. 2017).

Felciano, R.M., et al., "Predictive Systems Biology Approach to Broad-spectrum, Host-directed Drug Target Discovery in Infectious Diseases," Pacific Symposium on Biocomputing, pp. 17-28, World Scientific, United States (2013).

Fick, J., et al., "Predicted Critical Environmental Concentrations for 500 Pharmaceuticals," Regulatory Toxicology and Pharmacology 58(3):516-523, Elsevier, Netherlands (Dec. 2010).

Frasson, P., et al., "Free and Cued Selective Reminding Test: an Italian Normative Study," Neurological Sciences 32(6):1057-1062, Springer-Verlag Italia, Italy (Dec. 2011).

Fukumoto, S., and Martin, T.J., "Bone as an Endocrine Organ," Trends in Endocrinology and Metabolism 20(5):230-236, Elsevier Science Pub. Co., United States (Jul. 2009).

Hou, Y., et al., "Supramolecular Assemblies Based on Natural Small Molecules: Union Would Be Effective," Materials Today Bio 15:100327, 18 Pages, Elsevier Ltd., United Kingdom (Jun. 2022).

Ivanov, P.C., "The New Field of Network Physiology: Building the Human Physiolome," Frontiers in Network Physiology 1:711778, 15 Pages, Frontiers Media S.A., Switzerland (Jun. 2021).

Jeurissen, S.M.F., et al., "Basil Extract Inhibits the Sulfotransferase Mediated Formation of DNA Adducts of the Procarcinogen 1'-hydroxyestragole by Rat and Human Liver S9 Homogenates and in HepG2 Human Hepatoma Cells," Food and Chemical Toxicology 46(6):2296-2302, Elsevier Science Ltd, United Kingdom (Jun. 2008).

Kasprzyk-Hordern, B., et al., "The Removal of Pharmaceuticals, Personal Care Products, Endocrine Disruptors and Illicit Drugs During Wastewater Treatment and Its Impact on the Quality of Receiving Waters," Water Research 43(2):363-380, Pergamon Press, United Kingdom (Feb. 2009).

Kramer, A., et al., "Causal Analysis Approaches in Ingenuity Pathway Analysis," Bioinformatics 30(4):523-530, Oxford University Press, United Kingdom (Feb. 2014).

Kumar, R., et al., "Causal Reasoning Identifies Mechanisms of Sensitivity for a Novel AKT Kinase Inhibitor, GSK690693," BMC Genomics 11:419, 12 Pages, BioMed Central, United Kingdom (Jul. 2010).

Lehn, J-M., "Toward Complex Matter: Supramolecular Chemistry and Self-organization," Proceedings of the National Academy of Sciences of the United States of America 99(8):4763-4768, National Academy of Sciences, United States (Apr. 2002).

Magni, E., et al., "Mini-mental State Examination: a Normative Study in Italian Elderly Population," European Journal of Neurology 3(3):198-202, Wiley, United Kingdom (May 1996).

Martin, F., et al., "Assessment of Network Perturbation Amplitudes by Applying High-throughput Data to Causal Biological Networks," BMC Systems Biology 6:54, 18 Pages, BioMed Central, United Kingdom (May 2012).

Monaco, M., et al., "Forward and Backward Span for Verbal and Visuo-spatial Data: Standardization and Normative Data From an Italian Adult Population," Neurological Sciences 34(5):749-754, Springer-Verlag Italia, Italy (May 2013).

Pigliautile, M., et al., "Normative Data for the ACE-R in an Italian Population Sample," Neurological Sciences 36(12):2185-2190, Springer-Verlag Italia, Italy (Dec. 2015).

Pollard Jr., J., et al., "A Computational Model to Define the Molecular Causes of Type 2 Diabetes Mellitus," Diabetes Technology Therapeutics 7(2):323-336, Mary Ann Liebert, United States (Apr. 2005).

Romagnoli, C., et al., "In Vitro Behavior of Human Adipose Tissue-Derived Stem Cells on Poly(e-caprolactone) Film for Bone Tissue Engineering Applications," Biomed Research International 2015:323571, 12 Pages, Wiley, United States (Oct. 2015).

Roxburgh, C.S.D., and Mcmillan, D.C., "Cancer and Systemic Inflammation: Treat the Tumour and Treat the Host," British Journal of Cancer 110(6):1409-1412, Nature Publishing Group on behalf of Cancer Research UK, United Kingdom (Mar. 2014).

Zeileis, A., et al., "Colorspace: a Toolbox for Manipulating and Assessing Colors and Palettes," Journal of Statistical Software 96(1):1-49, Foundation for Open Access Statistics, United States (Nov. 2020).

Stear, E.B., "Systems Theory Aspects of Physiological Systems," IFAC Proceedings Volumes 6(4):495-500, Elsevier, Netherlands (Aug. 1973).

Verlicchi, P., et al., "Occurrence of Pharmaceutical Compounds in Urban Wastewater: Removal, Mass Load and Environmental Risk After a Secondary Treatment—a Review," The Science of the Total Environment 429:123-155, Elsevier, Netherlands (Jul. 2012).

Vos, T., et al., "Global, Regional, and National Incidence, Prevalence, and Years Lived With Disability for 310 Diseases and Injuries, 1990-2015: a Systematic Analysis for the Global Burden of Disease Study 2015," The Lancet 388(10053):1545-1602, Elsevier, Netherlands (Oct. 2016).

Co-pending Application, U.S. Appl. No. 18/410,096, inventors Mercati, V., et al., filed on Jan. 11, 2024 (Not Yet Published).

Co-pending Application, U.S. Appl. No. 18/744,862, inventors Mercati, V., et al., filed on Jun. 17, 2024 (Not Yet Published).

Abubakar, A.R. and Haque, M., "Preparation of Medicinal Plants: Basic Extraction and Fractionation Procedures for Experimental

(56)          References Cited

OTHER PUBLICATIONS

Purposes," Journal of Pharmacy & Bioallied Sciences 12(1):1-10, Medknow Publications, India (Jan.-Mar. 2020).

Hill, J.A., et al., "A Multi-Parameter, High-Content, High-Throughput Screening Platform to Identify Natural Compounds that Modulate Insulin and Pdxl Expression," PLoS One 5(9): e12958 pp. 1-9, PLoS, United States (Sep. 2010).

Shoemaker, R., et al., "The NCI60 Human Tumour Cell Line Anticancer Drug Screen," Nature Reviews Cancer 6: 813-823, Springer Nature, Germany (Oct. 2006).

Tai, Y.T., et al., "Isolation and Characterization of Human Multiple Myeloma Cell Enriched Populations," Journal of Immunological Methods 235(1-2):11-19, Elsevier, Netherlands (Feb. 2000).

Bigler, D., et al., "Gene Profiling and Promoter Reporter Assays: Novel Tools for Comparing the Biological Effects of Botanical Extracts on Human Prostate Cancer Cells and Understanding Their Mechanisms of Action," Oncogene 22(8):1261-1272, Nature Publishing Group, United Kingdom (Feb. 2003).

Wang, T.J., et al., "A Randomized Clinical Efficacy Trial of Red Yeast Rice (Monascus pilosus) Against Hyperlipidemia," The American Journal of Chinese Medicine 47(2):323-335, Institute for Advanced Research in Asian Science and Medicine, Singapore (Mar. 2019).

Co-pending Application, U.S. Appl. No. 19/169,541, inventors Mercati, V., et al., filed on Apr. 3, 2025 (Not yet Published).

Hu, D.G., et al., "The Expression Profiles of ADME Genes in Human Cancers and Their Associations with Clinical Outcomes" Cancers 12(11):3369, MDPI, Switzerland (Nov. 2020).

Jeurissen, S.M.F., et al., "Basil Extract Inhibits the Sulfotransferase Mediated Formation of DNA Adducts of the Procarcinogen 1'-hydroxyestragole by Rat and Human Liver S9 Homogenates and in HepG2 Human Hepatoma Cells," Food and Chemical Toxicology 46(6):2296-2302, Elsevier, Netherlands (Jun. 2008).

Madshus, I.H., "Regulation of Intracellular pH in Eukaryotic Cells," The Biochemical Journal 250(1):1-8, Portland Press, United Kingdom (Feb. 1988).

Schlosser, P., et al., "Genetic Studies of Urinary Metabolites Illuminate Mechanisms of Detoxification and Excretion in Humans," Nature Genetics 52(2):167-176, Nature Publishing Group, United Kingdom (Feb. 2020).

* cited by examiner

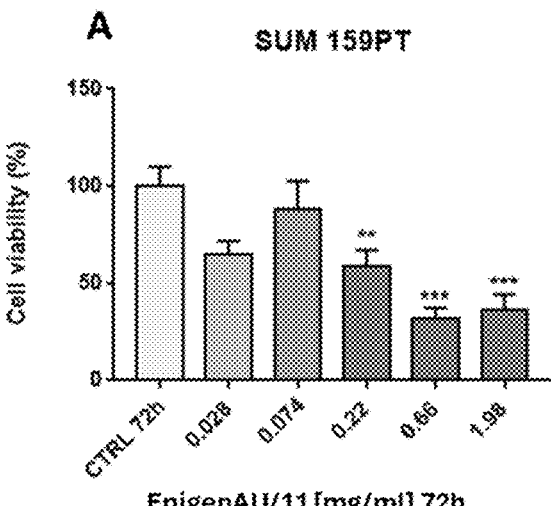
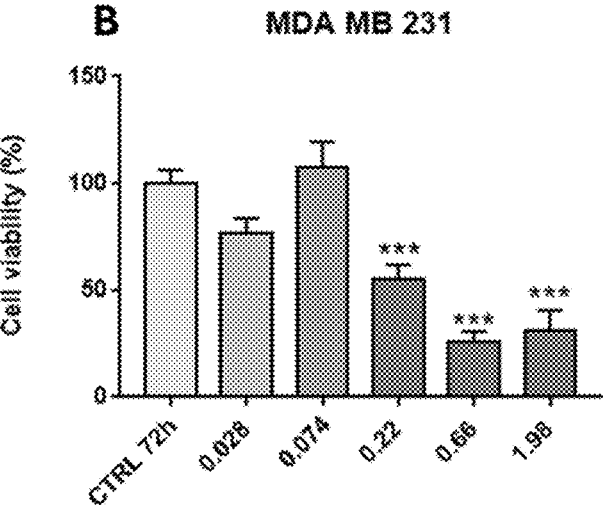
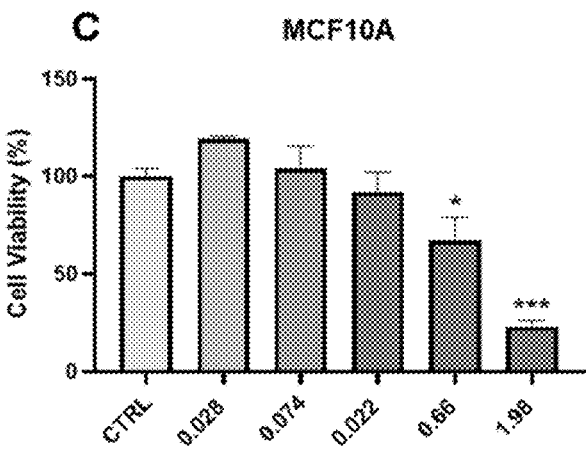
Fig. 4

| Canonical Pathways | EpigenAU/11 [50 mg/ml] 24 hrs | Cisplatin [150 μg/ml] 24 hrs |
|---|---|---|
| Class I MHC mediated antigen processing and presentation | -7.95 | -6.26 |
| Mitotic G2-G2/M phases | -7.07 | -5.86 |
| RHO GTPase cycle | -7.03 | -5.82 |
| Microautophagy Signaling Pathway | -5.15 | -5.75 |
| Neddylation | -6.71 | -5.68 |
| Mitotic Metaphase and Anaphase | -7.09 | -5.57 |
| Signaling by NOTCH4 | -4.64 | -5.29 |
| Interleukin-1 family signaling | -4.74 | -5.00 |
| Deubiquitination | -6.20 | -4.90 |
| DNA Replication Pre-Initiation | -4.74 | -4.54 |
| KEAP1-NFE2L2 pathway | -4.74 | -4.54 |
| Processing of Capped Intron-Containing Pre-mRNA | -10.19 | -4.45 |
| Synthesis of DNA | -4.94 | -4.13 |
| Cell Cycle Checkpoints | -7.25 | -4.04 |
| Intra-Golgi and retrograde Golgi-to-ER traffic | -5.92 | -3.92 |
| Major pathway of rRNA processing in the nucleolus and cytosol | -5.52 | -3.84 |
| Protein Sorting Signaling Pathway | -5.17 | -3.67 |
| Actin Cytoskeleton Signaling | -4.65 | -3.55 |
| RNA Polymerase II Transcription | -7.52 | -3.55 |
| RHO GTPases Activate Formins | -5.00 | -3.55 |
| Integrin Signaling | -4.75 | -3.43 |
| Mitotic Prometaphase | -6.38 | -3.41 |
| ISG15 antiviral mechanism | -5.39 | -3.00 |
| SRP-dependent cotranslational protein targeting to membrane | -4.71 | -3.00 |
| RNA Polymerase I Transcription | -4.90 | -2.45 |
| Mitotic Prophase | -4.95 | -2.32 |
| Estrogen Receptor Signaling | -4.51 | -2.19 |
| Glucose metabolism | -4.81 | -2.11 |
| RNA polymerase II transcribes snRNA genes | -4.64 | -2.11 |
| SUMOylation of DNA damage response and repair proteins | -5.29 | -1.16 |
| TP53 Regulates Transcription of DNA Repair Genes | -5.01 | -1.00 |
| Nucleotide Excision Repair | -4.64 | -0.58 |
| G alpha (i) signalling events | | 1.23 |
| Breast Cancer Regulation by Stathmin1 | | 1.69 |
| Gustation Pathway | | 1.89 |
| Class A/1 (Rhodopsin-like receptors) | | 2.18 |
| CREB Signaling in Neurons | | |
| BBSome Signaling Pathway | | |
| Olfactory Signaling Pathway | | |
| Expression and translocation of olfactory receptors | | |

DOWNMODULATION
(CUT-OFF ≤ -2.30)

BELOW THRESHOLD

Fig. 12

| HALLMARKS | CANONICAL PATHWAYS | EpigenAU/11 [50 mg/ml] 6 hrs | Cisplatin [150 µg/ml] 6 hrs |
|---|---|---|---|
| STEMNESS | Human Embryonic Stem Cell Pluripotency | | 0,22 |
| | Transcriptional regulation by RUNX2 | | -0,63 |
| EPITHELIAL-MESENCHYMAL TRANSITION | Gap Junction Signaling | | 0,38 |
| | Integrin Signaling | | -0,28 |
| | Cell Junction organization | | -1,63 |
| ENERGETIC METABOLISM AND INSULIN SENSITIVITY | Regulation of Insulin-like Growth Factor (IGF) transport and uptake by IGFBPs | | -1,51 |
| | PIP3 activates AKT signaling | | -1,07 |
| | Superpathway of Inositol Phosphate Compounds | | 1,89 |
| | 3-phosphoinositide Degradation | | 1,07 |
| GROWTH FACTOR | Role of Tissue Factor in Cancer | | -2,04 |
| | PDGF Signaling | | 1,34 |
| | Melanocyte Development and Pigmentation Signaling | | 0,45 |
| | Neurotrophin/TRK Signaling | | 1,13 |
| | Signaling by EGFR | | -1,00 |
| | Signaling by MET | | -0,38 |
| | Prolactin Signaling | | 1,63 |
| | Thrombopoietin Signaling | | 1,00 |
| CELL DAMAGE | ERK5 Signaling | | -0,45 |
| | Cachexia Signaling Pathway | | |
| | Degradation of the extracellular matrix | | -2,00 |
| REGULATION OF MITOSIS/PROLIFERATION | Mitotic Prometaphase | 0,82 | |
| | ESR-mediated signaling | | |
| | RAF/MAP kinase cascade | | -0,54 |
| | Acute Myeloid Leukemia Signaling | | 0,00 |
| | Estrogen-Dependent Breast Cancer Signaling | | 0,82 |
| | Assembly of collagen fibrils and other multimeric structures | | -0,83 |
| | P2Y Purigenic Receptor Signaling Pathway | | 1,00 |
| | ERBB Signaling | | 1,00 |
| | MAPK6/MAPK4 signaling | | -2,00 |
| | PI3K/AKT Signaling | | |
| | 3-phosphoinositide Biosynthesis | | 1,29 |
| | Neddylation | | 0,83 |
| | D-myo-inositol (1,4,5,6)-Tetrakisphosphate Biosynthesis | | 0,83 |
| | D-myo-inositol (3,4,5,6)-tetrakisphosphate Biosynthesis | | 0,83 |
| | D-myo-inositol-5-phosphate Metabolism | | 1,07 |
| | Extracellular matrix organization | | -1,27 |
| | Thyroid Cancer Signaling | | -0,54 |
| | PI Metabolism | -1,90 | |
| | Adrenergic Receptor Signaling Pathway (Enhanced) | 0,33 | |
| | Gene and protein expression by JAK-STAT signaling after IL-12 stimulation | 1,34 | |
| | PXR/RXR Activation | 2,00 | |

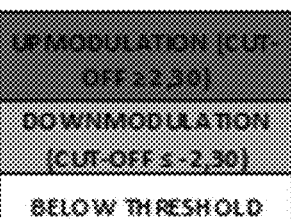

UPMODULATION (CUT-OFF ≥ 2,30)
DOWNMODULATION (CUT-OFF ≤ -2,30)
BELOW THRESHOLD

Fig. 13 A

| HALLMARKS | CANONICAL PATHWAYS | EpigenAU/11 [50 mg/ml] 6 hrs | Cisplatin [150 µg/ml] 6 hrs |
|---|---|---|---|
| INFLAMMATION | IL-6 Signaling | | -0.23 |
| | Senescence-Associated Secretory Phenotype (SASP) | | -1.41 |
| | Class I MHC mediated antigen processing and presentation | | -0.43 |
| | Tumor Microenvironment Pathway | | -1.50 |
| | Signaling by the B Cell Receptor (BCR) | | -0.82 |
| | Interleukin-1 family signaling | | -2.11 |
| | Interleukin 4 and Interleukin-13 signaling | | -1.21 |
| | Interleukin-10 signaling | | -1.67 |
| | IL-17A Signaling in Fibroblasts | | -2.11 |
| | IL-33 Signaling Pathway | | -1.34 |
| | Oncostatin M Signaling | | 0.00 |
| | Acute Phase Response Signaling | | -0.89 |
| | CD40 Signaling | 0.33 | |
| OTHERS | Role of Chondrocytes in Rheumatoid Arthritis Signaling Pathway | | -2.06 |
| | Cardiac Hypertrophy Signaling (Enhanced) | | -0.35 |
| | Pulmonary Fibrosis Idiopathic Signaling Pathway | | -0.71 |
| | Coronavirus Pathogenesis Pathway | | -2.83 |
| | Deubiquitination | | -1.67 |
| | Pulmonary Healing Signaling Pathway | | -1.15 |
| | Hepatic Fibrosis Signaling Pathway | | -0.33 |
| | Cellular response to heat stress | | -1.67 |
| | Role of Osteoclasts in Rheumatoid Arthritis Signaling Pathway | | -0.58 |
| | Synaptic Long Term Potentiation | | -0.82 |
| | Cardiac Hypertrophy Signaling | | 0.30 |
| | Role of IL-17F in Allergic Inflammatory Airway Diseases | | -2.24 |
| | Pathogen Induced Cytokine Storm Signaling Pathway | | |
| | Osteoarthritis Pathway | | -1.71 |
| | Cholecystokinin/Gastrin-mediated Signaling | | 0.00 |
| | Sleep REM Signaling Pathway | 0.26 | |
| | White Adipose Tissue Browning Pathway | 1.34 | |

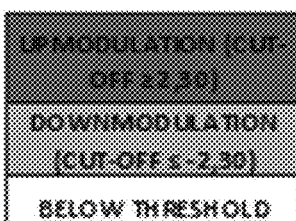

UPMODULATION (CUT-OFF 2.50)

DOWNMODULATION (CUT-OFF ≤ -2.50)

BELOW THRESHOLD

Fig. 13 B

| BIOLOGICAL ACTIVITIES | DESIRED | COMBINATION | EpigenAU/11 | CISPLATIN |
|---|---|---|---|---|
| Migration of tumor cell lines | | -5.97 | -5.57 | -2.90 |
| Invasion of tumor cell lines | | -5.32 | -5.43 | -3.78 |
| Cell movement of tumor cell lines | | -6.21 | -5.37 | -3.07 |
| Invasion of cells | | -5.23 | -5.11 | -3.26 |
| Growth of solid tumor | | -4.24 | -4.14 | -3.66 |
| Cell survival | | -4.27 | -3.89 | -2.10 |
| Cell viability | | -4.46 | -3.71 | -2.13 |
| Cell proliferation of carcinoma cell lines | | -4.55 | -3.44 | 0.00 |
| Migration of cells | | -5.87 | -3.27 | -2.72 |
| Cell movement | | -5.90 | -3.11 | -2.28 |
| Vasculogenesis | | -3.98 | -2.94 | -2.55 |
| Proliferation of lung cancer cell lines | | 0.00 | -2.64 | -2.48 |
| Growth of tumor | | -3.55 | -2.55 | 0.00 |
| Migration of sarcoma cell lines | | 0.00 | -2.53 | 0.00 |
| Colony formation of colorectal cancer cell lines | | 0.00 | -2.48 | 0.00 |
| Formation of colorectal cancer cell lines | | 0.00 | -2.33 | 0.00 |
| Growth of malignant tumor | | -3.59 | -2.21 | -2.13 |
| Angiogenesis | | -4.16 | -2.12 | 0.00 |
| Sphere formation of colorectal cancer cell lines | | 0.00 | -2.04 | 0.00 |
| Neoplasia of tumor cell lines | | -3.48 | 0.00 | -3.19 |
| Metastasis of tumor cell lines | | -3.55 | 0.00 | -2.73 |
| Cell viability of tumor cell lines | | -3.91 | 0.00 | -2.56 |
| Formation of vessel | | 0.00 | 0.00 | -2.45 |
| Neoplasia of cells | | 0.00 | 0.00 | -2.45 |
| Cell movement of sarcoma cell lines | | 0.00 | 0.00 | -2.32 |
| Cancer of cells | | 0.00 | 0.00 | -2.25 |
| Formation of blood vessel | | 0.00 | 0.00 | -2.24 |
| Chemotaxis of tumor cell lines | | 0.00 | 0.00 | -2.22 |
| Advanced malignant tumor | | -3.93 | 0.00 | -2.10 |
| Cell movement of carcinoma cell lines | | -4.67 | 0.00 | -2.06 |
| Migration of vascular endothelial cells | | 0.00 | 0.00 | -2.05 |
| Binding of mononuclear leukocytes | | -2.84 | 0.00 | -2.04 |
| Synthesis of DNA | | 0.00 | 0.00 | -2.04 |
| Proliferation of cancer cells | | -2.64 | 0.00 | -2.03 |
| Synthesis of nitric oxide | | -3.16 | 0.00 | -2.01 |
| Cell proliferation of tumor cell lines | | -5.39 | 0.00 | 0.00 |
| Invasion of carcinoma cell lines | | -4.99 | 0.00 | 0.00 |
| Migration of carcinoma cell lines | | -4.27 | 0.00 | 0.00 |
| Invasion of tumor | | -4.10 | 0.00 | 0.00 |
| Metastasis | | -3.87 | 0.00 | 0.00 |
| Invasive tumor | | -3.77 | 0.00 | 0.00 |
| Invasive cancer | | -3.76 | 0.00 | 0.00 |
| Invasion of tumor cells | | -3.68 | 0.00 | 0.00 |

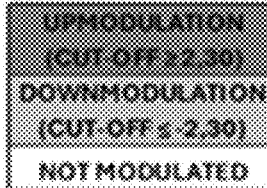

UPMODULATION (CUT-OFF ≥ 2.30)
DOWNMODULATION (CUT-OFF ≤ 2.30)
NOT MODULATED

Fig. 15 A

| BIOLOGICAL ACTIVITIES | DESIRED | COMBINATION | EpigenAU/11 | CISPLATIN |
|---|---|---|---|---|
| Metastasis of cells | | 3.66 | 0.00 | 0.00 |
| Invasion of solid tumor | | 3.38 | 0.00 | 0.00 |
| Migration of breast cancer cell lines | | 3.38 | 0.00 | 0.00 |
| Cell movement of breast cancer cell lines | | 3.38 | 0.00 | 0.00 |
| Invasion of breast cancer cell lines | | 3.24 | 0.00 | 0.00 |
| Cell proliferation of hepatoma cell lines | | 2.90 | 0.00 | 0.00 |
| Growth of lung tumor | | 2.81 | 0.00 | 0.00 |
| Growth of blood vessel | | 2.80 | 0.00 | 0.00 |
| Proliferation of tumor cells | | 2.79 | 0.00 | 0.00 |
| Cell viability of carcinoma cell lines | | 2.75 | 0.00 | 0.00 |
| Migration of ovarian cancer cell lines | | 2.70 | 0.00 | 0.00 |
| Growth of subcutaneous tumor | | 2.56 | 0.00 | 0.00 |
| Cell movement of ovarian cancer cell lines | | 2.54 | 0.00 | 0.00 |
| Cell movement of colorectal cancer cell lines | | 2.51 | 0.00 | 0.00 |
| Cell viability of breast cancer cell lines | | 2.48 | 0.00 | 0.00 |
| Development of carcinoma cell lines | | 2.47 | 0.00 | 0.00 |
| Cell proliferation of ovarian cancer cell lines | | 2.41 | 0.00 | 0.00 |
| Migration of colorectal cancer cell lines | | 2.31 | 0.00 | 0.00 |
| Subcutaneous tumor | | 2.27 | 0.00 | 0.00 |
| Metastasis of adenocarcinoma cell lines | | 2.27 | 0.00 | 0.00 |
| Vascularization | | 2.22 | 0.00 | 0.00 |
| Cell proliferation of breast cancer cell lines | | 2.21 | 0.00 | 0.00 |
| Colony formation of carcinoma cell lines | | 2.19 | 0.00 | 0.00 |
| Migration of stomach cancer cell lines | | 2.15 | 0.00 | 0.00 |
| Oxidative stress | | | 0.00 | 0.00 |
| Development of mesenchymal tumor | | 0.00 | | 0.00 |
| Growth of epithelial tissue | | 0.00 | 0.00 | 2.38 |
| Cell proliferation of fibroblasts | | 3.16 | 0.00 | 0.00 |
| Development of epithelial tissue | | 3.14 | 0.00 | 0.00 |

UPMODULATION
(CUT-OFF ≥ 2.30)
DOWNMODULATION
(CUT-OFF ≤ 2.30)
NOT MODULATED

Fig. 15 B

| Hallmarks | Biological Activities | Desired | EpigenAU/11 [50 mg/ml] |
|---|---|---|---|
| ANGIOGENESIS | Angiogenesis | | -2.77 |
| | Cell proliferation of vascular endothelial cells | | -2.56 |
| | Vasculogenesis | | -2.47 |
| | Endothelial cell development | | -2.18 |
| | Development of endothelial tissue | | -2.18 |
| | Migration of vascular endothelial cells | | -2.09 |
| IMMUNE SYSTEM AND INFLAMMATORY PROCESS | Recruitment of leukocytes | | -3.01 |
| | Recruitment of myeloid cells | | -2.70 |
| | Recruitment of phagocytes | | -2.69 |
| | Recruitment of mononuclear leukocytes | | -2.37 |
| | Maturation of dendritic cells | | -2.20 |
| | Synthesis of prostaglandin | | -2.13 |
| | Binding of mononuclear leukocytes | | -2.09 |
| TUMOR VIABILITY AND PROLIFERATION | Cell movement of tumor cell lines | | -3.95 |
| | Migration of tumor cell lines | | -3.78 |
| | Cell viability | | -3.47 |
| | Cell survival | | -3.41 |
| | Mitosis | | -3.15 |
| | Proliferation of vascular cells | | -3.06 |
| | Proliferation of connective tissue cells | | -2.96 |
| | Differentiation of connective tissue cells | | -2.82 |
| | Invasion of tumor cell lines | | -2.78 |
| | Cell movement of breast cancer cell lines | | -2.78 |
| | Adhesion of tumor cell lines | | -2.76 |
| | Invasion of carcinoma cell lines | | -2.76 |
| | Invasive cancer | | -2.76 |
| | Growth of tumor | | -2.74 |
| | Advanced malignant tumor | | -2.69 |
| | Metastasis | | -2.69 |
| | Migration of tumor cells | | -2.66 |
| | Migration of breast cancer cell lines | | -2.59 |
| | Binding of tumor cell lines | | -2.28 |
| | Migration of cancer cells | | -2.27 |
| | Metastasis of cells | | -2.25 |
| | Metastasis of tumor cell lines | | -2.23 |
| | Mitogenesis | | -2.20 |
| | Synthesis of prostaglandin E2 | | -2.13 |
| | Cell movement of tumor cells | | -2.11 |
| | Migration of carcinoma cell lines | | -2.10 |
| | Proliferation of tumor cells | | -2.07 |
| | Cell death of cancer cells | | -2.06 |
| | Cell movement of carcinoma cell lines | | -2.01 |
| | Organismal death | | |

DOWNMODULATION (CUT-OFF ≤ -2)

UPMODULATION (CUT-OFF ≥ 2)

Fig. 17

SIZE DISTRIBUTION BY INTENSITY

Workflow for Treating Squamous Cell Carcinoma with EpigenAU/11 and Cisplatin

Workflow for Treating Squamous Cell Carcinoma with
EpigenAU/11, Cisplatin, and Their Combination

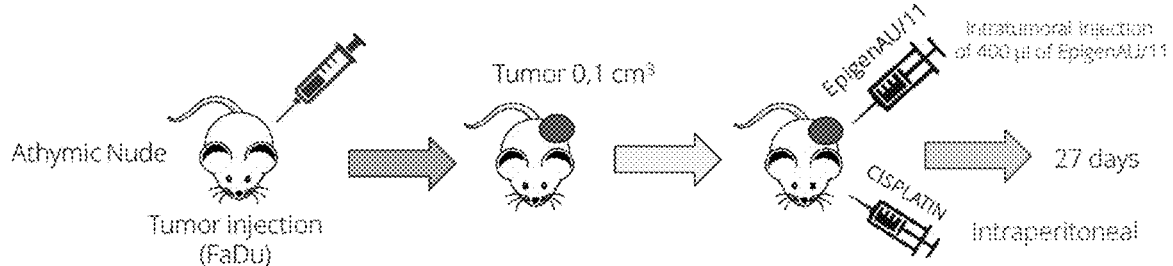

Athymic Nude

Tumor injection
(FaDu)

Tumor 0.1 cm³

EpigenAU/11

Intratumoral injection
of 400 µl of EpigenAU/11

CISPLATIN 27 days

Intraperitoneal

FaDu is a cell line
isolated from a
hypopharyngeal
tumor of a
squamous cell
carcinoma
patient.

| CONDITION |
| --- |
| VEHICLE |
| EpigenAU/11 50 mg/ml everyday |
| Cisplatin 2 mg/kg every other day |
| EpigenAU/11 50 mg/ml everyday + Cisplatin 2 mg/kg every other day |

Fig. 23

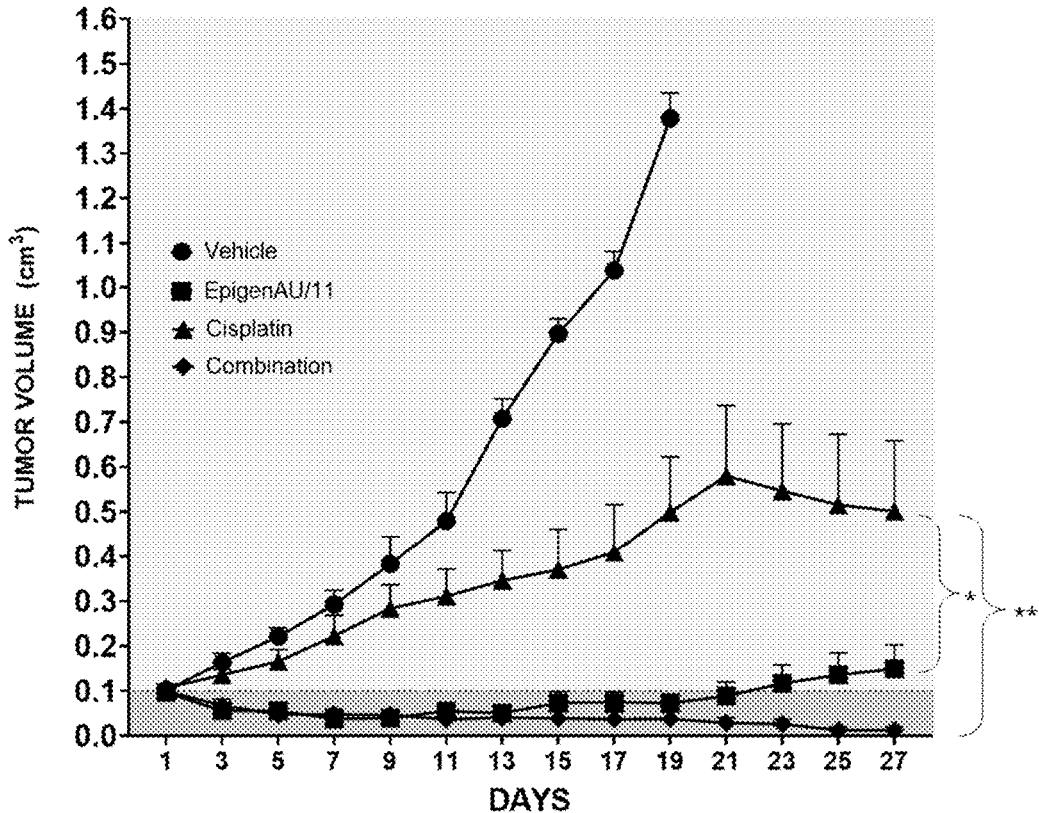

Fig. 24

11

BENEFIT SCORE CALCULATION

Evaluation of *in vivo* pathological parameters (ie calculation of tumor mass size)

Calculation of benefit score for each treatment

10

RISK SCORE CALCULATION

Evaluation of *in vivo* parameters related to animal suffering:

➤ BEHAVIORAL PARAMETERS:

1. Loss of Spontaneous activity
2. Loss of Cleaning
3. Loss of Curiosity
4. Loss of Reactivity
5. Loss of Straightening reflex
6. Loss of Physical strength
7. Impairment of Palpebral opening
8. Palpebral reflex
9. Tremors
10. Pallor
11. Stereotypies
12. Passivity

➤ ANIMAL WEIGHT LOSS

Data normalization and calculation of risk score for each treatment, summing each value obtained

CALCULATION OF BENEFIT/RISK SCORE FOR EACH TREATMENT APPLING:

$$\frac{BENEFIT\ SCORE}{RISK\ SCORE}$$

12

Fig. 30

| HALLMARKS | ANNOTATED SIDE EFFECTS | IPA BIOLOGICAL ACTIVITIES (with healthy trends) |
|---|---|---|
| NEPHROTOXICITY | Damage of kidney | Injury of renal glomeruly |
| | | Damage of kidney |
| | | Injury of kidney |
| | | Cisplatin-inducedf acute kidney injury |
| | | Acute kidney injury |
| | Failure of kidney | Failure of kidney |
| | | Acute renal failure |
| | Increase of azotemia/uremia | Uremia |
| | | Azotemia |
| | Clearance of creatinine | Increased clearance of creatinine |
| | | Increased levels of creatinine |
| | | Quantity of creatinine in blood |
| | Hematuria | Hematuria |
| | Hyperuricemia | Hyperuricemia |
| OTOTOXICITY | Tinnitus | Tinnitus |
| | Hearing loss | Hearing loss |
| HEMATOLOGY | Suppression of bone marrow | Suppression of bone marrow |
| | Decrease of production of myelocites | Proliferation of myeloblast |
| | | Proliferation of promyelocytes |
| | | Expansion of myelocytes |
| | | Expansion of metamyelocytes |
| | | Cell division of myeloblasts |
| | Leukopenia | Leukopenia |
| | | Leukopenia of bone marrow |
| | Thrombocytopenia | Thrombocytopenia |
| | Anemia | Anemia |
| | | Chemotherapy-induced Anemia |
| GASTROINTESTINAL TRACT | Nausea | Nausea |
| | Vomiting | Vomiting |
| | Anorexia | Anorexia |
| NEUROTOXICITY | Peripheral neuropathy | Distal peripheral neuropathy |
| | | Peripheral neuropathy |
| | | Progressive peripheral neuropathy |
| | | Severe peripheral neuropathy |
| | Ageusia | Ageusia |
| ANAPHYLACTIC-LIKE REACTIONS | Edema | Edema of skin |
| | | Edema |
| | | Periorbital edema |
| | Dyspnea | Dyspnea |
| | Tachycardia | Tachycardia |
| | Hypotension | Hypotension |
| GENERAL TOXICITY | Cisplatin toxicity | Citotoxicity of Cisplatin |
| | | Toxicity of Cisplatin |
| | | Cisplatin-induced acute kidney injury |

UP-MODULATION
DOWN-MODULATION

Fig. 31

| HALLMARKS | BIOLOGICAL ACTIVITIES | EpigenAU/11 | Cisplatin |
|---|---|---|---|
| ANGIOGENESIS | Angiogenesis | -3,03 | -2,98 |
| | Development of vasculature | -3,02 | -2,03 |
| | Vascularization | -3,13 | 0,00 |
| | Vasculogenesis | -3,15 | 0,00 |
| METASTATISATION | Adhesion of tumor cell lines | -2,10 | 0,00 |
| | Cell movement of tumor cell lines | -3,48 | 0,00 |
| | Cell movement of tumor cells | -2,97 | 0,00 |
| | Differentiation of tumor cell lines | -2,02 | 0,00 |
| | Interaction of tumor cell lines | -2,10 | 0,00 |
| | Invasion of tumor | -3,72 | -2,76 |
| | Invasion of tumor cell lines | -3,46 | 0,00 |
| | Invasion of tumor cells | -2,97 | -2,11 |
| | Metastasis of cells | -3,46 | 0,00 |
| | Metastasis of tumor cell lines | -3,32 | 0,00 |
| | Migration of cancer cells | -2,70 | 0,00 |
| | Migration of tumor cell lines | -3,29 | 0,00 |
| | Migration of tumor cells | -3,07 | 0,00 |
| | Shape change of tumor cell lines | -2,78 | 0,00 |
| PREMETASTATIC NICHE FORMATION | Fibrogenesis | 0,00 | -2,10 |
| TUMOR VIABILITY | Cancer of cells | -2,13 | -2,11 |
| | Cell cycle progression | -2,25 | 0,00 |
| | Cell death of cancer cells | 0,00 | -2,48 |
| | Cell survival | -3,93 | 0,00 |
| | Cell transformation | -2,31 | 0,00 |
| | Cell viability | -3,95 | -2,17 |
| | Cell viability of cancer cells | -2,06 | 0,00 |
| | Cell viability of tumor cell lines | -3,14 | 0,00 |
| | Cell viability of tumor cells | 0,00 | -2,67 |
| | Epithelial-mesenchymal transition | -2,09 | 0,00 |
| | Microtubule dynamics | -4,21 | 0,00 |
| | Neoplasia of cells | -2,75 | -2,24 |
| | Neoplasia of tumor cell lines | -3,51 | 0,00 |
| | Organization of cytoplasm | -4,12 | 0,00 |
| | Organization of cytoskeleton | -4,15 | 0,00 |
| | Proliferation of cancer cells | -2,16 | 0,00 |

Fig. 32 A

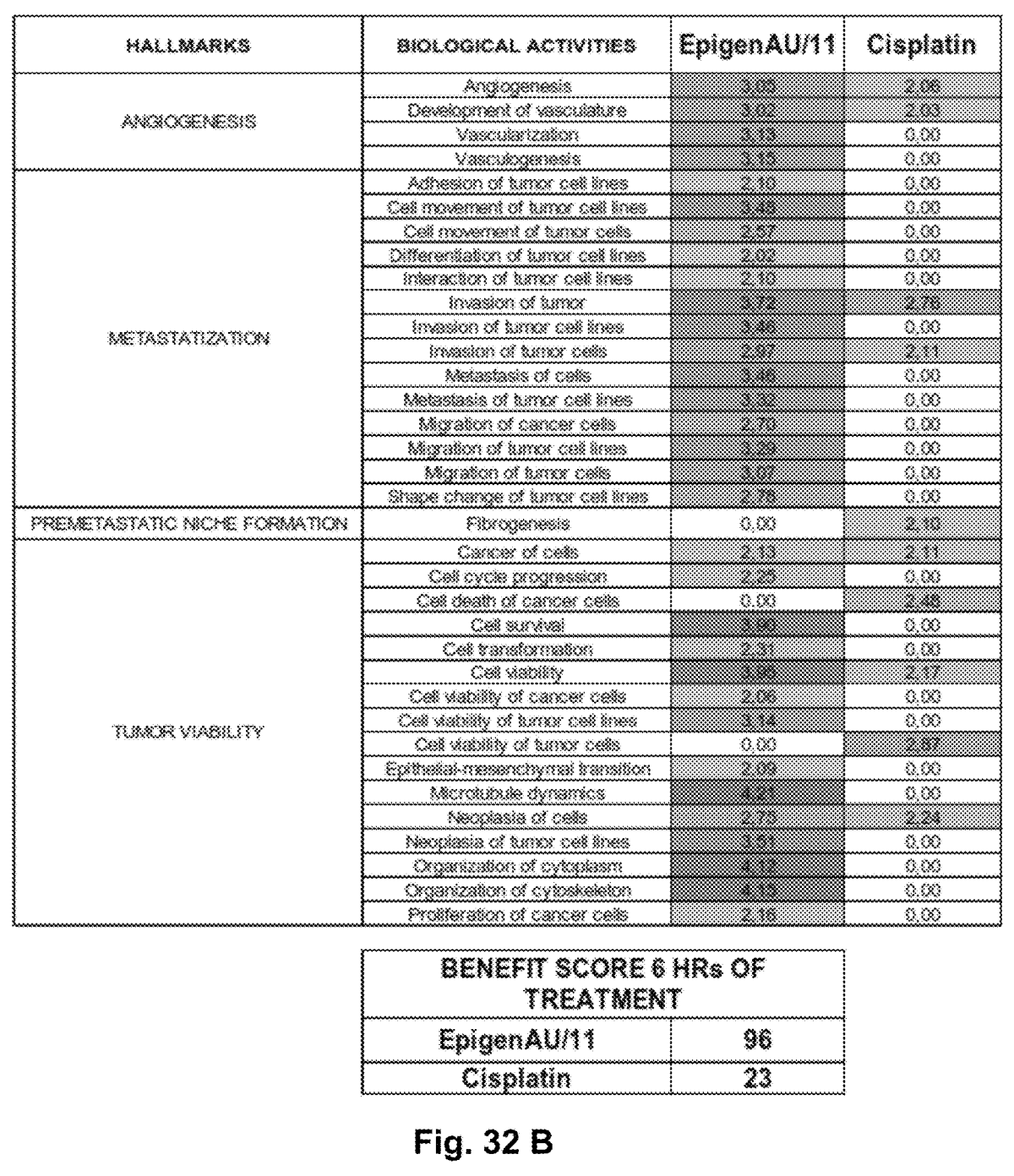

| HALLMARKS | BIOLOGICAL ACTIVITIES | EpigenAU/11 | Cisplatin |
|---|---|---|---|
| ANGIOGENESIS | Angiogenesis | | 2.06 |
| | Development of vasculature | | 2.00 |
| | Vascularization | | 0.00 |
| | Vasculogenesis | | 0.00 |
| METASTATIZATION | Adhesion of tumor cell lines | | 0.00 |
| | Cell movement of tumor cell lines | | 0.00 |
| | Cell movement of tumor cells | | 0.00 |
| | Differentiation of tumor cell lines | | 0.00 |
| | Interaction of tumor cell lines | | 0.00 |
| | Invasion of tumor | | 2.78 |
| | Invasion of tumor cell lines | | 0.00 |
| | Invasion of tumor cells | | 2.11 |
| | Metastasis of cells | | 0.00 |
| | Metastasis of tumor cell lines | | 0.00 |
| | Migration of cancer cells | | 0.00 |
| | Migration of tumor cell lines | | 0.00 |
| | Migration of tumor cells | | 0.00 |
| | Shape change of tumor cell lines | | 0.00 |
| PREMETASTATIC NICHE FORMATION | Fibrogenesis | 0.00 | 2.10 |
| TUMOR VIABILITY | Cancer of cells | | 2.11 |
| | Cell cycle progression | | 0.00 |
| | Cell death of cancer cells | 0.00 | 2.48 |
| | Cell survival | | 0.00 |
| | Cell transformation | | 0.00 |
| | Cell viability | | 2.17 |
| | Cell viability of cancer cells | | 0.00 |
| | Cell viability of tumor cell lines | | 0.00 |
| | Cell viability of tumor cells | 0.00 | 2.87 |
| | Epithelial-mesenchymal transition | | 0.00 |
| | Microtubule dynamics | | 0.00 |
| | Neoplasia of cells | | 2.24 |
| | Neoplasia of tumor cell lines | | 0.00 |
| | Organization of cytoplasm | | 0.00 |
| | Organization of cytoskeleton | | 0.00 |
| | Proliferation of cancer cells | | 0.00 |

| BENEFIT SCORE 6 HRs OF TREATMENT | |
|---|---|
| EpigenAU/11 | 96 |
| Cisplatin | 23 |

Fig. 32 B

| HALLMARKS | BIOLOGICAL ACTIVITIES | COEFFICIENT OF IMPORTANCE | EpigenAU/11 | Cisplatin |
|---|---|---|---|---|
| ANGIOGENESIS | Angiogenesis | 1 | -3.35 | -2.88 |
| | Development of vasculature | 1 | -3.02 | -2.83 |
| | Vascularization | 1 | -3.13 | 0.00 |
| | Vasculogenesis | 1 | -3.15 | 0.00 |
| METASTATISATION | Adhesion of tumor cell lines | 2 | -2.19 | 0.00 |
| | Cell movement of tumor cell lines | 2 | -3.48 | 0.00 |
| | Cell movement of tumor cells | 2 | -2.57 | 0.00 |
| | Differentiation of tumor cell lines | 2 | -3.03 | 0.00 |
| | Interaction of tumor cell lines | 2 | -2.19 | 0.00 |
| | Invasion of tumor | 2 | -3.72 | -2.76 |
| | Invasion of tumor cell lines | 2 | -3.46 | 0.00 |
| | Invasion of tumor cells | 2 | -2.97 | -2.11 |
| | Metastasis of cells | 2 | -3.46 | 0.00 |
| | Metastasis of tumor cell lines | 2 | -3.32 | 0.00 |
| | Migration of cancer cells | 2 | -2.70 | 0.00 |
| | Migration of tumor cell lines | 2 | -3.29 | 0.00 |
| | Migration of tumor cells | 2 | -3.07 | 0.00 |
| | Shape change of tumor cell lines | 2 | -2.76 | 0.00 |
| PREMETASTATIC NICHE FORMATION | Fibrogenesis | 1 | 0.00 | -2.19 |
| TUMOR VIABILITY | Cancer of cells | 2 | -2.13 | -2.11 |
| | Cell cycle progression | 2 | -2.25 | 0.00 |
| | Cell death of cancer cells | 2 | 0.00 | -2.48 |
| | Cell survival | 2 | -3.90 | 0.00 |
| | Cell transformation | 2 | -2.31 | 0.00 |
| | Cell viability | 2 | -3.95 | -2.17 |
| | Cell viability of cancer cells | 2 | -2.96 | 0.00 |
| | Cell viability of tumor cell lines | 2 | -3.14 | 0.00 |
| | Cell viability of tumor cells | 2 | 0.00 | -2.87 |
| | Epithelial-mesenchymal transition | 2 | -2.08 | 0.00 |
| | Microtubule dynamics | 2 | -4.21 | 0.00 |
| | Neoplasia of cells | 2 | -2.73 | -3.24 |
| | Neoplasia of tumor cell lines | 2 | -3.51 | 0.00 |
| | Organization of cytoplasm | 2 | -4.12 | 0.00 |
| | Organization of cytoskeleton | 2 | -4.15 | 0.00 |
| | Proliferation of cancer cells | 2 | -2.16 | 0.00 |

Fig. 32 C

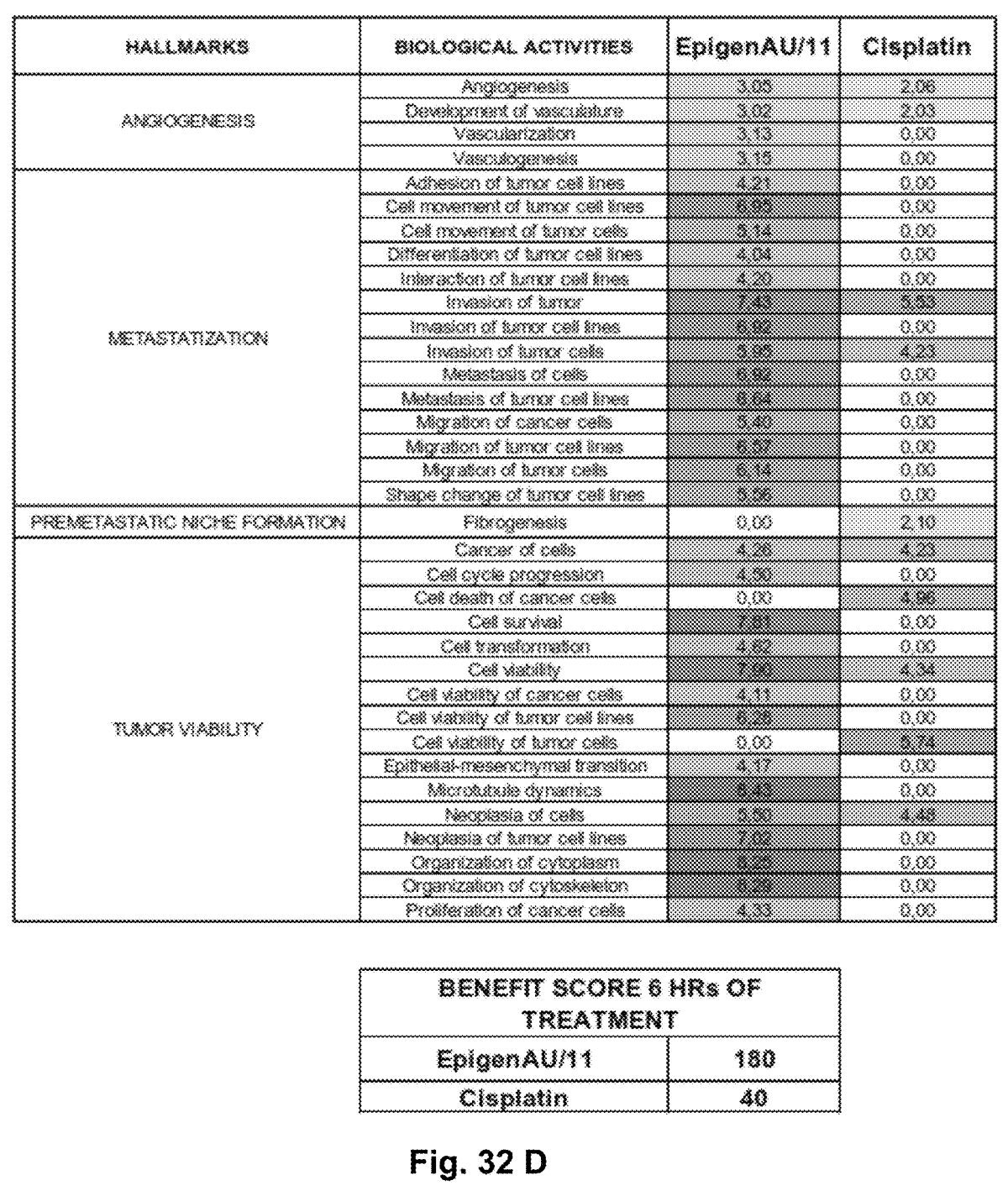

| HALLMARKS | BIOLOGICAL ACTIVITIES | EpigenAU/11 | Cisplatin |
|---|---|---|---|
| ANGIOGENESIS | Angiogenesis | 3.05 | 2.06 |
| | Development of vasculature | 3.02 | 2.00 |
| | Vascularization | 3.13 | 0.00 |
| | Vasculogenesis | 3.15 | 0.00 |
| METASTATIZATION | Adhesion of tumor cell lines | 4.21 | 0.00 |
| | Cell movement of tumor cell lines | | 0.00 |
| | Cell movement of tumor cells | | 0.00 |
| | Differentiation of tumor cell lines | 4.04 | 0.00 |
| | Interaction of tumor cell lines | 4.20 | 0.00 |
| | Invasion of tumor | | |
| | Invasion of tumor cell lines | | 0.00 |
| | Invasion of tumor cells | | |
| | Metastasis of cells | | 0.00 |
| | Metastasis of tumor cell lines | | 0.00 |
| | Migration of cancer cells | | 0.00 |
| | Migration of tumor cell lines | | 0.00 |
| | Migration of tumor cells | | 0.00 |
| | Shape change of tumor cell lines | | 0.00 |
| PREMETASTATIC NICHE FORMATION | Fibrogenesis | 0.00 | 2.10 |
| TUMOR VIABILITY | Cancer of cells | 4.28 | 4.23 |
| | Cell cycle progression | 4.66 | 0.00 |
| | Cell death of cancer cells | 0.00 | |
| | Cell survival | | 0.00 |
| | Cell transformation | 4.62 | 0.00 |
| | Cell viability | | 4.34 |
| | Cell viability of cancer cells | 4.11 | 0.00 |
| | Cell viability of tumor cell lines | | 0.00 |
| | Cell viability of tumor cells | 0.00 | |
| | Epithelial-mesenchymal transition | 4.17 | 0.00 |
| | Microtubule dynamics | | 0.00 |
| | Neoplasia of cells | | 4.48 |
| | Neoplasia of tumor cell lines | | 0.00 |
| | Organization of cytoplasm | | 0.00 |
| | Organization of cytoskeleton | | 0.00 |
| | Proliferation of cancer cells | 4.03 | 0.00 |

| BENEFIT SCORE 6 HRs OF TREATMENT | |
|---|---|
| EpigenAU/11 | 180 |
| Cisplatin | 40 |

Fig. 32 D

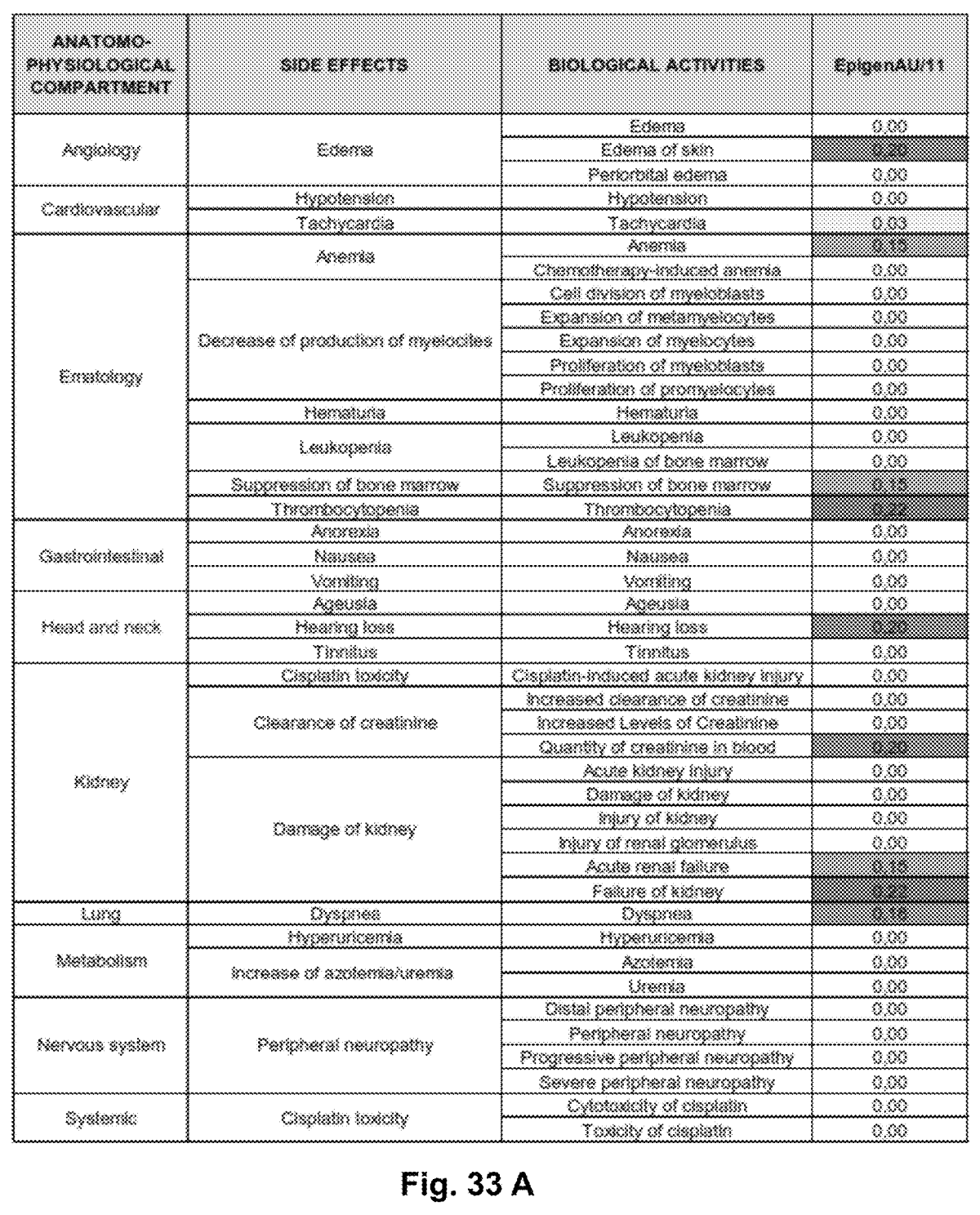

| ANATOMO-PHYSIOLOGICAL COMPARTMENT | SIDE EFFECTS | BIOLOGICAL ACTIVITIES | EpigenAU/11 |
|---|---|---|---|
| Angiology | Edema | Edema | 0.00 |
| | | Edema of skin | |
| | | Periorbital edema | 0.00 |
| Cardiovascular | Hypotension | Hypotension | 0.00 |
| | Tachycardia | Tachycardia | 0.00 |
| Ematology | Anemia | Anemia | |
| | | Chemotherapy-induced anemia | 0.00 |
| | Decrease of production of myelocites | Cell division of myeloblasts | 0.00 |
| | | Expansion of metamyelocytes | 0.00 |
| | | Expansion of myelocytes | 0.00 |
| | | Proliferation of myeloblasts | 0.00 |
| | | Proliferation of promyelocytes | 0.00 |
| | Hematuria | Hematuria | 0.00 |
| | Leukopenia | Leukopenia | 0.00 |
| | | Leukopenia of bone marrow | 0.00 |
| | Suppression of bone marrow | Suppression of bone marrow | |
| | Thrombocytopenia | Thrombocytopenia | |
| Gastrointestinal | Anorexia | Anorexia | 0.00 |
| | Nausea | Nausea | 0.00 |
| | Vomiting | Vomiting | 0.00 |
| Head and neck | Ageusia | Ageusia | 0.00 |
| | Hearing loss | Hearing loss | |
| | Tinnitus | Tinnitus | 0.00 |
| Kidney | Cisplatin toxicity | Cisplatin-induced acute kidney injury | 0.00 |
| | Clearance of creatinine | Increased clearance of creatinine | 0.00 |
| | | Increased Levels of Creatinine | 0.00 |
| | | Quantity of creatinine in blood | |
| | Damage of kidney | Acute kidney injury | 0.00 |
| | | Damage of kidney | 0.00 |
| | | Injury of kidney | 0.00 |
| | | Injury of renal glomerulus | 0.00 |
| | | Acute renal failure | |
| | | Failure of kidney | |
| Lung | Dyspnea | Dyspnea | |
| Metabolism | Hyperuricemia | Hyperuricemia | 0.00 |
| | Increase of azotemia/uremia | Azotemia | 0.00 |
| | | Uremia | 0.00 |
| Nervous system | Peripheral neuropathy | Distal peripheral neuropathy | 0.00 |
| | | Peripheral neuropathy | 0.00 |
| | | Progressive peripheral neuropathy | 0.00 |
| | | Severe peripheral neuropathy | 0.00 |
| Systemic | Cisplatin toxicity | Cytotoxicity of cisplatin | 0.00 |
| | | Toxicity of cisplatin | 0.00 |

Fig. 33 A

| ANATOMO-PHYSIOLOGICAL COMPARTMENT | SIDE EFFECTS | BIOLOGICAL ACTIVITIES | Cisplatin |
|---|---|---|---|
| Angiology | Edema | Edema | 0.00 |
| | | Edema of skin | 0.06 |
| | | Periorbital edema | 0.00 |
| Cardiovascular | Hypotension | Hypotension | 0.00 |
| | Tachycardia | Tachycardia | 0.00 |
| Ematology | Anemia | Anemia | 0.00 |
| | | Chemotherapy-induced anemia | 0.00 |
| | Decrease of production of myelocites | Cell division of myeloblasts | 0.00 |
| | | Expansion of metamyelocytes | 0.00 |
| | | Expansion of myelocytes | 0.00 |
| | | Proliferation of myeloblasts | 0.00 |
| | | Proliferation of promyelocytes | 0.00 |
| | Hematuria | Hematuria | 0.00 |
| | Leukopenia | Leukopenia | 0.00 |
| | | Leukopenia of bone marrow | 0.00 |
| | Suppression of bone marrow | Suppression of bone marrow | |
| | Thrombocytopenia | Thrombocytopenia | |
| Gastrointestinal | Anorexia | Anorexia | 0.00 |
| | Nausea | Nausea | 0.00 |
| | Vomiting | Vomiting | 0.00 |
| Head and neck | Ageusia | Ageusia | 0.00 |
| | Hearing loss | Hearing loss | 0.00 |
| | Tinnitus | Tinnitus | 0.00 |
| Kidney | Cisplatin toxicity | Cisplatin-induced acute kidney injury | 0.00 |
| | | Cytotoxicity of cisplatin | 0.00 |
| | | Toxicity of cisplatin | 0.00 |
| | Clearance of creatinine | Increased clearance of creatinine | 0.00 |
| | | Increased Levels of Creatinine | 0.00 |
| | | Quantity of creatinine in blood | |
| | Damage of kidney | Acute kidney injury | 0.00 |
| | | Damage of kidney | 0.00 |
| | | Injury of kidney | 0.04 |
| | | Injury of renal glomerulus | 0.00 |
| | Failure of kidney | Acute renal failure | 0.00 |
| | | Failure of kidney | |
| Lung | Dyspnea | Dyspnea | 0.00 |
| Metabolism | Hyperuricemia | Hyperuricemia | 0.00 |
| | Increase of azotemia/uremia | Azotemia | 0.00 |
| | | Uremia | 0.00 |
| Nervous system | Peripheral neuropathy | Distal peripheral neuropathy | 0.00 |
| | | Peripheral neuropathy | 0.00 |
| | | Progressive peripheral neuropathy | 0.00 |
| | | Severe peripheral neuropathy | 0.00 |

Fig. 33 B

| RISK SCORE 6 HRs OF TREATMENT | |
|---|---|
| EpigenAU/11 | 1,70 |
| Cisplatin | 0,80 |

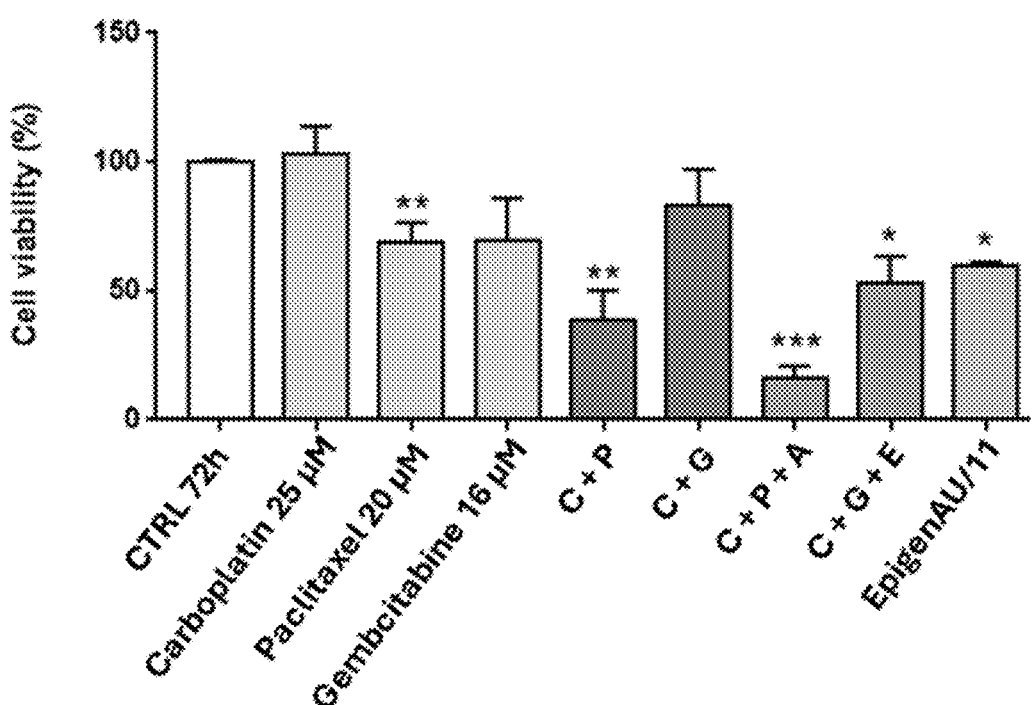
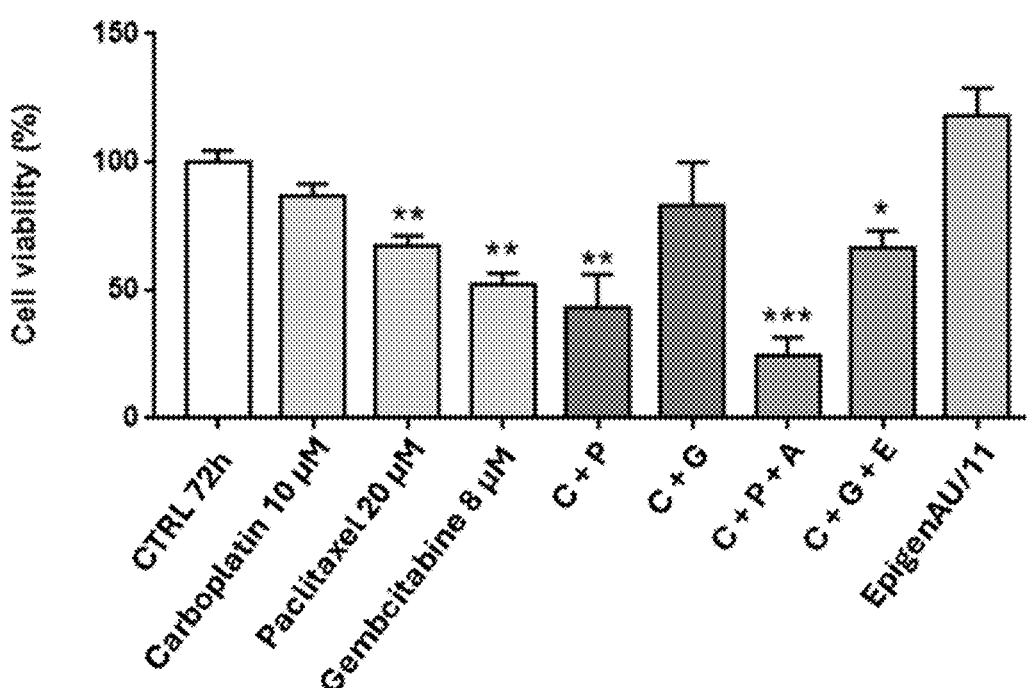
Fig. 38

Figure 44:
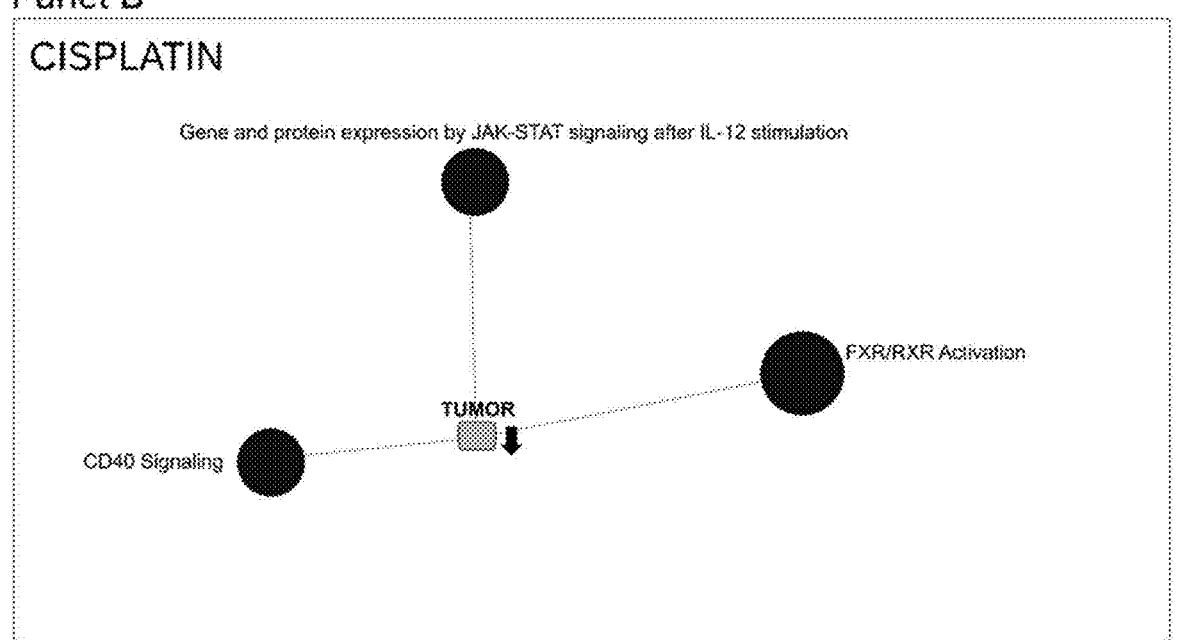
Figure 44:
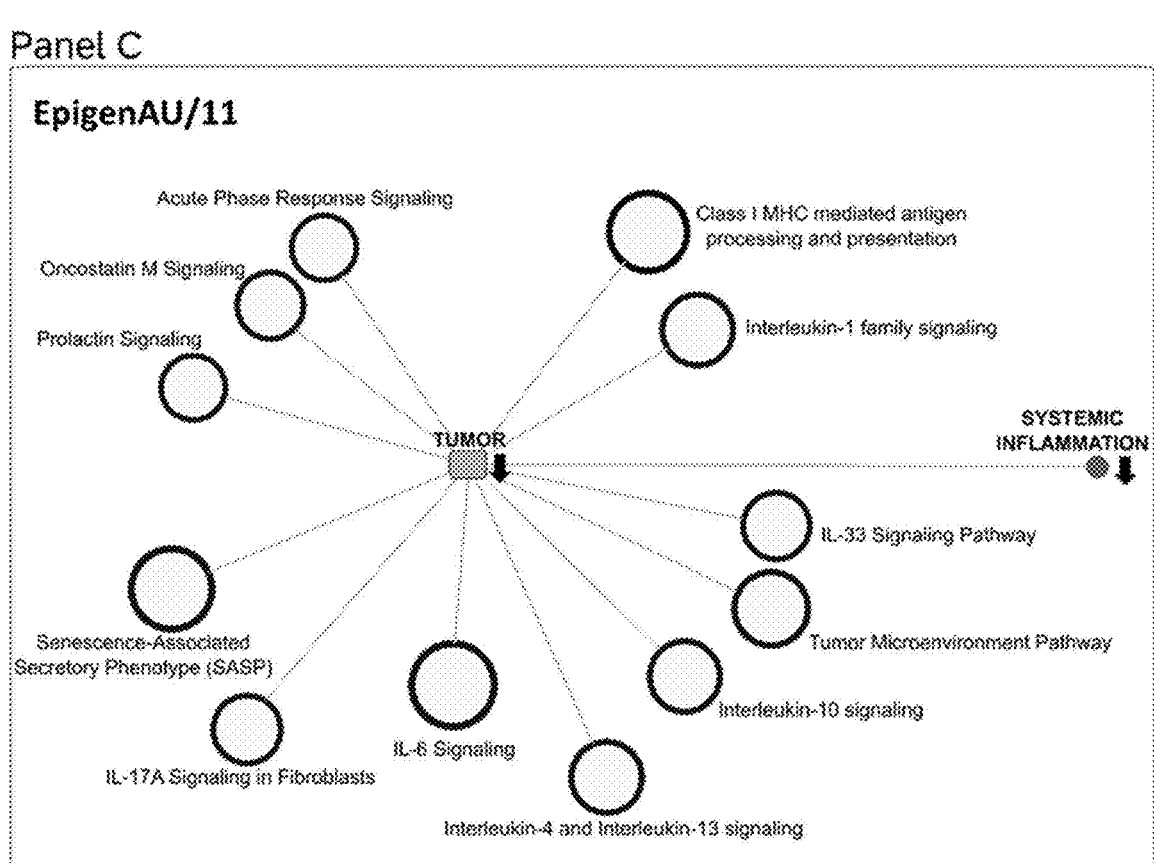

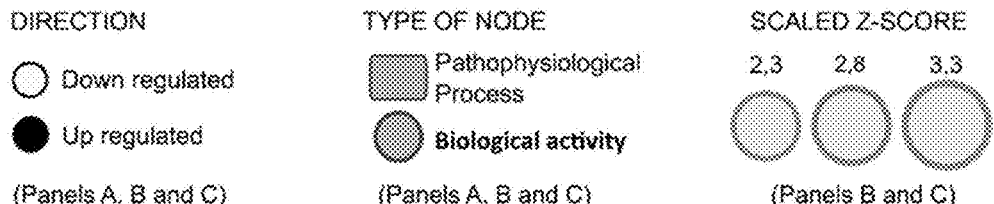
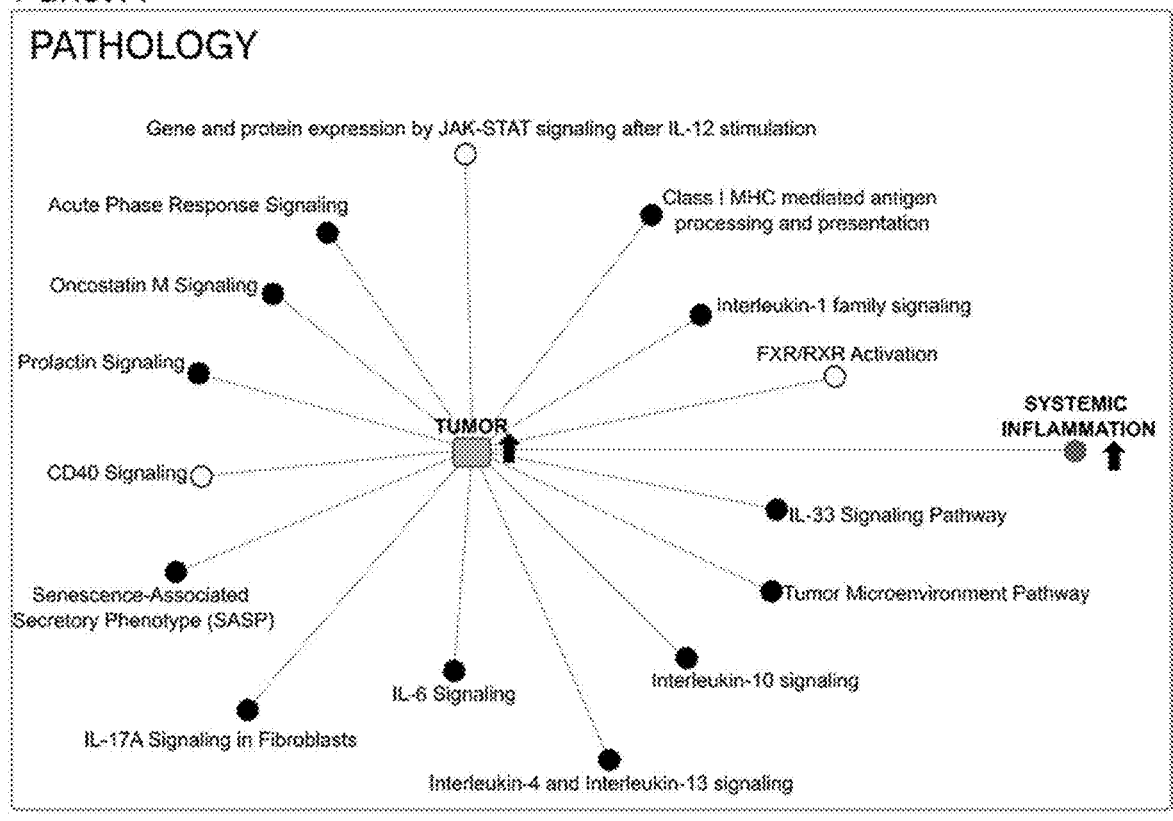
Fig. 44 A

Panel B

Panel C

EPIGEN AU/11: A NATURAL MATRIX FOR RESTORING HOMEOSTASIS IN CANCER CELL-INFILTRATED TISSUE

TECHNICAL FIELD OF THE INVENTION

The present invention relates to a new composition of matter consisting of 100% natural matter, exerting a therapeutic or adjuvant effect in the treatment of cancer, having a physiological (as opposed to pharmacological) mode of action.

In particular, the invention relates to the exclusive selection and use of native matrices, appropriately processed through specific processes and methods, to create final products intended for therapeutic or adjuvating purposes, for restoring or adjuvating the organism in restoring healthy physiological states in cancer patients. Every phase of the production process of such products is under the aegis of the One Health principle (which is a principle that recognizes the interconnectedness of human health, animal health, and environmental health), therefore, the use of artificial forces or substances is not permitted.

Indeed, in the field of the present invention, a fundamental requirement is represented by the fact that the final product, that is a product comprising or consisting of one or more natural matrices, must maintain the natural intelligence i.e. the imprint of the domain of the living to which each constituent of the product belongs, thereby maintaining a network capable of interconnecting and recognizing itself with other networks, whether natural or artificial, that is, originally natural networks that have acquired a degree of artificiality due to interaction with artificial components. This interconnection is deemed to be fundamental to rebalance any disturbances in the network of events that are active in each interacting biological system. Every matrix identified will present bio-physical specifications such that it will represent an invention on its own.

Each network of each native natural matrix comprised in the product, which will contribute to forming the network of the final matrix of the product of the invention, can be defined as a UVCB substance (i.e. Substances of Unknown or Variable composition, Complex reaction products, or Biological materials) according to the REACH (Registration, Evaluation, Authorisation, and Restriction of Chemicals) definition since, being a product processed respecting its self-assembly peculiarities, it cannot be determined nor validated on the basis of small molecule chemistry protocols.

Each network will be characterized by the establishment of connections within the matrices in the final product and within the physiological actions exerted by the product on the receiving organism. The production validation of the product can be carried out and confirmed using probabilistic models based on the link between the conservation of a physiological activity profile and descriptors of the matrix per se generated using multiple bio-physical analytical systems, including spectroscopy (NIR and other techniques), mass spectrometry, and paper or X-ray crystallography (fractal measurements). Although useful, the conventional molecular chemical definitions of individual substances contained in matter cannot be used for validating this kind of products as they are not representative of the overall effectiveness and quality thereof.

The selection of matrices intended for administration must be validated according to the updated and specific current taxonomic criteria for the animal, plant and mineral kingdoms. In case of use in combination with natural physical phenomena, it will be necessary to validate the relationship between action and effectiveness on a case-by-case basis, considering sound effects (music or other forms) and those in the field of wave-particles, including those of a quantum nature.

In the current state of the art, it will not always be possible to outline a fully described mechanism of action; however, it will be possible to validate the action and reaction in the interconnection of the respective networks, already validated at a biophysical level.

The invention aims to select and provide new entities or products, as well as systems capable of rebalancing, activating, or limiting physiological functions in specific metabolic states of living organisms, that are always in continuous transformation.

The preparations conceived in this way can rebalance the psycho-neuro-endocrine-immunological system, considered as a single system that governs and manages all the other systems.

The invention contributes to a new state of the art that goes beyond the alchemical technologies in the medical field, the beginning of which can be traced back to the early years of the sixteenth century, bringing products and processes back to the conceptual One Health objective already mentioned. The invention proposes a new declination of artificial technologies and of those that naturally self-assemble matter, recognizing existing rules or finding new ones in order to guarantee the constitution of entities that can be validated, mainly based on the concept of validating of their effect and activity on other organisms. The latter, being living beings in continuous transformation, require an evaluation of their physiological state within defined intervals, which is a concept that today falls within the personalized medicine. The present invention fits into the concept of scientificity, understood as the set of knowledge that can demonstrably validate the effects of theoretical modes of action. Today, these methods find application in the establishment of interconnections between all forms of life, in a context in which technological innovations advance at such a pace as to risk compromising the interconnection between human-generated (artificial) intelligence and natural.

Since the activities of the invention herein disclosed are not currently covered by the state of the art, it will be necessary to consider the entire product cycle, from the end user to the social context concerned, under the concept of One Health.

The operational paradigm within which the invention was prepared has been herein denominated as "Bios Physiological Health".

This paradigm aims to introduce into the field of medical art an innovative approach for the treatment and self-management of health using natural matrices, alone or in combination, in order to rebalance the normal physiological states of various living entities, including humans, through endogenous physiological actions triggered by the product. It is a matter of identifying, selecting, and assembling natural entities which possess emerging properties, validable through the final product's physiological mode of an action and other methods evolved in recent decades.

A reading of the context according to both technical-scientific and humanistic canons, integrated in their transversality, constitutes the foundation of the proposed invention. Although some of the properties of each matrix part of the product may already be known the emerging properties of the new composition are unexpected.

Of particular relevance is the role of determining the genetic and epigenetic aspects determining the network representing natural matrices and their description at the level of their specific isotopic abundance.

In order to fulfil the Bios Physiological Health paradigm, each phase of processing, from the selection of the reproductive material to the agricultural and industrial phases, up to the methods of use, must preserve as much as possible the integrity of the native programming heritage, inserted into the natural intelligence of each entity of creation, at least as far as known in our terrestrial dimension. It will be essential to validate matrices coming from epigenetic realities similar to the reference one, recognized as a Reference Standard for its specific emerging properties on the metabolism of other living beings, including humans. By way of example, one of the factors that negatively influences epigenetic differentiations is represented by different soil conditions, together with circadian, monthly, and annual variations. To preserve the properties of the natural system, which are the only ones that can claim physiological interconnection with the whole of creation, it is not possible to use substances derived from alchemical processes, such as distillation, other processes of synthesis or hemi synthesis, or products derived from genetic modifications or genetically modified organisms. A new interpretation of the mysteries of natural programming, responsible for the vital evolution of organic and inorganic matter, is needed. The consolidation of scientific evolution in recent decades allows us to reposition the understanding of the genesis of a progress based on reductionist determinism, founded on the development of alchemical processes starting from the beginning of the 16th century, which in medicine, with Paracelsus, marked the beginning of the current evolutionary process, known as the Anthropocene.

The term Anthropocene describes the current phase of human evolution and can be dated back to different eras. If considered in the context of this invention, the key date can only be 1492, which represents the end of the humanistic/ neo platonic period of the early Renaissance. This period was represented politically by Cosimo the Elder and Lorenzo de'Medici, with artists and scientists such as Piero della Francesca, Luca Pacioli, Leonardo and Dürer. In the 16th century, alchemical research seen as a human possibility of dominion over nature, has evolved until today under the aegis of artificial intelligence as opposed to the natural one, inspired from the biblical thought according to which "man will dominate over all creation", with the aim of improving divine creation.

1492 is a symbolic date: in that year Lorenzo de'Medici and Piero della Francesca died, while Columbus discovered America. The human species abandoned the fifteenth-century Neoplatonic path to follow the Judeo-Catholic one, where the alchemical practices of Paracelsus applied to medicine marked the transition to the Renaissance mannerism of the 1500s, which, up to the present day, has led us towards a full-blown and irreversible sixth extinction.

The present invention, with the demonstration of feasibility of the resulting industrial discoveries in the medical field, but in principle adaptable to any production field, intends to address the change in evolutionary paradigms. We often talk about defending biodiversity without ever addressing the real problem, guiltily obscured, of the billions of tons of exogenous and non-biodegradable artificial substances released into the planetary system, with the certainty of irreversibly poisoning the sources of life, while the "carpe diem" approach prevails over the survival instinct of the species.

The invention is presented primarily in the patent context, with the hope of opening new areas of research that explore and share natural intelligence, rather than artificial intelligence, which, can do very little to stop or slow down the sixth extinction, or to lay the foundations of an alternative progress to the current one. The inventor Valentino Mercati, together with his collaborator Jacopo Lucci, has undertaken the path of researching in nature itself what can be useful to the living systems, and has developed a knowledge in the agricultural and industrial production system for over 40 years, presenting numerous patent applications following this operational strategy. The patents filed in the past relating to the present inventive process are essentially based on instrumental and diagnostic readings based on principles related to chemistry for the connection of physiological actions with the emerging properties of natural matrices and the innate defences of each individual living being with which they interconnect.

The analyses that followed and inspired the approach herein disclosed were unthinkable just a few decades ago, due to the technological impossibility of reading the genetic and epigenetic information written in the cells of every living organism, and the role of atomic isotopic differentiations in the molecular self-assembly and interconnections of every single unity/individuality with the "universe". The conceptual difficulty in moving from the reassuring management parameters of the artificiality of molecules—at least partly purified and linked by powerful thermodynamic forces that allow strong bonds such as covalent ones, which acts on reduced molecular scopes of other organisms- to natural matrices, mysterious by definition and, still viewed today as part therapeutically unreliable, is extremely high.

If a new inventive interpretation is needed for a new medical state of the art after five centuries of alchemical reductionism, this interpretation must connect the most distant concepts and processes in a single application field. This is due, as already expressed, to a philosophical legacy that questions the human condition: the human species was created like all the others by the original vital intelligence with the purpose of life itself, as far as we can assume, to dominate on creation, or has it been experimentally endowed with different faculties from other organisms, already favourably inserted into creation, to constitute a new ecological niche at the service of the universe?

The answer to this dilemma does not arise for the current invention: humanity will have to return to the Neoplatonic thought of the early Renaissance, and the experimental duality of the human species must emancipate itself from the mindset of dominance in order to share its unique faculties within the universe with all of creation. Humanity will need to reconsider the warning of Leonardo da Vinci: "Man can only create his own offspring . . . " and reflect on the melancholic thoughts of wise figures like Piero della Francesca, Luca Pacioli, and Dürer, regarding the impossibility of understanding and representing the beauty of creation and deciphering its mysteries.

The era has arrived for the acquisition of new research centres in molecular and cellular biology, with an indispensable focus on bioinformatics and the new physical sciences. Today, the inventor can base research strategies and socio-economic applications in new therapeutic fields, particularly those that are complex and/or chronic-degenerative, where the restoration of metabolic balance for organisms either naturally or artificially disturbed will become an integral part of a future that is already present.

The present invention represents a new vision of the medical art, which reconsiders scientific evolution from a perspective different from reductionist determinism. This alternative progress, in conflict with universal or planetary rules, will have to rely not so much on artificial intelligence and technological advancement, but on the evolution of the laws that regulate our universe and life itself. The transition from the artificial treatment of singled out symptoms, even if seen from a systemic perspective with modern techniques of systems biology, to a holistic approach that embraces the whole, represents the basis of the present progress.

The present invention addresses the need of providing a product consisting of natural matrices for the treatment of cancer, or for adjuvating the treatment of cancer, when combined with an anticancer drug.

BACKGROUND OF THE INVENTION

Cancer cells, driven by their inherent nature, orchestrate significant intra- and extra-cellular modifications at the structural and metabolic levels. These alterations aim to bolster and facilitate cellular development, creating optimal conditions for tumour proliferation while concurrently establishing mechanisms for immune evasion.

The tumour organizes itself through a dense and complex network of actions carried out in order to set up an optimal organization for its own survival and proliferation, thus activating a wide and multifaceted corollary of genetic and metabolic mechanisms.

These peculiarities impact this type of cell transversely, often regardless of the nature of the tumour or the tissue where it develops.

Carcinogenesis is a process that arises and develops in the complexity of a cellular transformation both in its internal processes and in the surrounding environment, establishing an interaction network both with other tumour cells, the environment and the organism; the origin and development of the tumour microenvironment, understood as a vital network of relationships within which the tumour prolifer- ates, turns out to be a fundamental and crucial aspect for the management and treatment of the pathology.

Development, structuring into a 3D conformation, cre- ation of new blood vessels, extracellular acidification, and a glycolytic switch are essential processes that feed into the larger design of tumour microenvironment. In this context, a key aspect is represented by the metabolic transformation orchestrated by cancer cells and that involves a shift in energy production.

Unlike healthy cells, cancer cells exhibit a preference for glycolytic-type anaerobic metabolism over oxidative metabolism. This predilection for anaerobic metabolism, a hallmark feature known as the Warburg effect, appears paradoxical given the increased energy demands of cancer cells, even in the presence of oxygen. Although cancer cells use less efficient energy systems, such as the glycolytic system, they produce a higher amount of energy than healthy cells, with higher ATP production than noncancer cell lines.

The selection of glycolytic metabolism proves advanta- geous for the cancer cell. Despite the availability of oxygen, the rapid glycolytic process efficiently meets cellular energy requirements while inducing alterations in the intra- and extra-cellular environment conducive to tumour survival and development.

The implications of glycolytic metabolism manifest both upstream and downstream in the cellular processes. Upstream, cancer cells necessitate a heightened influx of glucose and nutrients, thus further strengthening their pro- liferative advantage over normal cells by reducing free glucose availability. Downstream, the process results in the production of metabolites such as lactate and H+, leading to extracellular acidification as a consequence of their effort.

Acidification of extracellular pH (pHe) is a useful strategy for evasion from immune system control.

These aspects are established within the tumour context to perpetuate changes in the extracellular and peritumoral environment. For instance, the need to bring more nutrients to the cells and the acidification of the neighbouring envi- ronment is interpreted by the organism as the need to counter the establishment of a hypoxic zone, leading to the stimu- lation of angiogenesis and thus the perpetuation of a vicious cycle beneficial for tumour establishment and progression.

The tumour microenvironment and the Warburg effect are therefore key aspects in understanding tumour pathophysi- ology; in this context, intra- and extracellular pH and ATP glycolytic production are extremely useful parameters in order to assess possible efficacy of tumour therapy.

Modifying the physiological parameters of the tumour poses an important opportunity to alter its establishment and growth and allow the body to regain greater efficiency in fighting it.

The complex view of pathology and the attempt at an interaction characterized by the same degree of complexity lays the foundation for a new and innovative treatment of cancer, which is based on targeting the sum of the physi- ological aspects that distinguish it from its healthy counter- part, thus abandoning the reductionist vision of a therapy targeted towards a single molecular entity.

As research and development in oncology unmistakably gravitate towards personalized and precision medicine, a therapeutic strategy addressing the fundamental character- istics underpinning the establishment and proliferation of tumours could prove a highly effective additional desirable tool in the fight against a diverse array of tumour forms.

As known in the art, several anticancer drug show lack of specificity, trigger drug resistance, show potent toxicity side effects in the whole patient's organism and have a limited efficacy for certain cancers.

In recent years, there has been a growing interest in the potential of plant-based medicines for cancer treatment. Natural products often exhibit a variety of mechanisms of action that could complement or even provide alternatives to conventional treatments. Indeed, various plant-based mate- rials have shown promise in targeting cancer cells with greater specificity than traditional chemotherapy, together with a lower toxicity and synergistic effects with conven- tional drugs and are also investigated for their potential in cancer prevention and supportive care.

Despite the growing interest in plant-based cancer thera- pies, there are several regulatory and practical challenges that must be addressed before these treatments can become mainstream options for cancer patients.

One of the key challenges with plant-based medicines is the lack of standardization in terms of their composition and potency. Unlike conventional drugs, which are rigorously formulated to contain specific concentrations of active ingre- dients, plant-based medicines vary in quality due to differ- ences in growing conditions, harvest times, and processing methods. This can make it difficult to determine the appro- priate dosage or ensure consistent therapeutic outcomes. Due to these reasons regulatory bodies are at present not prepared to accept plant-based material for cancer therapy notwithstanding the strong experimental data demonstrating their promising efficacy.

Plant-based medicines offer promising alternatives with potentially lower toxicity, fewer side effects, and comple- mentary effects when used alongside conventional treat- ments. However, the use of plant-based treatments for cancer is hindered by regulatory issues, including a lack of standardization, insufficient clinical evidence, and concerns about interactions with conventional therapies. To fully realize the potential of plant-based medicines in cancer care, further research, clinical trials, and regulatory frameworks are needed to ensure their safety, efficacy, and integration into mainstream cancer treatment strategies.

In fact, the conceptual framework thus far applied to the study of matrices severely hampered their use as its deterministic inspiration forced such inherently structurally variable matrices into a framework devised for highly structurally reproducible single molecules. As a practical outcome, matrices historically stopped representing a viable source of therapy and were relegated to an improvised, non-scientific, adverse to innovation ghetto represented by traditional use. The shift of paradigm granted by the hereby discussed application, based on the passage from a deterministic validation of properties to a probabilistic one based on functional redundancy logics, will grant an industrially viable source of innovation for manufacturers.

SUMMARY OF THE INVENTION

The present invention relates to a product consisting of natural matrices from *Filipendula, Laurus, Brassica, Withania, Cynara, Curcuma* and *Agave*, which is effective in the treatment of cancer and, when combined with known anticancer drugs, is capable of adjuvating their anticancer therapeutic effect (e.g. by enhancing their activity and/or reducing drug-resistance) and which acts with a physiological mechanism of action by modifying a whole pathological state rather than one or few biological functions and by showing therapeutic functional resilience, i.e. by maintaining the desired therapeutic effect notwithstanding batch-to-batch differences in the chemical composition.

The experiments carried out by the inventors demonstrate that the product can be standardized, provide robust in vitro and in vivo experimental evidence of its therapeutic effect and of its adjuvating effect when combined with conventional anticancer drugs, and also provide safety data as well as means for defining the unit of activity of the product, quality control, as well as pharmacokinetics, ADME and biodegradability evaluation of the product.

Furthermore, the inventors also demonstrate the naturality of the product and its natural native intelligence.

The present invention also relates said product or a composition comprising said product for use in the treatment or in adjuvating the treatment cancer in a subject in need thereof, as well as a method of treatment or adjuvating the treatment cancer in a subject in need thereof comprising the administration of said product or composition. In addition, the invention relates to the above medical use or treatment wherein the product or composition is administered in simultaneous or subsequent administration, in combination with a known anticancer drug.

The extensive characterisation study of the claimed product is depicted in detail by the figures and by the experiments provided in the present specification.

As appreciable by the reader, several experiments have been carried out simultaneously on different batches of the product, and demonstrate that the product of the invention maintains a repeatable and conserved functional resilience with respect to its therapeutic efficacy, which allows the definition of a unit of activity of the product i.e. of a standardised measurement of the product's potency or effectiveness that defines the amount of the product required to produce a specific, desired therapeutic effect or to achieve a particular biological response in a given system. This measurement ensures consistency and reproducibility of the product's effect across different doses, formulations, or batches in conditions in which reproducibility based on chemical characterization is irrelevant based on the intimate nature of the product.

Therefore, an object of the present invention is:

a product consisting of:

20-50% in weight of component a.

49-80% in weight of component b.

and 0.6-1.2% in weight of component c.

for a total of 100% wherein component a. is a coextract of *Filipendula* leaves and flowers, *Laurus* leaves, *Brassica* seeds and *Withania* roots, the % in weight of the raw materials for the preparation thereof consisting of 17.5-32.5% in weight of *Filipendula* leaves and flowers, 17.5-32.5% in weight of *Laurus* leaves, 17.5-32.5% in weight of *Brassica* seeds and 17.5-32.5% in weight of *Withania* roots for a total of 100%, and component b. is a coextract of *Cynara* leaves, *Curcuma* roots and *Tanacetum* flowers, the % in weight of the raw materials for the preparation thereof consisting of 10-19% in weight of *Cynara* leaves, 29-55% in weight of *Curcuma* roots, 29-55% in weight of *Tanacetum* flowers for a total of 100% and component c. is an extract of *Agave* leaves;

a unit of activity of the product as defined in the claims and in the specification, said unit being the defined as the necessary and sufficient amount of said product that, when administered, separately, to HuDe, FaDu and A431 cells in culture, induces after 24 hours from said administration, the following cell mortality:

A 40-50% mortality of healthy cells HuDe;

A ≥90% mortality of FaDu tumour cells;

A ≥65% mortality of A431 tumour cells;

in a cell culture plate wherein

HuDe cells seeded at about 7,000 cells per well in 200 µl of the appropriate medium; FaDu cells, seeded at about 12,500 cells per well in 200 µl of the appropriate medium, and A431 cells seeded at about 8,500 cells per well in 200 µl of the appropriate culture medium; cells are cultured for 24 hours after treatment with said product and cell mortality is measured by assessing cell viability through nuclear staining;

a composition comprising the product as defined in the claims and in the specification and at least one of an antitumour active principle and a pharmaceutically acceptable carrier;

a therapeutic adjuvant or a vehicle for anticancer therapy consisting of the product as defined in the claims and in the specification and a pharmaceutically acceptable carrier;

a kit of parts for concomitant or sequential administration comprising separate vials of the therapeutic adjuvant or vehicle as defined in the claims and the specification and of at least one antitumour active principle;

the product according, the composition according, or the kit of parts as defined in the claims and the specification for use in the treatment of cancer;

a method of treatment of cancer wherein the product, the composition, or the kit of parts as defined in the claims and the specification is administered in a therapeutically effective amount to a patient in need thereof;

a method for determining the presence of native natural intelligence in a therapeutic or beneficial product, said product comprising or consisting of natural matrices as defined in the claims and in the specification.

GLOSSARY

Unless otherwise defined herein, scientific, and technical terms used in connection with the present invention shall have the meanings that are commonly understood by those of ordinary skill in the art. Further, unless otherwise required by context, singular terms shall include pluralities and plural terms shall include the singular.

In any point of the present specification or of the claims, the expression "comprising" or "comprise(s)" can be replaced by "consisting of" or "consist(s) of".

A "natural matrix" in the present application refers to a material consisting of a network represented by a broad number of components/constituents obtained (e.g. extracted) directly from a member of the natural kingdom or a naturally occurring portion thereof (i.e., from a natural raw source), without significant processing or synthetic alteration, wherein "without significant processing or synthetic alteration" is intended that no denaturing processes are used for obtaining the matrix from the raw source. In other words, the natural raw source is processed only by manual, mechanical or gravitational means e.g. by dissolution in water or other naturally occurring solvents, such as water, water-alcohol solutions etc.; by flotation; by extraction with water or other naturally occurring solvents; by steam distillation or by heating solely to remove water or any other naturally occurring solvent; or extracted from air by any means and with the provision that "natural matrix" excludes said member of the natural kingdom "as such" i.e. non-processed. In particular, according to the invention, a natural matrix is a 100% natural and biodegradable material, consisting of natural components that have not been denatured by the process for the production of the matrix from the starting raw materials without intentional addition of synthetic products along the whole process. In the present description, 100% biodegradable is considered as "readily biodegradable" according to an OECD biodegradability test. These features guarantee the maintenance of the matrix effect which is conferred to the matrix by the presence of structural interactions by its components (material interactions) and functional interactions that become evident upon exposure of a biological system to the natural matrix (immaterial interactions). In other words, a natural matrix, or a mixture of natural matrices, are materials obtained from entities that are self-assembled in nature and processed so to preserve their native bio-physical characteristics which determine their physiological interaction with other living organisms, such as the human organism. Their emerging properties can be expressed by contributing to the rebalancing of metabolic processes or states of the receiving organism and/or of some organs or tissues alongside the physiological actions that will be activated in each specific context. According to the present invention the natural matrix can be from a material obtained from any source in the life kingdoms i.e., Monera, Protista, Fungi, Plantae and Animalia. The term hence encompasses a plant natural matrix, an animal natural matrix, a fungi natural matrix, a Protista (archaea or bacteria) natural matrix, a Monera natural matrix. A natural matrix may also comprise natural inorganic materials such as minerals obtained from natural raw materials. A synonym of natural matrix or one or more natural matrices in the present description is "complex natural system" or "natural material" as defined below.

An example of naturally occurring portion of an organism may be represented by e.g., roots, leaves, bark, fruit, flower, of a plant or sections thereof, organs, tissues.

In any part of the description the general term natural matrix can be substituted with:

a plant natural matrix or a natural matrix obtained from a plant, an animal natural matrix or a natural matrix obtained from an animal or from an animal product such as eggs or milk, a fungi natural matrix or a natural matrix obtained from a fungus, a Protista natural matrix or a natural matrix obtained from a Protista, a Monera natural matrix or a natural matrix obtained from a Monera, or with a plant material and/or extract, an extract from an animal tissue or organ, fungi and/or a fungi extract, or a mixture thereof wherein the extraction process does not encompass denaturing steps (e.g., temperature or the use of denaturing solvents).

Plant is synonymous with herb.

The term "natural" matrix emphasizes the retaining the integrity and complexity of networks of constituents/components as in the original natural source due to the absence of denaturing treatments for the obtainment thereof. A natural matrix hence does not encompass compositions of natural origin that are enriched in specific molecules of artificial synthesis or isolated from a natural raw material. In addition, a natural matrix is obtainable only with processes that do not act through extensive processing or chemical modification, isolation, purification, or molecular extraction.

Due to the supramolecular self-assembly of the constituents/components of a natural matrix and the presence of functional interactions among them, the whole matrix behaves as a complex network that does not interact with a single target molecule but that interacts with a network of recipients (also organised as a network) in the receiving organism. Therefore, the interaction natural matrix-receiving organism is not, as for common pharmaceutical APIs the result of a point-to-point interaction, but the result of an "interactor" networks (i.e., the matrix)-"receiver" network (i.e., the organism to whom the matrix is administered) interaction.

The term natural matrix can be also substituted in any part of the description and claims with complex natural system.

Nowhere in the description and in the claims the term natural matrix can be interpreted as "a product of nature" as such, rather, a natural matrix is a product obtained from a natural organism and processed (e.g. extracted) therefrom by techniques that do not substantially alter biological structure and the relevant supramolecular and functional interconnections among the components within the matrix as mentioned above, i.e., without the use of denaturing techniques and that does not comprise additional isolated or synthesised molecules or classes of molecules.

Emerging properties according to the present description and to the art, the term defines the properties of a natural matrix or of a natural material according to the present specification, i.e., properties that are not represented by the mere sum of properties of each singled out constituent/component of said matrix/material but by the both functional and structural interactions among all constituents/components of the matrix/material that are also the result of the supramolecular self-assembly of said components/constituents within the matrix/material itself.

"Emerging properties" hence refer to technical effects, such as therapeutic or homeostasis-adjuvating properties (i.e., beneficial effect), that the interactions and relationships among the constituents/components of a natural matrix exert on a receiving living system. By definition, emergent properties are properties that are not immediately evident or even predictable based solely on the individual characteristics of each constituent/component of the matrix. Instead, they "emerge" when all the constituents/components of the matrix networks interact with one another and with the living system receiving network in a dynamic and complex way. Emerging properties have been broadly discussed in the art in various scientific and systems-oriented fields, including physics, chemistry, biology, and complex systems theory.

Emerging properties are hence properties that cannot be predicted a priori by the quali-quantitative knowledge of each component of a given composition or matrix and that, consequently, cannot be ascribed to one or more specific API. Hence, although multidrug compositions can show unpredicted synergic effects, the properties of said compositions are still ascribed to the specific APIs and quantities thereof contained therein.

In the case of emerging properties, characteristic of natural matrices, the observed emerging properties cannot be reconducted to specific APIs and are maintained in different batches of a given matrix or a given mixture of matrices notwithstanding the different quali-quantitative composition of said batches (functional resilience see below).

Synthetic according to the present description has the meaning conventionally accepted in chemistry. Conventionally, in chemistry, the term "synthetic" refers to the origin or source of a material or substance. Synthetic substances or materials are produced by man through artificial synthesis i.e., through laboratory chemical reactions usually by reacting simpler chemicals to create more complex ones through processes that often use different pathways, temperature conditions, pressure conditions, energy sources and/or catalysers from those used by living organisms.

Examples: Synthetic substances or materials include plastics, pharmaceutical drugs, and many industrial chemicals. For example, nylon is a synthetic polymer made through chemical synthesis, and aspirin is a synthetic drug produced through specific chemical reactions.

Functional resilience (also indicated as "redundancy") according to the present description is intended as a therapeutic or beneficial (homeostasis adjuvant) resilience of a therapeutic or beneficial product comprising or consisting of one or more natural matrices; the term describes the maintenance of the therapeutic or beneficial properties of different batches of a given product comprising (or consisting of one or more natural matrices) notwithstanding the different batch to batch qualitative and quantitative composition, which is necessarily present (inherent) in products comprising or consisting of one or more natural matrices. As known by the skilled person, each time a different batch of starting raw material is used, the resulting natural matrix has a unique quali-quantitative composition at the molecular level which is typical of the individual diversity between living organisms also of the same species.

A healthy physiological state refers to the condition of an organism's body, organ, apparatus, system or body district, and its internal processes when they are functioning optimally and within normal parameters for that individual, i.e., the state to which homeostasis tends. A healthy physiological state, in the context of one or more biological activities known to contribute to hallmarks of a given disease or pathological condition or of an altered physiological state, refers to the state in which said one or more biological activities are operating optimally and within normal (healthy) parameters. This state is characterized by the absence of significant aberrant cellular or molecular processes associated with the specific disease under consideration. When the modification trend of one or more biological activities which concurs to a pathological, pre-pathological condition is known, the healthy physiological state can be considered represented by the opposite modification trend for each of said activities.

The term considers the hallmarks of a particular disease, which are distinctive features or characteristics that are typically observed in individuals affected by that disease. These hallmarks can include specific cellular behaviours, molecular pathways, canonical pathways, or physiological responses that play a key role in the development or progression of the disease.

In summary, a healthy physiological state in the context of a specific disease or pathological/altered condition is a state in which the one or more biological activities related to the known hallmarks of that disease or pathological condition are modulated in a direction that is consistent with a non-pathological/non-altered state, in other words, opposed to the pathological/altered state.

A healthy physiological state according to the invention, therefore, also indicates the direction of the modulation of one or more biological activities that are known hallmarks of a pathological condition in homeostasis, i.e., before the onset of a pathological condition, in other words the homeostatic direction of the modulation of one or more biological activities ascribed to a specific system, district, apparatus or organ of a healthy subject.

Altered physiological states and altered homeostasis are closely related concepts that describe deviations from the normal functioning and balance of the body's internal environment. While they overlap, there are some distinctions between the two terms:

Altered Physiological States: This term encompasses a broad range of changes in the body's normal functioning, including disruptions in organ systems, biochemical processes, and cellular functions. Altered physiological states can result from various factors such as disease, injury, medication, environmental factors, and psychological stress. Examples include fever, inflammation, hormonal imbalances, and impaired organ function.

Homeostasis (altered): Homeostasis refers to the body's ability to maintain a stable internal environment despite external or pre-pathological changes. This stability is achieved through regulatory mechanisms that control variables such as body temperature, blood pressure, pH balance, and blood glucose levels within narrow ranges. Altered homeostasis occurs when these regulatory mechanisms fail to maintain balance, leading to deviations from the body's normal set points. These deviations can be temporary or chronic and may involve compensatory mechanisms to restore balance.

In summary, altered physiological states describe the observable changes in the body's normal functioning, while altered homeostasis refers to the underlying disruption of the body's regulatory mechanisms that maintain internal stability.

An altered homeostasis underlies altered physiological states, as disruptions in homeostatic mechanisms that can lead to physiological imbalances and manifestations of illness or dysfunction. A product adjuvating homeostasis is a product that adjuvates the body to restore the stability of its internal environment when altered.

Hallmark of a disease or of a pathological or medical condition according to the present description has the meaning conventionally used in the art. Hallmarks of a disease are known to be indicators that can mark the progression or control of a given disease or pathological or pre-pathological condition and taken together are usually representative of the general pathological state associated to a given pathology. These hallmarks (also called 'key indicators') are typically a set of features or patterns that a physician would monitor, over time, to track the onset, the progression or regression of a particular illness. In summary, a hallmark of a disease is a defining feature or characteristic whose modification is indicative of a given pre-medical or medical condition, aiding in its identification, diagnosis, monitoring and understanding. By way of example, for neurodegenerative diseases (NDDs) at least the following eight hallmarks of NDD are known in the art: (pathological protein) aggregation, synaptic and neuronal network (dysfunction), (aberrant) proteostasis, cytoskeleton (abnormalities), (altered) energy homeostasis, DNA and RNA (defects), inflammation (increase), and neuronal cell death (increase). In cancer research, the hallmarks of cancer are a set of distinctive characteristics that are commonly found in cancer cells. These hallmarks include (sustained) proliferative signalling, (evasion of) growth suppressors, (resistance to) cell death, (enabling) replicative immortality, (inducing) angiogenesis, and (activating) invasion and metastasis.

Hallmarks of a disease, parameters related to said hallmarks (e.g., biomarkers), one or more biological activities associated to said hallmarks etc. are a framework to study a disease or a pathological or medical condition using an integrated/holistic approach.

The hallmarks of an altered physiological state typically include observable changes in various aspects of the body's functioning, which may manifest through symptoms, signs, or laboratory findings.

Altered physiological states typically reflect disruptions in the body's homeostatic mechanisms, leading to deviations from normal physiological parameters. These imbalances may involve alterations in temperature regulation, fluid and electrolyte balance, acid-base balance, glucose metabolism, or other regulatory processes.

Overall, the hallmarks of an altered physiological state provide valuable clues for healthcare providers to identify the underlying cause, assess severity, and guide appropriate interventions to restore normal functioning and promote recovery.

A reference drug is a drug that is commonly selected or chosen as the standard or preferred treatment for a specific medical condition or illness. It is often established based on factors such as its effectiveness, safety profile, cost, and clinical experience. The reference drug serves as a benchmark for comparison with other drugs, especially when assessing generic versions, new treatments, or alternative therapies. It is typically the first drug of choice recommended by medical guidelines or by healthcare providers for treating a particular condition.

Native natural intelligence, represents the intrinsic ability of natural matrices to conserve and transmit biological and physical-chemical information necessary for interacting and integrating with other living networks, using logics inherent to the living organism that receives them, as they are already known to it, and therefore endogenous in relation to it. This intelligence is an expression of natural autopoiesis, that is, the ability to self-organize and adapt to environmental stimuli without artificial intervention, which would transmit a message according to point-like logics and through mediators unknown to the living organism receiving them, and therefore exogenous in relation to it.

The expression Physiological Interconnection, defined as "endogenous" physiological interconnection, describes the ability of a natural matrix to interact in a harmonious and functional way with the biological systems of the recipient based on the fact that they both belong to the domain of what is living (endogenous), stimulating internal responses to restore balanced physiological states. This interaction is based on natural dynamics, without artificial interventions, and represents a reciprocal dialogue between the matrix and the organism, promoting self-regulation and physiological recovery.

Self-assembled entities in nature defines complex systems made up of multiple components that spontaneously organize into functional structures through chemical-physical interactions that occur in natural environments and conditions. These systems, found in living organisms or natural matrices, exhibit emergent properties that arise from their dynamic interactions and cannot be replicated artificially.

When referring to a subject in need of a beneficial or therapeutic treatment, the description relates to a human being, either affected by a pathological condition, in particular, cancer.

Unit of activity refers to a standardized measurement of a therapeutic product potency or effectiveness. It defines the amount of the therapeutic product required to produce a specific, desired therapeutic effect or to achieve a particular biological response in a given system. This measurement ensures consistency and reproducibility of the therapy's effect across different doses, formulations, or batches. The unit of activity can vary depending on the type of medicament and the way its effects are assessed. It may be defined based on different factors, such as:

DETAILED DESCRIPTION OF THE FIGURES

FIG. 1

Dysregulated pH creates a perfect storm for cancer progression. Cancer cells have a reversed pH gradient compared with normal differentiated adult cells, including a constitutively higher intracellular pH (pHi) and a lower extracellular pH (pHe), which facilitates the indicated adaptive behaviours.

FIG. 2

Graphs reporting cell number of tumour cell lines treated for 72 hours with EpigenAU/11 at two different concentrations (0.66 mg/ml and 0.22 mg/ml). Tumour cell lines were stained with HCS NuclearMask Red. Results are expressed as survival ratio (%) between treated and the corresponding untreated cells (set as 0% as reference and not represented in the graph).

The numbers, indicated with the negative value, represent the reduction of the cells' vitality. Therefore, by way of example, −x % with reference to the vitality corresponds to a x % of cell mortality.

FIG. 3

Graphs illustrating the differential ATP levels in tumour cell lines after 72 hours of treatment with EpigenAU/11 (0.22 mg/ml) or cisplatin (CDDP, 15 µg/ml). The Cell Titer-Glo® 3D Viability Assay was used to quantify ATP as a marker of cell viability. Results are expressed as the survival ratio (%) between treated cells and their corresponding untreated controls.

FIG. 4

Histograms illustrating normalized ATP levels in breast cancer spheroids (4A SUM159PT, 4B MDA-MB-231) and non-cancerous spheroids (4C MCF 10A) after 72-hour treatment with EpigenAU/11 at different concentrations. ATP content, measured by Cell Titer-Glo® 3D, is expressed as a percentage of viability, with untreated controls set at 100%. A significant reduction in ATP levels was observed in cancer spheroids at 0.22 mg/ml, while non-cancerous MCF 10A spheroids maintained high viability. Two-way ANOVA confirmed a significant interaction between cell type and concentration (p<0.05), with multiple comparison tests performed post hoc.

FIG. 5

Histograms illustrating normalized ATP levels in bladder, breast, endometrial, epithelial, and head and neck cancer organoids after 72-hour treatment with EpigenAU/11 at 0.66 mg/ml. ATP content, measured by Cell Titer-Glo® 3D, is expressed as a percentage of viability, with untreated controls for each organoid type set as 100% (controls histograms at 100% not represented in the graph).

FIG. 6

The heatmap represents the efficacy of various treatments on a patient-derived gastric cancer organoid model over a 72-hour period. Each row corresponds to a different treatment, with the intensity of the shade indicating the level of cell mortality: survival decrease from white to black, with black representing a High cell mortality (strong cytotoxic effect), and white a Low cell mortality (minimal cytotoxic effect).

FIG. 7

The heatmap represents the efficacy of various treatments on ovarian-origin peritoneal carcinomatosis organoid model over a 72-hour period. Each row corresponds to a different treatment, with the intensity of the shade indicating the level of cell mortality: survival decrease from white to black, with black representing a High cell mortality (strong cytotoxic effect), and white a Low cell mortality (minimal cytotoxic effect).

FIG. 8 (A-B)

Figure 8:
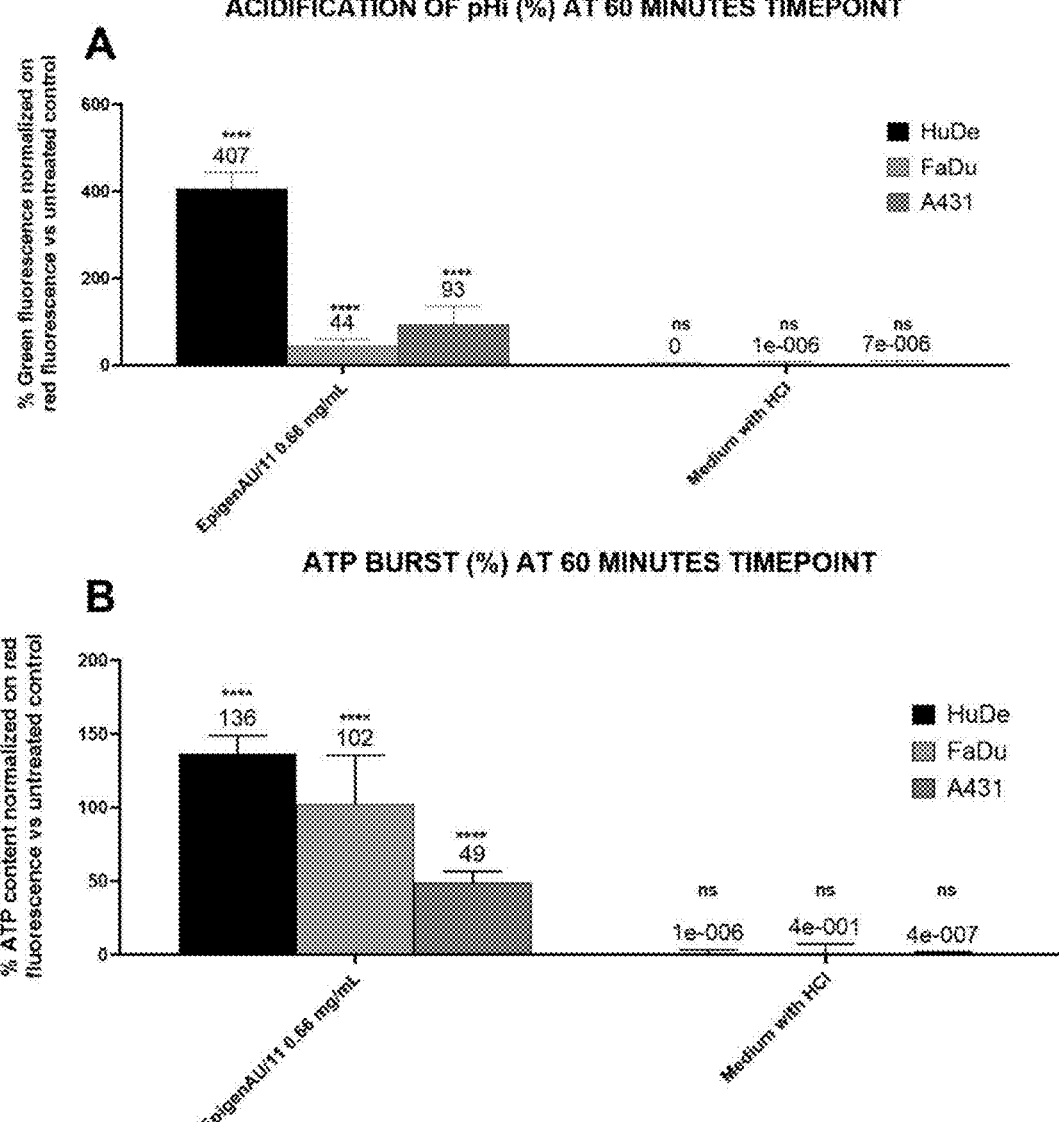

Intracellular pH and ATP Levels Following EpigenAU/11 Treatment. Intracellular pH (panel A) and ATP levels (panel B) were measured in squamous cell carcinoma lines (FaDu and A431) and healthy HuDe cells after treatment with EpigenAU/11 (0.66 mg/ml) and hydrochloric acid (HCl) for one hour. FIG. 8 A illustrates the changes in intracellular pH across the different cell lines, indicating a significant increase in pH only in cells treated with EpigenAU/11. Cells were labelled with pHrodo™ Green AM Intracellular pH Indicator according to manufacturers' instructions. pH values were normalized with respect to cell number, measured by Nuclear Mask Red staining. To the untreated control was applied 0% as reference (not reported in the graph) and the pH variation of samples treated with EpigenAU/11 was calculated as percentage vs the untreated condition.

FIG. 8 B illustrates the ATP levels assessed using the CellTiter-Glo® Luminescent Cell Viability Assay, following the manufacturer's protocol. ATP values were normalized with respect to cell number, measured by Nuclear Mask Red staining. The untreated control was set to 0% as a reference (not plotted in the graph), and the ATP quantity detected in samples treated with EpigenAU/11 was calculated as a percentage relative to the untreated condition. Ordinary two-way ANOVA with α=0.05 was applied, considering only values capable of returning p<0.05 as significant (****p<0.0001).

FIG. 9

Analysis of cell viability in explanted biopsies from the FaDu (9A) and A431 (9B) cell lines was performed after 72 hours of ex vivo treatment. Biopsies were treated with EpigenAU/11 at a concentration of 50 mg/ml, with a measured pH of 5.6, while the acid treatment group received hydrochloric acid (HCl) adjusted to the same pH of 5.6. Cell viability was analysed using a flow cytometer with the Pacific Blue™ Annexin V/SYTOX™ AADvanced™ Apoptosis Kit, following the manufacturer's instructions. Viability is expressed as a percentage, with untreated controls set at 100%. One-way ANOVA analysis followed by Dunnett's test confirmed significant differences among the groups. Data are represented as mean±SD; *p<0.03;***p<0.0002.

FIG. 10

Cell viability analysis of FaDu, A431, and HuDe cell lines after 24-hour treatments. Cells were treated with EpigenAU/11 DoE 2 at a concentration of 0.66 mg/ml or a combination of citric and lactic acids, using the same concentrations found in EpigenAU/11. Tumour cell lines were stained with HCS NuclearMask Red to assess cell viability. Results are expressed as survival ratio (%) between treated and the corresponding untreated cells, with untreated controls set at 0% as reference (not represented in the graph).

FIG. 11

Analysis of cell viability in explanted biopsies from the FaDu cell lines was performed after 72 hours of ex vivo treatment. Biopsies were treated with EpigenAU/11 at a concentration of 50 mg/ml or Cisplatin 150 μg/ml. Cell viability was analysed using a flow cytometer with the Pacific Blue™ Annexin V/SYTOX™ AADvanced™ Apoptosis Kit, following the manufacturer's instructions. Viability is expressed as a percentage, with untreated controls set at 100%. One-way ANOVA analysis followed by Dunnett's test confirmed significant differences among the groups. Data are represented as mean±SD; *p<0.05; **p<0.02.

FIG. 12

Gene expression pathway modulation following 24-hour treatment with EpigenAU/11 and cisplatin. This heatmap provides an overview of the sustained gene expression changes induced by each treatment over an extended period, focusing on pathways related to cell cycle regulation, DNA replication, mitosis, and DNA repair. Upregulated (positive numbers) and downregulated (negative numbers) pathways are indicated by shade intensity, with dark grey signifying upmodulation and light grey indicating downmodulation and white indicates up or down modulation below threshold.

FIG. 13 (A-B)

Gene expression pathway modulation following 6-hour treatment with EpigenAU/11 and cisplatin. This heatmap (divided in two subsequent panels 13 A and 13 B) illustrates the differential impact of each compound on various cellular pathways, categorized by hallmarks such as stemness, epithelial-mesenchymal transition, energy metabolism, growth factor signalling, cell damage, mitosis regulation, and inflammation. Pathways that are significantly upregulated (positive numbers) or downregulated (negative numbers) are indicated with dark grey signifying upmodulation and light grey indicating downmodulation and white indicates up or down modulation below threshold.

FIG. 14

Analysis of cell viability in explanted biopsies from the FaDu cell lines was performed after 72 hours of ex vivo treatment. Biopsies were treated with EpigenAU/11 at a concentration of 50 mg/ml, cisplatin at 150 μg/ml and combinations of EpigenAU/11 with cisplatin. Cell viability was analysed using a flow cytometer with the Pacific Blue™ Annexin V/SYTOX™ AADvanced™ Apoptosis Kit, following the manufacturer's instructions. Viability is expressed as a percentage, with untreated controls set at 100%. The combination treatments showed enhanced reductions in viability compared to single-agent treatments. Statistical analysis was conducted using one-way ANOVA followed by Dunnett's test, confirming significant differences among the groups. Data are represented as mean±SD; *p<0.002; **p<0.001.

FIG. 15 (A-B)

Dendrogram (divided in two subsequent panels 15 A and 15 B) displaying genome-wide gene expression profiling after 6 hours of treatment on biopsies derived from the FaDu graft, using EpigenAU/11, cisplatin and their combination with numbers and shades representing the intensity of upregulation (positive number dark grey) and downregulation (negative number light grey). White indicates up or down modulation below threshold. Clustering of pathways highlights shared and distinct effects of EpigenAU/11, cisplatin, and their combination on key cancer processes.

FIG. 16

Analysis of cell viability in explanted biopsies from the A431 cell lines was performed after 72 hours of ex vivo treatment. Biopsies were treated with EpigenAU/11 at a concentration of 50 mg/ml or Cisplatin 150 µg/ml. Cell viability was analysed using a flow cytometer with the Pacific Blue™ Annexin V/SYTOX™ AADvanced™ Apoptosis Kit, following the manufacturer's instructions. Viability is expressed as a percentage, with untreated controls set at 100%. One-way ANOVA analysis followed by Dunnett's test confirmed significant differences among the groups. Data are represented as mean±SD; **p<0.02.

FIG. 17

Gene expression modulation in A431 ex vivo model after 2-hour treatment with EpigenAU/11 at 50 mg/ml. The heatmap displays downregulation and upregulation of various pathways related to cancer progression and cellular responses. Numbers and shades representing the intensity of upregulation (positive number dark grey) and downregulation (negative number light grey) indicates the magnitude of expression changes, with a scale ranging from −5 (strong downregulation) to +5 (strong upregulation), highlighting the impact of EpigenAU/11 on cellular pathways over a short treatment duration.

FIG. 18

FTIR spectrum of reference standard EpigenAU/11 DoE2.

FIG. 19 (A-E)

Detection of supramolecular structures in EpigenAU/11 DoE2 (19 A and B) and exosomes (19 C and D):

19A: overlay of the average of particle size distributions as a function of intensity of three instrumental replications of conditions; line A—not filtered; line B—filtered at 0.45 µm; line C—filtered at 0.10 µm;

19B: Correlogram showing the correlation coefficient ($g_2-1$) as a function of time (µs) for three experimental conditions; line A—not filtered (average of three instrumental replications), line B—filtered 0.45 µm (average of three instrumental replications), line C—filtered 0.10 µm (average of three instrumental replications)

19C: overlay of particle size distributions as a function of intensity of three instrumental replications 19D: overlay of correlation functions of three instrumental replications 19 E: Distribution of the average particles concentration as a function of size (nm).

FIG. 20

Experimental workflow for treatment with EpigenAU/11 and cisplatin in a murine model with subcutaneous A431 cell xenografts.

FIG. 21

Tumour growth curve of A431 xenografts in athymic mice over 15 days of treatment. Mice were treated with vehicle (saline solution), EpigenAU/11 (50 mg/ml, intratumoral), or cisplatin (2 mg/kg, intraperitoneal, every two days). Tumour volume was measured every other day. Data are represented as mean±SEM; p<0.02; **p<0.001. One-way ANOVA followed by Fisher's LSD test was used for statistical analysis.

FIG. 22

Representative images of A431 xenografts from each treatment group (vehicle, EpigenAU/11, and cisplatin) at days 1, 7, and 15. Each image corresponds to a single example from the respective treatment arm, illustrating tumour size and appearance over time.

FIG. 23

Experimental workflow for treatment with EpigenAU/11 and cisplatin in a murine model with subcutaneous FaDu cell xenografts.

FIG. 24

Tumour growth curve of FaDu xenografts in athymic mice over 27 days of treatment. Mice were treated with vehicle (saline solution), EpigenAU/11 (50 mg/ml, intratumoral, daily), cisplatin (2 mg/kg, intraperitoneal, every two days), or a combination of EpigenAU/11 and cisplatin. Tumour volume was measured every other day. Data are represented as mean±SEM; *p<0.05; **p<0.02. One-way ANOVA followed by Fisher's LSD test was used for statistical analysis.

FIG. 25

Representative images of FaDu xenografts from each treatment group (vehicle, EpigenAU/11, cisplatin and combo) at days 1, 19, and 27. Each image corresponds to a single example from the respective treatment arm, illustrating tumour size and appearance over time.

FIG. 26

Graphs reporting cell number of tumour cell lines treated for 24 hours with DoEs 1, 2, 3, and 4.2 EpigenAU/11 at 0.66 mg/ml. Tumour cell lines were stained with HCS Nuclear-Mask Red. Results are expressed as survival ratio (%) between treated and the corresponding untreated cells (set as 0% as reference and not represented in the graph).

FIG. 27

Targeted metabolomics: shown is the % of 5 chemical classes, in the order: phenols, tannins, organic acids, sugars and derivatives thereof, inorganic compounds, of five batches of EpigenAU/11, DoEs 1, 2, 3, 4 and 4.2. Each batch differs from one another in the quali-quantitative composition.

FIG. 28 (A-D)

Cell viability analysis of FaDu, A431, and HuDe cell lines after 24-hour treatments. Cells were treated with EpigenAU/11 different DoEs whose composition is described in detail in example 9.1 at a concentration of 0.66 mg/ml.

Tumour cell lines were stained with HCS NuclearMask Red to assess cell viability. Results are expressed as survival ratio (%) between treated and the corresponding untreated cells, with untreated controls set at 0% as reference (not represented in the graph).

28 A DoE 1, 1.1, 1.2, 1.3

28 B DoE 2, 2.1, 2.2, 2.3

28 C DoE 3, 3.1, 3.2, 3.3

28 D DoE 4, 4.1, 4.2, 4.3

FIG. 29

Flowchart of the procedural process to calculate EpigenAU/11 and cisplatin benefit/risk score on the basis of transcriptional profiles obtained from in vitro or ex vivo experimentation.

FIG. 30

Flowchart of the procedural process to calculate EpigenAU/11 and cisplatin benefit/risk score on the basis of data obtained from in vivo experimentation in animal models.

FIG. 31

Annotated side effects of cisplatin and IPA corresponding biofunctions (BFs). The desired trend of modification of the biofunctions selected is indicated in the figure.

FIG. 32 (A-D)

Benefit scores calculation of EpigenAU/11 and cisplatin treatments after 6 hours of treatment.

32 A and C: Biological activities selected on the basis of their coherence with the therapeutic indication of the product under examination. Biological activities are grouped into activity characteristics (Hallmarks), in this figure to each characteristics a weight coefficient based on its relevance in the pathogenesis of interest, is assigned (panel A only mandatory steps according to the description were performed, panel C mandatory and optional steps according to the description were performed). 32 B and D Z-score values of the biological activities transformed into absolute values and the numbers thus obtained were exported into a table reporting the indication of the biological activities and their relative modulation values. The sum of each value for each treatment is considered as the benefit score (panel B only mandatory steps according to the description were performed, panel D mandatory and optional steps according to the description were performed)

FIG. 33 (A-C)

Risk scores calculation of EpigenAU/11 and cisplatin treatments after 6 hours of treatment.

33 A risk score calculation of EpigenAU/11 after 6 hours of treatment

33 B risk score calculation of cisplatin after 6 hours of treatment

33 C summary of risk scores of EpigenAU/11 and cisplatin after 6 hours of treatment

FIG. 34 (A-D)

34 A and C Benefit/Risk scores obtained with EpigenAU/11 and cisplatin treatments after 6 hours (34 A only mandatory steps according to the description were performed, 34 C mandatory and optional steps according to the description were performed).

34 B and D Calculation of the fold change of the score obtained with EpigenAU/11 compared to that obtained with cisplatin: the EpigenAU/11 score is twice that of cisplatin (34 B only mandatory steps according to the description were performed, 34 D mandatory and optional steps according to the description were performed)

FIG. 35

35 A Benefit/Risk scores obtained with in vivo EpigenAU/11 and cisplatin treatments.

35 B Calculation of the fold change of the score obtained with EpigenAU/11 compared to that obtained with cisplatin: the EpigenAU/11 score is three times that of cisplatin.

FIG. 36

Graphical comparison of the obtained fold changes of benefit/risk scores of the benefit/risk score calculated according to the invention, columns 1 and 2 on the ex vivo sample, 3 from the in vivo animal model (first column: only mandatory steps according to the description were performed, second column: mandatory and optional steps according to the description were performed)

FIG. 37

Cell viability analysis of FaDu and A431 cell lines after 24-hour treatments. Cells were treated with EpigenAU/11 at a concentration of 0.66 mg/ml, either alone or in combination with cisplatin. Tumour cell lines were stained with HCS NuclearMask Red to assess cell viability. Results are expressed as survival ratio (%) between treated and the corresponding untreated cells, with untreated controls set at 0% as the reference (not represented in the graph).

FIG. 38

Histograms illustrating normalized ATP levels in breast cancer spheroids (MDA-MB-231 and SUM159PT) after a 72-hour treatment with EpigenAU/11 alone or in combination with various chemotherapy agents (carboplatin, paclitaxel, and gemcitabine), as well as the chemotherapy agents alone or in combination with each other. ATP content, measured using the Cell Titer-Glo® 3D Viability Assay, is expressed as a percentage of viability, with untreated controls set at 100%. One-way ANOVA analysis confirmed a significant interaction between treatment type and cell line ($p < 0.05$), with multiple comparison tests performed post hoc-. C=carboplatin, P=paclitaxel, G=gemcitabine, A=EpigenAU/11. In the combination experiments the amount of EpigenAU/11 used was 0.22 mg/ml

FIG. 39 (A-D)

39A bladder 38, 39B bladder 41, 39C breast 203, 39D Endometrium 12. Histograms illustrating normalized ATP levels in bladder, breast, and endometrial tumour organoids after treatment with EpigenAU/11 (0.66 mg/ml) and various chemotherapeutic agents. Bladder organoids (Bladder 41 and Bladder 38): Treated with cisplatin (C, 5 μg), gemcitabine (G, 70 μg), or their combination for 72 hours. Breast organoids (Breast 203): Treated sequentially with paclitaxel (P, 50 nM)+carboplatin (C, 100 nM) for 72 hours, followed by epirubicin (E, 1 μM)+cyclophosphamide (Cy 7 μM) for an additional 72 hours. Endometrial organoid (Endometrium 12): Treated with carboplatin (C, 100 nM), paclitaxel (P, 100 nM), or their combination for 72 hours. ATP content, measured by CellTiter-Glo® 3D, is expressed as a percentage of cell viability, with untreated controls set at 100%. Statistical analysis was performed using one-way ANOVA followed by Dunnett's test, with significant differences denoted by $p < 0.002$ () and $p < 0.0001$ (**). Data are presented as mean±SD.

FIG. 40

Vitality assays on Head and Neck Squamous Cell Carcinoma 10847 and 10632 organoid models following treatment with EpigenAU/11 (0.66 mg/ml) and radiotherapy at different doses (0, 4, and 8 Gy). HNSCC 10847 (left) represents a radiotherapy-sensitive model, whereas HNSCC 10632 (right) represents a radiotherapy-resistant model. Data represent mean±standard deviation of triplicate experiments. ATP content, measured by CellTiter-Glo® 3D, is expressed as a percentage of cell viability, with untreated controls set at 100%. Statistical significance was assessed using one-way ANOVA followed by Dunnett's test, with significant differences denoted by *$p < 0.05$, $p < 0.01$, *$p < 0.001$, and ns=not significant.

FIG. 41

Pharmacokinetics experimental Design over the 48 hours of experiment and status of the data analysis in each collected organ.

FIG. 42

Time-Course perturbation of genes involved in ADME in Liver samples from untreated mice, mice treated with Physiological Solution, or mice treated with EpigenAU/11.

FIG. 43

Time-Course perturbation of genes possibly involved in renal ADME in Kidney samples from Untreated mice, mice treated with Physiological Solution, or mice treated with EpigenAU/11.

FIG. 44 (A-C)

Network analysis of squamous carcinoma (44 A) and treatment with reference drug (44 B) vs. treatment with EpigenAU/11 (44 C). The grey squares represent both the fundamental nodes characterizing the pathophysiological or altered physiological state and the specific sites through which the pathology interconnects with the body. The arrows next to the nodes indicate the specific modulation for each situation described, and the intensity is shown through multiples of the arrows themselves. The grey squares are in turn linked to a network of biological activities, the modulation of which, has been demonstrated experimentally. These biological activities are represented by black (upregulation) or white (downmodulation) circles whose amplitude is directly proportional to the magnitude of their experimentally proved modulation. The network analysis shows that EpigenAU/11 influences the body in a systemic way, modulating a higher number of desired activities, according to the trend concurring to the healthy physiological state, than treatment with reference drug.

DETAILED DESCRIPTION OF THE INVENTION

Cancer cells, leveraging characteristics inherent to their nature, drive profound modifications both within and outside their environment. These transformations, at structural and metabolic levels, are essential for stimulating cellular proliferation, creating favourable conditions for tumour growth, and developing strategies to evade immune surveillance. Tumours evolve within a complex network of interconnected biological processes that ensure their survival and expansion, activating a dynamic series of genetic and metabolic pathways. These pathways influence tumour cells across various tissues and environments, demonstrating the tumour's ability to adapt and thrive in multiple biological contexts.

Carcinogenesis progresses within an intricate framework of cellular transformation, shaped by internal processes and the surrounding environment. This complexity fosters a web of interactions among tumour cells, the tumour microenvironment, and the host organism. The tumour microenvironment—a critical network supporting tumour growth—plays a pivotal role in cancer progression and response to treatment, influencing key aspects of tumour biology, from growth dynamics to therapeutic outcomes.

Within this complex context, the balance of pH between the intracellular and extracellular spaces emerges as a hallmark of cancer cell physiology, supporting the activation of metabolic and physiological pathways that promote tumour cell proliferation and environmental adaptation. Unlike healthy cells, cancer cells exhibit a unique pH profile characterized by intracellular alkalinity and extracellular acidity. This pH imbalance is not merely a by-product of altered metabolism but rather a functional adaptation that allows cancer cells to secure a proliferative advantage, create immune-evasive niches, and establish adaptive pathways critical for survival and progression (FIG. 1).

Key drivers behind this pH regulation include the Warburg effect and oxidative phosphorylation, which contribute to extracellular acidification while supporting an alkaline intracellular environment. The Warburg effect, defined by a preference for glycolysis even in the presence of oxygen, forms part of a broader metabolic network that maintains an alkaline intracellular pH, enabling key enzymes in biosynthetic pathways and supporting rapid cell division. Meanwhile, extracellular acidification aids in the degradation of the extracellular matrix, facilitating tumour invasion and metastasis.

In addition to structural and metabolic advantages, cancer cells are also characterized by elevated levels of reactive oxygen species (ROS). While ROS are often associated with cellular damage, they serve as signalling molecules within cancer cells, promoting growth and survival. Elevated ROS levels, coupled with extracellular acidification from increased glycolysis, create a unique environment leading to cancer cell proliferation. However, cancer cells operate at a metabolic threshold that poses a vulnerability: any disruption to the balance of pH and ROS can induce metabolic stress, potentially leading to cell death. This metabolic vulnerability, unique to cancer cells, represents a potential target for therapeutic interventions.

This broader understanding of tumour biology, coupled with a holistic view of the interactions involved, forms the foundation for innovative cancer therapies. Tumours are not simply the result of isolated molecular anomalies but arise from a complex network of biological interactions involving physiological, environmental, and immunological factors. Moving beyond a reductionist approach focused on single pathways or molecules, therapeutic strategies that address the full spectrum of physiological distinctions between tumour and healthy cells offer a promising path forward. In this context, the unique pH balance and metabolic vulnerabilities of cancer cells provide new entry points for treatments aimed not only at tumour destruction but also at restoring physiological equilibrium.

An integrative approach to oncology therapy does not merely imply the concurrent use of different drugs; rather, it involves a network of synergistic interventions that address the complexities of the tumour microenvironment. Recognizing the critical connections between tumour cells, surrounding healthy cells, and the immune system, this approach seeks to restore the body's natural homeostasis and capacity to respond to tumour challenges, leading to more effective treatments with fewer side effects. By minimizing the adverse effects of traditional therapies, this strategy aims to improve patient quality of life.

As oncology research and development increasingly gravitates toward personalized and precision medicine, therapeutic strategies that target the fundamental characteristics driving tumour initiation and progression could become powerful tools in combating cancer. By leveraging the complexity of tumour biology and its surrounding microenvironment, comprehensive treatment protocols can be developed that not only inhibit tumour growth but also restore the body's natural ability to regulate and combat cancer more effectively. Such an approach has the potential to transform cancer therapy, offering more precise and less invasive treatment options with improved outcomes for patients.

The present invention relates to a new composition of matter, i.e. product, consisting of 100% natural materials, exerting a therapeutic effect in the treatment of cancer, or a therapeutic or adjuvant effect when combined with an anti-cancer drug, in the treatment of cancer. As disclosed in the present specification, figures and examples, the product of the invention exerts its therapeutic or adjuvant effect through a physiological (as opposed to pharmacological) mode of action.

To act with a physiological mode of action, a product must be 100% natural, to show a batch-to-batch therapeutic or adjuvant functional resilience (i.e. maintaining the therapeutic or adjuvant effect notwithstanding batch-to-batch different chemical composition) and to modify a whole pathological state rather than one or few functions. Natural materials, such as products comprising or consisting of natural matrices as the product of the invention, are entities which maintain at least in part the autopoietic properties of their starting materials which belong to the living domain, and display own properties which are represented by networks of material and immaterial relationships, that interact with the network of relationships of the treated subject (networks-to-network interactions) thereby recapitulating an interaction with features and complexities that are physiological-like.

Therefore, according to the present description, a product comprising or consisting of one or more natural matrices is a product which is 100% natural, which means that the product does not contain additional artificial substances, i.e., substances of chemical synthesis made by man through laboratory processes.

In addition, according to the present description, a product comprising one or more natural matrix, does also not contain any added isolated molecule, e.g., excipient/s or active principle/s even if of natural origin.

To note, natural matrices are fundamentally different from "substances", including singled out substances of natural origin. To describe natural materials or matrices, it is necessary to extend the reductionist approach and use the innovations of the last century. Conceptually, this means referring to systems theory. From an experimental point of view, preclinical evidence involves systems biology approaches such as omics sciences (e.g., transcriptomics) and bioinformatics evaluations.

These allow appropriate assessments of the matrix (the acting networks), the human body (the receiving network) and allow to consider the interaction between the two as a "networks over a network" interaction. A mechanism that accompanies, in each specific context, the coordinated redundancy and resilience that characterize physiology corresponds to a 'physiological mechanism of action' and could be characterized by a network paradigm, distinct from the targeted and non-targeted models that describe the PhIM and the mechanical/chemical/physical mechanism, respectively.

In particular, according to the invention, a natural matrix is a 100% natural and biodegradable material, consisting of natural components that have not been denatured by the process for the production of the matrix from the starting raw materials without intentional addition of synthetic products along the whole process.

As already stated, according to the present invention, in order to be defined natural, it is mandatory that the matrices are obtained through non-denaturing processes, so that the components of the matrices are not artificially denatured. When desired, the presence of additional indicators of maintenance of features that are present in the original raw material can be verified. In addition, a 100% natural product, is a product expected to be completely biodegradable. In the present description, a product which is "readily biodegradable" according to an OECD biodegradability test is considered as 100% biodegradable. These features, guarantee the maintenance of the matrix effect which is conferred to the matrix by the presence of structural interactions by its components (material interactions) and functional interactions that become evident upon exposure of a biological system to the natural matrix (immaterial interactions).

The invention relates to a product consisting of:

20-50% in weight of component a.

49-80% in weight of component b.

and 0.6-1.2% in weight of component c.

for a total of 100% wherein component a. is a (freeze-dry) coextract in water of *Filipendula* leaves and flowers, *Laurus* leaves, *Brassica* seeds and *Withania* roots, the % in weight of the raw materials for the preparation thereof consisting of 17.5-32.5% in weight of *Filipendula* leaves and flowers, 17.5-32.5% in weight of *Laurus* leaves, 17.5-32.5% in weight of *Brassica* seeds and 17.5-32.5% in weight of *Withania* roots for a total of 100%, and component b. is a (freeze-dry) coextract in water of *Cynara* leaves, *Curcuma* roots and *Tanacetum* flowers, the % in weight of the raw materials for the preparation thereof consisting of 10-19% in weight of *Cynara* leaves, 29-55% in weight of *Curcuma* roots, 29-55% in weight of *Tanacetum* flowers for a total of 100% and component c. is a "(freeze-dry) extract in water of *Agave* leaves.

According to the invention, 0.66 mg/ml of the product, as defined above and in the rest of the specification and claims, when administered separately to HuDe, FaDu and A431 cells in a cell-based assay, are capable of inducing, after 24 hours from administration, the following cell mortality:

A mortality ≤61% of healthy cells HuDe;

A mortality ≥71% of FaDu tumour cells;

A mortality ≥55% of A431 tumour cells or, in a preferred embodiment

A mortality ≤61% of HuDe healthy cells,

A mortality ≥71% of FaDu tumour cells, and

A mortality ≥65% of A431 tumour cells;

in a cell culture plate wherein

HuDe cells seeded at about 7,000 cells per well in 200 µl of the appropriate medium; FaDu cells, seeded at about 12,500 cells per well in 200 µl of the appropriate medium, and A431 cells seeded at about 8,500 cells per well in 200 µl of the appropriate culture medium; cells are cultured for 24 hours after treatment with said product and cell mortality is measured by assessing cell viability through nuclear staining.

Preferably the cell culture plate for each cell type is a 96 wells plate.

According to the invention, hence, the product has the formula as defined above, and shows the measurable cytotoxicity on HuDe, FaDu and A431 cells which are well-known and available to the skilled person.

The test could be carried out, mutatis mutandis, on healthy vs. tumour cells in order to demonstrate the cytotoxic selectivity against tumour cells of the product of the invention.

The cell-based assay indicated above is a classic in vitro assay for assessing the effectiveness and the specificity of antitumour medicaments. As clear from the examples and the results obtained, the product of the invention, tested in various preparations according to the specification and the claims, has shown a strong cytotoxic selectivity against tumour cells while the mortality of the non tumour cells is lower than the one of different tumour cells which is a strongly desired characteristic in antitumour therapy. The skilled person can carry out the assay according to common standard procedures. I any case in the examples section a detailed description on how the cell-based assay for assessing the cytotoxicity and hence verifying this desired feature of the product of the invention is provided.

Hence, the product of the invention induces a minimal/low cytotoxic effect (low mortality e.g. not higher than 45%) on non tumour cells, and a strong cytotoxic effect (high mortality e.g. a mortality higher than 45%) on tumour cells.

The mortality, i.e. the opposite of the viability, of the cells can be measured according to any common technique known to the skilled person. Non limiting examples of a possible techniques commonly used in the art can be quantification of ATP levels, Methylthiazolyl Tetrazolium (MTT) assay, Trypan Blue Exclusion test, Annexin V/PI staining (flow cytometry), Lactate Dehydrogenase (LDH) Release Assay, Caspase Activity Assay, Neutral Red Uptake Assay, Real-Time Cell Analysis (RTCA), Colony Formation Assay and the like.

According to the invention the HuDe, FaDu and A431 cell mortality induced by 0.66 mg/ml of the product herein describe and claimed can be calculated by applying, mutatis mutandis, the protocol described in detail below for the assessment of the Unit of Activity.

According to an embodiment of the invention, the product has the following formula:

30-40% in weight of system a.
60-70% in weight of a system b
and
0.6-1.2% in weight of system c.
for a total of 100%.

The product of the invention can be prepared as disclosed in the examples. However, components a. b. and c. could be prepared as a mixture of extracts of each plant material in the same proportions as in each single component.

Although the preferred extraction mode is through a water extract, also watery extracts (e.g. water and alcohol, wherein the water to alcohol ratio is 1:0 to 1:1) are encompassed by the present invention.

In one embodiment, component a. is a freeze-dried coextract in water of Filipendula leaves and flowers, Laurus leaves, Brassica seeds and Withania roots, the % in weight of the raw materials for the preparation thereof consisting of 17.5-32.5% in weight of Filipendula leaves and flowers, 17.5-32.5% in weight of Laurus leaves, 17.5-32.5% in weight of Brassica seeds and 17.5-32.5% in weight of Withania roots for a total of 100%;

component b. is a freeze-dried coextract in water of of Cynara leaves, Curcuma roots and Tanacetum flowers, the % in weight of the raw materials for the preparation thereof consisting of 10-19% in weight of Cynara leaves, 29-55% in weight of Curcuma roots, 29-55% in weight of Tanacetum flowers for a total of 100%; and component c. is a freeze-dried extract in water of Agave leaves.

In a particular embodiment (e.g. DoEs 1, 2, 3 and 4 as described in the examples), component a. is a freeze-dried coextract in water of Filipendula leaves and flowers, Laurus leaves, Brassica seeds and Withania roots, the % in weight of the raw materials for the preparation thereof consisting of 25% in weight of Filipendula leaves and flowers, 25% in weight of Laurus leaves, 25% in weight of Brassica seeds and 25% in weight of Withania roots, and component b. is a (freeze-dry) coextract in water of Cynara leaves, Curcuma roots and Tanacetum flowers, the % in weight of the raw materials for the preparation thereof consisting of 14.30% in weight of Cynara leaves, 42.85% in weight of Curcuma roots, 42.85% in weight of Tanacetum flowers;

component c. is a freeze-dried extract in water of Agave leaves.

In a non limiting example each of the starting plant materials used for the preparation of the product of the invention, can be individually selected among the species indicated below, Filipendula is selected between Filipendula ulmaria and Filipendula vulgaris or a mixture thereof, Laurus is selected from Laurus azorica and Laurus nobilis or a mixture thereof, Brassica is selected from Brassica rapa, Brassica nigra, Brassica oleracea botrytis cymosa or a mixture thereof, Withania is selected from Withania siniensis and Withania somnifera or a mixture thereof, Cynara is selected from Cynara cardunculus scolymus and Cynara flavescens or a mixture thereof, Curcuma is selected from Curcuma zedoaria and Curcuma longa or a mixture thereof, Tanacetum is selected from Tanacetum cinerariifolium, Tanacetum parthenium and Tanacetum vulgare or a mixture thereof, and Agave is selected from Agave americana and Agave sisilana or a mixture thereof.

Preferably all the plant species used are selected among the plant species as indicated above.

In a preferred embodiment Filipendula is Filipendula vulgaris, Laurus is Laurus nobilis, Brassica is Brassica oleracea botrytis cymosa, Withania is Withania somnifera, Cynara is Cynara cardunculus scolymus, Curcuma is Curcuma longa or a mixture thereof, Tanacetum is Tanacetum, Agave is Agave sisilana.

The table below summarises possible embodiments of the invention.

| Genus and plant parts | Species and plant parts | Preferred Species and plant parts | Range % w/w | % w/w | | Range % w/w | Range % w/w | % w/w | % w/w |
|---|---|---|---|---|---|---|---|---|---|
| Filipendula leaves and flowers | Filipendula vulgaris and/or Filipendula ulmaria leaves and flowers | Filipendula vulgaris leaves and flowers | 17.5-32.5% | 25% | Component a | 20-50% | 30-40% | 36.05% | 30.00% |
| Laurus leaves | Laurus azorica and/or Laurus nobilis leaves | Laurus nobilis leaves | 17.5-32.5% | 25% | | | | | |
| Brassica seeds | Brassica rapa and/or Brassica | Brassica oleracea L. | 17.5-32.5% | 25% | | | | | |

-continued

| Genus and plant parts | Species and plant parts | Preferred Species and plant parts | Range % w/w | % w/w | | Range % w/w | Range % w/w | % w/w | % w/w |
|---|---|---|---|---|---|---|---|---|---|
| | *nigra* and/or *Brassica oleracea botrytis cymosa* seeds | *botrytis cymosa* seeds | | | | | | | |
| *Withania* roots | *Withania siniensis* and/or *Withania somnifera* roots | *Withania somnifera* roots | 17.5-32.5% | 25% | | | | | |
| | | | Tot 100% | 100% | | | | | |
| *Cynara cardunculus* leaves | *Cynara cardunculus scolymus* and/or *Cynara flavescens* leaves | *Cynara scolymus* leaves | 10-19% | 14.30% | Component b | 49-80% | 60-70% | 63.06% | 69.11% |
| *Curcuma* roots | *Curcuma zedoaria* and/or *Curcuma longa* roots | *Curcuma longa* roots | 29-55% | 42.85% | | | | | |
| *Tanacetum* flowers | *Tanacetum parthenium* and/or *Tanacetum vulgare* flowers | *Tanacetum parthenium* flowers | 29-55% | 42.85% | | | | | |
| | | | Tot 100% | 100% | | | | | |
| *Agave* leaves | *Agave americana* and/or *Agave sisilana* leaves | *Agave sisalana* leaves | 100% | 100% | Component c | 0.6-1.2% | 0.6-1-2% | 0.89% | 0.89% |
| | | | | | | Tot 100% | Tot 100% | 100% | 100% |

As disclosed in the Examples, the product of the invention, as defined above and in the claims, has been thoroughly characterised by the Applicant.

The present invention also encompasses the definition of the potency of the product in terms of Arbitrary Units (AU or a.u. or also arb. unit), i.e. the determination of a unit of activity (UoA) of the product of the invention as the amount of product necessary and sufficient to obtain a defined biological effect.

In the biomedical field, the term "arbitrary units" is often used when measuring and expressing data where the exact physical units are either difficult to define or are not essential for the specific context of the experiment.

Using arbitrary units allows researchers to normalize measurements across different experiments or conditions focusing on a measurement of a biological outcome rather than on a physical property (e.g. weight) of the therapeutic agent used in order to induce such biological outcome, making it easier to appreciate equivalence in the induction of a biological outcome, and making it possible to disregard the measurement of physical properties when these are irrelevant given the nature of the therapy.

In the present specification determination of UoA was based on the performance of the elected standard (DoE2).

1UoA is herein defined as the necessary and sufficient amount of EpigenAU/11 capable of inducing 24 hours from its administration, separately, to HuDe, FaDu and A431 cells:

A 40-50% mortality of HuDe healthy cells;
A ≥90% mortality of FaDu tumour cells;
A ≥65% mortality of A431 tumour cells;
in a cell culture plate wherein
HuDe cells seeded at about 7,000 cells per well in 200 μl of the appropriate medium; FaDu cells, seeded at about 12,500 cells per well in 200 μl of the appropriate medium, and A431 cells seeded at about 8,500 cells per well in 200 μl of the appropriate culture medium; cells are cultured for 24 hours after treatment with said product and cell mortality is measured by assessing cell viability through nuclear staining.

According to the invention, about 7,000 HuDe cells/well are seeded in the appropriate culture medium; about 12,500 FaDu cells/well are seeded in the appropriate culture medium and about 8,500 A431 cells/well are seeded in the appropriate culture medium. The cells are cultured at 37° C. with 5% CO2.

In order to assess the Unit of Activity, the reference DoE2, (diluted 20×) was seeded at a final concentration of 0.66 mg/ml and the cells were treated for 24 hours before measuring the cell mortality, assessment of cell viability was made through nuclear staining with NuclearMask—an the Fluorescence intensity, indicative of cell viability, was measured using the Varioskan™ LUX Multimode Microplate Reader; Emission/Excitation: 622 nm/645 nm.

In order to ensure repeatability of the criteria above, the following experimental conditions should be followed:
1. Cell Culture Conditions:
HuDe, FaDu and A431 cell lines should be cultured according to their conventional specified protocols, wherein:
HuDe cells are cultured in MEM medium with 10% FBS, 1% penicillin/streptomycin, and 1% sodium pyruvate, seeded at about 7,000 cells per well.
FaDu cells are cultured in EMEM medium with 10% FBS, 1% penicillin/streptomycin, seeded at about 12,500 cells per well.
A431 cells are cultured in DMEM medium with 10% FBS, 1% penicillin/streptomycin, seeded at about 8,500 cells per well.

2. Experimental Setup:

Cells are cultured in a humid incubator at 37° C. with 5% CO2.

In a preferred embodiment the seeding and treatment steps are carried out using an Assist Plus robot to ensure precision.

3. Treatment with EpigenAU/11 (DOE2):

EpigenAU/11 should be solubilised as described in the experimental section and added to the cells to reach a final concentration of 0.66 mg/mL in a total volume of 200 μL per well.

In a preferred embodiment the product is solubilised at a 20× concentration, therefore the amount of product calculated in terms of a given number of AUs can be provided for a final, standard, solubilisation in a constant volume.

Cells are hence exposed to the treatment with 0.66 mg/mL EpigenAU/11 for 24 hours.

4. Assessment of Cell Viability:

Preferably the assessment of cell viability is made through nuclear staining with NuclearMask-Red according to the manufacturer's instructions.

Fluorescence intensity, indicative of cell viability, is preferably measured using the Varioskan™ LUX Multimode Microplate Reader; Emission/Excitation: 622 nm/645 nm.

The Unit of Activity is therefore the effectiveness achieved under these specific experimental conditions which ensures reproducibility and reliability in determining the anticancer potential of EpigenAU/11.

Mortality (also intended as "decrease in vitality") measurement can be carried out as indicated above.

The results provided in the experimental section, where the product of the invention has been combined with different anticancer drugs (antitumour active principle), see FIGS. 15, 24, 37, 38, 39, examples 4, 7 and 13, show that the combination with different anticancer drugs results in a enhancement of the anticancer drug therapeutic effect and even in a synergistic effect. One of the results obtained in the experiments is the decrease of drug resistance which is a strongly advantageous effect (see, e.g., FIG. 7, example 2.4.1, therefore, the product of the invention can be advantageously combined with one or more anticancer drug. A non limiting example of suitable anticancer drugs to be used in combination with the product of the invention is represented by chemotherapeutics, antibodies or therapeutically active fragments thereof, small molecules etc. A non limited example of suitable chemotherapeutics is represented by Cisplatin, Paclitaxel, Gemcitabine, Epirubicin, Cyclophosphamide, Carboplatin, Oxaliplatin, Mitomycin C, Bleomycin, Doxorubicin, Busulfan, Dacarbazine, Temozolomide, Ifosfamide, Melphalan, Clofosfamide, Lomustine, Bendamustine. A non limited example of suitable antibodies is provided by monoclonal antibodies such as Rituximab, Trastuzumab, Bevacizumab, Pembrolizumab, Ipilimumab, Nivolumab, Atezolizumab, Cetuximab.

The product or composition of the invention can be also advantageously combined with radiotherapy as clear from the examples. Indeed, the experimental data demonstrate the adjuvating effect in the treatment of cancer of the product of the invention when combined with radiotherapy.

Advantageously, the product of the invention, suitably diluted with an appropriate pharmaceutically acceptable carrier (e.g. water or brine etc.), can be used in anticancer therapy as an adjuvant or vehicle for known anticancer drugs, a non limiting example of which, is provided above.

Therefore, the invention also relates to a composition comprising the product according to anyone of the embodiments herein disclosed and at least one of an anticancer active principle and a pharmaceutically acceptable carrier.

When more than one anticancer drug is comprised in the composition of the invention, these can be anticancer drugs commonly co-administered.

Possible examples of combinations are provided in the example section.

The at least one anticancer active principle according to the invention can be any known anticancer drug, by way of example, as defined above or combinations thereof.

The composition or the therapeutic adjuvant according to the invention can be readily formulated by the skilled person for oral, nasopharyngeal, oropharyngeal, aerosol, systemic injection, microneedle injection, intratissutal injection, endovenous, topical, rectal, vaginal, ocular, intratissutal administration.

A non limitative example of formulation forms can be a suspension, a solution, a freeze-dried material, a cream, an ointment, a spray, a tablet, a soft gelatine capsule, a hard gelatine, a gel, an emulsion, an eye drop, an enema, a suppository, a vaginal ovule, a powder, a granule, loaded vesicles, loaded liposomes.

The invention also relates to a kit of parts for concomitant, simultaneous or sequential administration comprising separate vials of the therapeutic adjuvant or vehicle according to the invention and of at least one anticancer active principle (e.g., as defined above).

Concomitant administration generally means using two or more treatments in a narrow time range (e.g. within 5, 10, 15, 20 minutes or the like), but not necessarily together in the same dose or at the exact same moment. According to the invention two different anticancer drugs can be, each, resuspended or diluted in the adjuvant or vehicle of the invention and then administered separately, or the adjuvant and one or more anticancer drugs can be administered separately (the adjuvant being administered separately from the one or more drugs).

Simultaneous administration refers to giving treatments or medications at the exact same time, in the case of the kit of the invention this can also mean directly resuspending or diluting one or more anticancer drug in the vehicle or adjuvant of the invention.

Sequential administration means giving to the patient in need thereof either one or more anticancer drug diluted or resuspended in the adjuvant or vehicle of the invention, or the adjuvant and one or more anticancer drug one after the other, with a time gap between them.

When more than one anticancer drug is administered, these can be anticancer drugs commonly administered concomitantly, simultaneously, or sequentially according to combinations known in the art.

Possible examples of combinations are provided in the example section.

The invention also relates to the product or the composition, or the adjuvant, or the kit of parts of the invention, for use in a medical treatment, in particular in the treatment of cancer.

According to an embodiment of the invention, the cancer can be osteosarcoma, breast cancer, bladder cancer, endometrial cancer, gastric cancer, ovarian cancer, squamous cell carcinoma, head cancer and neck cancer.

As disclosed in the examples section and discussed above, the product of the invention has shown anticancer effectiveness when used alone as well as in combination with one or more anticancer drug. In particular, the product has surprisingly shown the advantageous capability of decreasing of drug resistance on suitable models of resistant patients, the additive or even synergic anticancer effect in combination with various anticancer drugs thereby allowing either to reduce the amount of anticancer drug used or the duration of the therapy or both.

The invention hence also relates to a method of treatment of cancer wherein the product, composition, adjuvant, or kit of parts of the invention are administered in a therapeutically effective amount to a patient in need thereof.

To note, as clear from the examples, the Applicant has also provided a new method for calculating the benefit/risk ratio of the product of the invention and has demonstrated the naturality of the product and its physiological mode of action. In the example is provided a novel Method to Quantify Benefit/risk Ratio Profile Differences between EpigenAU/11 and Cisplatin through an in-depth evaluation of the benefit/risk score associated with treatments using EpigenAU/11 and cisplatin, with a particular focus on transcriptional and functional effects observed in ex vivo conditions (see FIGS. 29-34). The analysis was based on an integrated computer implemented approach utilizing transcriptomic data and advanced biological pathway analysis tools, such as Ingenuity Pathway Analysis (IPA), to identify gene expression changes and modification of relevant biological functions, addressing both therapeutic efficacy and potential adverse effects.

Benefit/risk ratio is a crucial parameter extremely helpful in terms of appreciation of the differences between such key features of a therapeutic option. Nevertheless, such a parameter is currently hard to be reassumed into an objectively calculated single numerical parameter that could facilitate a first approach to the comparison between therapeutic solutions. Here we provide a method capable of correctly predicting and objectivate the comparison between the benefit/risk ratio of two therapeutic solutions based on exclusively ex vivo transcriptomics data. Furthermore, the inventors provide an additional method to rationalize and summarize the benefit/risk ratio into a single numerical parameter from data obtained by in vivo on animal models concerning the same therapeutic product (see figs 35 and 36).

The benefit/risk assessment of a drug in the state of the art involves comparing its observed positive effects (benefits) with its observed negative effects (risks) for patients. The process normally begins with clinical trials to evaluate efficacy and safety. Benefits are assessed based on the drug's ability to treat or prevent a condition effectively. Risks are considered by identifying side effects, toxicity, and long-term impacts. Data from preclinical studies, clinical trials, and post-market surveillance help in this evaluation. The drug's safety profile, the severity of side effects, and the severity of the condition being treated are all factored in. Regulatory agencies like the FDA assess the evidence before approval, weighing if the benefits outweigh the risks. Ongoing monitoring ensures continued safety after approval. If risks outweigh benefits, a drug may be recalled or its usage restricted.

The invention provides new methods for determining a benefit/risk score of a new potential drug using as control a known reference drug whose side effects are known.

The methods can be advantageously used for a predictive evaluation of the benefit/risk ratio of a new product under evaluation, in particular when compared to the benefit/risk ratio obtained with the same methods on a reference drug for the treatment of the same pathology treated by the product under evaluation.

According to the invention, provides a computer implemented method for providing a benefit/risk score of a therapeutical product of interest based on transcriptional data (obtained through the use of data generated ex vivo or in vitro) (Method A) comprising the following steps 1. performing a transcriptomics analysis by
   1.1 providing samples of a biological substrate representing the pathology treated by said product and
   a. treating one or more of said samples with said product;
   b. treating one or more of said samples with a reference drug for the treatment of said pathology; and
   c. using one or more samples of said biological substrate as relevant control
   1.2 extracting RNA from each of said a. b. and c. samples
   1.3 performing a transcriptome raw data analysis from the RNAs extracted in 1.2 to obtain a list of differentially expressed genes (DEGs), in each of samples a. and b. identified based on their expression fold changes with respect to said c. thereby obtaining fold changes values for each DEG
   1.4 Performing an IPA core analysis on the list obtained in 1.3 thereby obtaining numerical values representing the variation in terms of magnitude and directionality (i.e. upregulated or downregulated) of biological activities related to the differential expression of said DEGs in each of samples a. and b. normalised with respect to samples c.
2. determining the benefit score by
   2.1 selecting the biological activities identified in 1.4 which are relevant to the therapeutic indications of said product (e.g. for the product of the invention, antitumoral activities),
   2.2 converting said numerical values into absolute values
   2.3 Summing said absolute values of each of said biological activities thereby obtaining the benefit score of the product under examination,
3. determining the risk score by
   3.1 providing the side effects associated with a reference drug for the treatment of said pathology (e.g. by database query)
   3.2 determining the IPA biological activities associated with said side effects,
   3.3 building a risk in silico model using IPA by establishing a relationship between gene expression pattern obtained at point 1.3 and the biological activities determined at point 3.2, for samples a. and b.
   3.4 inputting the relevant fold changes values for each DEGs of samples a. and b. obtained in 1.3 to the risk in silico model obtained at point 3.3. and using IPA to obtain data representing the direction and the magnitude of the regulation of each biological activity obtained at point 3.2 and transforming said data into corresponding numerical values;
   3.5 Summing each positive value obtained in 3.4 thereby obtaining a final value representing the risk score of the product under examination, wherein, when said final value is <than a predefined positive minimal value, it is automatically corrected to said positive minimal value
4. providing a benefit/risk score value of the product of interest as the ratio between the benefit score value obtained at point 2.3 and the risk score value obtained at point 3.5

According to the present description, absolute values in 2.2 means that the modulus of each value is therefore considered, and negative and positive signs are not considered.

Summing means that a summatory of each value is performed and the side effects considered in 3.1 are the ones indicated as common/frequent in the reference's drug leaflet.

The determination in 3.2 can be made by interrogating a suitable IA.

It is herein reminded that the value 0 in mathematics and in the present description is not considered as a positive or negative number. Therefore, the correction to the positive minimal value is necessarily applied when a 0 value is obtained in the risk score value provided by the methods herein disclosed.

Preferably the benefit/risk score value is calculated both for the product of interest as well as for the reference drug in order to allow comparison between the product of interest and the reference drug.

The invention further discloses a method for providing a benefit/risk score of a therapeutical product of interest for the treatment of a given pathology based on data obtained from in vivo animal models.

1. providing numerical values obtained from the following groups of animal models representing said pathology
   a. group treated with said product and
   b. group treated with a reference drug for the treatment of said pathology; and
   c. relevant control group
   said numerical values representing each of the following parameters: the therapeutical efficacy, the behavioural modifications indicative of animal suffering and the body weight-loss indicative of animal suffering observed in each of groups a. and b. normalised with respect to control group c
2. determining the benefit score by summing said therapeutical efficacy values thereby obtaining the benefit score value of the product under examination,
3. determining the risk score
3.1 identifying as risk parameters the modifications and the weight-loss indicative of animal suffering for which numerical values are provided in 1.
3.2 summing said numerical values of 3.1 (with reference to group a.) thereby obtaining a final value representing the risk score of the product under examination, wherein, when said final value is <than a predefined positive minimal value, it is automatically corrected to said positive minimal value
4. providing a benefit/risk score value of the product of interest as the ratio between the benefit score value obtained at point 2 and the risk score value obtained at point 3.2

Therapeutic efficacy parameters depend on the pathology of interest, e.g. for an anticancer drug said parameters are mainly represented by the tumour mass reduction and, optionally, by the presence or absence of metastasis; for an antidepressive drug said parameters can comprise behavioural modifications indicative of an amelioration of the depression gravity and so on. The parameters hence will be parameters commonly correlated with the assessment of therapeutic efficacy in the treatment of a given pathology.

Parameters indicative of behavioural modifications indicative of animal sufferings are parameters that are codified by standard tests commonly used in the art such as, e.g. Irwin test, used in official protocols for evaluating animal suffering in pre-clinical trials or stabulation.

Also in this case the benefit/risk score can be provided also for the reference drug.

Preferably, when applicable, both methods are carried out so to validate the results obtained with either one of them. The examples provided also demonstrate that the product of the invention, shows therapeutic or adjuvating resilience (i.e. different batches and even slightly different permutations in the relative ratio of the components a. b. and c. among batches still maintain the desired therapeutic effect) and behaves as a natural matrix itself, showing emerging properties achieving its effect through a network over networks interaction, thereby retaining a native natural intelligence.

The "natural native intelligence" of a natural matrix, such as a therapeutical plant-based natural matrix, such as the product of the invention, refers to the intrinsic, synergistic wisdom embedded within the complex relationships between plants, their biochemical properties, and their interactions with human biology and well-being. It encompasses the self-organizing, adaptive processes inherent in plants that support healing, balance, and regeneration, both within ecosystems and when applied to human health. The natural native intelligence of a plant-based matrix is observed in how the diverse compounds within a single plant work together in synergy. Unlike isolated pharmaceuticals, whole plants offer a balanced interaction of active and supportive components, reducing side effects and enhancing efficacy.

This synergy extends to how different plants in a matrix complement one another, creating holistic therapeutic effects.

In summary, the natural native intelligence of a therapeutical plant-based natural matrix represents the harmonious, innate wisdom of plants and ecosystems in supporting health and healing. It is expressed through plants' biophysical synergy, ecological balance, alignment with human biology, and capacity to guide holistic healing. This intelligence emphasizes cooperation and connection, offering a therapeutic pathway grounded in nature's own evolutionary wisdom.

The product of the invention, being itself a new natural matrix, possesses the natural native intelligence typical of natural matrices.

As demonstrated in the examples, the product or the therapeutic adjuvant according to any of the embodiments as defined herein, when used in therapy as disclosed, exerts its therapeutic or adjuvant effect on cancer through a physiological mechanism of action, through the modulation of a network of biological activities, on the altered physiological state underlying said cancer condition and shows therapeutic or adjuvating functional resilience among different batches of said product or adjuvant, said functional resilience being intended as the maintenance of the therapeutic or adjuvating properties among different batches of said product or adjuvant, notwithstanding their different batch to batch qualitative and quantitative composition.

This is held true, as demonstrated in the examples, even when different permutations in the formula within the ranges claimed are used.

In fact, the inventors also demonstrated in the examples below, that different batches of the product of the invention (see examples, EpigenAU/11 DoEs 1, 2, 3, 4 as well as permutations thereof in terms of relative amount of components a. b. and c. within the ranges claimed), notwithstanding their quali-quantitative different chemical composition, showed therapeutic/beneficial functional resilience by modulating the biological activities as described above, with the same pattern and with similar modulation values.

Figure 27:
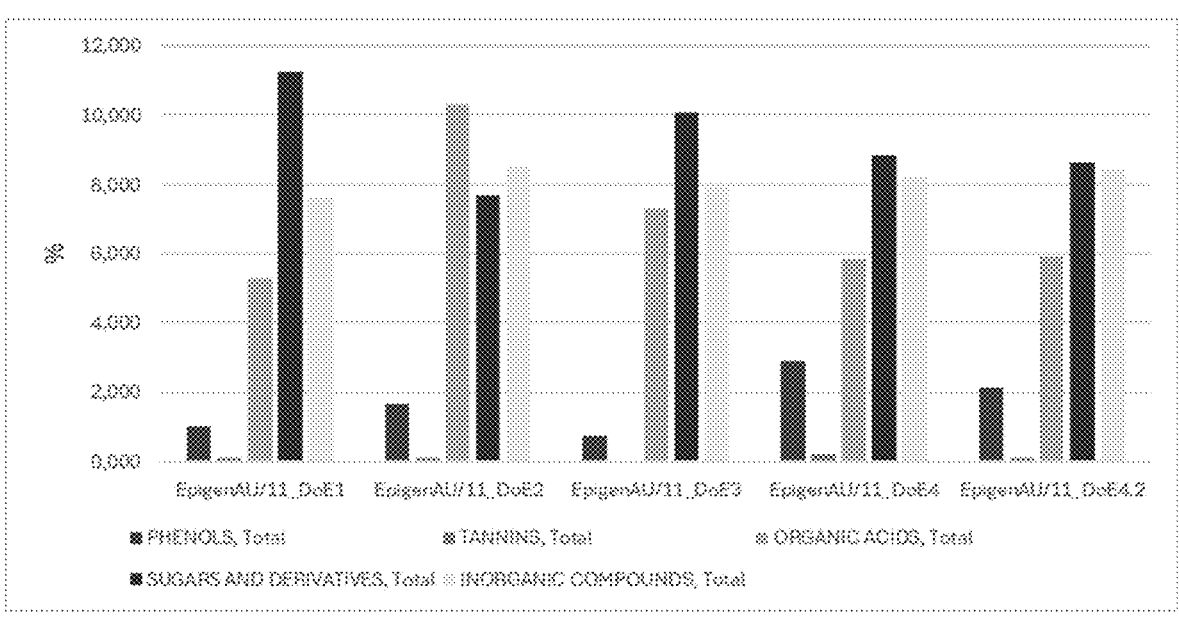

In fact, although different batches of a product comprising one or more natural matrices are, by definition, batches wherein the qualitative and quantitative composition is necessarily variable as thoroughly discussed above, according to one embodiment, a qualitative and/or quantitative analysis of each batch was performed to demonstrate the existing qualitative and/or quantitative difference in the molecular composition of each batch (FIG. 27). This can be achieved through conventional techniques; a non-limiting example comprises chromatography. spectrophotometry, atomic absorption spectroscopy (AAS), atomic emission spectroscopy (AES), inductively coupled plasma (ICP) techniques, chromatography coupled with detectors, and the like or combinations thereof. The analysis can be focused on a limited number of selected classes of substances (e.g., FIG. 27) or on all the components of the product.

As expected for products comprising or consisting of natural matrices, although each batch was prepared following standardised procedures to obtain a priori a high degree of homogeneity between different batches, the detailed quali-quantitative analysis of all the tested batches clearly demonstrated relevant batch-to-batch quali-quantitative differences that would have lead, with conventional validation methods used for synthetic or isolated drugs, to the discard of batches that were indeed therapeutically valid, as well as the impossibility to hypothesise the presence of an API.

In example 15 a quality control procedure for the manufacturing of the product of the invention is provided. For the desiderata of the quality control, the performance of DoE2, which was thoroughly characterised and tested by the inventors, is taken as the quality manufacturing goal. Therefore, the inventors provide, in the present specification, a procedure for standardising the product for manufacturing commercial, safety and repeatability.

It is herein reminded that, due to their own nature, natural matrices are variable in their composition even when obtained from the same kind of raw source, by way of example, the skilled person knows very well that a natural matrix obtained from an individual of a plant species, will never be absolutely identical to another natural matrix obtained from a different individual of the same plant species, even among plants in the same field, due to the genetic and epigenetic variability of each living organism.

Following the experiment reported in FIG. 27, notwithstanding the different qualitative and quantitative chemical composition of all the batches analysed, the authors surprisingly found that, in all the batches tested, the different molecular entities within each matrix appeared to interact in a redundant manner with each other both functionally and possibly structurally providing the same therapeutic or beneficial (homeostasis-adjuvant) effect despite their differences in quali-quantitative molecular composition.

Indeed, the batches showed a functional (therapeutical or beneficial) resilience despite the variability in their qualitative and quantitative molecular composition.

In other words, the authors surprisingly found that different batches of the same product showed a consistent regulation (in terms of trend and magnitude) of all the examined biological activities, relevant to the desired therapeutical or beneficial effect, notwithstanding batch-to-batch qualitative and quantitative composition differences, herein also defined as "functional resilience effect". The observed maintenance of the biological activity is likely due to the fact that, as said above, the emerging properties of a natural matrix are due to the matrix networks acting as a whole entity with distinctive properties, and may not be ascribable to each single molecule as if it were in isolation, the therapeutic action being through a non-pharmacological mechanism of action different from the classical therapeutic products based on the pharmacological relationship between structure and activity (SAR) which is the most relevant relationship in classical pharmacological activities between an active pharmaceutical ingredient (API) and the receptor targeted by said API, which is considered at the level of single molecules.

This agrees with the likelihood that the products analysed by the inventors, may exert their therapeutic or beneficial action by acting on a whole pathophysiological or altered physiological state.

According to the invention, the product or composition as defined and/or claimed, exerts its therapeutic or beneficial effect through a physiological mechanism of action, by adjuvating the reinstatement of cancer through a network of biological activities on the altered physiological state underlying said cancer condition and by showing therapeutic or beneficial functional resilience among different batches of said product or composition, said functional resilience being intended as the maintenance of the therapeutic or beneficial properties of different batches of said product or composition, notwithstanding their different batch to batch qualitative and quantitative composition.

In particular, due to all the reasoning on natural matrices provided above, together with all the experimental data gathered by the Applicant, it can be said that the product or composition according the invention is itself a natural matrix, representing native natural intelligence, said natural intelligence being the only capable to allow a physiological endogenous interconnection with other entities which are self-assembled in nature, such as the human species.

It is herein reminded that native natural intelligence, represents the intrinsic ability of natural matrices to conserve and transmit biological and physio-chemical information necessary for interacting and integrating with other living networks, using logics inherent to the living organism that receives them, as they are already known to it, and therefore endogenous in relation to it. This intelligence is an expression of natural autopoiesis, that is, the ability to self-organize and adapt to environmental stimuli without artificial intervention, which would transmit a message according to point-like logics and through mediators unknown to the living organism receiving them, and therefore exogenous in relation to it.

Therefore, as stated above, the product or therapeutic adjuvant of the invention is itself a natural matrix and represents native natural intelligence, said natural intelligence allowing a physiological endogenous interconnection with other entities which are self-assembled in nature, such as the human species.

Method ISO-16620-2; 2019 (AMS), is a method measuring the residual activity of 14C (which is an instable isotope) and its measurement is indicative of the naturality of a product. In fact, the decrease of 14C activity indicates the distance from "living" of a given compound. Hence, a product with a 14C activity of about 100% can be defined as a natural product. According to the invention, a 14C activity measured with ISO-16620-2; 2019 (AMS) method is a value higher than 99.0% percent.

According to invention the presence of said native natural intelligence within the product or adjuvant composition of the invention can be determined through the validation of the product's or composition's emerging properties in anti-cancer activity when the following conditions are met: their 14C activity measured with ISO-16620-2; 2019 (AMS) method is of ≥99.00%, miRNAs and exosomes are detected therein, the product or composition shows batch-to-batch therapeutic or beneficial functional resilience between different batches of said product or composition and said product or composition modulates a whole altered pathological condition.

According to the invention, the presence of native natural intelligence in a therapeutic or therapeutically adjuvant product or composition, wherein said product or composition comprises or consists of natural matrices, can be determined by validating that the product or composition is itself a natural matrix with emerging properties in anticancer activity (therapeutic or beneficial) when its 14C activity measured with ISO-16620-2; 2019 (AMS) method is of ≥99.00%, miRNAs and exosomes are detected in said product or composition, the product or composition shows batch-to-batch therapeutic or beneficial functional resilience between different batches of said product or composition and when the product or composition modulates a whole altered physiological state or pathological condition.

This can be done, with the product or composition of the invention, by performing the following steps on samples of said product or composition:

a. assessing the product or composition naturality by:

1. measuring the 14C activity in said product or composition with ISO-16620-2; 2019 (AMS) method, 2. assessing the presence of miRNAs in said product or composition, 3. assessing the presence of exosomes in said product or composition, b. assessing the presence of therapeutic or beneficial functional resilience between different batches of said product by comparing, batch to batch, the modulation of one or more biological activities underlying the product's desired therapeutic or beneficial effect on a relevant altered physiological state and/or on the pathological condition treated by said product or composition in a cell-based assay whose read-out is representative of the modulation of said one or more biological activities;

c. assessing from the read-out of said cell-based assay, whether the modulation of said biological activities underlying the desired therapeutic or beneficial effect results in the modulation of a whole altered physiological state or pathological condition; and determining that said product or composition is itself a natural matrix, representing native natural intelligence when:

the measured value for the 14C activity is ≥99.00%, miRNAs, exosomes and therapeutic or functional resilience are detected, and said modulation in c. results in the modulation of a whole altered physiological state or pathological condition.

The product is determined to be natural when the measured value for the 14C activity is ≥99.00%, miRNAs, exosomes are detected and to exert its activity through a physiological mechanism of action when it modifies a state and show therapeutic or beneficial functional resilience i.e. shows emerging properties. The sum of these features allows the determination of the product as a natural matrix itself, thereby representing native natural intelligence.

Assessment of the modification of a state and of functional resilience can be performed as follows.

The capability of a therapeutic or therapeutically adjuvant product of modifying a pathophysiological state or an altered physiological state (e.g., by adjuvating the homeostasis response of the organism) is a crucial feature for establishing its physiological mode of action. Indeed, a product acting with networks-to-network interaction is a product that is expected to modify a state rather than a single function when administered to a living organism.

In other words, this feature is likely to be satisfied by a therapeutic or therapeutically adjuvant product comprising one or more natural matrices or consisting of one or more natural matrices given the networks-network (product-receiver) interactions exerted by natural matrices. The Applicant's patent application PCT/IB2024/055892 discloses a method for defining the mode of action of a therapeutic or beneficial natural matrices-based product.

A product exerting a physiological mode of action is also expected to be 100% natural (see above) and to show the flexibility and self-administrating mechanisms that are observable in living organisms wherein different messages within the cell and among cells as well as different regulations of gene pathways can provide the same result notwithstanding the different messages triggered within the cell. For a therapeutic or beneficial product this equates to the functional resilience of different batches of the product (with a quali-quantitative variability in their chemical composition).

The present inventors determined whether product of the invention exerts its therapeutic or beneficial effect by modifying a pathological state and whether the product shows or not functional resilience (i.e., the maintenance of the therapeutic or beneficial properties of different batches of a given product comprising one or more natural matrices, notwithstanding its different batch to batch qualitative and quantitative composition).

According to the invention, this can be verified by carrying out a cell-based assay whose readout is representative of the modulation of the selected biological activities as defined above as disclosed e.g. in the examples and figures as described in the specification, and by analysing and interpreting the data obtained therefrom.

Assessment of functional resilience (therapeutic or beneficial).

As indicated in the glossary and in the specification above, in the present description and claims, functional resilience is the maintenance of a therapeutic or beneficial measurable efficiency in different batches of a product notwithstanding variability in their qualitative and quantitative molecular composition.

It is clear that the batches (such as the tested DoEs 1, 2, 3 and 4 of EpigenAU/11) are intended as batches that are identical in terms of manufacturing processes and type and amounts of each ingredient (as the main ingredients of the selected products are natural matrices, this means that each matrix in the product is produced from the same kind of starting materials and with the same procedures e.g. a given kind of extract from the same plant part of the same plant species), therefore, the variability in their qualitative and quantitative molecular composition cannot be ascribed to different manufacturing procedures or to different ingredients but can only originate from the inherent difference between natural matrices obtained with the same procedure from different organism/s of the same species. When different batches of the same product comprising one or more natural matrices maintain in a measurable and verifiable way their final modulatory activities underlying their therapeutic or beneficial properties irrespectively of their quali-quantitative composition, functional resilience of the product can be validated.

The invention hence also relates to a method for determining the presence of native natural intelligence in a therapeutic or therapeutically adjuvant product or composition, said product or composition comprising or consisting of natural matrices, through the validation of its therapeutic or beneficial emerging properties, the method comprising the following steps on samples of said product or composition:

a. verifying said product naturality by performing:

1. measuring of the 14C activity with ISO-16620-2; 2019 (AMS) method 2. assessing the presence of miRNAs in said product or composition, 3. assessing the presence of exosomes in said product or composition, b. assessing the presence of therapeutic or beneficial functional resilience between different batches of said product by comparing, batch to batch, the modulation of one or more biological activities underlying the product's desired therapeutic or beneficial effect on a relevant altered physiological state and/or on the pathological condition treated by said product or composition in a cell-based assay whose read-out is representative of the modulation of said one or more biological activities;

c. assessing from the read-out of said cell-based assay, whether the modulation of said biological activities underlying the desired therapeutic or beneficial effect results in the modulation of a whole altered physiological state or pathological condition; and determining that said product or composition is itself a natural matrix representing native natural intelligence, when the measured value for the 14C activity is ≥99.00%, miRNAs, exosomes and therapeutic or functional resilience are detected, and said modulation in c. results in the modulation of a whole altered physiological state or pathological condition.

According to an embodiment of the invention the method further comprises, before performing the one or more cell-based assay: (1) providing a list of hallmarks representative of said altered metabolism and/or pathological state; (2) identifying for each of said hallmarks one or more biological activities modifications underlying said pathological state thereby pinpointing a network of biological activities whose modulation concurs to said pathological state and (3) identifying one or more parameters whose modulation concurs to the modulation of said one or more biological activities underlying the therapeutic effect of the product tested and determining the modulation trend in terms of up or down modulation of said one or more biological activities, in said network, concurring to said pathological state or to a healthy state.

According to a preferred embodiment said altered physiological state is cancer and said hallmarks are selected from: angiogenesis, immune system and inflammatory process, tumour viability and proliferation, metastatisation, premetastatic niche formation, preferably, wherein the biological activities of (2) for the angiogenesis, immune system and inflammatory process, tumour viability and proliferation, metastatisation, premetastatic niche formation hallmarks are selected from the biological activities depicted in FIG. 17 and in FIG. 32.

The method below is a computer implemented method. More in detail (1) providing a list of hallmarks representative of the pathological state associated to a pathology i.e., providing a list of hallmarks representative of the disease or pathophysiological condition treated by the product of interest;

(2). identifying for each of said hallmarks one or more biological activities modifications underlying said pathology and determining the modulation thereof representing the pathophysiological state associated to said pathology and assessing the opposite modulation as the modulation pattern of each of said activities representing a healthy physiological state; and (3). identifying one or more marker and the modulation pattern thereof underlying the modification detectable in said pathological state for each of said one or more biological activities and setting for each of said parameters the modulation pattern opposite to the one identified, as the modulation pattern concurring to said healthy physiological state.

In case a therapeutic product is examined, according to an embodiment, the method of the invention may comprise the following steps:

(a) performing said at least one in vitro cell-based assay on the following groups of cells (a1) at least one control group and at least two test groups of cells having the diseased phenotype relevant to the intended use of the therapeutic product; or (a2) at least one group of cells with a healthy physiological phenotype; and at least one control group and at least two test groups of said cells with a healthy physiological phenotype wherein the diseased phenotype relevant to the intended use of the therapeutic product is induced, and treating each of said test groups of cells with one of said different batches of therapeutic product;

(b) determining the modulation or modulation pattern of each of said parameters on each of said groups of cells of step (a) and calculating the respective modulation values for each of said one or more biological activities;

(c) comparing said modulation values, wherein:

said therapeutic product is shown to exert its therapeutic effect through a physiological mechanism when at least 50% of said one or more biological activities for each hallmark are modulated by each product batch with the modulation trend of the network concurring to the healthy state, and the modulation values determined in (b) of each of said at least 50% one or more biological activities for said test groups of cells of (a1) differ, respectively, from the ones of said control group of cells of (a1) of at least 0.15, or at least 50% of said one or more biological activities for each hallmark are modulated by each product batch with the modulation trend of the network concurring to the healthy state, and the modulation values determined in (b) of each of said at least 50% one or more biological activities for said test groups of cells of (a2) differ, respectively, from the ones of said control group of cells of (a2) by at least 15%, and functional resilience of the product is demonstrated by the modulation values for each one or more biological activities of each said test groups of cells differing by less than 20% from the average of said values.

For EpigenAU/11 the cell-based assay identified is (a1).

This means, that the modulation value of a given biological activity of the test group is confronted, respectively, with the modulation value of the same biological activity of the control group, therefore the difference of at least 0.15 or of at least 15% is the difference between the modulation value of a given activity in the treated group of cells with respect to the modulation value of the same activity in the group of cells representing the control baseline.

The expression at least 50% of said one or more biological activities for each hallmark are modulated by each product batch with the modulation trend of the network concurring to the healthy state, means that, in case of a single biological activity for a given hallmark, in order to fulfil the requirement above, 100%, i.e., the single activity, must be modulated by the product tested, with the modulation trend concurring to the healthy state, The expression "the modulation values of each said at least 50% one or more biological activities determined in (b)" refers to the modulation values determined in (b) of that at least 50% of biological activities fulfilling the requirement of being modulated according to the modulation trend concurring to the healthy state. This applies, mutatis mutandis, to all the embodiments disclosed herein.

As previously indicated, the method of the invention comprises: (1) providing a list of hallmarks representative of the pathological state of interest (i.e., the pathological state treated by the product analysed or the pathological state that can stem from the altered physiological state on which the beneficial product analysed exerts its homeostasis adjuvating activity); (2) identifying for each of said hallmarks one or more biological activities modifications underlying said pathological state thereby pinpointing a network of biological activities whose modulation concurs to said pathological state and (3) identifying one or more parameters whose modulation concurs to the modulation of said one or more biological activities underlying the therapeutic effect of the product tested and determining the modulation trend in terms of up or down modulation of said one or more biological activities, in said network, concurring to said pathological state or to a healthy state.

All the embodiments above allow to determine whether a therapeutic or beneficial product exerts its therapeutic or beneficial effect by modifying a state or merely a limited number of activities or even a single function underlying the pathology an aberrant physiological state treated by said product and whether a therapeutic or beneficial product as the ones selected maintains a functional resilience as herein defined.

The modification of a state is a feature that cannot be obtained with a one-API pharmaceutical product, therefore, this feature rules out classical pharmaceutical modes of action. However, the modification of a state could, in principle, be obtained with a pharmaceutical product comprising a cocktail of APIs.

A physiological mode of action requires that the therapeutic or beneficial product regulates the state in a manner that involves an overall cellular response with a networks over network interaction, and not in a points over network interaction that is at the basis of APIs mode of action (be it a single API or a cocktail thereof).

This implies, besides the regulation of a state, also the capability of the product of acting with a functional resilience (either therapeutic or beneficial), i.e., providing the same batch to batch therapeutic/beneficial effect notwithstanding the different batch to batch quali-quantitative composition which, in other words, is the result of regulating the various parameters selected in variable ways and nevertheless providing a conserved functional result.

The present invention hence also provides modes for demonstrating the functional resilience of therapeutic or beneficial products.

As already explained in the glossary and in the description above, functional resilience (therapeutic or beneficial) is the capability of a given product of modulating one or more biological activities underlying a pathological state or an altered physiological state notwithstanding variability in the qualitative and quantitative composition of different batches of the same product and therefore notwithstanding the possibility of reaching the same final result triggering different signals within the cell i.e., showing bioequivalence intended as same final result. As already stated above is known that pharmaceutical (API based) products, with a different qualitative and quantitative composition are not considered bioequivalent.

The physiological mode of action, which implies an overall interaction with the cells of the subject treated and not with singled out cellular molecular targets, is the mode exerted by living organisms as the result of networks-network interactions. Physiological systems in the body often exhibit functional redundancy to maintain homeostasis and adapt to changes or disruptions, redundancy being a well-known physiological mechanism in the living for ensuring that a given goal is reached (e.g., a response of the organism in the production of various proteins, in the activation of various pathways etc.). When a therapeutic product interacts with these systems, it may engage multiple pathways or mechanisms, including redundant ones, to achieve its desired effect. This redundancy, which results in a functional resilience, contributes to the physiological mode of action of the product.

Functional resilience in therapeutic/beneficial products (intended as the ability of a therapeutic or beneficial product to maintain its intended functionality and effectiveness despite variability in its batch-to-batch qualitative and quantitative composition) is therefore an essential feature of a physiological mode of action.

The invention also relates, mutatis mutandis, to method of treatment or of adjuvating the treatment of cancer condition wherein the product or the composition or the therapeutic adjuvant or the kit of parts according to the invention is administered, alone or in combination with an antitumour active principle or in combination with the suitable radiotherapy in therapeutically effective amount to a patient in need thereof, preferably wherein said cancer is osteosarcoma, breast cancer, bladder cancer, endometrial cancer, gastric cancer, ovarian cancer, squamous cell carcinoma, head cancer and neck cancer.

In any part of the present description and claims the term comprising can be substituted by the term consisting of.

In any part of the description and of the claims, when reference to cytotoxic effect (i.e. mortality/vitality of the tested cells) is made, it is understood that the vitality values are the opposite of the mortality values and vice versa. Therefore, by way of example, $-x$ % with reference to the vitality corresponds to a x % of cell mortality.

In any part of the description or in the claims, when calculations are made, this can be carried out in a computer implemented mode.

Examples are reported below which have the purpose of better illustrating the embodiments disclosed in the present description, such examples are in no way to be considered as a limitation of the previous description and the subsequent claims, further, the examples below report all the studies performed on the product of the invention and support all the subject-matter claimed.

EXAMPLES

1. The System of the Invention: EpigenAU/11
1.1 EpigenAU/11 Composition:

The composition claimed, herein also denominated EpigenAU/11, is expressed in terms of weight % of each plant system and in weight % of each plant part used for the preparation of each system.

The table below reports the composition of different batches of EpigenAU/11 (each denoted by the label DoE followed by a number) wherein the starting materials (plant materials) used for the preparation of each plant system in each batch are different plants of the same species indicated in the table. The different batches were prepared in order to analyse their chemical quali-quantitative composition (which was expected to be different in each batch due to the fact that plants are living organisms and each individual is necessarily different from the other in terms of quali-quantitative composition although belonging to the same species) and their activity was tested in various assays in order fully characterise the EpigenAU/11 system and to prove the therapeutic functional resilience of the product, i.e. the maintenance of the therapeutic activity notwithstanding the batch-to-batch different quali-quantitative composition.

from light and moisture. The weight-to-weight percentages of each plant material used are reported in the table above.

Component B

Plant system 2: dried *Cynara cardunculus* leaves, *Curcuma longa* radix, *Tanacetum parthenium* flowers were subjected to co-extraction by water 100% (v/v) [drugs solvent ratio: 1/20] for 2 h at 50° C. and filtered to remove solid exhausted material. The co-extract was subjected to centrifugation. The supernatant was ultrafiltered (filter at 20000 Da), 2 fractions were obtained: permeate and the retained. The retained fraction was pasteurized then freeze-dried for 72 h. The resulting co-extract was stored until use

| PLANT SYSTEM | Genus and plant part within the product | Species within the product | Components (A, B and C) composition % DoE 1, 2, 3, 4 and all permutations thereof disclosed in the examples | % Plant systems in DoE 1, 2, 3 and 4 | % Plant systems in DoE 4.2 |
|---|---|---|---|---|---|
| COMPONENT A | Filipendula leaves and flowers | *Filipendula vulgaris* | 25% | 36.05% | 30% |
| | Laurus leaves | *Laurus nobilis* | 25% | | |
| | Brassica seeds | *Brassica oleracea botrytis cymosa* | 25% | | |
| | Withania roots | *Withania somnifera* | 25% | | |
| COMPONENT B | Cynara leaves | *Cynara cardunculus scolymus* | 14.30% | 63.06% | 69.11% |
| | Curcuma roots | *Curcuma longa* | 42.85% | | |
| | Tanacetum flowers | *Tanacetum parthenium* | 42.85% | | |
| COMPONENT C | Agave leaves | *Agave sisalana* | 100% | 0.89% | 0.89% |

1.2 EpigenAU/11 Preparation Process

EpigenAU/11 preparation: in general, EpigenAU/11 system consists of 3 components: plant system 1, plant system 2, and *agave* in the relative weight percentages defined in the description and in the claims. Specific embodiments of EpigenAU/11 composition were prepared, each being indicated as "DoE" followed by a number for practical reasons. The table above indicates the exact percentages of each component in the different EpigenAU/11 DoEs used in the following examples. In the examples where further DoEs are tested the exact formulation of each of them will be provided. The process described below (1.3), mutatis mutandis the relative percentages of each component, or starting plant material according to the table above as well as to the claims and various embodiments described, applies to all EpigenAU/11 possible formulations within the claims.

1.3 Preparation of Components A, B and C

Solvent: purified water was produced from drinking water by means of an Industrial Water Treatment Plant.

Component A:

Plant system 1: dried Laurel *nobilis* leaves, *Withania somnifera* radix, *Filipendula* ulmaria leaves and flowers and *Brassica oleracea* seed were subjected to co-extraction by water 100% (v/v) [drugs solvent ratio: 1/20] for 2 h at 50° C. and filtered to remove solid exhausted material. The co-extract was subjected to centrifugation. The supernatant was ultrafiltered (filter at 20000 Da), 2 fractions were obtained: permeate and the retained. The retained fraction was pasteurized then freeze-dried for 72 h. The resulting co-extract was stored until use at room temperature, away at room temperature, away from light and moisture. The weight-to-weight percentages of each plant material used are reported in the table above.

Component C

*Agave*: dried *Agave* sisalana leaves was subjected to extraction by water 100% (v/v) [drugs solvent ratio: 1/15] for 2 h at 50° C. and filtered to remove solid exhausted material. The extract was subjected to centrifugation. The supernatant was ultrafiltered (filter at 20000 Da), 2 fractions were obtained: permeate and the retained. The retained fraction was pasteurized then freeze-dried for 72 h. The resulting extract was stored until use at room temperature, away from light and moisture.

1.3.2. EpigenAU/11 System Assembly

The 3 components are combined according to the ratios in the description and in the claims in order to reach a 100% weight. Component A. (36.05%), component B. (63.06%), component C. (0.89%) weight to weight percentages were combined for preparing EpigenAU/11 DoEs 1, 2, 3 and 4; whereas component A. (30%), component B. (69.11%), component C. (0.89%) weight to weight percentages were combined for preparing EpigenAU/11 DoE 4.2.

1.3.3 EpigenAU/11 Solubilization

All the solubilised EpigenAU/11 DoEs used in the examples below were prepared by the following method: weigh the desired amount in a tube and add the solvent of interest (physiological solution or medium). Then, vortex for 2 minutes at room temperature using a multi reax and sonicate for 5 minutes at 35° C. at maximum power (Branson Ultrasonics). The extracts were then placed in a wheel mixer at 27 RPM for 30 minutes and centrifuged at 5000 RPM for 10 minutes. Finally, the supernatant was recovered and filtered through a 0.22 µm filter.

1.4 Summary of Protocols Used

| | |
|---|---|
| GENE EXPRESSION ANALYSIS | 2.1.2. Gene expression analysis<br>At the end of described treatment periods, tumour fragments were homogenized using Lysing Matrix Tubes J (MP Biomedicals) in RLT buffer (Qiagen, 1053393) added with β-mercaptoethanol (Sigma, M3148) and DX reagent (Qiagen, 19088) for gene expression analysis experiments. Total RNA was extracted from cells lysates using an QIAsymphony RNA Kit (Qiagen,) with the QIAsymphony SP instrument (Qiagen).<br>The quality and quantity of RNA was determined by A230, A260, A280 and A320 measurements on Varioskan™ LUX multimode microplate reader (Thermo Scientific™). Integrity of RNA was checked using a 2100 expert_Eukaryote Total RNA Nano Kit (Agilent). Whole transcriptome expression profile was evaluated using a Human Clariom™ S Pico Assay HT (Applied Biosystems, ThermoFisher Scientific) on a GeneTitan MC Instrument (Applied Biosystems, ThermoFisher Scientific), following the manufacturer's instructions. Briefly, 6 ng of total RNA was used to generate cDNA, then fragmented and labelled cDNA was hybridized to a Human Clariom S 96-array plate for 17 h at 45° C. Arrays were washed, stained and then scanned using the GeneTitan MC Instrument (Applied Biosystems, ThermoFisher Scientific) and CEL Intensity files were generated by Affymetrix GeneChip Command Console Software (AGCC, ThermoFisher Scientific). (computer implemented or assisted) |
| TRANSCRIPTOMICS DATA ANALYSIS | 2.1.3. Transcriptomics data analysis<br>Data analysis was performed using Transcriptomic Analysis Console Software (TAC, ThermoFisher Scientific) that provides quality control analysis, performs normalization and summarization, based on the Signal Space Transformation-Robust Multi-Chip Analysis (SST-RMA) analysis algorithm, and provides a list of differentially expressed genes (Limma Bioconductor package, p-value ≤ 0.05).<br>(computer implemented or assisted) |
| CELL BASED ASSAY | In this study, FaDu cells, a squamous cell carcinoma line (obtained from the American Type Culture Collection-ATCC HTB-43), capable of tumorigenesis in nude mice, were utilized. After inoculation subcutaneously into animals and generating masses, the biopsies were explanted and immediately frozen in liquid nitrogen and then transferred to −80° C. Upon thawing in Eagle's Minimum Essential Medium (EMEM) (ATCC, 30-2003), they were sectioned into approximately 40 mg pieces and cultured for either 6 hours (for gene expression analysis) or 72 hours (for cytofluorimetric analysis) in a humidified incubator at 37° C., with an atmosphere enriched with 5% CO2, in the absence or presence of EpigenAU/11 at 50 mg/ml or Cisplatin at 666 µM.<br>For gene expression analysis, at the end of the 6-hour treatment period, tumour fragments were homogenized using Lysing Matrix Tubes J in RLT buffer and followed the previously described process. For cytofluorimetric analysis, at the end of the 72-hour treatment period, the masses were collected and fragmented using a scalpel to create smaller pieces. These fragments underwent further processing to obtain single-cell suspensions using the gentleMACS Octo Dissociator with Heaters (Miltenyi Biotec, 130-096-427) in combination with a tissue dissociation kit (Miltenyi Biotec, 130-095-0929), following the manufacturer's instructions. Cellular debris was removed using the MACS Miltenyi Biotec Debris Removal Solution (Miltenyi Biotec, 130-109-398), and red blood cells were eliminated using Red Blood Cell Lysis Solution (10x) (Miltenyi Biotec, 130-095-0929) according to the manufacturer's protocol.<br>Following dissociation, cells were resuspended and stained with CD45 Monoclonal Antibody (30-F11), PE-Cyanine7, eBioscience™ (Invitrogen, 25-0451-82) at a concentration of 0.125 µg/test for 30 minutes on ice with occasional shaking. Cells were then washed in cold DPBS (ThermoFisher, 14190-094) at 1200 rpm for 5 minutes. CD45 Monoclonal Antibody was utilized to exclude all hematopoietic cells except mature erythrocytes and platelets. After removing the supernatant, cells were stained with Alexa Fluor® 488 Annexin V/Dead Cell Apoptosis Kit (ThermoFisher, V13241, A13201). Subsequently, the cells were resuspended in 500 µl 1X annexin-binding buffer and analysed using an Attune NxT flow cytometer (Life Technologies). |
| DEFINITION OF THE PATHOPHYSIOLOGICAL HALLMARKS OF THE DISEASE WITH WHICH TO INTERROGATE IPA | The alteration of healthy physiological state features of state-of-the-art "Cancer" were considered with particular attention to the following areas involved:<br>Cell damage<br>Energetic metabolism and insulin sensitivity<br>Epithelial-mesenchymal transition<br>Growth factor |

-continued

Inflammation
Regulation of mitosis/proliferation
Stemness
This knowledge was used to select and classify IPA core analysis
outputs (ie Canonical pathways).

2. Preclinical Data

The preclinical data reported below demonstrate a cancer-cells selective cytotoxicity of EpigenAU/11, the DoE used in the experiments reported was DoE2, similar data have been obtained with other DoEs listed above.

The EpigenAU/11 system has been developed through a research process that leverages the insights gained from previous formulations. This innovative candidate aims to play a discriminating role, specifically targeting tumour cells while preserving healthy cells. Rooted in a comprehensive understanding of the active processes in carcinogenesis, this approach highlights the necessity of addressing the intricate interactions within the tumour microenvironment to enhance therapeutic outcomes, all while seeking to maintain a favourable risk-benefit ratio.

2.1 EpigenAU/11 In Vitro Performance

This novel formulation was tested across a range of cell lines selected from both non-cancerous and various cancer types to assess any differential responses.

Cell Lines Used:

1 non-cancerous cell line of Human Dermal Fibroblasts (HuDe)

3 head and neck squamous cell carcinoma lines (FaDu, Detroit562, CAL-27)

1 skin squamous cell carcinoma line (A431)

2 osteosarcoma cell lines (U-2 OS, SaOS-2)

1 osteosarcoma cancer stem cell line (OCSC)

2 triple-negative breast cancer cell lines (MDA-MB-231, SUM159PT)

1 breast cancer stem cell line (BCSC)

1 melanoma cell line (M14)

1 human bladder transitional cell carcinoma line (UMUC3)

143B: A highly proliferative and invasive derivative of the osteoblastic osteosarcoma line.

MSC (BM-derived Mesenchymal Stromal Cells): Multipotent stromal cells derived from bone marrow.

Besides the significant histological differences among these lines, the selection encompassed over 350 known mutations in genes and proteins involved in key cellular processes, including cell division, proliferation, differentiation, mitogenesis, and transcription regulation. The list included well-established markers such as BRAF, CREB3L2, CREBBP, ERBB4, ESR1, KRAS, TP53, TP63, TPH1, VEGFC, as well as groups of genes and proteins like CDK(s), EIF(s), MAPK(s), PIK(s), and TRIM(s).

The screening aimed to determine whether EpigenAU/11 could induce cell death across a broad spectrum of cancer cell lines while demonstrating specificity towards a non-cancer cell line.

2.2 In Vitro Cytotoxicity Cell-Based Assay

Figure 2:
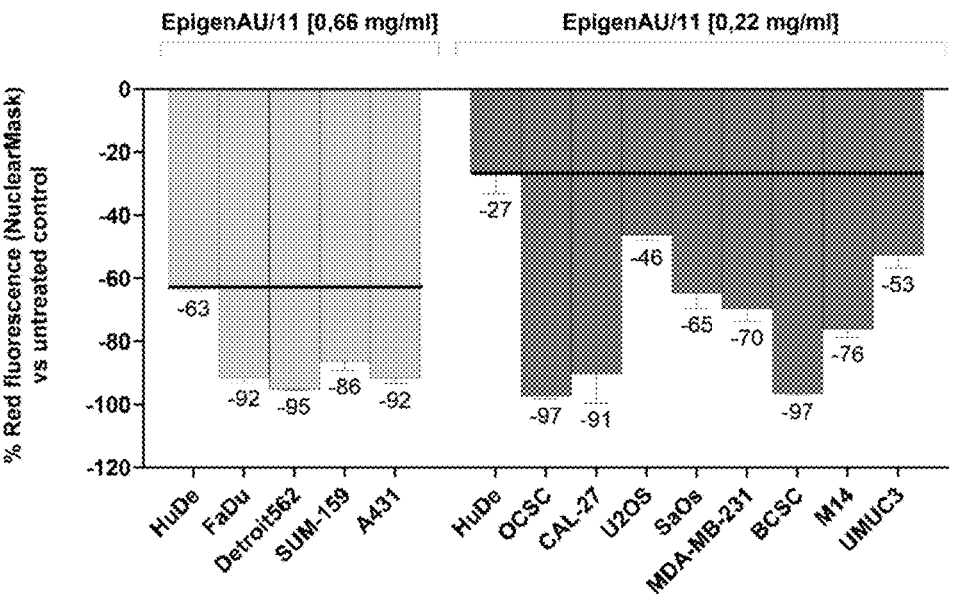

Cells, seeded in the appropriate amount in the medium indicated in their datasheet, were treated 24 hours after seeding with EpigenAU/11 at two different concentrations: 0.66 mg/ml and 0.22 mg/ml, for a duration of 72 hours. Notably, this treatment revealed a differential sensitivity to EpigenAU/11 between cancerous and non-cancerous cells. The quantification of viable cell nuclei demonstrated that, within the 72-hour timeframe, EpigenAU/11 consistently induced cell death in all selected cancer cell types while retaining a degree of selectivity for the non-cancerous HuDe cells (FIG. 2).

2.3 In Vitro 3D Spheroids Toxicity

In addition to the findings above, several partners contributed to the development of more complex in vitro models, including 3D spheroids, which better mimic the three-dimensional structure of tumours and their microenvironment. Notably, the group at IRCCS Istituto Ortopedico Rizzoli in Bologna explored in the inventor's account, the effects of EpigenAU/11 on osteosarcoma viability using three tumour spheroid lines derived from distinct osteosarcoma cell lines:

143B: A highly proliferative and invasive derivative of the osteoblastic osteosarcoma line.

SaOS-2: Derived from primary osteogenic osteosarcoma. Exhibits osteoblast-like behaviour in vitro, with low tumorigenicity and invasiveness, and a low frequency of metastasis.

U-2 OS: Derived from primary osteogenic osteosarcoma, this moderately differentiated line has low tumorigenicity and invasiveness, and is non-metastatic.

Additionally, two 3D spheroids from non-cancerous cell lines were included in the study:

MSC (BM-derived Mesenchymal Stromal Cells): Multipotent stromal cells derived from bone marrow.

HuDe (Human Dermal Fibroblasts): Non-cancerous dermal fibroblast cells.

The viability of both control and treated cells was assessed 72 hours after the start of treatment by quantifying ATP levels using the Cell Titer-Glo® 3D Viability Assay following the manufacturer's instructions. The results demonstrated a clear differential mortality between the cancerous and non-cancerous cells. While the cancer cells showed significant death rates, the healthy cells appeared unaffected and even exhibited an increase in ATP levels, indicating preserved vitality.

Figure 3:
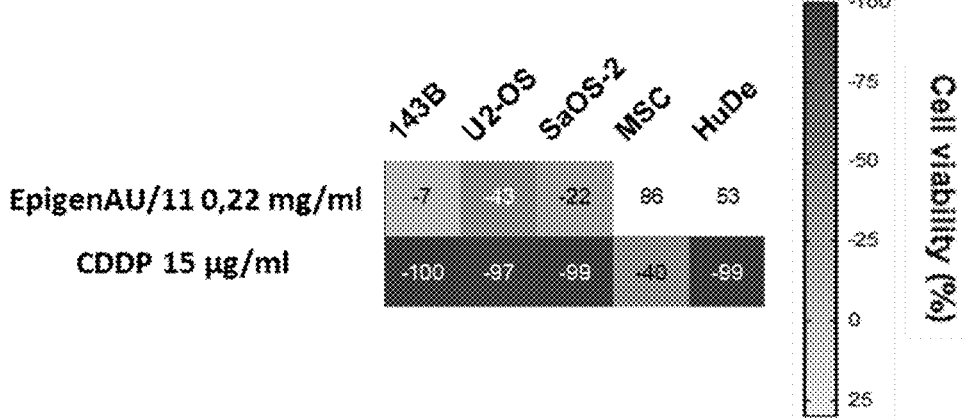

Cisplatin (CDDP), used as a comparative control, indiscriminately killed both cancerous and healthy cells (FIG. 3).

This stark contrast suggests that EpigenAU/11 may offer a more selective treatment option, sparing healthy tissue while targeting tumour cells. The differential effect observed with EpigenAU/11 highlights its potential as a candidate with a more favourable benefit/risk ratio, especially in complex, 3D tumour models.

Similarly, the Department of Pharmaceutical Sciences at the University of Pavia conducted viability assays explored in the inventor's account, on breast cancer and non-cancerous spheroids. Two triple-negative breast cancer lines were tested, MDA-MB-231 and SUM159PT, along with the non-cancerous mammary epithelial cell line, MCF 10A, derived from fibrocystic breast tissue.

Using the Cell Titer-Glo® 3D Viability Assay following the manufacturer's instructions, d the effects of EpigenAU/11 across a range of concentrations were examined. At the 0.22 mg/ml dose, a significant reduction of approximately 50% in cancer cell viability was observed, while the non-cancerous cells remained largely unaffected. Higher doses showed a gradual impact on non-cancerous cells, but the effect was still far less than that seen in tumour cells (FIG. 4). This further reinforces the potential of EpigenAU/11 to selectively impair tumour cells while preserving healthy ones, maintaining a more favourable risk-benefit profile.

2.4 In Vitro Leveraging Patient-Derived Organoids to Uncover EpigenAU/11's Therapeutic Potential in Complex Cancer Models Finally, the team from the Regina Elena National Cancer Institute in Rome conducted viability experiments in the inventor's account, to assess EpigenAU/11's effects across a range of patient-derived tumour organoids. These models represent an advanced approach in preclinical testing, offering a highly accurate in vitro platform that closely mimics the in vivo conditions of actual patient tumours. By preserving both the genetic and phenotypic diversity of the original tumour, organoids capture essential features such as tumour heterogeneity, cellular microenvironments, and complex interactions within the tissue structure. This high fidelity makes organoids especially valuable for assessing the therapeutic response of experimental candidates like EpigenAU/11.

Figure 5:
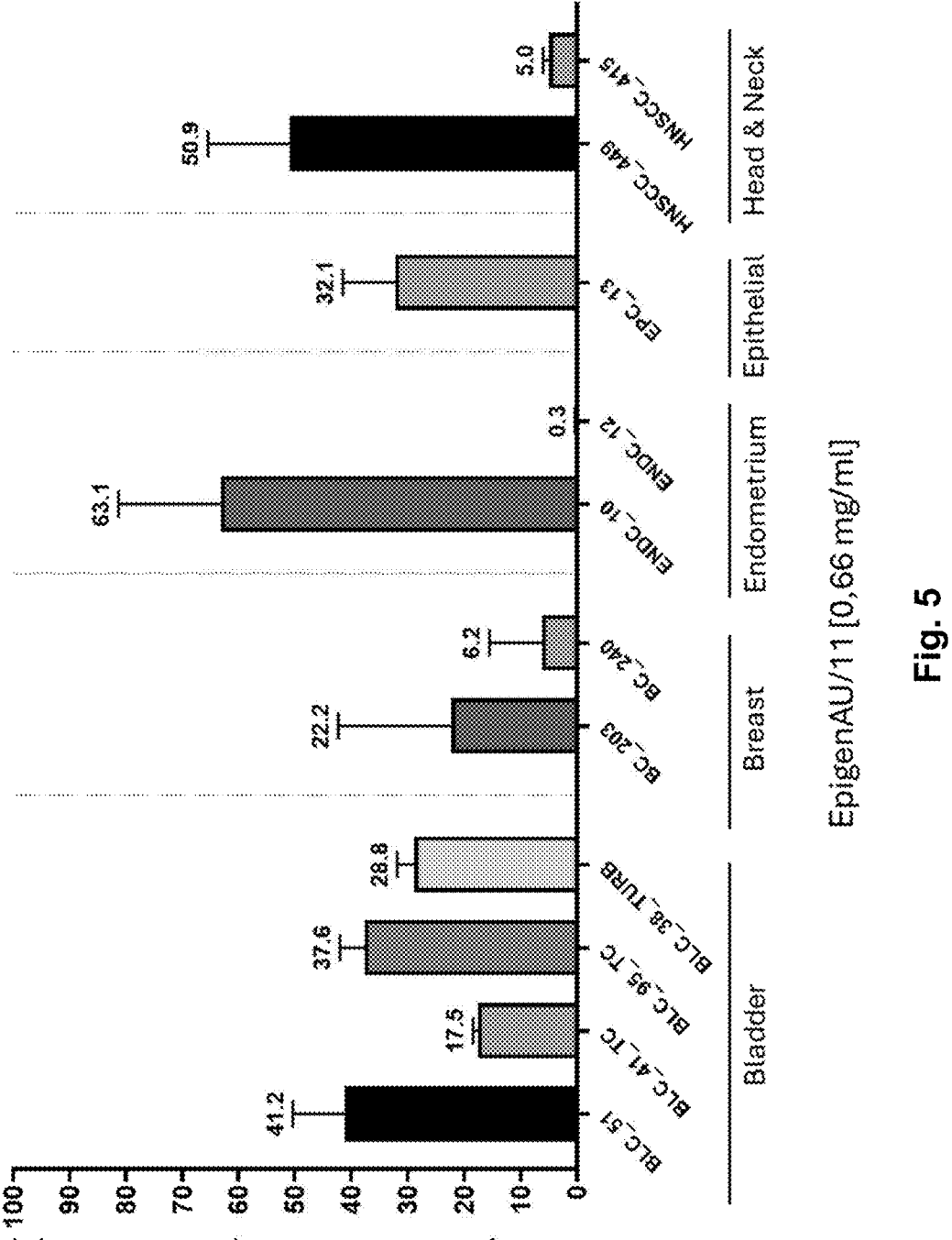

The study included organoids from primary bladder, breast, endometrial, epithelial, and head and neck cancer tissues, utilizing the Cell Titer-Glo® 3D Viability Assay following the manufacturer's instructions to measure ATP content as a proxy for cell viability. EpigenAU/11 treatment resulted in a substantial reduction in viability across these diverse cancer types, with mortality percentages consistently ranging from 40% to 100% depending on the tumour type (FIG. 5). These findings highlight EpigenAU/11's broad-spectrum efficacy and selective cytotoxic potential, marking it as a potent antitumour agent capable of inducing significant cell death even in complex cancer models.

2.4.1 In Vitro Leveraging Patient-Derived Organoids from Patients with Complex Treatment History For further, detailed analysis in more complex cases, the team employed the Opera Phenix Plus High-Content Screening System. With its high-resolution confocal imaging, this advanced system allowed precise and quantitative evaluation of cellular responses within each organoid. This setup enhanced the ability to observe real-time morphological changes, specific pathway activations, and detailed cell viability outcomes, making it a powerful tool in capturing EpigenAU/11's effects within intricate tumour models.

Figure 6:
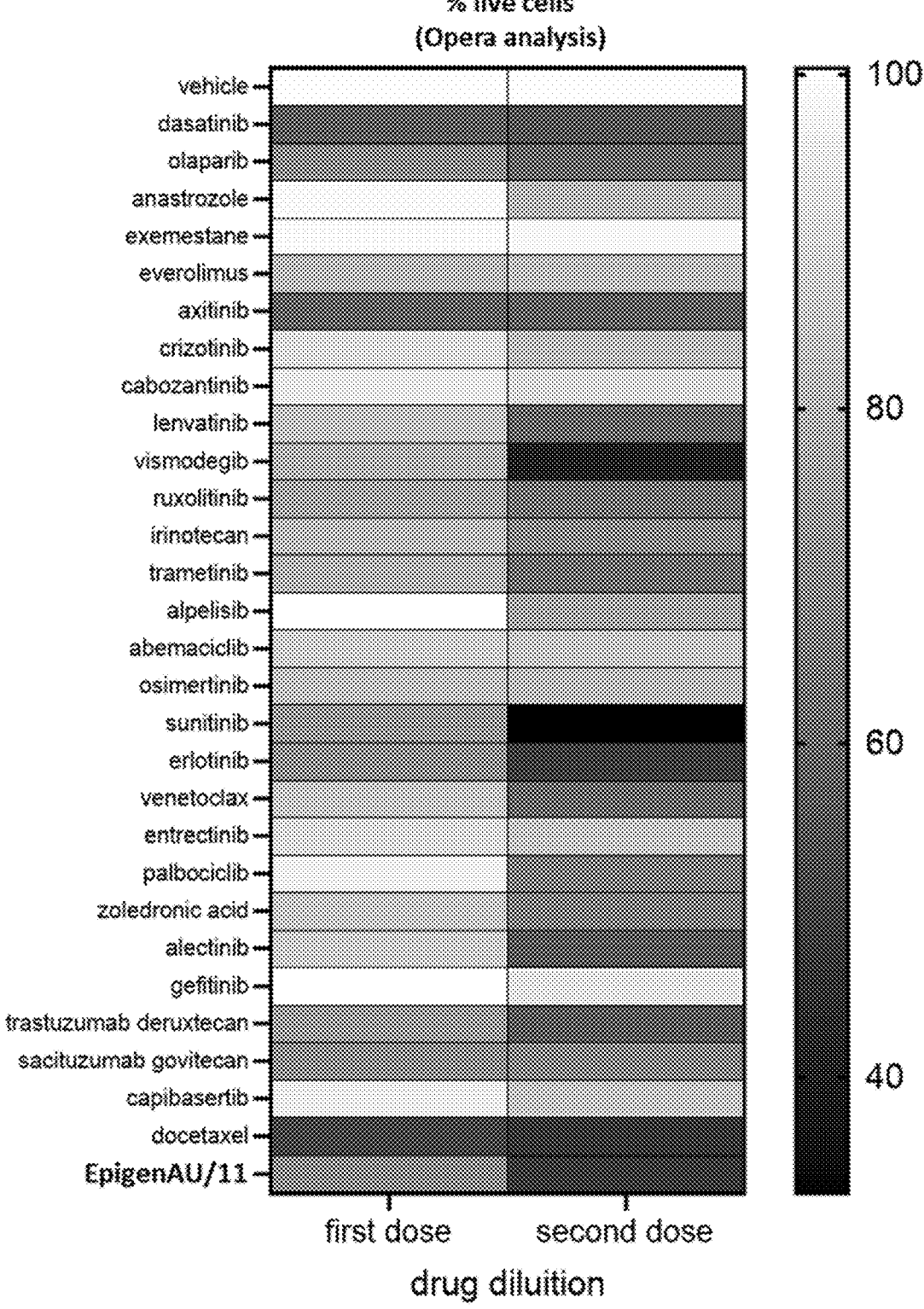

Highlighted within the study were two unique clinical cases that demonstrated EpigenAU/11's potent efficacy in organoids (produced upon informed consent of the patients) derived from tumours with high mutational burdens. The first involved a gastric cancer organoid model derived from a patient with an extensive treatment history, having undergone seven distinct lines of therapy, including multiple chemotherapy agents, monoclonal antibodies, and targeted therapies. This model presented a particularly challenging profile due to its high degree of treatment resistance. However, within this model, EpigenAU/11 demonstrated a notably potent response. Following the second dose, EpigenAU/11 induced a remarkable increase in cell mortality, showing potency comparable to only two or three other agents within the extensive range of drugs tested (FIG. 6).

Figure 7:

The second case featured an ovarian-origin peritoneal carcinomatosis organoid model, derived from a patient who had previously undergone two lines of therapy, including the ongoing Carboplatin+Gemcitabine regimen. In this model, high-content screening revealed that only the ongoing therapy and EpigenAU/11 displayed meaningful cytotoxic activity against the cancer cells. EpigenAU/11's pronounced cytotoxicity in this resistant model was particularly notable, as the therapy induced tumours cell death where other treatments showed limited impact. This result further highlights EpigenAU/11's promise as a therapeutic option in complex cases where conventional therapies fail to elicit a sufficient response (FIG. 7).

EpigenAU/11 demonstrated robust efficacy across a wide range of cancer types and preclinical models, showing a strong cytotoxic effect on tumour cells while sparing non-cancerous cells. The compound exhibited consistent potency in various test environments, from traditional 2D cell cultures to advanced 3D spheroid systems and patient-derived organoids, including those from osteosarcoma, breast, bladder, and head and neck cancers. These models are instrumental in accurately assessing therapeutic potential as they reflect the complex interactions within the tumour microenvironment, where cancer cells employ structural and metabolic adaptations to support proliferation.

The ability of EpigenAU/11 to selectively induce cell death across diverse tumour types highlights its broad-spectrum activity. Each experiment reinforced the discriminative nature of EpigenAU/11 's mechanism, underscoring its potential in addressing the intricate network of factors that sustain tumour cell viability. By specifically targeting cancerous cells while preserving healthy tissue, EpigenAU/11 demonstrates a favourable risk-benefit profile.

Furthermore, dose-response studies have highlighted EpigenAU/11's specificity, aligning with a therapeutic approach that minimizes collateral damage to normal tissues which is a critical aspect in cancer treatment. This approach supports a model of restoring physiological balance rather than focusing solely on tumour eradication, emphasizing the need to consider the unique metabolic behaviours and complex interactions within the tumour microenvironment. The findings reflect that cancers arise from multifaceted interactions influenced by physiological, environmental, and immunological factors, rather than isolated molecular anomalies alone.

3. Understanding EpigenAU/11: Early Intracellular pH Changes, ATP Burst, and Metabolic Adaptation The investigation into EpigenAU/11's cellular effects was carried out with DoE2 formulation and identified two critical and interconnected metabolic events: an early acidification of intracellular pH (pHi), corresponding to an increase in ATP levels. This link between pHi and ATP production aligns with previous findings, where acidification was shown to influence key metabolic pathways, including glycolysis, which cancer cells rely on for rapid ATP generation, even under low-oxygen conditions (Madshus, 1988). Cancer cells are known to naturally exhibit higher levels of intracellular acidification compared to healthy cells, a characteristic that supports their rapid proliferation. This heightened acidification is part of a metabolic reprogramming that allows cancer cells to favour glycolysis over oxidative phosphorylation for energy production, regardless of oxygen availability. This glycolytic preference contributes to an acidic microenvironment, which further supports cancer cell growth and enhances resistance to stress.

This intrinsic difference in pHi between healthy and cancerous cells sets the stage for how they respond differently to external agents, such as EpigenAU/11, that alter metabolic pathways. By examining EpigenAU/11's impact on intracellular acidification and ATP dynamics, we gain insight into how it disrupts cancer cell metabolism selectively, exploiting these pre-existing vulnerabilities.

3.1 Intracellular pH Acidification as a Primary Response to EpigenAU/11

The inventors found that treatment with EpigenAU/11 induces a marked acidification in intracellular pH across various tumour cell lines. This acidification was measured at two EpigenAU/11 concentrations (0.22 mg/ml and 0.66 mg/ml) over intervals of 5 and 60 minutes. Both cancerous and healthy cells exhibited an immediate acidification effect, particularly pronounced at the higher concentration (0.66 mg/ml) as early as 5 minutes after treatment. At the lower concentration, or with longer exposure (60 minutes), the acidification response varied according to the tumour type, reflecting a dose-dependent effect of EpigenAU/11 on cellular pH.

For cancer cells, which are already metabolically constrained by their reliance on glycolysis, this additional acidification intensifies their metabolic stress. The forced shift in pHi due to EpigenAU/11 treatment places further strain on the cells' ability to maintain homeostasis, pushing them toward an unsustainable metabolic state. In healthy cells, while acidification is also observed following EpigenAU/11 treatment, their metabolic systems are inherently more flexible and resilient. This adaptability allows them to manage fluctuations in pHi and energy demands without significant stress, as they are equipped with a balanced oxidative and glycolytic capacity. Unlike cancer cells, which are heavily reliant on glycolysis and already operate under metabolic strain, healthy cells can effectively compensate for such shifts, maintaining stability without adverse consequences, which is an established characteristic of non-transformed cells.

3.2 ATP Burst as a Result of Intracellular Acidification

Following the initial acidification triggered by EpigenAU/11, a rapid increase in ATP levels was observed. This ATP burst appears to be a compatible consequence of the shift in intracellular pH, representing an adaptive response to the metabolic stress introduced by EpigenAU/11 (M Madshus I H. Regulation of intracellular pH in eukaryotic cells. Biochem J. 1988 Feb. 15; 250(1):1-8. doi: 10.1042/bj2500001. PMID: 2965576; PMCID: PMC1148806.).

In cancer cells, this ATP surge reflects an urgent need for energy as they attempt to stabilize their intracellular environment under acidic conditions. However, due to their heavy reliance on glycolysis, cancer cells may struggle to sustain this heightened energy demand, potentially leading to an accumulation of metabolic by-products and increased cellular stress. These metabolic disruptions, such as the possibility of reactive oxygen species (ROS) build-up and other by-products accumulating under acidic conditions, could overwhelm cancer cells already limited metabolic flexibility. This state of heightened metabolic stress may contribute to the observed increase in cell mortality, as cancer cells are less capable of adapting to the dual pressures of acidification and elevated ATP requirements.

In contrast, healthy cells demonstrate a greater capacity to accommodate these metabolic changes. With a more balanced oxidative and glycolytic metabolism, healthy cells are better equipped to absorb transient ATP fluctuations and handle acidification without experiencing severe stress. This metabolic flexibility allows healthy cells to manage fluctuations in pHi and energy demands without significant stress, supported by a balanced oxidative and glycolytic capacity.

3.3 Evaluating the Differential Effects of EpigenAU/11 and different Acid on Cell Viability By measuring intracellular pH changes, the inventors sought to elucidate the dynamic responses elicited by EpigenAU/11 treatment, potentially differentiating its action from that of general acidic treatments. We treated two squamous cell carcinoma lines, FaDu and A431, along with healthy HuDe cells, with EpigenAU/11 at the aforementioned concentration for one hour. As a control, hydrochloric acid (HCl) was added to the culture medium, ensuring that the pH remained stable and did not exceed the buffering capacity of the system.

Intriguingly, the results revealed that only treatment with EpigenAU/11 resulted in a significant decrease in intracellular pH, whereas HCl showed no observable effects (FIGS. 8 A and B). This observation aligns with the known ability of cells to efficiently pump out HCl, preventing it from impacting the intracellular environment. In contrast, EpigenAU/11 appears capable of entering and remaining within the cell, resulting in a stable and notable intracellular acidification.

This finding reinforces that the action of EpigenAU/11 is multipronged, highlighting its potential to induce selective cytotoxic effects in cancer cells through unique intracellular dynamics that HCl does not achieve.

To further substantiate these findings, an ex vivo test was conducted using explanted biopsies from the FaDu and A431 cell lines. These biopsies were generated by injecting the cells into immunocompromised mice, thereby creating a more intricate three-dimensional structure that closely mimics the tumour microenvironment. After the biopsies were explanted, they were treated ex vivo with either EpigenAU/11 at the maximum tolerated dose established in animal studies (50 mg/ml), with a measured pH of 5.6, or hydrochloric acid (HCl), which was added to the culture medium to achieve the same pH of 5.6, for a duration of 72 hours. Following the 72-hour treatment period, cell viability was analysed using flow cytometry.

Figure 9:
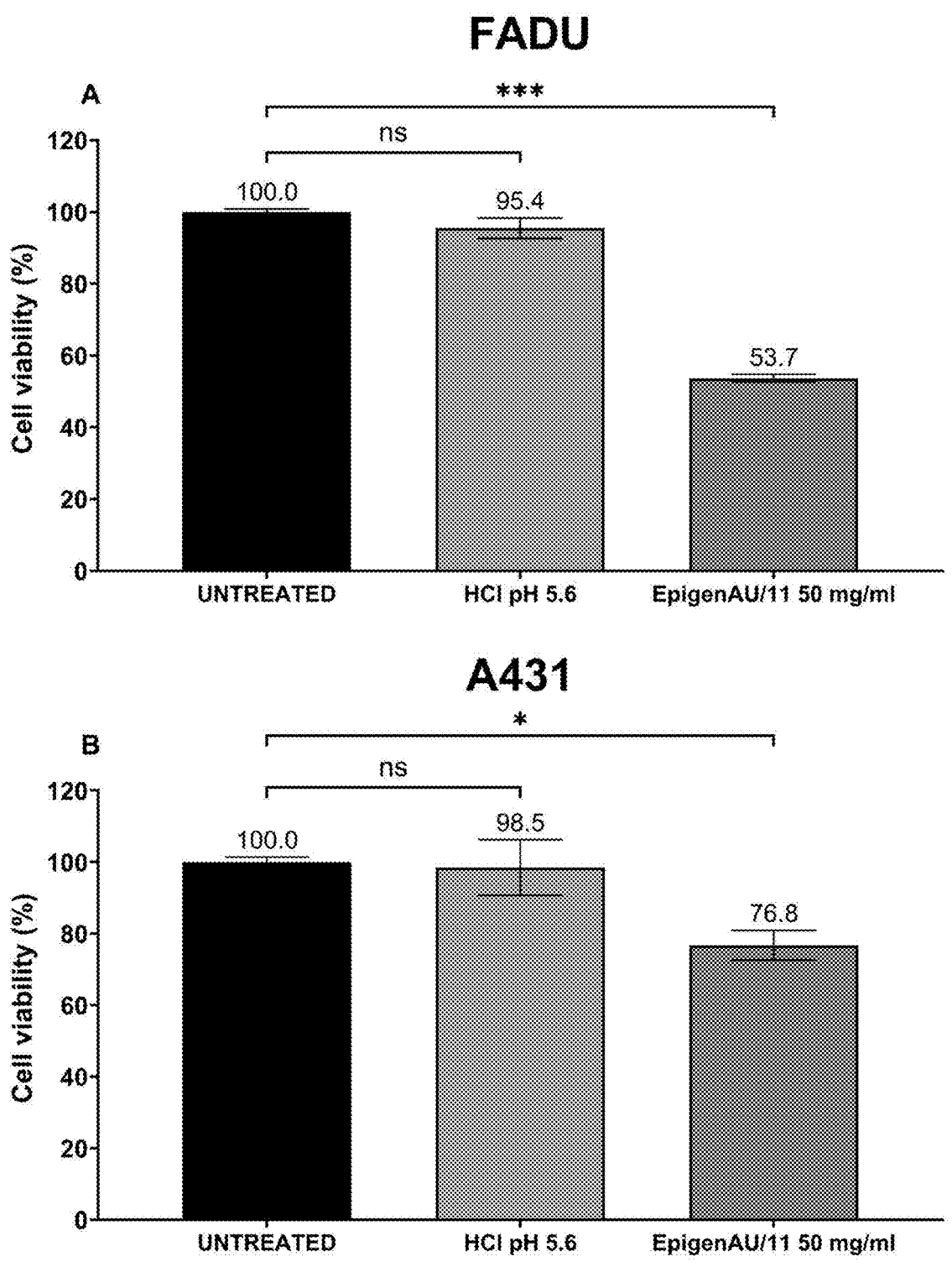

The results revealed that EpigenAU/11 induced approximately 50% cell death in the FaDu grafts and around 25% in the A431 grafts, while HCl treatment showed no significant signs of cell death (FIG. 9). These experiments highlight the unique effectiveness of EpigenAU/11, showcasing its capacity to selectively induce cell death in cancer cells. Importantly, this effect emphasizes that the mechanisms behind EpigenAU/11's action extend beyond mere acidification, pointing to its potential to interact with cellular systems in ways that conventional acids cannot achieve.

Further investigations prompted the inventors to perform HPLC-UV analysis on the EpigenAU/11 sample, resulting in the identification of two biologically relevant and abundant organic acids: citric acid (5.64%) and lactic acid (4.66%). The other acids measured, including fumaric, tartaric, propionic, shikimic, acetic, succinic, and malic acids, were found to be below the limits of quantification. This discovery raised the question of whether citric and lactic acids in EpigenAU/11 could be responsible for the differential cytotoxic effects observed in cancerous versus healthy cells. Both acids are known to play critical roles in cellular metabolism; citric acid is integral to the Krebs cycle, while lactic acid is a product of glycolysis. Literature indicated that high concentrations (beyond those vehiculated by EpigenAU/11 treatment) of these acids could lead to cytotoxic effects, prompting the inventors to explore their potential impact in our context.

There was hence a particular interest in determining whether the quantities of citric and lactic acids present in the extracts that constitute EpigenAU/11 could be responsible for the selective cytotoxic effects observed in cancerous versus healthy cells were the primary factors contributing to selective cell death. This investigation aimed to clarify whether the observed effects could be attributed solely to these two organic acids within the formulation, i.e. whether potential API's could be identified in the formulation.

To explore this, an in vitro experiment was conducted on the three cell lines—FaDu, A431, and HuDe—by treating them for 24 hours with either EpigenAU/11 at a concentration of 0.66 mg/ml or a combination of citric and lactic acids. The quantities of the two acids used in the combination matched the concentrations found in EpigenAU/11, allowing for a direct comparison between the effects of the full extract and the isolated acids.

Figure 10:
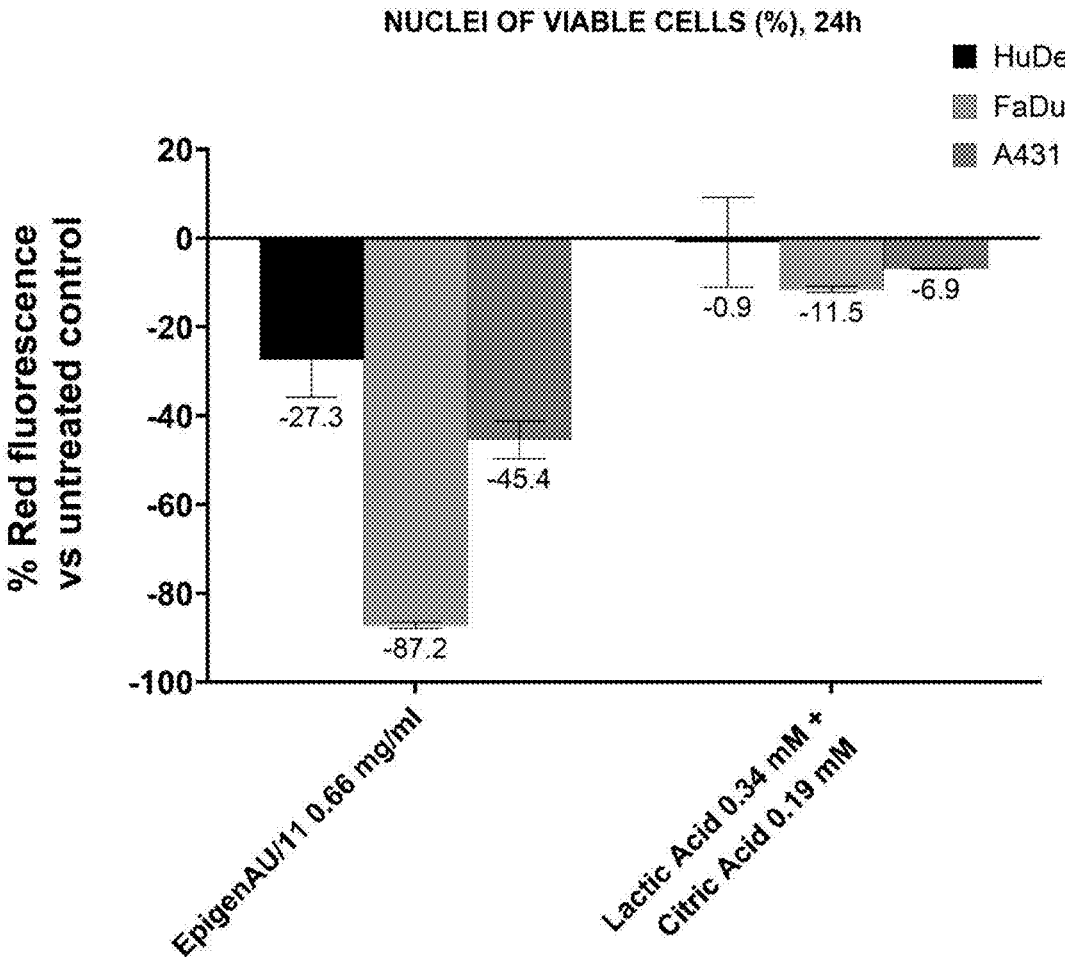

The results showed that while EpigenAU/11 induced significant cytotoxicity, particularly in the cancerous cell lines, the combination of citric and lactic acids at the same concentrations resulted in almost negligible mortality (FIG. 10). For example, in the FaDu tumour cells, EpigenAU/11 caused 87.2% cell death, whereas the citric and lactic acid combination induced only 11.5% cell death. This clear distinction suggests that the selective cytotoxic effects of EpigenAU/11 are not recapitulated by treatment with these two organic acids and that EpigenAU/11's effects are emerging properties of the natural matrices system. Similar results were obtained with others of the EpigenAU/11 DoEs herein disclosed.

4. Gene Expression Ex Vivo Studies

The gene expression ex vivo studies of EpigenAU/11 vs Cisplatin demonstrate that the EpigenAU/11 systems regulates a whole pathological status as opposed to the typical API's regulatory effect on one or few functions. The data below were obtained with the EpigenAU/11 formulation DoE2.

4.1 Cytotoxicity of EpigenAU/11 vs Cisplatin on Biopsies

Additional ex vivo tests, applying methodologies consistent with those used in previous sections, were conducted to evaluate and compare the efficacy of EpigenAU/11 and cisplatin on head and neck tumour tissue. To ensure relevance to prior findings, both EpigenAU/11 and cisplatin were administered at doses reflective of those used in animal models, replicating in vivo conditions as closely as possible within the ex vivo environment. This approach allowed the inventors to assess each compound's effects within a realistic tissue structure, providing continuity with earlier in vivo findings.

Figure 11:
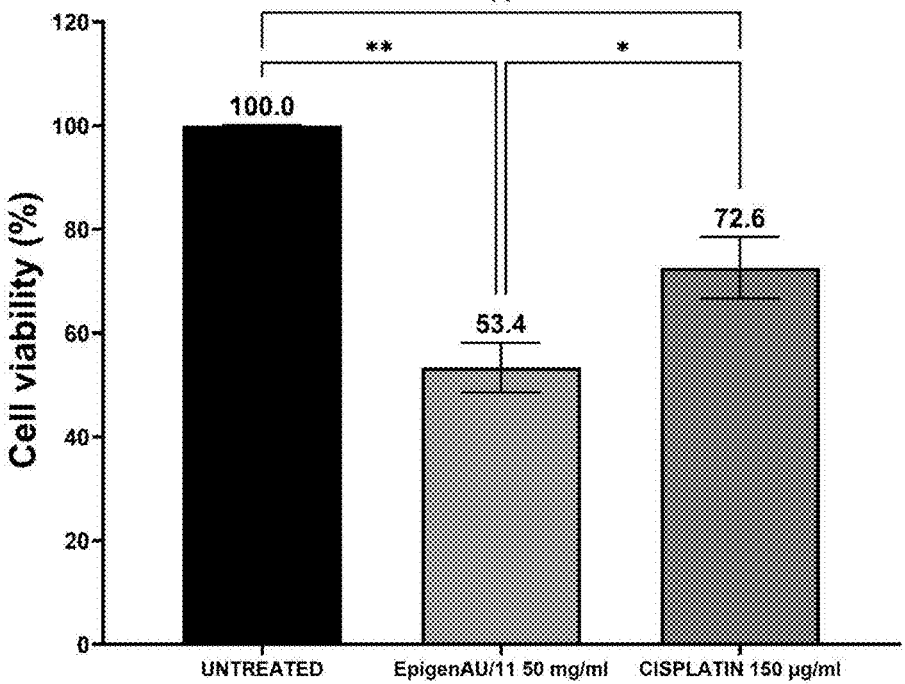

As shown in FIG. 11, the results indicate a substantial difference in cell mortality after 72 hours of treatment on an explanted biopsy from a FaDu graft. Specifically, EpigenAU/11 induced approximately 50% cell death, a significantly higher mortality rate than that observed with cisplatin, which induced around 25% mortality under the same conditions. This suggests that EpigenAU/11 elicits a faster and more pronounced cellular response, with an earlier onset of cell death relative to cisplatin, potentially engaging distinct or additional pathways.

4.2 Genome-Wide Gene Expression Profiling (Computer Implemented)

To further elucidate the mechanistic differences between EpigenAU/11 and cisplatin, genome-wide gene expression profiling was conducted to capture the relevant cellular responses to each treatment. This analysis aimed to reveal unique features of each approach and identify potential areas of complementarity (see also example 11).

As shown in FIG. 12, functional interpretation of the gene expression profiles after 24 hours of treatment reveals considerable overlap between EpigenAU/11 and cisplatin. Both treatments induce a gene expression landscape consistent with cell cycle arrest and subsequent cell death. This shared response suggests that both EpigenAU/11 and cisplatin effectively disrupt cell division and trigger apoptotic pathways at 24 hours time point.

However, profiling at an earlier stage, 6 hours post-treatment, provides a more detailed and informative view of the differences between the two compounds. In line with expectations, cisplatin treatment primarily induces cell cycle arrest, particularly with enhanced prometaphase pathway activity, and initiates pathways associated with cell damage. This response is typical for cisplatin's mechanism, which involves direct DNA damage leading to cell cycle interruption and cell death (FIGS. 13 A and B).

In contrast, EpigenAU/11 (FIG. 13) elicits a more complex and comprehensive response that targets multiple hallmarks of carcinogenesis. Specifically, EpigenAU/11 reduces the activity of pathways associated with a proliferation-promoting tumour microenvironment, including pathways related to stemness, epithelial-mesenchymal transition, energy metabolism and insulin sensitivity, growth factors, cell damage, mitotic regulation, and inflammation. This broad-based interaction suggests that EpigenAU/11 engages with cancer cells in a multifaceted manner, disrupting a range of pathways essential for sustaining tumour growth and survival.

The ability of EpigenAU/11 to modulate these diverse pathways implies a potentially desirable therapeutic approach, as it can interact with cancer cells on multiple fronts. By impairing the pathways that cancer cells rely on to support their physiology, promote proliferation, and implement compensatory mechanisms for therapeutic evasion, EpigenAU/11 may present a more versatile and comprehensive strategy for targeting cancer cells compared to cisplatin.

4.3 Study on Combined Effects of EpigenAU/11 and Cisplatin in Cytometry-Based Mortality Analysis In addition to the initial cytometry experiment on the FaDu, a further ex vivo study was conducted to evaluate the combined effects of EpigenAU/11 (Formulation DoE2) and cisplatin. This experiment aimed to assess the impact of administering EpigenAU/11 and cisplatin in combination, using doses identical to those previously tested in vivo to ensure consistency across experimental models. Specifically, EpigenAU/11 was applied at the same concentration as in earlier studies, and cisplatin was administered at 150 µg/m, aligning with prior in vivo applications.

Figure 14:
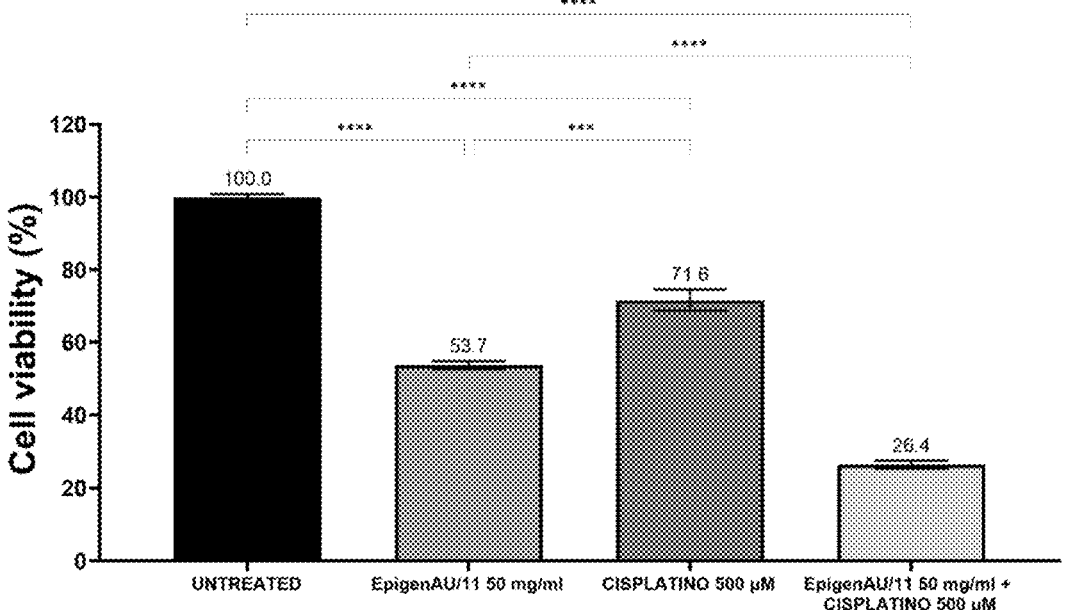

As shown in FIG. 14, the results were consistent with previous findings: EpigenAU/11 alone led to an approximate 50% reduction in cell viability, while cisplatin alone achieved around a 30% reduction. Notably, the combination treatment produced a significantly enhanced effect, reducing cell viability by approximately 74%. This substantial increase in efficacy with the combination suggests a synergistic interaction between EpigenAU/11 and cisplatin, potentially amplifying therapeutic outcomes beyond what either agent achieves independently. These findings demonstrated the superior efficacy of the combination treatments, suggesting an advantageous interaction between EpigenAU/11 and cisplatin that could enhance therapeutic outcomes.

4.4 Study on Combined Effects of EpigenAU/11 and Cisplatin in a Genome-Wide Gene Expression Profiling (Computer Implemented)

A genome-wide gene expression profiling was performed after 6 hours of treatment on biopsies derived from the FaDu, using the same doses as in the cytometry-based mortality analysis: EpigenAU/11 (DoE2 formulation) at 50 mg/ml and cisplatin at 150 µg/ml, both alone and in combination with EpigenAU/11 and the same profiling conditions of 4.2. This analysis aimed to elucidate the distinct and combined effects of EpigenAU/11 and cisplatin on various pathways associated with cancer progression and cellular responses (FIG. 15).

The expression data reveal that EpigenAU/11 alone induced substantial downregulation across a broad range of cancer-related pathways. Specifically, pathways such as tumour cell invasion, cell movement, angiogenesis, and cell viability show significant decreases in activity, indicating EpigenAU/11's capacity to target essential processes for tumour growth and metastasis. This effect on angiogenesis and cell movement suggests that EpigenAU/11 may limit both the formation of new blood vessels, critical for tumour nourishment, and the migratory potential of cancer cells, which is essential for metastasis.

Similarly, cisplatin showed a comparable downregulatory effect across many of the same pathways, indicating that, at this concentration, cisplatin can inhibit key tumour-supportive functions.

In contrast, the combination treatments of EpigenAU/11 and cisplatin demonstrated a markedly enhanced modulation of gene expression modulating various pathways not modulated by either EpigenAU/11 or cisplatin alone. Both combinations lead to strong downregulation across multiple cancer-related pathways, with effects seen in cell proliferation, cell survival, and immune-related responses. This enhanced modulation indicates a synergistic or potentiating effect of EpigenAU/11 when combined with cisplatin, allowing even the local dose of cisplatin to achieve downregulation levels comparable to or exceeding those of the systemic dose when used alone.

Moreover, the combined treatment of cisplatin and EpigenAU/11 not only downregulates pathways involved in cellular growth and movement but also appears to impact immune system-related pathways, suggesting that the combination could potentially create an immunostimulatory environment within the tumour microenvironment. This may facilitate immune cell recruitment and increase tumour visibility to immune surveillance, further amplifying the anti-tumour response.

The data also highlighted the broad-spectrum impact of the combination treatments on cellular stress responses. For instance, pathways associated with apoptosis, cell cycle arrest, and cellular senescence are highly modulated in the combination groups, supporting the hypothesis that EpigenAU/11 might sensitize tumour cells to cisplatin-induced cytotoxicity, thereby enhancing cell death mechanisms beyond what either agent achieves alone. This synergy might stem from EpigenAU/11's ability to prime cancer cells by modulating the tumour microenvironment and weakening cellular defences, making them more susceptible to the DNA-damaging effects of cisplatin.

In summary, the genome-wide profiling of gene expression elucidated EpigenAU/11's potential as both a standalone and a combination therapy. The ability of EpigenAU/11 to potentiate the effects of cisplatin underscores its promise in enhancing therapeutic efficacy. These findings provide compelling support for further investigation into EpigenAU/11 as a multifaceted therapeutic agent capable of impacting several hallmark cancer processes, ultimately contributing to a more comprehensive and effective cancer treatment strategy.

4.5 Cytotoxicity of EpigenAU/11 vs Cisplatin on A431 Cells

Figure 16:
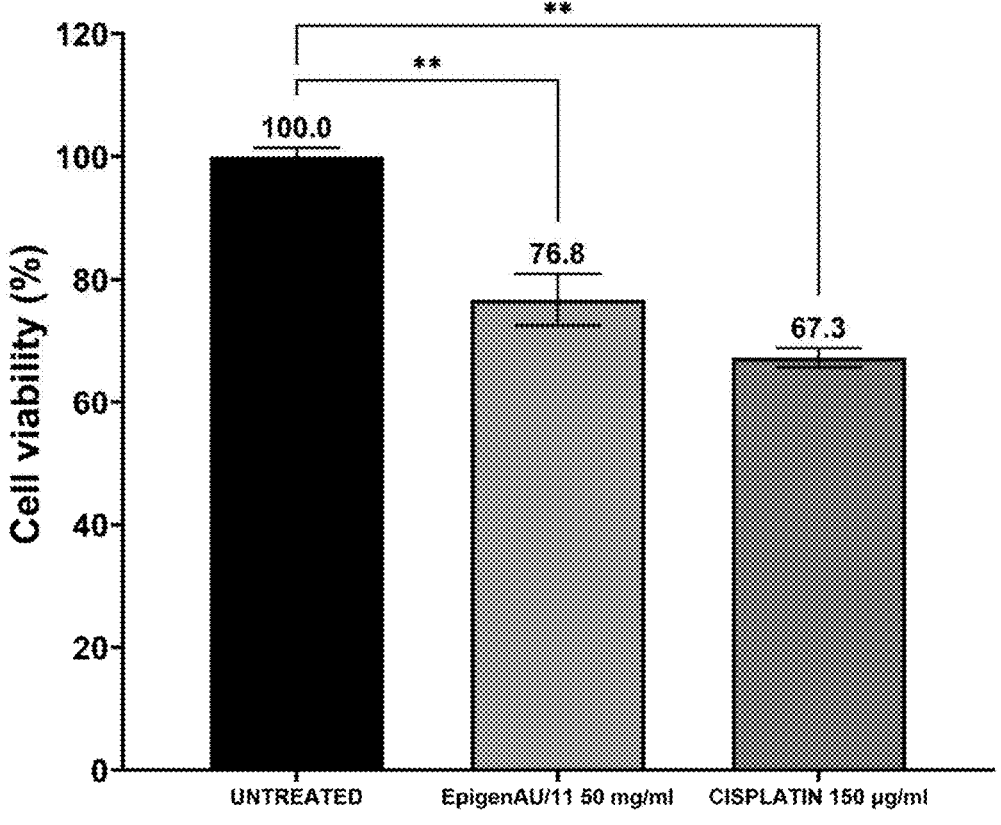

Following the previously described ex vivo tests with the FaDu cells, a similar experiment was conducted using A431 cells to further validate EpigenAU/11's effects. Flow cytometry analysis revealed that EpigenAU/11 (DoE2 formulation) induced approximately 25% cell death, while cisplatin induced around 30%. These results suggest that even in this model, EpigenAU/11 demonstrates promising cytotoxic effects, comparable to cisplatin (FIG. 16).

4.6 Study on Combined Effects of EpigenAU/11 and Cisplatin in a Genome-Wide Gene Expression Profiling on A431 Cells (Computer Implemented)

A genome-wide gene expression profiling was conducted as in the paragraphs above, to evaluate the early effects of EpigenAU/11 treatment at the 2-hour mark in A431 cells. EpigenAU/11 DoE2 formulation was used. The analysis revealed significant modulations in three hallmark cancer pathways:

Angiogenesis: The results indicated a pronounced downregulation of genes involved in angiogenesis, with expression levels reduced by up to −3.95. This suggests that EpigenAU/11 may impede the tumour's ability to establish new blood vessels, thereby restricting nutrient and oxygen supply essential for tumour growth and survival.

Inflammatory Response: Genes associated with inflammation exhibited a notable upregulation, with some expression levels reaching +3.54. While inflammation can, in some contexts, support tumour progression, this response could also stimulate an immune-mediated reaction against tumour cells, potentially aiding in the recognition and destruction of cancer cells.

Inhibition of Cell Proliferation and Viability: Several genes linked to cellular proliferation and viability were significantly downregulated (with values as low as −3.78), indicating that EpigenAU/11 exerts an inhibitory effect on the growth and survival mechanisms of A431 cells. This early suppression of proliferative capacity suggests that EpigenAU/11 may effectively curtail tumour expansion by directly targeting cellular mechanisms essential for tumour cell vitality.

These initial findings suggest that EpigenAU/11 exerts a multifaceted impact on tumour cells, affecting key pathways associated with angiogenesis, inflammation, and cell proliferation. By simultaneously modulating these critical cancer-related processes, EpigenAU/11 appears to undermine the tumour's capacity to sustain its growth and may promote conditions unfavourable for tumour survival (FIG. 17).

All the data obtained in the experiment 4 above were confirmed with other EpigenAU/11 DoEs formulations within the ranges claimed.

5. Bio-Chemical and Physical Characterisations of EpigenAU/11

As reference standard DoE2 of EpigenAU/11 was used for a qualitative and quantitative characterization of as many primary and secondary metabolites as possible was carried out using an "omic" approach, the targeted metabolomics analysis, based on the use of multiple analytical methodologies.

The analytical methods used for the characterization are described in the relevant table below. The same analytical methods were used for other batches (DoEs) of EpigenAU/11 in the subsequent examples. The most appropriate analytical techniques have been adopted based on the chemical nature of the classes of compounds present. The analysis with chromatographic methods combined with different detection techniques (e.g., LC each combined with a suitable detector), made it possible to identify and quantify, as appropriate, the organic compounds. The inductively coupled plasma analysis using a single quadrupole mass spectrometer (ICP-MS) or an optical emission spectrometer (ICP-PAD) made it possible to establish the levels of elements present, while the anions were determined by ion chromatography and conductivity detector.

The table below summarizes all the methods used in examples 5 and 6.

| Class of Compounds | Characteristics | Method | Short description |
|---|---|---|---|
| Phenols | Phenols polar | UHPLC-qToF | Sample extraction and reverse phase chromatography analysis by UHPLC coupled to a quadrupole-time-of-flight mass spectrometer. (A) |
| Tannins | Tannins | UHPLC-qToF | Sample extraction and reverse phase chromatography analysis by UHPLC coupled to a quadrupole-time-of-flight mass spectrometer. (A) |
| Organic acids | Organic acids mono-, di-, tri-carboxylic | HPLC-UV | Sample extraction and analysis by HPLC coupled to UV detector. B) |
| Sugars and Derivatives | Monosaccharides | IC-PAD | Sample extraction and analysis by ion chromatograph coupled to pulsed amperometric detector. (C) |
| | Disaccharides | IC-PAD | Sample extraction and analysis by ion chromatograph coupled to pulsed amperometric detector. (C) |
| Inorganic Compounds | Elements | ICP-MS, ICP-OES IC-CD | Acid mineralization of the sample in a microwave oven and analysis of the conductively induced plasma by means of a single quadrupole mass spectrometer, or optical emission spectrometer. (D) Sample extraction and analysis by ion chromatograph coupled to conductometric detector. (D) |
| miRNAs | miRNA | Sequencing | After sample extraction protocol the samples were analysed by RNA-Seq technique (Genomix4Life ) (E). |

5.1 Targeted Metabolomics Analysis of DoE2

The analysis was performed with the methos reported in the table above and the results are summarised in the table below:

| METHOD | COMPOUNDS | EpigenAU/ 11 DoE2 | METHOD | COMPOUNDS | EpigenAU/ 11 DoE2 |
|---|---|---|---|---|---|
| | PHENOLS, Total | 1.643 | | TANNINS, Total | 0.115 |
| | FLAVONOIDS, Total | 0.126 | | CONDENSED TANNINS, Total | 0.115 |
| | FLAVANONES, Total | 0.001 | A | Procyanidin B2 | 0.115 |
| A | Naringenin & Pinobanksin (AS: Naringenin) | 0.001 | | TANNIN MONOMERS, Total | <LoQ |
| | FLAVONES, Total | 0.040 | | GALLOTANNINS MONOMERS, Total | <LoQ |
| A | Acacetin | <LoQ | A | Gallic acid | <LoQ |
| A | Apigenin-7-O-glucuronide | <LoQ | | ORGANIC ACIDS, Total | 10.331 |
| A | Hispidulin | <LoQ | | MONOCARBOXYLIC ACIDS, Total | 4.660 |
| A | Isorhoifolin | <LoQ | B | Lactic acid | 4.660 |
| A | Isovitexin | 0.003 | | DICARBOXYLIC ACIDS, Total | 0.035 |
| A | Linarin | 0.005 | B | Fumaric acid | 0.035 |
| A | Luteolin-7-O-Rutinoside | 0.012 | | TRICARBOXYLIC ACIDS, Total | 5.636 |
| A | Orientin & Homoorientin (AS: Orientin) | <LoQ | B | Citric acid | 5.636 |
| A | Vicenin-2 | 0.011 | | SUGARS AND DERIVATIVES, Total | 7.683 |
| A | Vitexin-2"-O-rhamnoside | 0.009 | | MONOSACCHARIDES, Total | 6.591 |
| | FLAVONOLS, Total | 0.085 | C | Arabinose | <LoQ |
| A | Isorhamnetin-3-O-glucoside | <LoQ | C | Fructose | 4.402 |
| A | Kaempferol-3-O-rutinoside | 0.047 | C | Galactose | 0.118 |
| A | Kaempferol-7-O-neohesperidoside | <LoQ | C | Glucose | 2.071 |
| A | Luteolin-4'-O-glucoside & Kaempferol-3-O-glucoside & Quercitrin (AS: Quercitrin) | 0.016 | C | Mannose | <LoQ |

-continued

| METHOD | COMPOUNDS | EpigenAU/11 DoE2 | METHOD | COMPOUNDS | EpigenAU/11 DoE2 |
|---|---|---|---|---|---|
| A | Quercetin | <LoQ | C | Rhamnose | <LoQ |
| A | Rutin | 0.023 | | DISACCHARIDES, Total | 1.092 |
| | PHENOLS, Total | 1.643 | C | Lactose | <LoQ |
| | FLAVONOIDS, Total | 0.126 | C | Maltose | 0.887 |
| | FLAVANONES, Total | 0.001 | C | Sucrose | 0.205 |
| A | Naringenin & Pinobanksin (AS: Naringenin) | 0.001 | | INORGANIC COMPOUNDS, Total | 8.531 |
| | FLAVONES, Total | 0.040 | | MACROELEMENTS, Total | 8.459 |
| A | Acacetin | <LoQ | D | Calcium | 0.583 |
| A | Apigenin-7-O-glucuronide | <LoQ | D | Magnesium | 0.585 |
| A | Hispidulin | <LoQ | D | Phosphorus | 1.027 |
| A | Isorhoifolin | <LoQ | D | Potassium | 5.998 |
| A | Isovitexin | 0.003 | D | Sodium | 0.266 |
| A | Linarin | 0.005 | | MICROELEMENTS, Total | 0.041 |
| A | Luteolin-7-O-Rutinoside | 0.012 | D | Chromium | 0.0014 |
| A | Orientin & Homoorientin (AS: Orientin) | <LoQ | D | Cobalt | 6.68316E−05 |
| A | Vicenin-2 | 0.011 | D | Copper | 0.0023 |
| A | Vitexin-2"-O-rhamnoside | 0.009 | D | Iron | 0.0166 |
| | FLAVONOLS, Total | 0.085 | D | Manganese | 0.0107 |
| A | Isorhamnetin-3-O-glucoside | <LoQ | D | Molybdenum | 7.36657E−05 |
| A | Kaempferol-3-O-rutinoside | 0.047 | D | Nickel | 0.0011 |
| A | Kaempferol-7-O-neohesperidoside | <LoQ | D | Selenium | 3.42504E−06 |
| A | Luteolin-4'-O-glucoside & Kaempferol-3-O-glucoside & Quercitrin (AS: Quercitrin) | 0.016 | D | Tin | <LoQ |
| A | Quercetin | <LoQ | D | Vanadium | 5.06679E−05 |
| A | Rutin | 0.023 | D | Zinc | 0.009 |
| | PHENOLIC ACIDS, Total | 0.014 | | OTHER ELEMENTS, Total | 0.031 |
| A | Protocatechuic acid | 0.014 | D | Aluminum | 0.023 |
| | PHENYLPROPANOIDS, Total | 1.502 | D | Antimony | <LoQ |
| | COUMARINS, Total | <LoQ | D | Arsenic | 8.05812E−06 |
| A | Scopoletin | <LoQ | D | Barium | 0.0007 |
| | HYDROXYCINNAMIC ACIDS, Total | 1.502 | D | Boron | 0.002 |
| A | 3,4-Dicaffeoylquinic acid & 3,5-Dicaffeoylquinic acid (AS: 3,4-Dicaffeoylquinic acid) | 0.324 | D | Cadmium | <LoQ |
| A | 4,5-Dicaffeoylquinic acid | 0.194 | D | Gadolinium | <LoQ |
| A | 4-Coumaric acid | 0.008 | D | Gallium | 6.63549E−06 |
| A | Caftaric acid | 0.034 | D | Gold | <LoQ |
| A | Cryptochlorogenic acid & Chlorogenic acid (AS: Chlorogenic acid) | 0.789 | D | Iridium | <LoQ |
| A | Curcumin | 0.056 | D | Lead | 2.37893E−05 |
| A | Cynarin | 0.016 | D | Lithium | 0.00017 |
| A | Demethoxycurcumin | 0.023 | D | Lutetium | <LoQ |
| A | Ferulic acid | 0.005 | D | Mercury | <LoQ |
| A | Neochlorogenic acid | 0.053 | D | Palladium | <LoQ |
| | PHLOROGLUCINOLS, Total | <LoQ | D | Platinum | <LoQ |
| A | Arzanol | <LoQ | D | Rubidium | 0.0020 |
| | SALICYLATES, Total | <LoQ | D | Ruthenium | <LoQ |
| A | Salicylic acid | <LoQ | D | Strontium | 0.0017 |
| | SIMPLE PHENOLS, Total | 0.001 | D | Tellurium | <LoQ |
| A | Protocatechualdehyde | <LoQ | D | Thallium | <LoQ |
| A | Vanillin | 0.001 | D | Thorium | <LoQ |
| | | | D | Titanium | 0.0011 |

-continued

| METHOD | COMPOUNDS | EpigenAU/ 11 DoE2 | METHOD | COMPOUNDS | EpigenAU/ 11 DoE2 |
|--------|-----------|-------------------|--------|-----------|-------------------|
| | | | D | Uranium | <LoQ |
| | | | D | Ytterbium | <LoQ |

Note 1.
Bold indicate chemical macro classes.
Note 2.
% = compound concentration expressed as percentage of the whole matrix.
Note 3.
(d %) = percentage deviation: (|Gold (%) − Test(%)|/(Gold (%) ) × 100).
Note 4.
The term "Total" refers to the sum of the value of the various compounds which forms the corresponding group.
Note 5.
<LdQ = below the limit of quantification.
Note 6.
/ = percentage deviation not quantifiable.

5.2 Spectroscopy FTIR Characterization (Computer Implemented)

Fourier transform infrared spectroscopy (FTIR, Fourier Transform Infrared Spectroscopy) is an analytical technique used to obtain the absorption or emission spectrum of a sample and is based on the analysis of the interaction between infrared radiation and matter. FTIR spectroscopy can be affected by weak interactions between plant matrix components, such as hydrogen bonds, van der Waals forces, dipole-dipole interactions and hydrophobic interactions. These interactions can alter the position, intensity and shape of peaks in the spectrum, changing the absorption characteristics of various functional groups. Thus, weak interactions within plant matrices significantly influence the data obtained by FTIR spectroscopy. Therefore, the FTIR spectrum, is characteristic of each material (in this case a vegetal biological matrix). Thus, FTIR spectroscopy can be regarded as a descriptive means of system properties, allowing a detailed view of the physicochemical properties of a plant matrix to be obtained.

FTIR Instruments and Set Up.

Alpha spectrometer from BRUKER Optics. Instrument is equipped with a GLOBAR source emitting in the Far and Mid-Infrared regions, a ROCKSOLID interferometer (Michelson type), a KBr beam splitter, and an RT-DLATGS detector.

Resolution: 2 cm−1
Spectral range: 5000-300 cm−1
Background scans: 50
Scans for sample acquisition: 50

5.2.1 Preparation of the Sample

The EpigenAU/11 DoE2 sample was transferred into the appropriate sample holder for ATR-FTIR analysis of solids and liquids. Approximately 10 mg of the sample were deposited and pressed onto the diamond crystal of the ATR support. Before recording the measurement, it was verified that the entire sample holder was properly covered.

Sample Acquisition

The sample, at least three measurements were repeated to verify the reproducibility of the data. The replicates were then averaged to obtain a representative spectrum of the sample for characterization.

Figure 18:
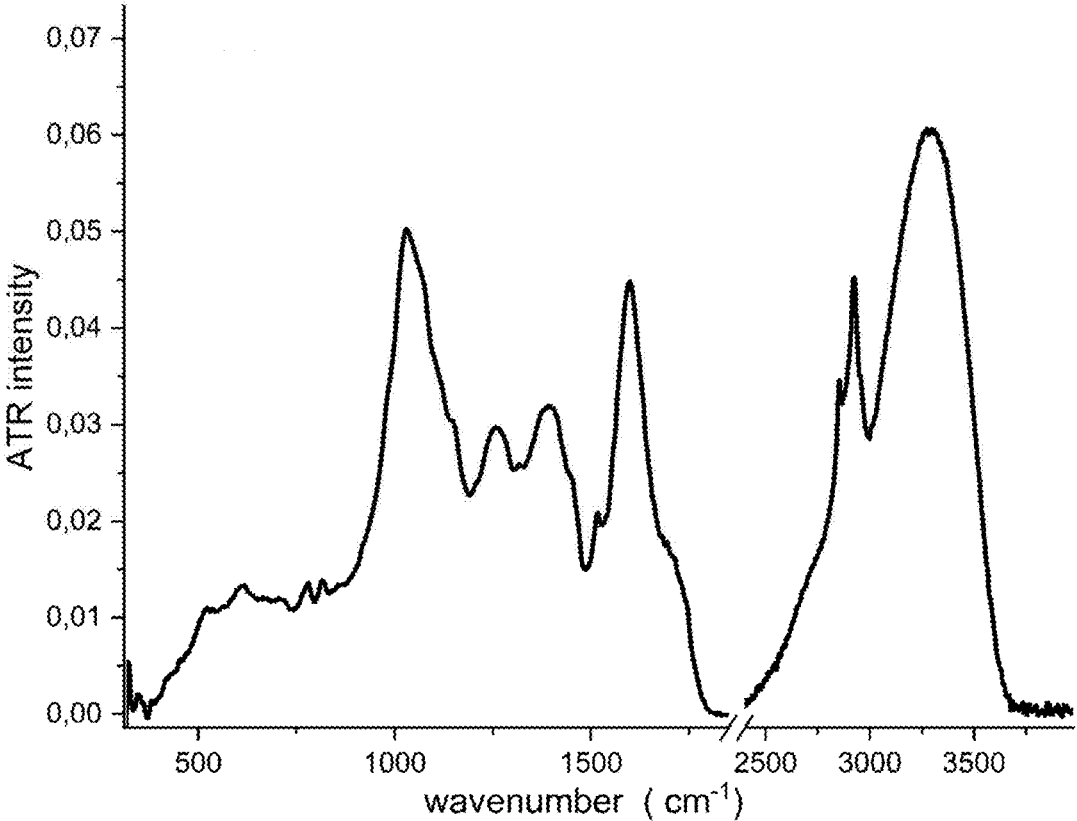

The results are reported in FIG. 18.

5.3 Isotopic Abundance

The analysis of isotopic abundance is a way to describe matter from an atomic point of view.

This description, from an atomic perspective, is significant because phenomena such as the Geometric Isotope Effect (GIE) and the Kinetic Isotope Effect (KIE) are associated with isotopic abundance.

The Geometric Isotope Effect (GIE) refers to the impact of isotopic substitution on the geometric structure of molecules, particularly in the context of hydrogen bonding.

This subtle change can lead to alterations in the overall molecular geometry, affecting both intra- and intermolecular interactions. These structural modifications may influence the physical, chemical, and even biological properties of the material, making the GIE a significant phenomenon in understanding isotopic effects at a molecular level.

The Kinetic Isotope Effect (KIE) describes the change in the rate of a chemical reaction due to the substitution of one isotope for another in a molecule. This effect occurs because isotopes have different masses, leading to variations in bond vibrational energies and reaction activation energies. The KIE can be classified as:

1. Primary KIE: Observed when the isotopic substitution occurs directly at the bond being broken or formed during the rate-determining step of a reaction. For instance, replacing hydrogen with deuterium can significantly slow the reaction due to the stronger and heavier deuterium bond.

2. Secondary KIE: Observed when the isotopic substitution occurs at a site adjacent to the reactive centre, indirectly influencing the reaction rate through changes in molecular geometry or electronic effects.

Isotopic abundance analysis was first performed on the reference standard of product EpigenAU/11, DoE2.

The sample was sent to Istituto San Michele all'Adige (Fondazione Edmund Mach) and tested for stable isotopes as follows:

δ18O: Method PDP 7011:2010 REV. 0 (TC-IRMS), UNIT ‰ vs V-SMOW.

δ13C: Method PDP 7009:2017 REV. 2 (EA-IRMS), UNIT vs ‰ V-PDB

δ15N: Method PDP 7009:2017 REV. 2 (EA-IRMS), UNIT ‰ vs V-AIR.

δ34S: Method PDP 7013:2010 REV. 0 (EA-IRMS), UNIT ‰ vs V-CDT.

14C-activity was also tested by Chelab (Tentamus Company):

14C-activity: Method ISO-16620-2; 2019 (AMS), UNIT % modern carbon (pMC).

The results were as follows.

| Product | δ18O (‰) | δ13C (‰) | δ15N (‰) | δ34S (‰) | 14C-activity (%) |
|---|---|---|---|---|---|
| EpigenAU/11 DoE 2 | +25.6 ± 1 | −28.4 ± 0.3 | +3.2 ± 0.6 | +4.7 ± 1 | 100.4 ± 0.21 |

Thus, an isotopic characterization was carried out for the reference standard DoE2. In addition, the measured values for the 14C activity of the reference standard of pMC correspond to those for substances from purely bio-based carbon. There is no evidence of a synthetic source in the analysed material.

As stated in the specification, according to Method 28-16620-2; 2019 (AMS), a value of 14C of about 1000 is indicative of the naturality of the product.

Hence, this data alone is sufficient to confirm the product's naturality.

To confirm that the production process from starting materials did not alter the nature of the material itself, a study of the isotopic abundance during different steps of the manufacturing process was conducted, the results are reported below.

The results are reported in the tables below depicting the δ ratio of the main isotopes.

| Samples | δ18O (‰) | δ13C (‰) | δ15N (‰) | δ34S (‰) | % in final formulation |
|---|---|---|---|---|---|
| Raw material blending | +27.6 ± 1 | −28.8 ± 0.3 | +3.3 ± 0.6 | +2.7 ± 1 | 36.05 |
| Aqueous extract | +28.5 ± 1 | −28.5 ± 0.3 | +2.6 ± 0.6 | +3.9 ± 1 | |
| Plant system 1 (SP1) | +27.2 ± 1 | −28.4 ± 0.3 | +2.8 ± 0.6 | +4.1 ± 1 | |

| Samples | δ18O (%) | δ13C (%) | δ15N (%) | δ34S (%) | % in final formulation |
|---|---|---|---|---|---|
| Raw material blending | +25.5 ± 1 | −28.5 ± 0.3 | +4 ± 0.6 | +4.6 ± 1 | 63.06 |
| Aqueous extract | +26.7 ± 1 | −28.1 ± 0.3 | +4.4 ± 0.6 | +6.1 ± 1 | |
| Plant system 2 (SP2) | +25.2 ± 1 | −28.7 ± 0.3 | +3.7 ± 0.6 | +5.8 ± 1 | |

| Samples | δ18O (%) | δ13C (%) | δ15N (%) | δ34S (%) | % in final formulation |
|---|---|---|---|---|---|
| Raw material | +22.7 ± 1 | −13.4 ± 0.3 | +2.4 ± 0.6 | +11.6 ± 1 | 0.89 |
| Aqueous extract | +24.5 ± 1 | −13.9 ± 0.3 | +2.5 ± 0.6 | +12 ± 1 | |
| Agave | +23 ± 1 | −13.6 ± 0.3 | +2.8 ± 0.6 | +11.2 ± 1 | |

| Sample | δ18O (%) | δ13C (%) | δ15N (%) | δ34S (%) | % of final formulation |
|---|---|---|---|---|---|
| DoE 2 experimental values | −25.60 ± 1 | −28.4 ± 0.3 | +3.2 ± 0.6 | +4.7 ± 1 | 100 |
| DoE 2 theoretical values | −25.90 | −28.47 | +3.37 | +5.24 | |

The assessment of the isotopic abundance of the materials along the production process shows that the production process does not alter the abundance ratios thus substantiating the fact that the process conserves the native biophysical characteristics of the starting materials.

In addition, the process of mixing the individual systems to obtain the finished product in the right percentages is efficient and does not alter isotopic abundance, returning a finished product consistent with expectations.

6. Identification of Extracellular Vesicles and miRNA Content in EpigenAU/11

6.1 miRNAs Characterisation

The analytical methods used for the characterization of DoE2 are described in the relevant table in example 5. above. The same analytical methods were used for other batches (DoEs) of EpigenAU/11 in the subsequent examples.

Through NanoSight analysis, a high concentration of particles within EpigenAU/11 samples, specified in the examples below, that are compatible with the size range of extracellular vesicles were identified. These particles, primarily between 30 and 120 nm, suggest the presence of extracellular vesicles within EpigenAU/11. Leveraging this insight, small RNA sequencing was performed using the sRNAtoolbox framework to explore the RNA content within these vesicle-sized particles.

Among the RNA sequences identified, reads that aligned to mature microRNAs (miRNAs) or their isoforms were found, annotated from the genome of *Arabidopsis thaliana*, which is the best-annotated plant genome to date.

Qualitative miRNA characterization was also performed on ultracentrifuged samples from each batch (Method E). The results show high metabolomic complexity together with the presence of miRNAs typical of living matter.

| miRNA Family | miRNA | miRNA Family | miRNA |
|---|---|---|---|
| miR159 | ath-miR159a | miR168 | ath-miR168a-3p |
| | ath-miR159b-3p | | ath-miR168a-5p |
| | ath-miR159c | | ath-miR168b-5p |
| miR160 | ath-miR160c-5p | miR171 | ath-miR171c-5p |
| miR162 | ath-miR162b-3p | miR1888 | ath-miR1888a |
| miR164 | ath-miR164a | miR319 | ath-miR319a |
| miR165 | ath-miR165a-3p | | ath-miR319b |
| | ath-miR165b | | ath-miR319c |
| miR166 | ath-miR166a-3p | miR394 | ath-miR394a |
| | ath-miR166b-3p | miR396 | ath-miR396a-5p |
| | ath-miR166c | | ath-miR396b-3p |
| | ath-miR166d | miR5660 | ath-miR5660 |

-continued

| miRNA Family | miRNA | miRNA Family | miRNA |
|---|---|---|---|
| | ath-miR166e-3p ath-miR166g | miR8175 | ath-miR8175 |

6.2 Detection of Supramolecular Structures in the EpigenAU/11 System Natural Matrix

6.2.1. Dynamic Light Scattering

The method of dynamic light scattering (DLS) is the most common measurement technique for particle size analysis in the nanometre range. DLS measures the hydrodynamic size of particles, by the mechanism of light scattering from a laser that passes through solution and analyses modulation of the intensity of scattered light as a function of time. Brownian motion of particles correlates with their hydrodynamic diameter. The smaller the particle, the faster it will diffuse than a larger one and the DLS instrument will generate a correlation function that is mathematically linked with particle size and its time-dependent light scattering capacity.

DLS has been used to measure the particle size of dispersing colloidal samples, to study the stability of formulations, and to detect the presence of aggregation or agglomeration. This method is also most suitable for analysing the size distribution of already isolated exosomes and micro vesicles.

The analysis was carried out by AlfatestLab.

Sample Preparation:

Reference standard DoE2 was dispersed at arbitrary concentration of 10 mg/ml in 0.22 μm filtered demineralized water.

After dispersion sample was vortexed for 2 minutes to provide complete dispersion.

Analysis Parameters:

Measurement cell: Plastic, (DTS0012)

Detector: Back scattering 1730 (NIBS)

Laser wavelength: 633 nm

Measurement number: 3

Correlation time: adaptive

Measurement position: automatic

Attenuator: automatic

Temperature: 25° C.

Temperature equilibration time: 120 seconds

Dispersant: Water

Dispersant refractive index: 1.33

Dispersant viscosity: 0.8872 cP at 25° C. (water)

Sample was Analysed at Three Different Conditions:

Unfiltered

After filtration with 0.45 μm Nylon syringe filter

After filtration with 0.1 μm Nylon syringe filter 0.1 μm filtration was performed on 0.45 μm filtered sample.

Before each filtration step, sample dispersions were vortexed for 30 seconds. Filtered dispersions were left at rest at room temperature for about 15 minutes and then analysed after a gentle manual stirring.

Results:

Averaged results of Z-Average and PdI obtained from 3 repeated measurements are reported in the table below. Z-Average is the intensity weighted mean diameter, PdI is the polydispersity index.

| Condition | Z-Average (nm) | PdI | Peak1 nm | Peak1 % | Peak2 nm | Peak2 % |
|---|---|---|---|---|---|---|
| Not Filtered | 2468 | 0.896 | 1122 | 83.6 | 178.7 | 16.4 |
| 0.45 μm-filtered | 190.3 | 0.177 | — | — | — | — |
| 0.1 μm-filtered | 142.1 | 0.217 | — | — | — | — |

Figure 19:
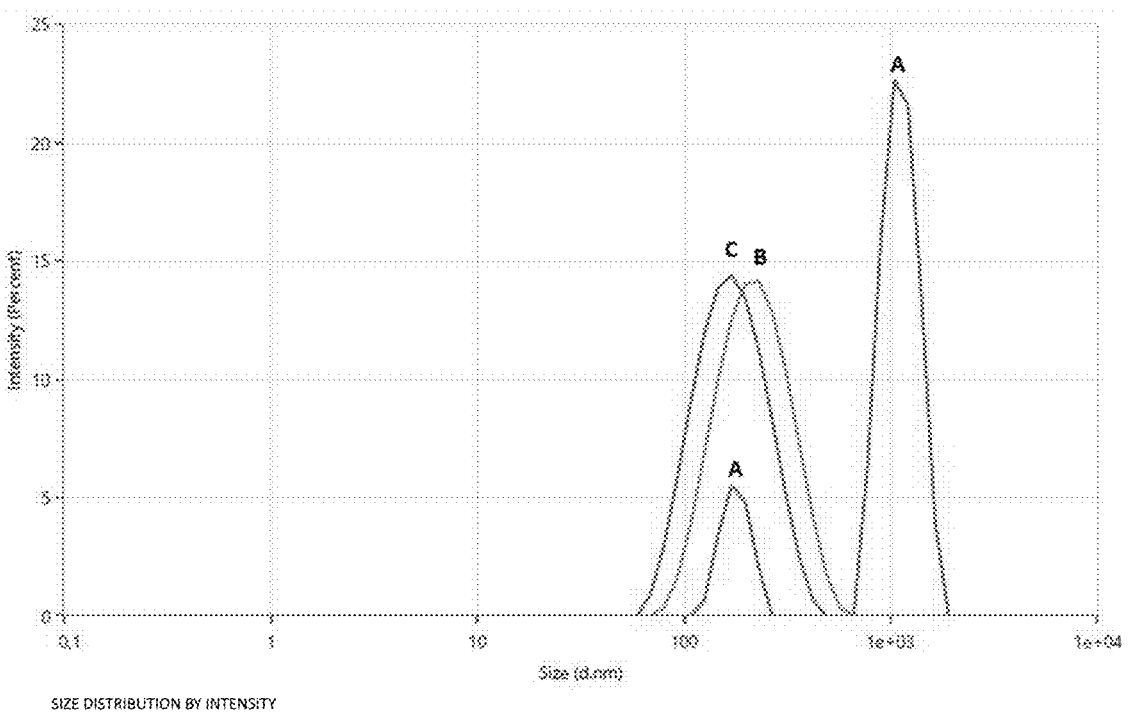
Figure 19:
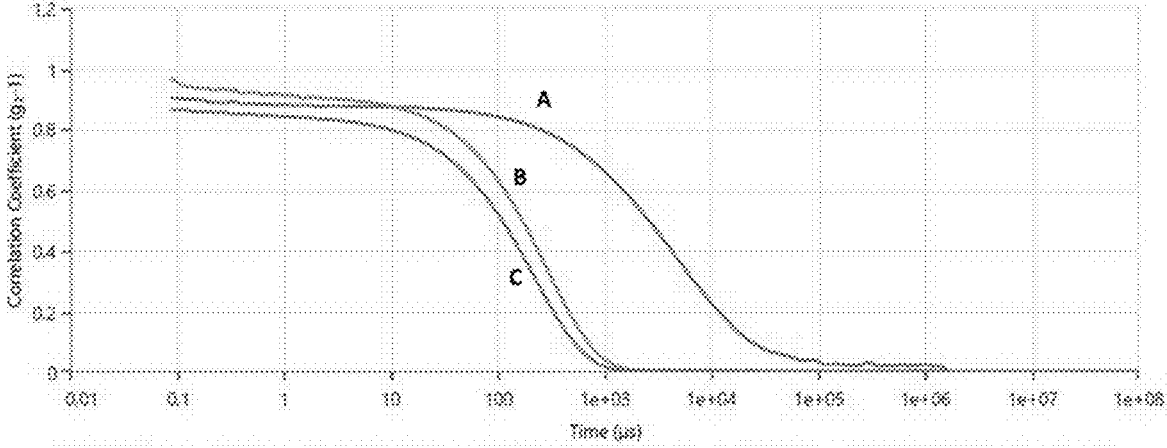
Figure 19:
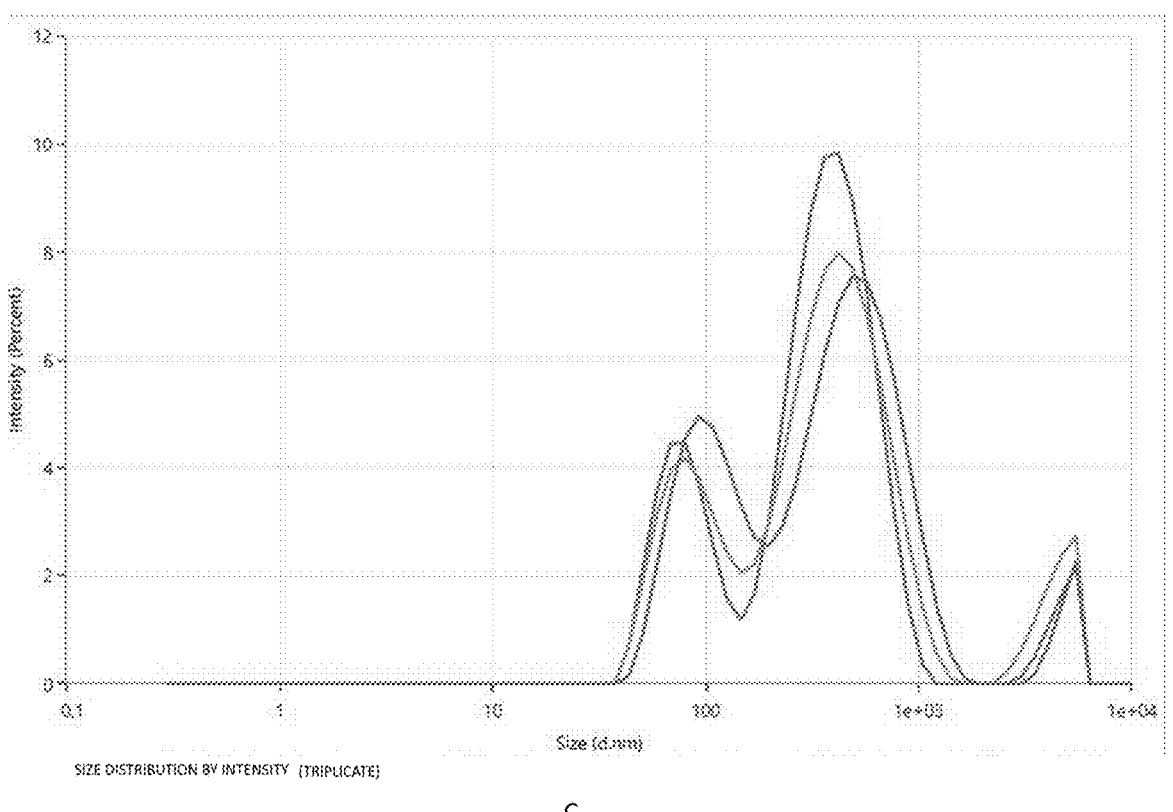
Figure 19:
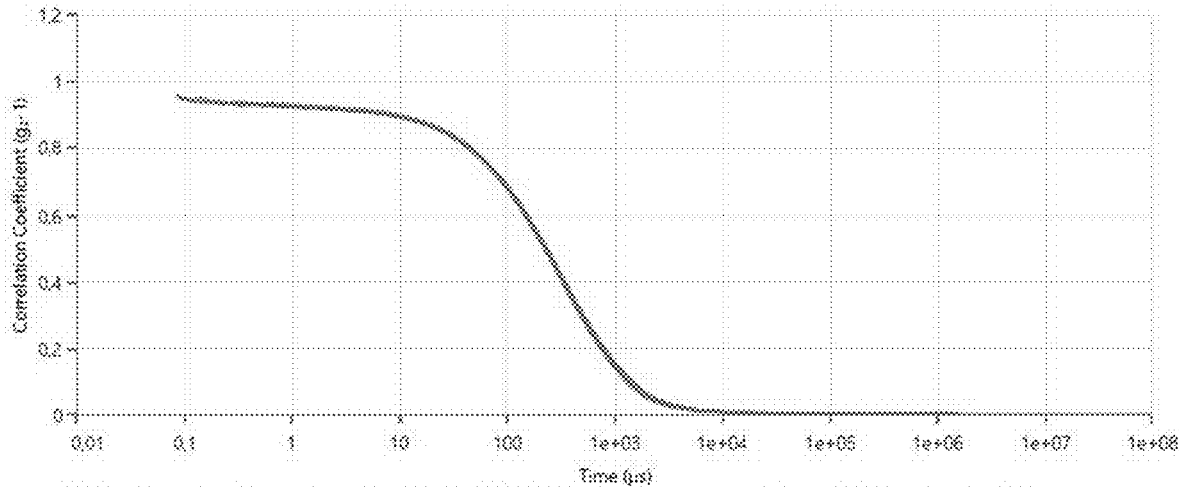
Figure 19:
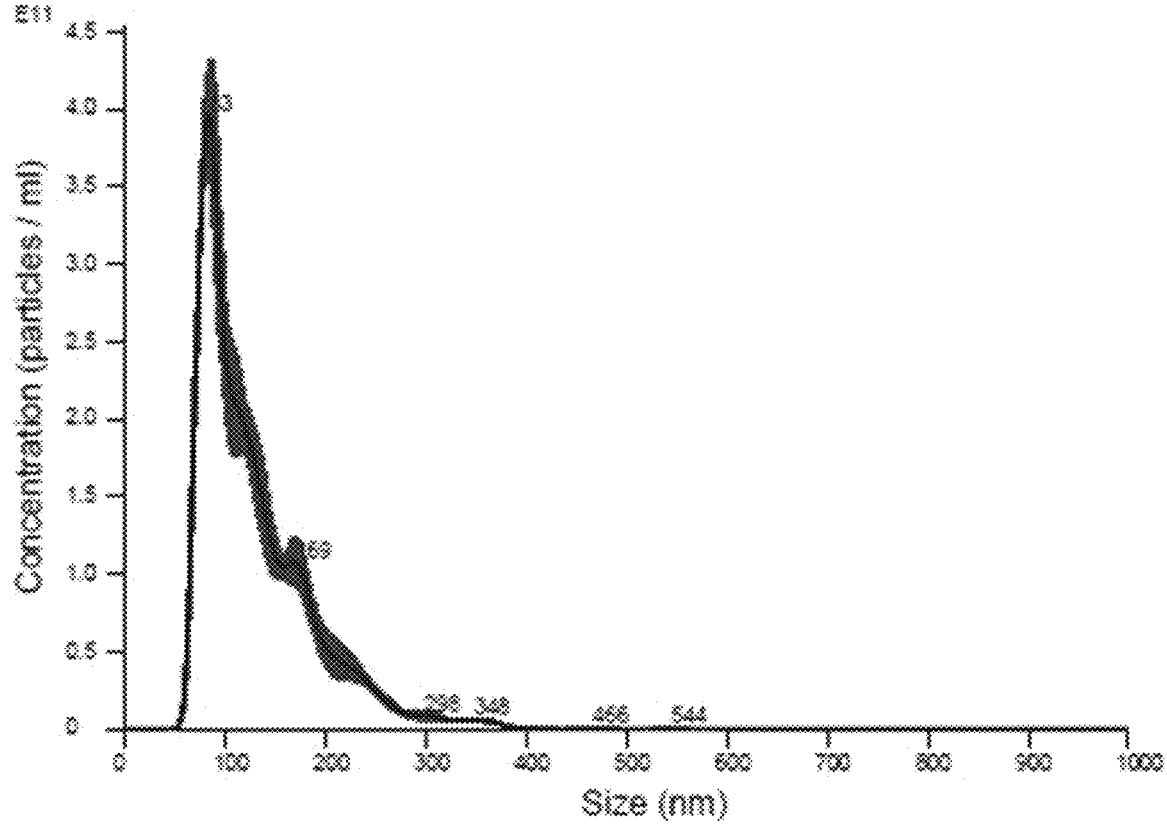

Correlogram evaluation (FIGS. 19 A and B) provides data quality information about DLS results. The graph shows the progress of a correlation function (y-axis) during time (x-axis) that should have a sigmoid shape. The intercept value on y-axis is linked to signal/noise ratio, i.e., how much scattering signal from the sample is reaching detectors and is successfully separated from background noise. The closer intercept is to 1, the better is the signal to noise ratio.

The position (on the x-axis, time) of the inflection point of the correlogram is related to the size of the particles: the longer the decay time of the correlation, the larger the particle size. The slope of this section of the curve is related to the polydispersity index (PdI) and thus to the dispersion of the sample size population: the steeper the decay, the less dispersed the particle size and the lower the PdI value. Finally, the section of the curve following the inflection point is related to the presence of large particles. In general, the absence of large particles and aggregates is evidenced by a curve tending to zero in this area.

As result show water dispersion provided the formation of large particles over 1 μm. The noisy right part of correlogram of unfiltered water dispersion suggests the presence of not characterized larger particles. Filtration caused a clear shift in the correlogram and size distribution. In particular, filtration at 0.10 μm shows a single-mode distribution with particle sizes larger than the filtration size. Indeed, it appears that the substructures that make up the particle separate during filtration and then return to form the original complex. Thus, the data suggest the presence of supramolecular aggregates consisting of noncovalent intermolecular interactions. Data quality of filtered samples is good.

6.2.2. Detection of Exosomes in EpigenAU/11 DoE2

Preparation of Ultracentrifuged Samples

The starting sample (reference standard DoE2) from which the ultra centrifugate is prepared was weighed and resuspended in a volume of VIB or vesicles isolation buffer (20 mM MES; 2 mM CaCl$_2$); 100 mM NaCl, pH 6.0) maintaining the ratio of 5 mL of buffer per 500 mg of sample. The sample was incubated under stirring at room temperature for 20-24 h to promote solubilisation. After incubation, several centrifugations were performed at 4° C. and at increasing speeds to isolate particles between 30-500 nm in size. The T-1250 rotor (Thermo Fisher Scientific, 11718-5) and the Thermo Scientific™ Sorvall™ WX+ultracentrifuge (Thermo Fisher Scientific™ 75000080, No: 15342177) were used for the ultracentrifugation. The sample was centrifuged at 700×g for 20 minutes; the pellet was discarded while the supernatant was filtered through a 0.45 μm filter and centrifuged at 10000×g for 30 minutes. The supernatant was then moved to ultracentrifugation tubes and centrifuged at 40000×g for 70 minutes. The supernatant was moved on a new ultracentrifuge tube and stored on ice, while the pellet (also indicated ad 40K pellet) was resuspended in VIB and centrifuged again at 40000×g for 70 minutes. The pellet was finally resuspended in 600 μL of 25 mM Trehalose (Merck, T0167) in PBS and stored at 4° C. to be used within 24 h, or at −30° C. for long-term storage. For some samples, ultracentrifugates were also produced at higher speeds, 100000×g. The resulting pellets, also called 100K pellets, were isolated from the supernatant of the first centrifugation at 40000×g and centrifuged again for 70 minutes at 100000×g. Supernatant was discarded and the 100K pellet was resuspended in VIB buffer and centrifuged at the same conditions. As for the 40K pellet, the new one was resuspended in 600 μL of 25 mM Trehalose in PBS and stored at 4° C. to be used within 24 h, or at −30° C. for long-term storage.

Extracellular Vesicles Analysis with DLS:

The analysis was carried out by AlfatestLab.

Analysis Parameters:

Measurement cell: Plastic (ZEN0040)

Detector: Back scattering 173° (NIBS)

Laser wavelength: 633 nm

Measurement number: 3

Correlation time: adaptive

Measurement position: automatic

Attenuator: automatic

Temperature: 25° C.

Temperature equilibration time: 120 seconds

Dispersant: Water

Dispersant refractive index: 1.33

Dispersant viscosity: 0.8872 cP at 25° C. (water)

Averaged results of Z-Average and PdI obtained from 3 repeated measurements are reported in the table below. Z-Average is the intensity weighted mean diameter, PdI is the polydispersity index (FIGS. 19C and 19D).

Results:

| Sample name | Z-Average (nm) | PdI | Peak1 nm | Peak1 % | Peak2 nm | Peak2 % | Peak3 nm | Peak3 % |
|---|---|---|---|---|---|---|---|---|
| EpigenAU/11 DoE2 100K | 241.8 | 0.5 | 459.8 | 68 | 89.2 | 25.2 | 4621 | 6.8 |

Analysis of Micro Vesicle Size and Concentration by Nano-Sight

The Malvern NanoSight NS300 uses the technology of Nanoparticle Tracking Analysis (NTA). This unique technology utilizes the properties of both light scattering and Brownian motion to obtain the size distribution and concentration measurement of particles in liquid suspension. A laser beam is passed through the sample chamber, and the particles in suspension in the path of this beam scatter light in such a manner that they can easily be visualized via 20× magnification microscope onto which is mounted a camera.

The analysis was carried out by AlfatestLab.

Analysis Parameters:

Dispersant: PBS 1×

Equipped laser: Blu 488 nm

Camera level: 16

Syringe pump velocity: 50

Number of videos: 5

Video duration: 60 seconds

Detection threshold: 7

Sample was diluted in 1×PBS (1:50000), filtered at 200 nm and subsequently mixed using a vortex mixer for 20 seconds. Sample was then analysed.

Results of the analysis performed on the sample (average of five repeated measurements):

| Sample name | Concentration (particles/ml) | Average diameters (nm) | Mode (nm) |
|---|---|---|---|
| EpigenAU/11 DoE2 100K | $2.77 \times 10^{13} \pm 1.57 \times 10^{12}$ | $128.6 \pm 0.8$ | $81.3 \pm 2.1$ |

Where:

Concentration (particles/ml) is the sum of concentration of all particles detected.

The average diameter is the average of all diameters found with respect to their populousness.

The mode is the value of the main peak that has the largest number of particles.

Thus, the data suggest that there are a large number of particles in the range of 30 and 120 nm compatible with the size of extracellular vesicles.

Negative control resulted non suitable for NTA analysis

7. In Vivo Activity OF EpigenAU/11 Formulation

The tests were carried out with DoE2 formulation.

7.1 In Vivo Antitumour Efficacy of EpigenAU/11 in the Context of Squamous Cell Carcinomas To further evaluate the antitumour efficacy of EpigenAU/11, the study transitioned from in vitro models to more complex and biologically relevant systems.

Animal models offer several advantages, including the ability to evaluate tumour growth in a living organism and assess the compound's systemic effects, which are critical for understanding its full therapeutic potential. Although the athymic (nude) mice used in this study lack an adaptive immune response, they provide a suitable platform for examining tumour behaviour and treatment efficacy in vivo.

7.1.1. Epidermoid Carcinoma (A431 Cells)

In this investigation, an in vivo trial using A431 cells, derived from epidermoid carcinoma, a type of squamous cell carcinoma was performed. This carcinoma, commonly affecting the skin, serves as an appropriate model for studying squamous tumours. While cisplatin is not typically the first-line treatment for A431 epidermoid carcinomas, it remains a cornerstone chemotherapeutic agent in the management of other squamous cell carcinomas, such as those found in the head and neck cancers. Cisplatin demonstrated significant cytotoxic effects in the previously reported in vitro studies on squamous cell carcinoma lines, including A431 and FaDu cells, leading the inventors to explore its efficacy in this in vivo model. Understanding the effects of cisplatin and EpigenAU/11 in an animal model should help illuminate their broader therapeutic applications, even in tumours not traditionally treated with cisplatin.

Figure 20:
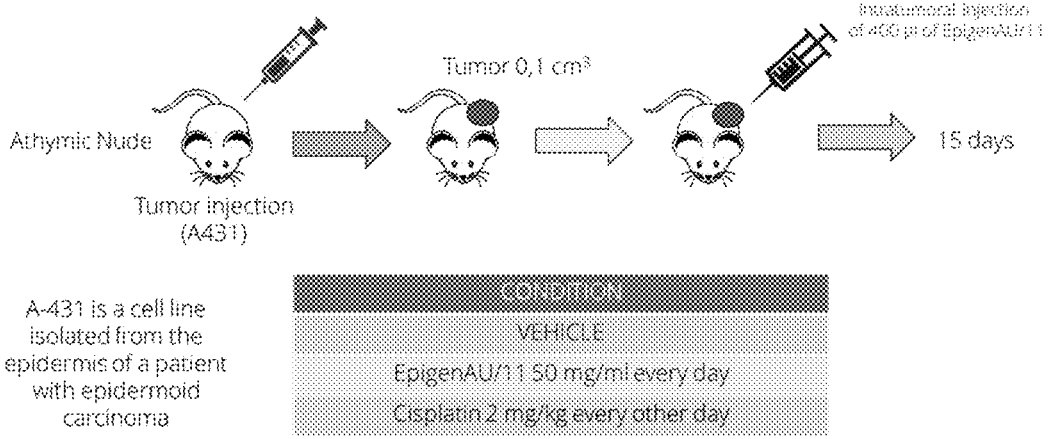

In this trial, athymic mice were subcutaneously injected with $1 \times 10^6$ A431 cells into their flank to develop xenograft tumours. Once the tumours reached a measurable volume of 0.1 cm$^3$, the mice were assigned to one of three treatment arms, each designed to evaluate distinct therapeutic strategies (FIG. 20):

EpigenAU/11 Arm: Mice received daily intratumoral injections of EpigenAU/11 at a concentration of 50 mg/ml.

Cisplatin Arm: Cisplatin was administered intraperitoneally at a dose of 2 mg/kg every two days, following a standard treatment schedule used in squamous carcinoma treatment regimens. Although cisplatin is not typically used for epidermoid carcinomas, its strong efficacy in vitro warranted exploration of its effects in this in vivo model.

Vehicle Control Arm: Mice in this group received injections of a physiological solution (vehicle), following the same schedule used for EpigenAU/11 and cisplatin, to serve as a control group for assessing the baseline tumour growth without active treatment.

All treatments were initiated when tumours reached a volume of 0.1 cm³, allowing for consistent tumour size across groups at the start of therapy.

The response in mice was evaluated using criteria akin to the RECIST 1.1 guidelines, including progressive disease (PD): defined as a ≥35% increase from baseline tumour size; partial response (PR): indicating a ≥50% reduction from baseline; and stable disease (SD): reflecting intermediate variations from baseline.

Figure 21:
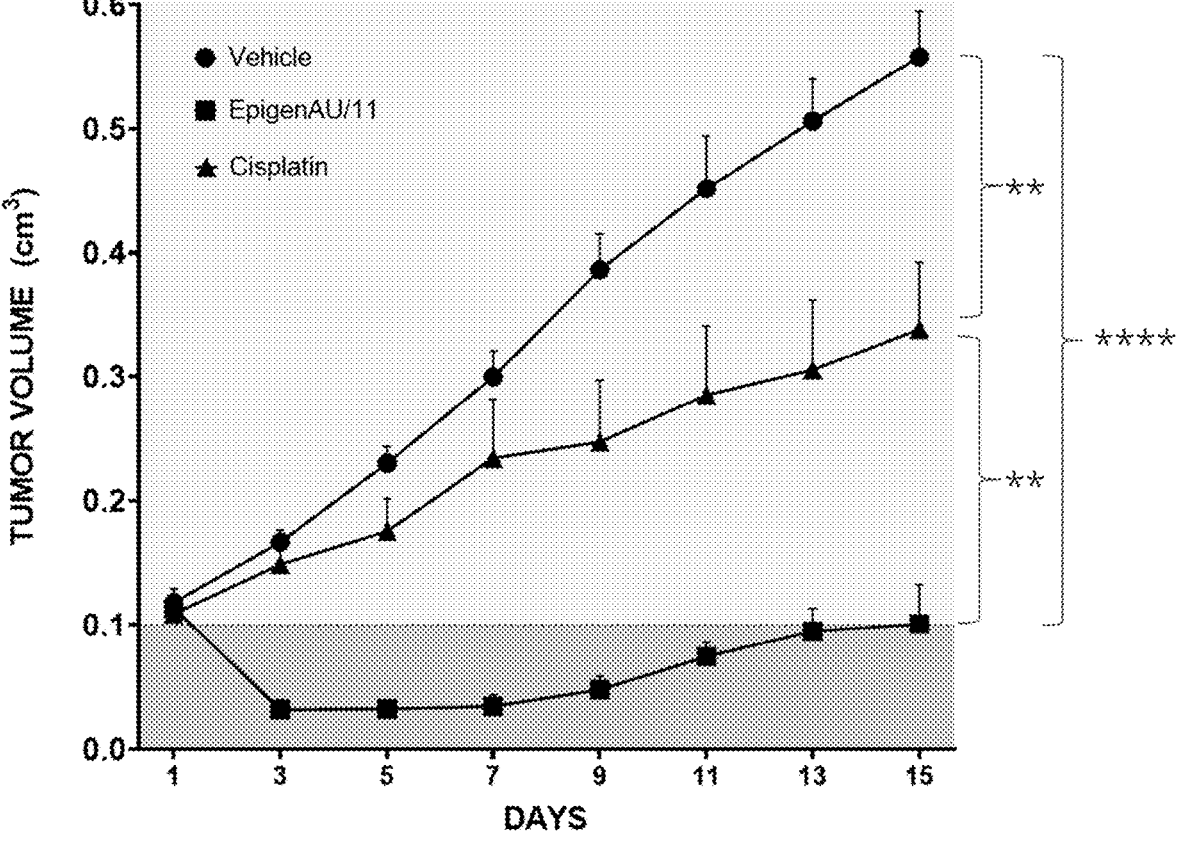

Results presented in the FIG. 21 highlight distinct differences between the treatment arms over a span of 15 days. Mice treated with the vehicle (saline solution) consistently exhibited tumour growth, with the tumours reaching sizes six times their initial volume by the end of the trial, indicative of progressive disease (PD). In contrast, mice treated with cisplatin experienced a slowing of tumour growth, particularly during the latter half of the trial, resulting in stabilization of the tumour mass, classifying them under stable disease (SD). EpigenAU/11, however, demonstrated a notable partial response (PR) as early as three days into treatment, with a marked reduction in tumour size. By day 15, the tumours in the EpigenAU/11-treated mice had slightly regrown but returned to their baseline size, showing a sustained partial response.

Figure 22:
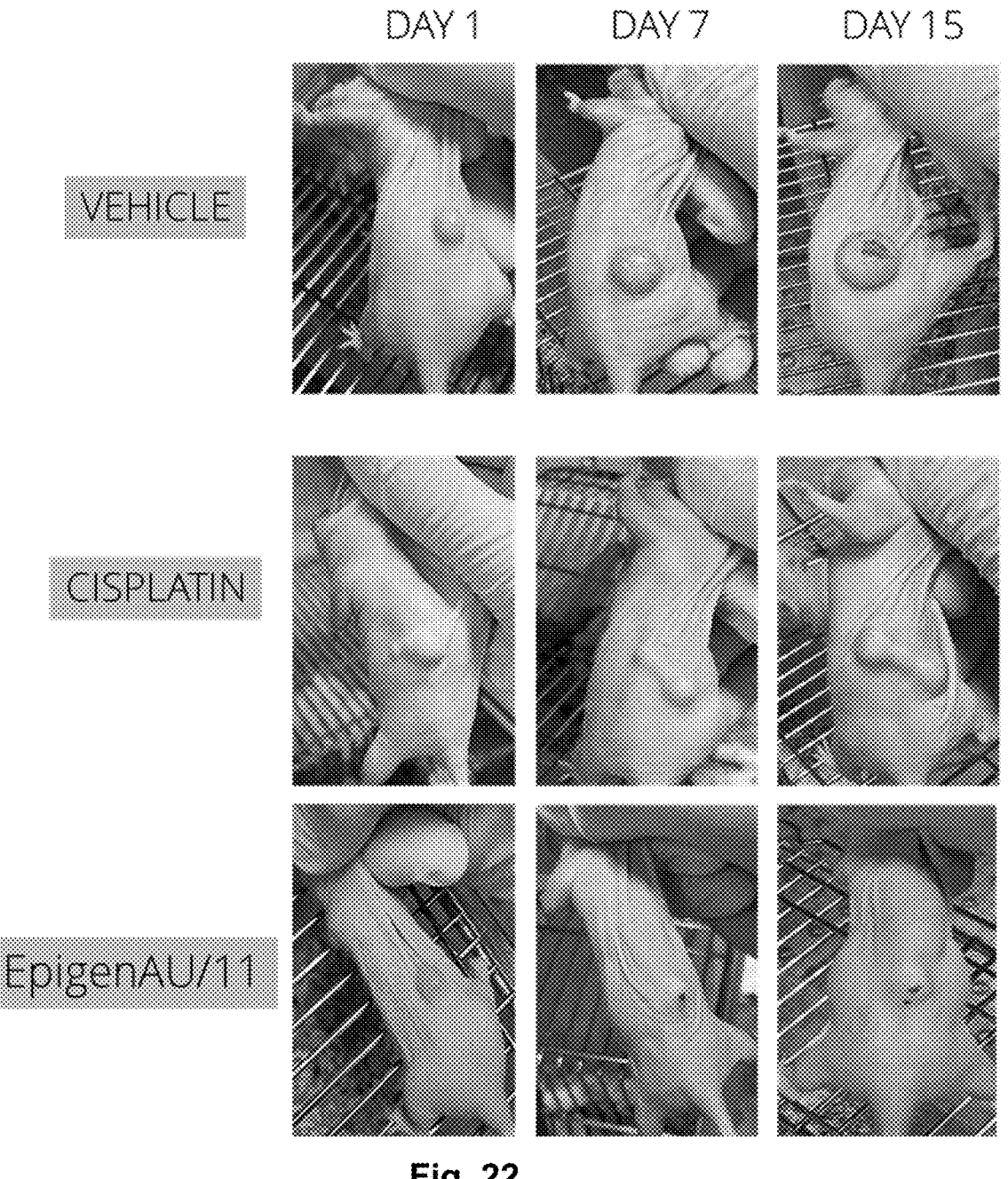

These results underscore the antitumour efficacy of EpigenAU/11 in this in vivo model, confirming its ability to reduce tumour size significantly within a short period, The visual representation of the treated tumours in the FIG. 22 further reinforces this, clearly illustrating the difference in tumour growth across the treatment groups.

At the end of the 15-day period, the tumours were excised and weighed to confirm the observed effects. The average tumour mass in the vehicle-treated group was approximately 626 mg across six mice. In the cisplatin-treated group, the average tumour mass was significantly lower at 368 mg. Notably, the EpigenAU/11-treated group had the smallest average tumour mass at just 169 mg, corroborating the tumour volume reductions observed during the trial. The Table below displays the average weights of tumour masses (in mg) extracted from athymic mice at the end of the 15-day treatment period. The table includes the mean tumour weights for the Vehicle Control, Cisplatin, and EpigenAU/11 treatment groups, illustrating the differences in tumour burden across the various treatment arms.

|  | VEHICLE | EpigenAU/11 | Cisplatin |
| --- | --- | --- | --- |
|  | 730 mg | 160 mg | 570 mg |
|  | 760 mg | 270 mg | 580 mg |
|  | 600 mg | 86 mg | 250 mg |
|  | 690 mg | 310 mg | 550 mg |
|  | 590 mg | 190 mg | 140 mg |
|  | 390 mg | Not found | 120 mg |
| MEAN | 626 mg | 169 mg | 368 mg |

Additionally, the body weight of the mice was monitored throughout the treatment period. Mice treated with the vehicle exhibited a slight increase in body weight of 2.5%, while those treated with EpigenAU/11 showed a similar 2.2% weight gain, indicating that EpigenAU/11 did not negatively affect the general health of the animals. In stark contrast, the cisplatin-treated mice experienced a substantial 10.3% decrease in body weight over the 15 days, reflecting the known systemic toxicity and side effects of cisplatin treatment.

The table below shows the average body weights (in grams) of athymic mice at the end of the 15-day treatment period for each experimental group: Vehicle Control, Cisplatin, and EpigenAU/11.

| VEHICLE | EpigenAU/11 | Cisplatin |
| --- | --- | --- |
| +2.5% (SD ± 1.8%) | +2.2% (SD ± 1.8%) | −10.3% (SD ± 2.6%) |

7.1.2 Head and Neck Carcinoma (FaDu Cells)

Following the investigation with A431 cells, the focus was shifted to FaDu cells, which are derived from head and neck squamous cell carcinoma (HNSCC). HNSCC represents a diverse group of malignancies that arise in the mucosal surfaces of the head and neck region, including the oral cavity, pharynx, and larynx. These tumours are notably aggressive and often associated with poor prognosis, making effective treatment strategies essential.

Cisplatin is considered the gold standard chemotherapeutic agent for treating HNSCC, frequently utilized in both neoadjuvant and adjuvant settings. Its mechanism of action primarily involves the formation of DNA cross-links, which inhibits DNA replication and ultimately triggers apoptosis in rapidly dividing tumour cells. Despite its efficacy, the effectiveness of cisplatin can be limited by various factors, including the development of resistance and significant side effects, which necessitate the exploration of combination therapies that could enhance its therapeutic outcomes.

In light of the promising results observed in vitro, where no interference was detected between EpigenAU/11 and traditional chemotherapeutic agents, this study aimed to investigate whether EpigenAU/11 could enhance the efficacy of cisplatin in an in vivo setting. Given the critical need for improved treatment strategies in HNSCC, understanding the potential interplay between EpigenAU/11 and cisplatin could offer new avenues for enhancing therapeutic efficacy while minimizing adverse effects.

In this investigation, an in vivo trial utilizing FaDu cells was performed to explore this interaction. The distinct dosing schedules employed for each treatment resulted in four specific treatment arms (FIG. 23).

EpigenAU/11 Arm: Mice received daily treatment with EpigenAU/11 at a concentration of 50 mg/ml, incorporating intratumoral administrations.

Cisplatin Arm: Cisplatin was administered intraperitoneally at a dosage of 2 mg/kg every two days, following the standard treatment protocol.

Combination Arm: Mice in this arm experienced a combined treatment approach, receiving both EpigenAU/11 daily (intratumoral) and cisplatin every two days (intraperitoneal).

Vehicle Control Arm: Animals in this arm served as the vehicle control group, receiving a physiological solution according to the same schedule used for cisplatin and EpigenAU/11.

All treatments commenced when tumours reached a volume of 0.1 cm³.

The response in mice was evaluated using criteria akin to RECIST 1.1 guidelines. This study was extended to 27 days to assess the prolonged effects of EpigenAU/11, cisplatin, and their combination over a longer treatment period (FIG. 24). In the vehicle control group, tumours exhibited rapid growth, reaching nearly 1 cm³ within just a few days, necessitating the sacrifice of the mice on the 19th day. In contrast, and in line with established reports, cisplatin treatment significantly slowed tumour progression, ultimately leading to a stabilization of the disease.

Both the EpigenAU/11 monotherapy and combination therapy arms demonstrated partial tumour regression (PR). A notable difference between these two arms emerged around day 23, when tumour regrowth was observed in the EpigenAU/11 group but not in the combination group.

Figure 25:
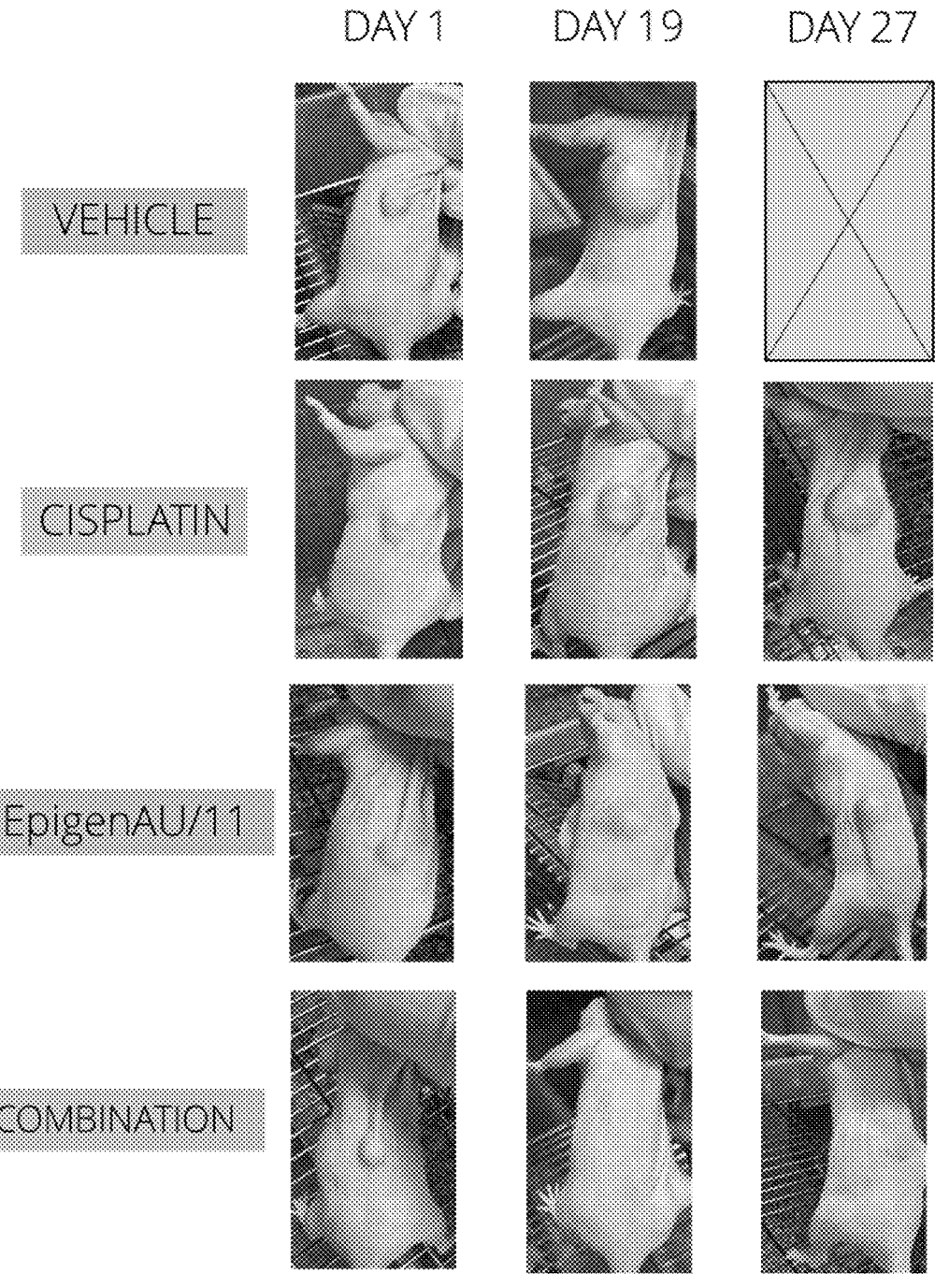

The visual representation of the treated tumours in FIG. 25 further reinforces this, clearly illustrating the difference in tumour growth across the treatment groups.

The animals were sacrificed at day 27, and tumour masses were excised and weighed to further confirm the observed effects.

In the vehicle-treated group, the average tumour mass was approximately 1307 mg across five mice. The cisplatin-treated group showed significantly smaller tumour masses, with an average of 454 mg. The EpigenAU/11-treated group had an average tumour mass of just 210 mg, and only four out of five mice had detectable tumour masses, corroborating the tumour volume reductions observed during the trial. Interestingly, in the combination therapy arm, only two out of five mice had remaining tumours at the end of the trial, with an average tumour mass of just 62 mg, underscoring the profound efficacy of the combination treatment in nearly eliminating tumour presence.

The Table below reports the data on tumour Masses Explanted After 27 Days of Treatment (Vehicle 19 days). Average tumour weights (in mg) for each treatment group are shown.

|  | VEHICLE | EpigenAU/11 | Cisplatin | Combination |
|---|---|---|---|---|
|  | 1550 mg | 330 mg | 180 mg | 120 mg |
|  | 1170 mg | 450 mg | 850 mg | 190 mg |
|  | 1310 mg | 220 mg | 510 mg | Not found |
|  | 1200 mg | 90 mg | 140 mg | Not found |
|  | — | Not found | 640 mg | Not found |
| MEAN | 1307 mg | 210 mg | 454 mg | 62 mg |

Additionally, throughout the treatment period, the body weight of the mice was closely monitored as an indicator of overall health and treatment-related toxicity. Mice treated with the vehicle control showed a slight body weight increase of 7.7%, while those treated with EpigenAU/11 exhibited a comparable 7.1% weight gain, indicating that EpigenAU/11 did not induce significant systemic toxicity. However, the cisplatin-treated mice and those receiving the combination therapy experienced notable decreases in body weight, with losses of −22.8% and −20.8%, respectively, over the 27-day period, reflecting the well-known systemic toxicity of cisplatin. The table below summarizes the percentage change in body weight of mice in each treatment group from the beginning to the end of the trial.

| VEHICLE | EpigenAU/11 | Cisplatin | Combination |
|---|---|---|---|
| +7.7% | +7.1% | −22.8% | −20.8% |
| (SD ± 5.3%) | (SD ± 5.7%) | (SD ± 7.3%) | (SD ± 6.6%) |

Furthermore, to better understand the potential systemic toxicity of the treatments, an Irwin test was conducted, evaluating a range of physiological and behavioural parameters, including general behaviour, CNS excitement, movement coordination, muscle tone, reflex responses, and autonomic signs. The results revealed that mice treated with cisplatin, or the combination of cisplatin and EpigenAU/11 exhibited a notable 30-40% reduction in overall biological functions, including diminished activity, reflex impairment, and changes in muscle tone. These reductions are consistent with the known side effects of cisplatin, which include neurotoxicity and general systemic stress.

In contrast, mice treated with EpigenAU/11 alone did not show any significant alterations in these parameters, maintaining normal behavioural and physiological function throughout the study. This distinction underscores EpigenAU/11's favorable safety profile, highlighting its potential to deliver therapeutic efficacy without the severe side effects typically associated with traditional chemotherapeutic agents like cisplatin. The Table below shows the results of the Irwin test, highlighting differences in key physiological and behavioural parameters between the treatment groups at the end of the trial. Parameters assessed include general behaviour, central nervous system (CNS) excitement, movement coordination, muscle tone, reflex responses, and autonomic signs.

| IRWIN TEST | | | | |
|---|---|---|---|---|
| 19 DAYS Vehicle | 27 DAYS EpigenAU/11 | 27 DAYS Cisplatin | 27 DAYS Combination | Limits |
| Behaviour | | | | |
| Spontaneous activity | | | | |
| 4 | 3.7 | 2.5 ! | 3.3 | 4-0 |
| Passivity 0 | 0.3 | 1.6 ! | 0.5 | 0.4 |
| Cleaning 4 | 3.8 | 2.9 | 3.3 | 4-0 |
| Curiosity 4 | 3.8 | 2.6 | 2.8 ! | 4-0 |
| Reactivity 4 | 3.9 | 2.2 ! | 2.3 ! | 4-0 |
| S.N.C. excitement | | | | |
| Tremors 0 | 0.1 | 0.8 | 0.5 | 0-4 |
| Movement | | | | |
| Stereotipies 0 | 0 | 0 | 1 | 0-4 |
| Straightening reflex 4 | 3.8 | 2.6 ! | 2.5 ! | 4-0 |
| Muscolar tone | | | | |
| Physical strength 4 | 3.8 | 2.7 ! | 3.3 ! | 3-0 |
| Reflexes | | | | |
| Palpebral reflex 4 | 3.8 | 2.8 ! | 3 ! | 4-0 |
| Autonomic signes | | | | |
| Pollor 0 | 1.2 | 2 ! | 2.3 ! | 0-4 |
| Palpebral opening 4 | 3.5 | 2 ! | 2.5 ! | 4-0 |

! = The symbol indicates that the results are statistically different from vehicle treated animals.

Preliminary analysis of the excised tumours is currently ongoing. However, early Haematoxylin and Eosin (H&E) staining data revealed notable differences in mitotic activity across the treatment groups. Specifically, mitotic counts (measured per 2.37 $mm^2$ at 10× magnification) were significantly reduced in the cisplatin group (14) and the combination group (20) compared to the vehicle control group (28). Interestingly, the EpigenAU/11-treated group exhibited an increased mitotic count (34), suggesting that while EpigenAU/11 was effective in reducing tumour mass, its mechanism of action may not be directly linked to reducing mitotic activity as seen with cisplatin. The combination treatment's ability to reduce mitotic activity while maintaining strong tumour control points to a complex interplay between EpigenAU/11 and cisplatin, possibly involving complementary mechanisms that warrant further investigation. The Table below shows the results of Haematoxylin and Eosin (H&E) staining analysis showing mitotic counts in tumour sections from vehicle, cisplatin, EpigenAU/11, and combination treatment groups. Mitotic figures were counted in a 2.37 mm$^2$ area at 1Ox magnification.

| MITOSIS (Amount of mitosis in 2.37 mm$^2$; 10x) | |
| --- | --- |
| TREATMENT | MITOSIS |
| Vehicle | 28 ($\pm$5) |
| EpigenAU/11 | 34 ($\pm$4) |
| Cisplatin | 14 ($\pm$8) |
| Combination | 20 ($\pm$1) |

8. Biodegradability Test According to OECD 301F:1992

Biodegradation is the process by which organic substances are decomposed by microorganisms into the simplest natural building blocks (e.g., $CO_2$, $H_2O$, and $NH_3$) that can be integrated into natural biogeochemical cycles.

The evaluation of the biodegradability of chemicals is one of the main issues in environmental risk assessment. Biodegradability tests are designed to evaluate, under batch conditions, a chemical substance as the sole carbon source for the survival of microfauna. The ready biodegradation tests (RBT) are the basis of the integrated testing strategy on pure substance biodegradation. They are a series of tests (from no. 301A to 301F and no. 310) proposed by the Organization for Economic Co-operation and Development (OECD). Microorganisms and the tested substance are usually incubated in a buffered pH 7 medium containing N, P, and a trace element (named the "mineral medium"). The kinetics of biodegradation is monitored during at least 28 days by the evaluation of metabolic parameters such as oxygen consumption, carbon dioxide production, or dissolved organic carbon consumption. The RBT measures ultimate biodegradability, or complete biodegradation and a chemical can be classified as readily biodegradable if has passed one of the RBTs.

The term primary biodegradation indicates the structural modification of a substance caused by a biological event, which results in the loss of a specific property of that substance. It can be calculated from supplemental chemical analysis for parent compounds made at the beginning and end of the tests (OECD 301, 310).

On the test item, EpigenAU/11, the analysis for the evaluation in an aqueous medium of the aerobic biodegradability has been performed following screening method described in OECD 301 F: 1992

The method is based on the determination of oxygen consumption by an agitated solution or suspension of the test chemical in a mineral medium inoculated with non adapted microorganisms, with measurement taking place automatically over a period of 28 days in a respirometer placed in a closed environment and in the dark and at a controlled temperature of 22$\pm$2° C.; the carbon dioxide developed is adsorbed by potassium hydroxide. Biodegradability is expressed as the percentage of oxygen consumed (corrected by blank consumption) relative to theoretical uptake (ThOD) or COD if determination of the former is not possible. The percentage of primary biodegradability is also calculated by an additional specific chemical analysis performed at the beginning and end of the test.

Reagents and Substances

This method involves working with the following reagents and substances:

A) Test substance reference standard EpigenAU/11 DoE2 in 50 mg/l dilution in mineral medium;

B) Mineral medium for solubilization of the test substance consisting of the following 4 solutions (A, B, C and D) brought to 11 with ultrapure water:

10 ml Solution A: 8.50 g $KH_2PO_4$+21.75 g $K_2HPO_4$+33.40 g $Na_2HPO_4$ di-hydrate+0.50 g $NH_4Cl$ brought to 1 lt with ultrapure water and with final pH at 7.4;

1 ml Solution B: 27.50 g $CaCl_2$) anhydrous made to 1 lt with ultrapure water;

1 ml Solution C: 22.50 g $MgSO_4$ heptahydrate brought to 1 lt with ultrapure water;

1 ml Solution D: 0.25 g $FeCl_3$ hexahydrate brought to 1 lt with ultrapure water.

C) Bacterial inoculum: The test substance was added to appropriate inoculum and obtained by taking activated sludge in equal aliquots.

D) Chemical Standard for BOD determination at 5 to 28 days consisting of various solutions of Sodium Acetate anhydrous analytical purity.

Assay Execution

Sample Preparation

The sample was treated according to the procedure reported in the respirometric-manometric method no. 301F (OECD). To be able to have the correct registration by using the BOD sensor and enough material to perform the planned instrumental analysis. Sodium acetate was used as the reference substance. Tests were done at a constant temperature of 22 C.

Inoculum Preparation

The inoculum was prepared by collecting 9 samples of activated sludge from different places and mixing them in equivalent volume. The inoculum is oxygenated, stirred and fed with glucose, peptone, dibasic potassium phosphate, and the values of redox potential, oxygen consumption and total dry matter are monitored daily. The dry substance was determined at 100 C to measure the same quantity (30 mg/mL) in the vessels containing the test substance.

Inoculum Composition

The inoculum was obtained by mixing active sludge from 8 different sectors and river water taken from two different rivers in equal parts. The assembled inoculum was oxygenated, stirred and fed with glucose, peptone and monopotassium orthophosphate. Oxygen, redox, and total suspended solid values were monitored daily. Before the use of inoculum, the total dry matter is determined.

The composition of the microfauna was determined by optical microscope analysis.

Reference Substance

Manometric respirometric method also requires the conduct of another test with ultrapure water fortified with a standard (sodium acetate) to assess proper performance and instrumental reliability.

Blank

Blank analysis was performed on inoculated mineral media to assess the contribution of the liquid and inoculum to the BOD value of the finished product.

Conditions of the Assay:

The containers are placed inside thermostat refrigerators set at 22$\pm$2° C. and kept in constant agitation by mechanical movement of the anchor; all this is carried out for 28 days by measuring every 6 h automatically and via wireless the oxygen depression value, which at 28 days will be the absolute biodegradability value of the sample under investigation.

Test Results

EpigenAU/11:

| Sample name | Analysis duration [d] | Sampling time [h] | Last value of BOD [mg/l] | Average BOD [mg/l] | SD BOD [mg/l] |
|---|---|---|---|---|---|
| EpigenAU/11 Blend 50 mg-L in mineral medium + inoculum. Test 1 | 28 | 6 | 58.7 | 59.5 | 2.5 |
| EpigenAU/11 Blend 50 mg-L in mineral medium + inoculum Test 2 | 28 | 6 | 34.5 | | |
| EpigenAU/11 Blend 50 mg-L in mineral medium + inoculum. Test 3 | 28 | 6 | 56.3 | | |
| EpigenAU/11 Blend 50 mg-L in mineral medium + inoculum. Test 4 | 28 | 6 | 62.0 | | |
| EpigenAU/11 Blend 50 mg-L in mineral medium + inoculum. Test 5 | 28 | 6 | 60.9 | | |

The values in bold were excluded from the calculations for evaluating the ready biodegradability of the product, as they were considered abnormal.

Blank:

| \ name | Analysis duration [d] | Sampling time [h] | Last value of BOD [mg/l] | Average BOD [mg/l] | SD BOD [mg/l] |
|---|---|---|---|---|---|
| Mineral medium + inoculum Test 1 | 28 | 6 | 7.8 | 10.1 | 2.1 |
| Mineral medium + inoculum Test 2 | 28 | 6 | 10.5 | | |
| Mineral medium + inoculum Test 3 | 28 | 6 | 12.0 | | |

The test shows a contribution to BOD between inoculum and mineral medium of 10.1 mg/l, a value that should be used for BOD correction of EpigenAU/11 product 50 mg/l mixture.

The mean value falls within the positive range of the test, which is between 10 and 50 mg/l.

Reference Substance:

| | ThOD | BOD (ppm) | | | | |
|---|---|---|---|---|---|---|
| Sample | (mg/l) | Day 1 | Day 7 | Day 14 | Day 21 | Day 28 |
| Sodium Acetate 50 mg/L | 31 | 10.2 | 25.6 | 28.7 | 30.3 | 32.5 |

The positivity of the test results from the following evidence:

A) The obtained value (32.5 ppm Biochemical Oxygen Demand, BOD) of the chemical standard is within the positivity range of the test, which is 31±5 ppm Theoretical demand of Oxygen (ThOD) so the chemical control was positive.

B) After only 7 days, the BOD value is 78.77% of the total;

C) After 14 gg the BOD value stands at 88.31% of the total.

The calculation of biodegradation is done at each sampling time for the reference substance, test sample and blank.

Total biodegradation of sample has been calculated using the equation:

BOD: (average of mg/L of $O_2$ consumed of the test substance)–(average of mg/L of $O_2$ consumed of the blank)/mg/L test substance in the container.

There is no evidence of nitrite and nitrate production, based on that no correction for nitrification/denitrification was performed.

mg/l $O_2$ consumed by the test substance: 59.5 mg/L.

mg/l $O_2$ consumed by the blank: 10.1 mg/L.

mg/l $O_2$ consumed by nitrification in the product: / mg/l test chemical in the container: 50 mg/L

BOD average calculated=0,988 mg of 02 for mg test substance.

In order to calculate the percentage degradation and thus the ready biodegradation, Chemical Oxygen Demand (COD) was evaluated by hot acid dichromate oxidation in ultrapure deionized water; tests were conducted on a 50 mg/l of EpigenAU/11 solution obtaining cod of 67.1 mg/l.

COD=(mg/l $O_2$ consumed by the test substance)/ (mg/l test substance in the container)

COD=1.342 mg of $O_2$ for mg of test substance.

Average of percentage degradation at 28 days: BOD average corrected by blank deduction/COD pure substance= (0.988/1.342)*100=73.6%

Interpretation of Results

Validity Criteria

The test is considered valid when:

the average biodegradation rate of the reference substance is above 60% after 14 days of incubation;

the difference of the extremes of the replicate values at the plateau at the end of the test is less than 20%;

the oxygen demand of the blank is not more than 60 mg O$_2$/L.

Interpretation

A substance is considered readily biodegradable when the level of biodegradation reached within 10 days after the start of degradation, considered to be the time when 10% of the substance has been degraded (10-day window), exceeds 60% and in addition the level of biodegradation reached at 28 days is >60%.

Results

Validity criteria of the test were satisfied.

The assessment regarding the biodegradability of the substance EpigenAU/11 blend at concentration 50 mg/l is that during the conducted experiment the product showed ready biodegradability under the conditions applied in the manometric respirometric test developed according to EC regulation 440/2008 updated to reg. 640/2012—part c: methods for determining ecotoxicity—method c.4. Part v—(method c.4-d)+OECD 301F: 1992; in fact, the product exceeded 60% biodegradation within ten days after reaching 10%, meeting the validity criteria of the method.

Product EpigenAU/11 at 50 mg/L concentration showed no toxic effects on the activity of microorganisms at the tested concentration reaching 73.6% of the associated theoretical COD value and thus showing well-present biotic activity.

Approximately 3.30 mg/L of total suspended solids were found at the end of the test, which attested to a decrease in active matter (bacteria) compared to the 30 mg/L inoculated; this biomass was completely depleted and devoid of the viable forms found at the beginning of the test, a typical situation of mud at the end of its life due to nutrient deficiency.

On the basis of results obtained, interpreted in accordance with OECD 301F:1992, the test item Product EpigenAU/11 resulted readily biodegradable in aerobic conditions.

9. Functional Reproducibility and Comparison of Different Batches (DoEs) OF EpigenAU/11

In PCT/IB2024/054526, the Applicant has disclosed a method for quality control and validation of therapeutic or beneficial products comprising natural matrices. As such products have a therapeutic effect that is not ascribable to a specific API and as their quali-quantitative composition is variable due to the variability of the plant raw material from which they derive, a new quality control and validation process, based on the biological activity of the product tested (the biological activity being analysed in cell based assays relevant to the therapeutic or beneficial effect of the product under examination and on the modification induced by the product batches to be validated compared to the activity of a reference batch of the product) and on the spectroscopy spectra of the reference product and other compliant batches for the determination of the acceptability spectroscopy values to be used in the subsequent validation.

The method has proved to be reliable and has been used in the present application in order to compare different batches (DoEs) of EpigenAU/11 for quality control and for comparative analysis of said DoEs.

The following examples show that, notwithstanding the plant origin and batch-to-batch quali-quantitative variability of EpigenAU/11 different DoEs, the product can undergo reliable quality control and support the formulation ranges claimed. The data provided also show that the product has to be treated as an "unity of activity" and not as a precisely defined sum of APIs.

Figure 26:
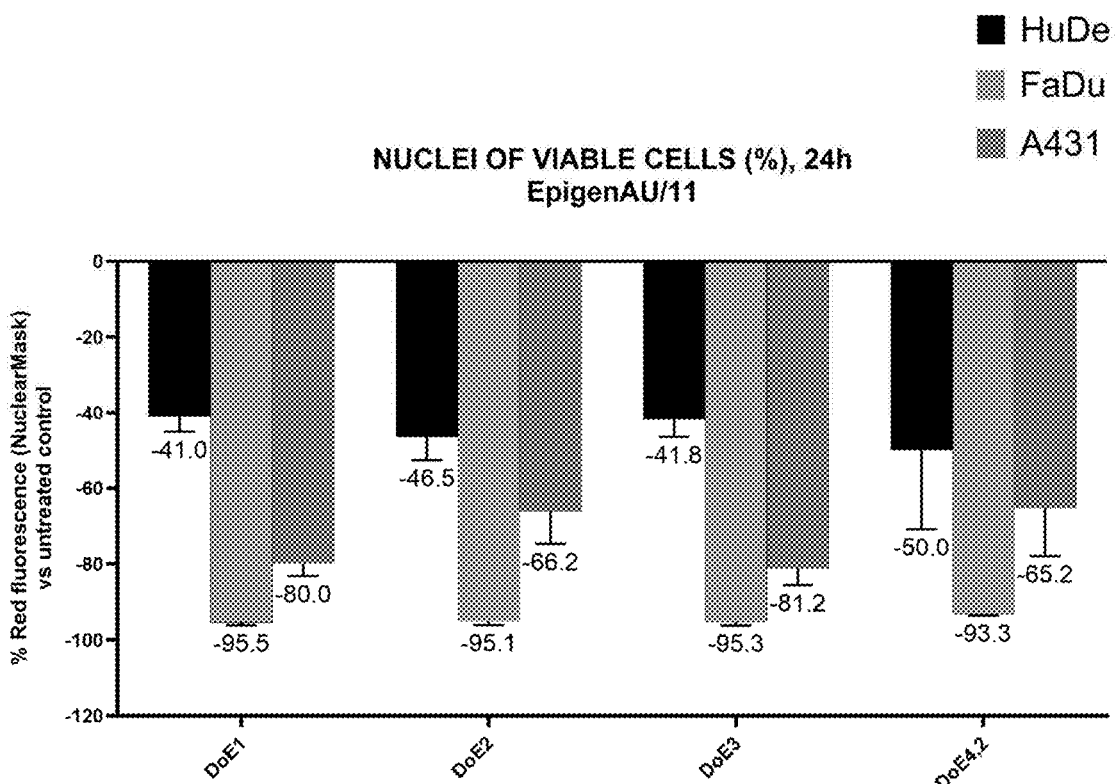

FIG. 26 shows graphs reporting cell number of tumour cell lines treated for 24 hours with EpigenAU/11 at 0.66 mg/ml (see example 1 for protocols) testing different batches (DoEs 1, 2, 3 and 4.2) of EpigenAU/11. The graph clearly shows that the results on the cell-based assay testing cytotoxicity are totally superimposable for the four quality validated batches.

9.1 Description of EpigenAU/11 DoEs

The study of biological activity and chemical characterization has been extended to three additional formulations of EpigenAU/11.

To define the four formulations in the correct plant-system ratios, each has been identified using the term DoE (Design of Experiments). Furthermore, to achieve one of the invention's objectives, formulation permutations of the individual DoEs have also been generated. In all these formulations, the *Agave* content (0.89%) and its production batch have remained unchanged.

A summary table is provided below:

| Product | Batch SP1 + Batch SP2 | W/W Ratio |
|---|---|---|
| EpigenAU/11_DoE1 | 24B1643 + 24B1201 | 36.05% + 63.06% |
| EpigenAU/11_DoE2 | 23C3017 + 23B2816 | 36.05% + 63.06% |
| EpigenAU/11_DoE3 | 23C3017 + 24B1201 | 36.05% + 63.06% |
| EpigenAU/11_DoE4 | 24B1643 + 23B2816 | 36.05% + 63.06% |
| Product Permutation | Batch SP1 + Batch SP2 | W/W Ratio |
| CQ1_Lot2 | 23C3017 + 23B2816 | 10% + 89.11% |
| DoE2.1 | 23C3017 + 23B2816 | 20% + 79.11% |
| DoE2.2 | 23C3017 + 23B2816 | 30% + 69.11 |
| DoE2.3 | 23C3017 + 23B2816 | 50% + 49.11% |
| CQ1_Lot3 | 23C3017 + 24B1201 | 10% + 89.11% |
| DoE3.1 | 23C3017 + 24B1201 | 20% + 79.11% |
| DoE3.2 | 23C3017 + 24B1201 | 30% + 69.11 |
| DoE3.3 | 23C3017 + 24B1201 | 50% + 49.11% |
| DoE4.1 | 23C3017 + 23B2816 | 20% + 79.11 |
| DoE4.2 | 23C3017 + 23B2816 | 30% + 69.11% |
| DoE4.2 | 23C3017 + 23B2816 | 50% + 49.11% |

Note 1.
SP1 = Plant system 1
Note 2.
SP2 = Plant system 2
Note 3.
DoE = Design of Experiments
Note 4.
CQ1_LotX = CQ1 indicates "formulative poor quality" i.e. formulations considered a priori of poor quality;; X identifies the corresponding DoE.

The plant system code is provided merely to show that different lots of plant system 1 and 2 were used (obtained from different batches of the starting raw materials with the same preparation protocol indicated in example 1) and said different lots were used in different combinations for preparing DoEs 1-4 and their related permutations.

9.2 Targeted Metabolomic and miRNA-seq of DoEs 1, 2, 3, 4 and 4.2

To appreciate whether the final matrix constituting product A is characterized by the matrix effect, a series of analyses to grasp the product's features on different aspects was carried out on the batches reported above. A targeted metabolomics analysis capable of identifying most of such molecular components, was carried out on different batches of the product) together with the other analysis reported herein.

The product, as described above, consists of two distant arrays of plant coextracts and one extract assembled in given percentages and resulting in a new final plant matrix. Several analytical techniques were used to identify and quantify compounds belonging to major classes present in plants.

Although metabolomic analysis does not allow to appreciate the dynamic changes within the component of the matrix, it allows a "picture" of the composition in the moment the analysis is carried out.

In the following analysis each individual component (plant metabolite) is specifically researched, for this reason the analysis is called "targeted metabolomics". This analysis allows to capture a frame on the qualitative data, by determining the chemical compounds present in the material, and quantitative data, by defining the concentrations of each compound in the material.

For DoEs 1, 2, 3, 4 and 4.2, a qualitative and quantitative characterization of as many primary and secondary metabolites as possible was carried out using an "omic" approach, the targeted metabolomics analysis, based on the use of multiple analytical methodologies.

FIG. 27 shows the results, of targeted metabolomics referred to the main chemical classes (phenols, tannins, organic acids, sugars and derivatives thereof, inorganic compounds) of five batches of EpigenAU/11, DoEs 1, 2, 3, 4 and 4.2. The figure clearly shows that each batch tested differs from each other and from the reference standard EpigenAU/11_DoE2 in their quali-quantitative composition.

The analytical methods used for the chemical characterization of each batch are the same reported in Example 6. The most appropriate analytical techniques have been adopted based on the chemical nature of the classes of compounds present. The analysis with chromatographic methods combined with different detection techniques (e.g., LC each combined with a suitable detector), made it possible to identify and quantify, as appropriate, the organic compounds. The inductively coupled plasma analysis using a single quadrupole mass spectrometer (ICP-MS) or an optical emission spectrometer (ICP-PAD) made it possible to establish the levels of elements present, while the anions were determined by ion chromatography and conductivity detector.

The results, that are summarised in the tables below, show an appreciable composition variability of each batch and underline the impossibility to recapitulate the properties of the matrix as the sum of its single components. The work performed and reported herein (see cell-based assay results) together with the data below, demonstrates that the biological effect elicited by product cannot be recapitulated by the sum of the effects elicited by the single molecular components but is the result of interconnections and interactions among the components: the matrix effect. This translates into the impossibility to formally define a structure-activity relationship (SAR) according to the principles canonically applied to APIs.

| METH-OD | COMPOUNDS | Epigen AU/11 DoE1 (%) | Epigen AU/11 DoE2 (%) | Epigen AU/11 DoE3 (%) | Epigen AU/11 DoE4 (%) | Epigen AU/11 DoE4.2 (%) | DoE1 (d %) | DoE3 (d %) | DoE4 (d %) | DoE4,2 (d %) |
|---|---|---|---|---|---|---|---|---|---|---|
| | PHENOLS, Total | 1.019 | 1.643 | 0.737 | 2.899 | 2.124 | 37.98 | 55.15 | 76.48 | 29.31 |
| | FLAVO-NOIDS, Total | 0.070 | 0.126 | 0.065 | 0.077 | 0.195 | 44.35 | 48.04 | 38.48 | 54.78 |
| | FLAVA-NONES, Total | 0.001 | 0.001 | 0.001 | 0.001 | <LoQ | 7.69 | 0.00 | 0.00 | / |
| A | Naringenin & Pinobanksin (AS: Naringenin) | 0.001 | 0.001 | 0.001 | 0.001 | <LoQ | 7.69 | 0.00 | 0.00 | / |
| | FLAVONES, Total | 0.024 | 0.040 | 0.028 | 0.028 | 0.148 | 38.25 | 29.96 | 28.39 | 272.54 |
| A | Acacetin | <LoQ | <LoQ | 0.001 | <LoQ | 0.002 | / | / | / | / |
| A | Apigenin-7-O-glucuronide | <LoQ | <LoQ | <LoQ | <LoQ | <LoQ | / | / | / | / |
| A | Hispidulin | <LoQ | <LoQ | <LoQ | <LoQ | 0.002 | / | / | / | / |
| A | Isorhoifolin | <LoQ | <LoQ | <LoQ | <LoQ | <LoQ | / | / | / | / |
| A | Isovitexin | <LoQ | 0.003 | 0.002 | <LoQ | <LoQ | / | 41.38 | / | / |
| A | Linarin | 0.004 | 0.005 | 0.004 | 0.004 | <LoQ | 18.67 | 13.40 | 19.92 | / |
| A | Luteolin-7-O-Rutinoside | 0.009 | 0.012 | 0.010 | 0.017 | 0.024 | 29.23 | 19.38 | 44.29 | 99.31 |
| A | Orientin & Homoorientin (AS: Orientin) | 0.004 | <LoQ | 0.004 | <LoQ | <LoQ | / | / | / | / |
| A | Vicenin-2 | 0.008 | 0.011 | 0.007 | 0.007 | 0.010 | 29.24 | 33.61 | 34.19 | 7.58 |
| A | Vitexin-2"-O-rhamnoside | <LoQ | 0.009 | <LoQ | <LoQ | nd | / | / | / | / |
| | FLAVO-NOLS, Total | 0.044 | 0.085 | 0.036 | 0.048 | 0.047 | 47.99 | 57.20 | 43.78 | 44.39 |
| A | Isorhamnetin-3-O-glucoside | <LoQ | <LoQ | <LoQ | <LoQ | 0.023 | / | / | / | / |
| A | Kaempferol-3-O-rutinoside | 0.011 | 0.047 | 0.013 | 0.010 | 0.004 | 76.52 | 72.38 | 78.49 | 91.54 |
| A | Kaempferol-7-O-neohesperido-side | 0.022 | <LoQ | <LoQ | 0.020 | 0.007 | / | / | / | / |

| METH-OD | COMPOUNDS | Epigen AU/11 DoE1 (%) | Epigen AU/11 DoE2 (%) | Epigen AU/11 DoE3 (%) | Epigen AU/11 DoE4 (%) | Epigen AU/11 DoE4.2 (%) | DoE1 (d %) | DoE3 (d %) | DoE4 (d %) | DoE4,2 (d %) |
|---|---|---|---|---|---|---|---|---|---|---|
| A | Luteolin-4'-O-glucoside & Kaempferol-3-O-glucoside & Quercitrin (AS: Quercitrin) | 0.004 | 0.016 | 0.009 | 0.007 | 0.007 | 75.48 | 41.63 | 57.19 | 52.03 |
| A | Quercetin | <LoQ | <LoQ | <LoQ | <LoQ | <LoQ | / | / | / | / |
| A | Rutin | 0.008 | 0.023 | 0.014 | 0.011 | 0.006 | 65.33 | 36.74 | 53.17 | 73.24 |
|  | PHENOLIC ACIDS, Total | 0.034 | 0.014 | 0.016 | 0.017 | 0.018 | 154.07 | 14.81 | 28.15 | 32.23 |
| A | Protocate-chuic acid | 0.034 | 0.014 | 0.016 | 0.017 | 0.018 | 154.07 | 14.81 | 28.15 | 32.23 |
|  | PHENYL-PROPA-NOIDS, Total | 0.912 | 1.502 | 0.654 | 2.803 | 1.902 | 39.29 | 56.49 | 86.58 | 26.63 |
|  | COUMA-RINS, Total | <LoQ | <LoQ | <LoQ | <LoQ | <LoQ | / | / | / | / |
| A | Scopoletin | <LoQ | <LoQ | <LoQ | <LoQ | <LoQ | / | / | / | / |
|  | HYDROXY-CINNAMIC ACIDS, Total | 0.912 | 1.502 | 0.654 | 2.803 | 1.902 | 39.29 | 56.49 | 86.58 | 26.63 |
| A | 3,4-Dicaffeoyl-quinic acid & 3,5-Dicaffeoyl-quinic acid (AS: 3,4-Dicaffeoyl-quinic acid) | 0.237 | 0.324 | 0.121 | 0.789 | 0.414 | 26.82 | 62.53 | 143.52 | 27.80 |
| A | 4,5-Dicaffeoyl-quinic acid | 0.072 | 0.194 | 0.050 | 0.336 | 0.272 | 63.00 | 74.32 | 73.67 | 40.66 |
| A | 4-Coumaric acid | 0.006 | 0.008 | 0.008 | 0.004 | 0.006 | 25.60 | 1.42 | 47.40 | 25.34 |
| A | Caftaric acid | <LoQ | 0.034 | 0.018 | <LoQ | <LoQ | / | 47.64 | / | / |
| A | Cryptochloro-genic acid & Chlorogenic acid (AS: Chlorogenic acid) | 0.498 | 0.789 | 0.303 | 1.579 | 0.942 | 36.93 | 61.55 | 100.15 | 19.34 |
| A | Curcumin | 0.094 | 0.056 | 0.075 | 0.075 | 0.087 | 67.64 | 33.64 | 34.32 | 55.87 |
| A | Cynarin | <LoQ | 0.016 | <LoQ | 0.014 | 0.014 | / | / | 15.40 | 13.48 |
| A | Demethoxy-curcumin | <LoQ | 0.023 | 0.034 | <LoQ | 0.084 | / | 48.39 | / | 261.05 |
| A | Ferulic acid | 0.006 | 0.005 | 0.006 | 0.005 | 0.009 | 8.29 | 8.39 | 6.32 | 71.32 |
| A | Neochloro-genic acid | <LoQ | 0.053 | 0.038 | <LoQ | 0.074 | / | 27.47 | / | 40.70 |
|  | PHLORO-GLUCIN-OLS, Total | <LoQ | <LoQ | <LoQ | <LoQ | nd | / | / | / | / |
| A | Arzanol | <LoQ | <LoQ | <LoQ | <LoQ | nd | / | / | / | / |
|  | SALICYL-ATES, Total | <LoQ | <LoQ | <LoQ | <LoQ | 0.005 | / | / | / | / |
| A | Salicylic acid | <LoQ | <LoQ | <LoQ | <LoQ | 0.0047 | / | / | / | |
|  | SIMPLE PHENOLS, Total | 0.003 | 0.001 | 0.002 | 0.001 | 0.005 | 123.95 | 94.33 | 27.04 | 304.22 |
| A | Protocatechu-aldehyde | <LoQ | <LoQ | <LoQ | <LoQ | <LoQ | / | / | / | / |
| A | Vanillin | 0.003 | 0.001 | 0.002 | 0.001 | 0.005 | 123.95 | 94.33 | 27.04 | 304.22 |
|  | TANNINS, Total | 0.114 | 0.115 | 0.046 | 0.217 | 0.113 | 1.13 | 60.57 | 87.69 | 2.30 |

-continued

| METH-OD | COMPOUNDS | Epigen AU/11 DoE1 (%) | Epigen AU/11 DoE2 (%) | Epigen AU/11 DoE3 (%) | Epigen AU/11 DoE4 (%) | Epigen AU/11 DoE4. 2 (%) | DoE1 (d %) | DoE3 (d %) | DoE4 (d %) | DoE4, 2 (d %) |
|---|---|---|---|---|---|---|---|---|---|---|
| | CONDENSED TANNINS, Total | 0.114 | 0.115 | 0.046 | 0.217 | 0.113 | 1.13 | 60.57 | 87.69 | 2.30 |
| A | Procyanidin B2 | 0.114 | 0.115 | 0.046 | 0.217 | 0.113 | 1.13 | 60.57 | 87.69 | 2.30 |
| | TANNIN MONO-MERS, Total | <LoQ | <LoQ | <LoQ | <LoQ | <LoQ | / | / | / | / |
| | GALLO-TANNINS MONO-MERS, Total | <LoQ | <LoQ | <LoQ | <LoQ | <LoQ | / | / | / | / |
| A | Gallic acid | <LoQ | <LoQ | <LOQ | <LoQ | <LoQ | / | / | / | / |
| | ORGANIC ACIDS, Total | 5.272 | 10.331 | 7.295 | 5.835 | 5.909 | 48.97 | 29.38 | 43.52 | 42.81 |
| | MONO-CARBOXY-LIC ACIDS, Total | 1.116 | 4.660 | 2.473 | 1.116 | 0.929 | 76.05 | 46.92 | 76.05 | 80.07 |
| B | Lactic acid | 1.116 | 4.660 | 2.473 | 1.116 | 0.929 | 76.05 | 46.92 | 76.05 | 80.07 |
| | DICARBOX-YLIC ACIDS, Total | 0.062 | 0.035 | 0.052 | 0.040 | 0.042 | 79.20 | 50.94 | 16.51 | 20.23 |
| B | Fumaric acid | 0.062 | 0.035 | 0.052 | 0.040 | 0.042 | 79.20 | 50.94 | 16.51 | 20.23 |
| | TRI-CARBOXY-LIC ACIDS, Total | 4.094 | 5.636 | 4.770 | 4.678 | 4.938 | 27.37 | 15.37 | 17.00 | 12.38 |
| B | Citric acid | 4.094 | 5.636 | 4.770 | 4.678 | 4.938 | 27.37 | 15.37 | 17.00 | 12.38 |
| | SUGARS AND DERIV-ATIVES, Total | 11.253 | 7.683 | 10.090 | 8.846 | 8.648 | 46.48 | 31.33 | 15.14 | 12.56 |
| | MONO-SACCH-ARIDES, Total | 9.755 | 6.591 | 8.980 | 7.365 | 7.281 | 48.01 | 36.25 | 11.76 | 10.48 |
| C | Arabinose | <LoQ | <LoQ | <LoQ | <LoQ | <LoQ | / | / | / | / |
| C | Fructose | 6.041 | 4.402 | 6.162 | 4.281 | 4.157 | 37.25 | 39.99 | 2.75 | 5.55 |
| C | Galactose | 0.144 | 0.118 | 0.123 | 0.139 | 0.135 | 21.49 | 4.01 | 17.48 | 14.30 |
| C | Glucose | 3.570 | 2.071 | 2.695 | 2.946 | 2.989 | 72.40 | 30.14 | 42.26 | 44.33 |
| C | Mannose | <LoQ | <LoQ | <LoQ | <LoQ | <LoQ | / | / | / | / |
| C | Rhamnose | <LoQ | <LoQ | <LoQ | <LoQ | <LoQ | / | / | / | / |
| | DISACCH-ARIDES, Total | 1.499 | 1.092 | 1.110 | 1.481 | 1.366 | 37.22 | 1.65 | 35.57 | 25.10 |
| C | Lactose | <LoQ | <LoQ | <LoQ | <LoQ | <LoQ | / | / | / | / |
| C | Maltose | 0.926 | 0.887 | 0.608 | 1.205 | 1.091 | 4.37 | 31.44 | 35.81 | 22.90 |
| C | Sucrose | 0.573 | 0.205 | 0.502 | 0.276 | 0.276 | 179.48 | 144.95 | 34.53 | 34.63 |
| | IN-ORGANIC COM-POUNDS, Total | 7.645 | 8.531 | 7.938 | 8.238 | 8.475 | 10.38 | 6.95 | 3.43 | 0.65 |
| | MACRO-ELE-MENTS, Total | 7.571 | 8.459 | 7.859 | 8.171 | 8.404 | 10.49 | 7.09 | 3.40 | 0.64 |
| D | Calcium | 0.841 | 0.583 | 0.778 | 0.646 | 0.609 | 44.40 | 33.54 | 10.87 | 4.55 |
| D | Magnesium | 0.554 | 0.585 | 0.557 | 0.583 | 0.572 | 5.27 | 4.87 | 0.40 | 2.21 |
| D | Phosphorus | 0.884 | 1.027 | 0.969 | 0.942 | 0.933 | 13.86 | 5.65 | 8.21 | 9.12 |
| D | Potassium | 4.809 | 5.998 | 5.061 | 5.747 | 6.017 | 19.82 | 15.63 | 4.19 | 0.32 |
| D | Sodium | 0.482 | 0.266 | 0.495 | 0.253 | 0.272 | 81.14 | 86.01 | 4.88 | 2.36 |
| | MICRO-ELE-MENTS, Total | 0.045 | 0.041 | 0.051 | 0.035 | 0.037 | 10.47 | 23.95 | 13.48 | 9.76 |
| D | Chromium | 0.0005 | 0.0014 | 0.0006 | 0.0013 | 0.001 | 64.34 | 57.08 | 7.26 | 0.43 |

-continued

| METH-OD | COMPOUNDS | Epigen AU/11 DoE1 (%) | Epigen AU/11 DoE2 (%) | Epigen AU/11 DoE3 (%) | Epigen AU/11 DoE4 (%) | Epigen AU/11 DoE4. 2 (%) | DoE1 (d %) | DoE3 (d %) | DoE4 (d %) | DoE4, 2 (d %) |
|---|---|---|---|---|---|---|---|---|---|---|
| D | Cobalt | 4.33325E−05 | 6.68316E−05 | 4.53858E−05 | 6.47784E−05 | 6.77109E−05 | 35.16 | 32.09 | 3.07 | 1.32 |
| D | Copper | 0.0023 | 0.0023 | 0.0023 | 0.0024 | 0.002 | 0.48 | 2.05 | 2.53 | 1.97 |
| D | Iron | 0.0152 | 0.0166 | 0.0148 | 0.0170 | 0.018 | 8.52 | 10.72 | 2.20 | 10.33 |
| D | Manganese | 0.0193 | 0.0107 | 0.0213 | 0.0088 | 0.009 | 80.23 | 98.43 | 18.20 | 17.83 |
| D | Molybdenum | 4.3323 1E−05 | 7.3665 7E−05 | 4.4874 5E−05 | 7.2114 2E−05 | 7.6837 8E−05 | 41.19 | 39.08 | 2.11 | 4.31 |
| D | Nickel | 0.0006 | 0.0011 | 0.0007 | 0.0010 | 0.001 | 46.44 | 37.07 | 9.38 | 7.54 |
| D | Selenium | 8.53689E−06 | 3.42504E−06 | 3.42504E−06 | 8.53689E−06 | 7.10421E−06 | 149.25 | 0.00 | 149.25 | 107.42 |
| D | Tin | <LoQ | <LoQ | <LoQ | <LoQ | <LoQ | / | / | / | / |
| D | Vanadium | 3.0784E−05 | 5.06679E−05 | 3.0784E−05 | 5.06679E−05 | 5.5529E−05 | 39.24 | 39.24 | 0.00 | 9.59 |
| D | Zinc | 0.007 | 0.009 | 0.011 | 0.005 | 0.005 | 16.11 | 28.03 | 44.14 | 44.08 |
|  | OTHER ELEMENTS, Total | 0.029 | 0.031 | 0.028 | 0.032 | 0.034 | 7.25 | 9.47 | 2.22 | 8.23 |
| D | Aluminium | 0.016 | 0.023 | 0.016 | 0.023 | 0.025 | 29.56 | 31.06 | 1.51 | 10.46 |
| D | Antimony | <LoQ | <LoQ | <LoQ | <LoQ | <LoQ | / | / | / | / |
| D | Arsenic | 5.23436E−06 | 8.05812E−06 | 5.23436E−06 | 8.05812E−06 | 0.00001 | 35.04 | 35.04 | 0.00E+00 | 9.59 |
| D | Barium | 0.0017 | 0.0007 | 0.0014 | 0.0010 | 0.001 | 140.59 | 102.74 | 37.85 | 32.19 |
| D | Boron | 0.002 | 0.002 | 0.002 | 0.002 | 0.002 | 14.93 | 10.16 | 4.76 | 4.19 |
| D | Cadmium | 0.000 | <LoQ | 0.000 | <LoQ | <LoQ | / | / | / | / |
| D | Gadolinium | <LoQ | <LoQ | <LoQ | <LoQ | <LoQ | / | / | / | / |
| D | Gallium | 5.43842E−06 | 6.63549E−06 | 5.43842E−06 | 0.000007 | 0.000007 | 18.04 | 18.04 | / | 9.59 |
| D | Gold | <LoQ | <LoQ | <LoQ | <LoQ | <LoQ | / | / | / | / |
| D | Iridium | <LoQ | <LoQ | <LoQ | <LoQ | <LoQ | / | / | / | / |
| D | Lead | 3.67202E−05 | 2.37893E−05 | 3.54049E−05 | 2.51046E−05 | 0.000025 | 54.36 | 48.83 | 5.53 | 5.43 |
| D | Lithium | 0.00014 | 0.00017 | 0.00016 | 0.00015 | 0.00013 | 16.18 | 3.91 | 12.27 | 23.93 |
| D | Lutetium | <LoQ | <LoQ | <LoQ | <LoQ | <LoQ | / | / | / | / |
| D | Mercury | <LoQ | <LoQ | <LoQ | <LoQ | <LoQ | / |  | / | / |
| D | Palladium | <LoQ | <LoQ | <LoQ | <LoQ | <LoQ | / |  | / | / |
| D | Platinum | <LoQ | <LoQ | <LoQ | <LoQ | <LoQ | / | / | / | / |
| D | Rubidium | 0.0052 | 0.0020 | 0.0054 | 0.0018 | 0.002 | 155.70 | 165.36 | 9.66 | 8.94 |
| D | Ruthenium | <LoQ | <LoQ | <LoQ | <LoQ | <LoQ | / | / | / | / |
| D | Strontium | 0.0021 | 0.0017 | 0.0017 | 0.0020 | 0.002 | 25.84 | 4.77 | 21.07 | 13.81 |
| D | Tellurium | <LoQ | <LoQ | <LoQ | <LoQ | <LoQ | / | / | / | / |
| D | Thallium | 0.0000 | <LoQ | 0.0000 | <LoQ | <LoQ | / | / | / | / |
| D | Thorium | <LoQ | <LoQ | <LoQ | <LoQ | <LoQ | / | / | / | / |
| D | Titanium | 0.0014 | 0.0011 | 0.0014 | 0.0012 | 0.001 | 26.95 | 21.97 | 4.98 | 1.61 |
| D | Uranium | <LoQ | <LoQ | <LoQ | <LoQ | <LoQ | / | / | / | / |
| D | Ytterbium | <LoQ | <LoQ | <LoQ | <LoQ | <LoQ | / | / | / | / |

Note 1.
Bold indicate chemical macro classes.
Note 2.
% = compound concentration expressed as percentage of the whole matrix.
Note 3.
(d %) = percentage deviation: (|Reference DoE2 (%)-Test(%)|/(Reference DoE2 (%))×100).
Note 4.
The term "Total" refers to the sum of the value of the various compounds which forms the corresponding group.
Note 5.
<LdQ = below the limit of quantification.
Note 6.
/ = percentage deviation not quantifiable.
Note 7.
Nd = Not detectable In addition, qualitative miRNA characterization was also performed on ultracentrifuged samples from each batch (Method E) and the results show high metabolomic complexity together with the presence of miRNAs typical of living matter.

| miRNA Family | miRNA | DOE1_ 100K | DOE2_ 100K | DOE3_ 100K | DOE4_ 100K |
|---|---|---|---|---|---|
| miR159 | ath-miR159a |  | X | X | X |
|  | ath-miR159b-3p | X | X |  |  |
|  | ath-miR159c | X | X | X | X |
| miR160 | ath-miR160c-5p | X |  |  |  |
| miR162 | ath-miR162b-3p | X |  |  |  |
| miR164 | ath-miR164a | X | X |  |  |

-continued

| miRNA Family | miRNA | DOE1_ 100K | DOE2_ 100K | DOE3_ 100K | DOE4_ 100K |
|---|---|---|---|---|---|
| miR165 | ath-miR165a-3p | X |  |  | X |
|  | ath-miR165b |  | X | X |  |
| miR166 | ath-miR166a-3p | X | X | X | X |
|  | ath-miR166b-3p | X |  |  |  |
|  | ath-miR166c |  | X | X |  |
|  | ath-miR166d |  | X |  | X |
|  | ath-miR166e-3p |  | X |  | X |
|  | ath-miR166g | X | X |  | X |
| miR168 | ath-miR168a-3p |  | X |  |  |
|  | ath-miR168a-5p | X | X |  |  |
|  | ath-miR168b-5p |  |  | X |  |
| miR171 | ath-miR171c-5p |  | X |  |  |
| miR1888 | ath-miR1888a | X |  |  |  |

-continued

| miRNA Family | miRNA | DOE1_ 100K | DOE2_ 100K | DOE3_ 100K | DOE4_ 100K |
|---|---|---|---|---|---|
| miR319 | ath-miR319a | | | X | |
| | ath-miR319b | X | | | |
| | ath-miR319c | X | | X | |
| miR394 | ath-miR394a | | X | | |
| miR396 | ath-miR396a-5p | X | X | | |
| | ath-miR396b-3p | | X | | |
| miR5660 | ath-miR5660 | X | X | X | X |
| miR8175 | ath-miR8175 | X | X | X | X |

The results show that there are more or less marked quantitative fluctuations of the individual chemical and qualitative fluctuations of miRNA classes in the five batches of EpigenAU/11. These fluctuations, if taken as the reference parameter, would lead to an a priori expectation for these batches to have a different therapeutic action. The analysis here reported demonstrates that, despite the biological activity is maintained across all the different batches assessed, none of the single molecular components identified would respect the criteria set for a single API, thus demonstrating that the matrix cannot be considered as a compilation of APIs.

The product, through a physiological mechanism of action is capable to evoke, in biological systems, the same reaction relevant for the intended use.

This also highlights the fact that there are both structural and functional redundancy mechanisms maintained in products comprising or consisting of natural matrices, of a functional resilience (reaching the same result notwithstanding the individual differences among individuals of a same species) that is typical of the living matter.

9.3 Isotopic Abundance of DoEs 1, 2, 3, 4, 4.2

In order to evaluate the isotopic ratio between different batches of EpigenAU/11 product the analysis was performed on batches prepared from different starting materials.

The samples were sent to Istituto San Michele all'Adige (Fondazione Edmund Mach) and tested for stable isotopes as follows:

δ18O: Method PDP 7011:2010 REV. 0 (TC-IRMS), UNIT ‰ vs V-SMOW.
δ13C: Method PDP 7009:2017 REV. 2 (EA-IRMS), UNIT vs ‰ V-PDB
δ15N: Method PDP 7009:2017 REV. 2 (EA-IRMS), UNIT ‰ vs V-AIR.
δ34S: Method PDP 7013:2010 REV. 0 (EA-IRMS), UNIT ‰ vs V-CDT.

The results were as follows.
δ ratio of the main isotopes of the EpigenAU/11 batches:

| Product Batch | δ18O (‰) | δ13C (‰) | δ15N (‰) | δ34S (‰) |
|---|---|---|---|---|
| DoE 1 | +26.4 ± 1 | −28.4 ± 0.3 | +3 ± 0.6 | +5 ± 1 |
| DoE 2 | +25.6 ± 1 | −28.4 ± 0.3 | +3.2 ± 0.6 | +4.7 ± 1 |
| DoE 3 | +26.6 ± 1 | −28.6 ± 0.3 | +3.2 ± 0.6 | +5.4 ± 1 |
| DoE 4 | +26.1 ± 1 | −28.5 ± 0.3 | +3.6 ± 0.6 | +4.4 ± 1 |
| DoE 4.2 | +25.8 ± 1 | −28.3 ± 0.3 | +3.5 ± 0.6 | +4.7 ± 1 |

Also for these formulations the 14C activity of the gold standard provided no evidence of a synthetic source in the analysed material. The values δ18O, δ15N, δ34S and δ13C overlap among batches showing they are not affected by processing but only by the biological variability of the starting materials, thus confirming the high reproducibility of the production process according to conservation of this parameter. The analysis for the batches under study showed substantial similarity of values and maintenance of ratios during the manufacturing process (see also example 6 for reference).

10. Definition of the "Unit of Activity" of EpigenAU/11 Different Batches

All the assays carried out on various EpigenAU/11 formulations and DoEs, indicated that the product inherent quali-quantitative variable composition still results in a biological activity that is essentially maintained.

According to the results obtained in the cell viability assay on HuDe, FaDu and A431 cells (as in example 2) performed treating for 24 hrs with 0.66 mg/ml all the DoEs and permutations thereof within the ranges claimed, described in example 9.1, all DoEs and permutations tested maintain a relevant cytotoxicity against tumour cells and a selectivity in the protection of healthy cells.

In detail, the following protocol was used:
Cell Culture and Treatments

Human healthy Dermis fibroblasts (HuDe, IZSLER Brescia), and two cancer cell lines: human Pharynx Squamous Cell Carcinoma (FaDu, Cat #HTB-43, ATCC) and Epidermoid Carcinoma (A431, Cat #CRL-1555, ATCC), were kept in a humid incubator at 37° C., in an atmosphere enriched with 5% CO2. HuDe cells were amplified in Minimum Essential Medium (MEM, Cat #: 11095080, Gibco) containing 10% inactivated Foetal Bovine Serum (FBS, Cat #: 10270106, Gibco), streptomycin (100 µg/mL) and penicillin (100 U/mL) (Cat #: 15140122, Life Technologies) and sodium pyruvate (1 mM, Cat #: 11360039, Gibco); FaDu were amplified in Eagle's minimum essential medium (EMEM, Cat #: 30-2003 ATCC) containing 10% inactivated FBS, streptomycin (100 µg/mL) and penicillin (100 U/mL); A431 were amplified in Dulbecco's modified Eagle's medium (DMEM, Cat #: 31966-021, Gibco) containing 10% inactivated FBS, streptomycin (100 µg/mL) and penicillin (100 U/mL). Cells were cultured according to the supplier's specifications, enzymatically detached from the growth support and counted with an electronic cell counter (Invitrogen).

In vitro assays were performed in 96 well plates with a final volume of 200 µL/well. The following table summarises for each cell line, the respective culture medium and the number of cells seeded per well in the plates (Table below). The seeding and treatment steps were carried out with the robot Assist Plus, Integra.

| Cell Line | Passage number | Cell Medium | FBS | Penicillin/ Streptomycin | Supplement | n° cells/96 well |
|---|---|---|---|---|---|---|
| HuDe | P15 | MEM (Gibco) | 10% | 1% | 1% sodium pyruvate | 7.000 |
| FaDu | P16 | EMEM (ATCC) | 10% | 1% | \ | 12.500 |
| A431 | P36 | DMEM (Gibco) | 10% | 1% | \ | 8.500 |

Nuclear Staining, Cell Viability Assay

To determine the number of adherent cells, NuclearMask-Red (H10326, Life Technologies) staining was employed. This fluorescent dye binds specifically to nucleic acids, enabling accurate cell counting. The day before the experiment the three cell lines were seeded in a 96-multiwell plate black with clear bottom (Cat #: 732-3737, VWR) in a final volume of 190 µL/well. After 24 hours from seeding, EpigenAU/11 were solubilize as indicated in the section before in complete EMEM medium at a 20× concentration compared to the final concentration of 0.66 mg/mL. 10 µl of treatment was dispensed on cells using the Assist Plus robot in a final volume of 200 µL. Following 24-h exposition, treatments were removed, and cells were stained with NuclearMask according to the manufacturer's instructions. Fluorescence intensity, corresponding to cell number, was measured using the Varioskan™ LUX Multimode Microplate Reader.

1. Cell Culture Conditions:

Human healthy dermis fibroblasts (HuDe) and two cancer cell lines (FaDu and A431) were cultured according to the specified protocols, including:

HuDe cells: MEM medium with 10% FBS, 1% penicillin/streptomycin, and 1% sodium pyruvate, seeded at 7,000 cells per well.

FaDu cells: EMEM medium with 10% FBS, 1% penicillin/streptomycin, seeded at 12,500 cells per well.

A431 cells: DMEM medium with 10% FBS, 1% penicillin/streptomycin, seeded at 8,500 cells per well.

2. Experimental Setup:

Cells were cultured in a humid incubator at 37° C. with 5% CO2.

The seeding and treatment steps were carried out using Assist Plus robot (Integra Bioscience) to ensure precision.

3. Treatment with EpigenAU/11 (DoE2):

EpigenAU/11 should be solubilized as described and added to the cells at a 20× concentration to reach a final concentration of 0.66 mg/mL in a total volume of 200 µL per well.

Cells were exposed to the treatment for 24 hours.

4. Assessment of Cell Viability:

Nuclear staining with NuclearMask-Red was performed according to the manufacturer's instructions.

Fluorescence intensity, indicative of cell viability, should be measured using the Varioskan™ LUX Multimode Microplate Reader MET Emission/Excitation: 622 nm/645 nm Overall, the cell-based assays results show that all DoEs when 0.66 mg/ml are administered, separately, to HuDe, FaDu and A431 cells in culture induce after 24 hrs from administration A mortality ≤61% of healthy cells HuDe;

A mortality ≥71% of FaDu tumour cells;

A mortality ≥55% of A431 tumour cells;

In a cell culture in a 96 well in 200 µl format

Figure 28:
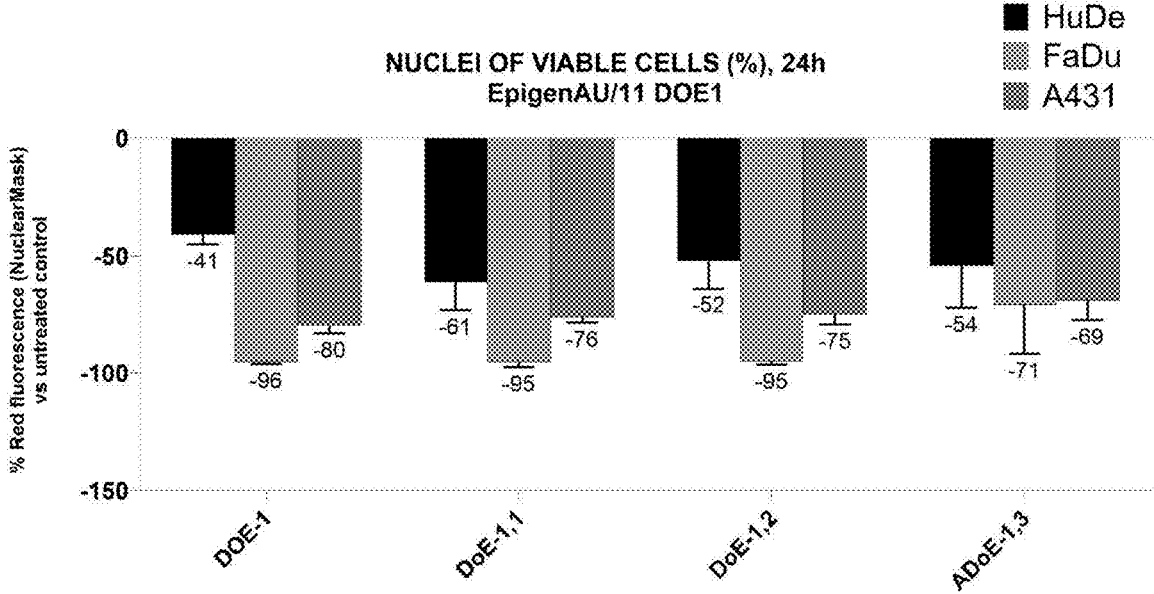
Figure 28:
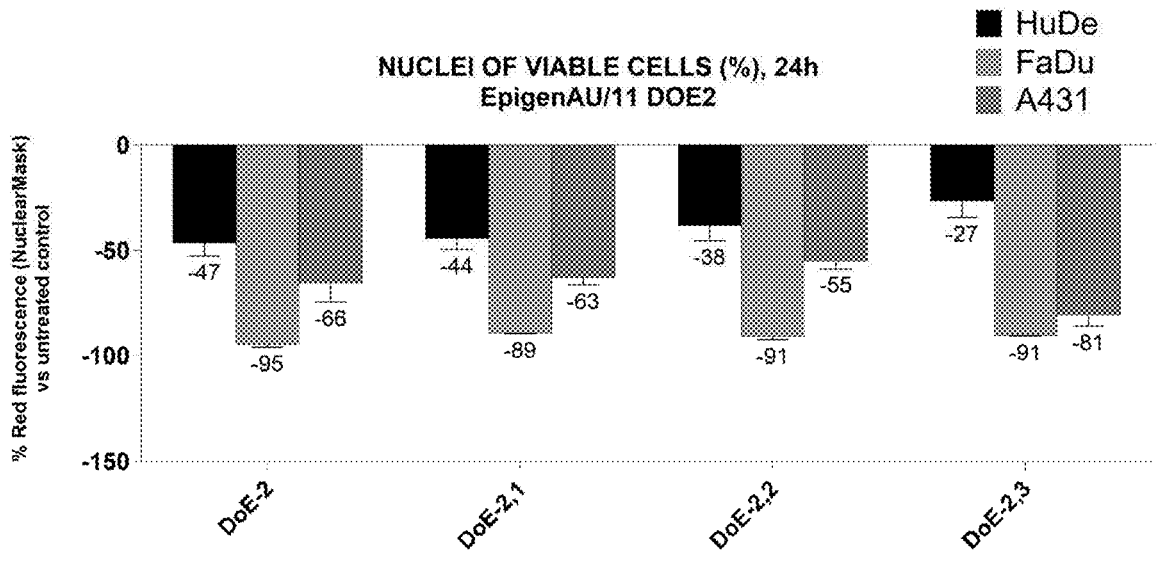
Figure 28:
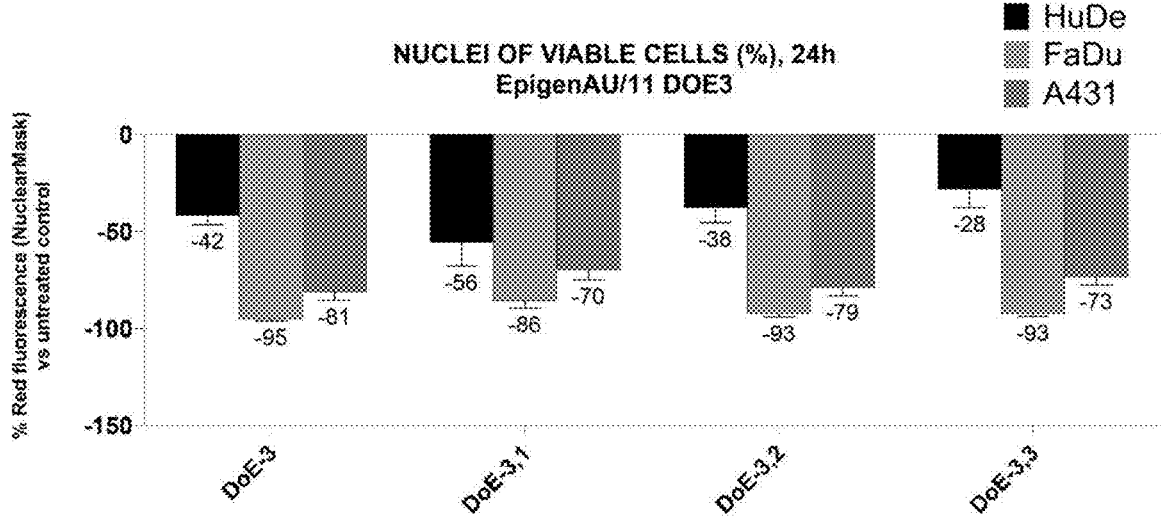
Figure 28:
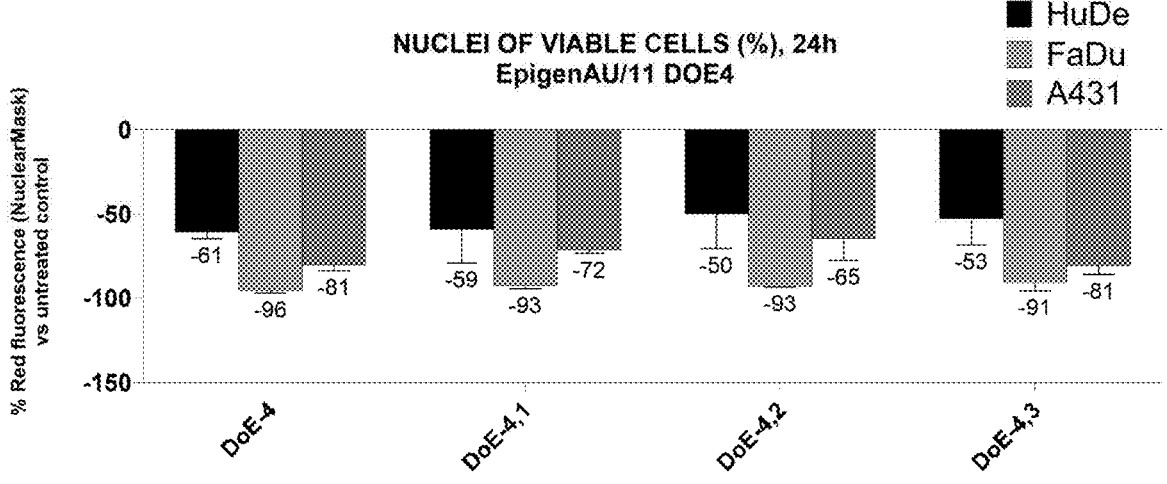
Figure 29:
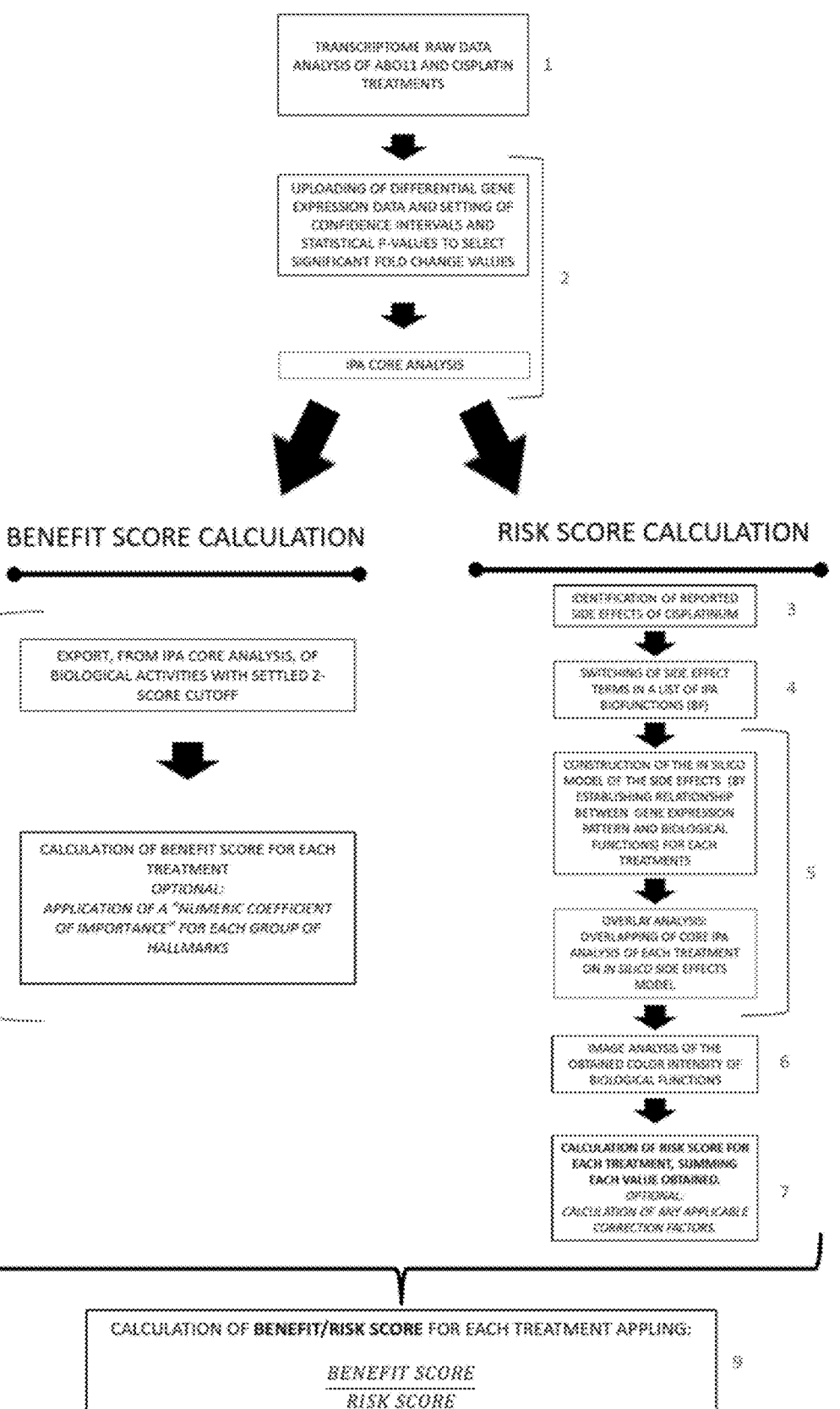
Figure 33:
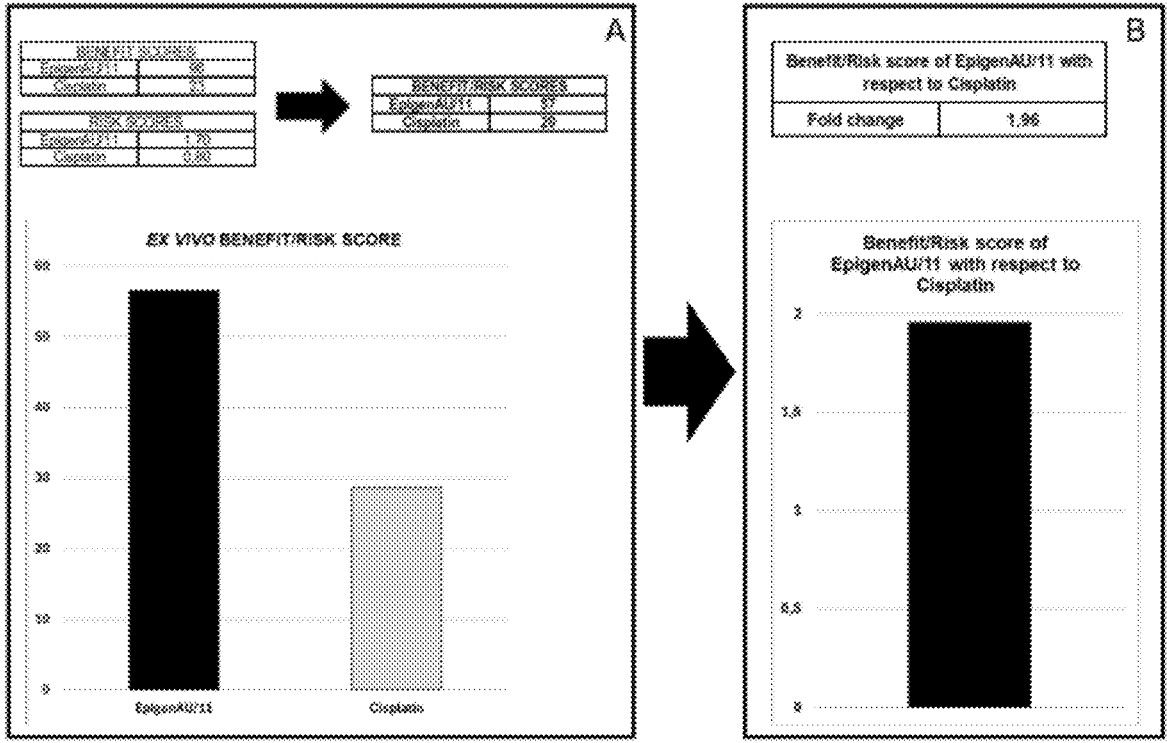

FIG. 28 (panels A to D) shows that, in particular, the same treatment with DoEs 1, 1.1, 1.2, 1.3; 2, 2.1, 2.2, 2.3, 3, 3.1, 3.2, 3.3, 4, 4.1, 4.2 and 4.3 when 0.66 mg/ml are administered, separately, to HuDe, FaDu and A431 cells in culture induce after 24 hrs from administration A mortality ≤61% of healthy cells HuDe;

A mortality ≥71% of FaDu tumour cells;

A mortality ≥65% of A431 tumour cells;

In a cell culture in a 96 well in 200 µl format.

According to the data provided in the experiments above, it can be affirmed that EpigenAU/11 acts through a physiological mechanism of action as it alters a state and not one or few functions and as it shows a strong therapeutic functional resilience in the cell-based assay as depicted in FIG. 28.

In addition, the analysis reported above also demonstrate that the product not only is composed of natural matrices but is a matrix itself, it is 100% natural, it is readily biodegradable and contains miRNAs and exosomes.

For therapeutic product it is essential to define the Unit of Activity, which, as explained in the glossary, is a standardized measurement of a therapeutic product potency or effectiveness defining the amount of the therapeutic product required to produce a specific, desired therapeutic effect or to achieve a particular biological response in a given system.

In order to define a Unit of Activity of EpigenAU/11, as a preferred features in anticancer treatments are the preservation of the healthy cells viability together with a strong cytotoxicity against tumour cells, a preferred cut-off of desired activity in terms of healthy and tumour cells cytotoxicity balance exerted by the product was defined based on all the studies performed on the DoE2 reference product, and 1 Unit of Activity was defined as the necessary and sufficient amount of EpigenAU/11 being capable of inducing, after 24 hours from administration, separately, to HuDe, FaDu and A431 cells:

A 40-50% mortality of healthy cells HuDe;

A ≥90% mortality of FaDu tumour cells;

A ≥65% mortality of A431 tumour cells;

in a cell culture plate wherein

HuDe cells seeded at about 7,000 cells per well in 200 µl of the appropriate medium; FaDu cells, seeded at about 12,500 cells per well in 200 µl of the appropriate medium, and A431 cells seeded at about 8,500 cells per well in 200 µl of the appropriate culture medium; cells are cultured for 24 hours after treatment with said product and cell mortality is measured by assessing cell viability through nuclear staining.

In more detail, the plate is a 96 well culture plate and the conditions are indicated in detail above.

In the case of EpigenAU/11 DoE2, 1 UoA is 0,132 mg.

Hence, for different lots of EpigenAU/11, the UoA as defined above, can be reached either by variating the amount of product until the desired mortality is obtained, or, alternatively, as demonstrated in the present specification, by modifying the formula in the ranges claimed until the desired UoA is obtained with an amount of product similar to the amount of DoE2 indicated above or both.

Therefore, the UoA as defined is the quantity of product necessary and sufficient to obtain a significant reduction of the tumour cells vitality while maintaining the vitality of the healthy cells within a physiologically tolerable range has been developed.

The UoA (Unit of Activity) as defined herein can be readily used by the skilled person for determining, batch to batch for different EpigenAU/11 batches in order to guarantee that each EpigenAU/11 UoA represents a reproducible biological activity independently from the variations in the product formulation within the ranges claimed.

The concept of EpigenAU/11 UoA has been developed in order to quantify the potency or biological effect of the product of the invention thereby ensuring consistency, safety, and efficacy in the production, formulation, and clinical application of the product. As the product of the invention can vary qualitatively and quantitatively maintaining, nevertheless, a consistency in the biological effect observed. the definition its UoA guarantees that each EpigenAU/11 UoA represents a reproducible biological activity independently from the variations in the product formulation within the ranges claimed. Therefore, the product can be prepared within the ranges claimed and will be considered providing the desired technical effects when a UoA as defined above can be determined for the formulation tested.

In other terms 1 EpigenAU/11 UoA is defined as the quantity of product needed to obtain a significant reduction of the tumour cells vitality while maintaining the vitality of the healthy cells within a physiologically tolerable range 11. New Benefit/Risk Assessment (Computer Implemented/Assisted)

11.1 Data Assembly 11.1.1 Ex Vivo Sample Treatment (Referring to Method A Step 1.1-1.2)

To perform the experiments, ex vivo tumour masses were generated from the FaDu head and neck squamous carcinoma cell line implanted in immunocompromised mice. Once the tumours reached an adequate size, they were excised, divided into 40 mg portions, and treated in triplicate with EpigenAU/11 and cisplatin for 6 hours. Subsequently, the masses were lysed, and RNA was extracted for transcriptional analysis.

11.1.2 Transcriptome Raw Data Analysis (Referring to Method A Step 1.3)

Whole transcriptome expression profile was evaluated. A Human Clariom™ S Pico Assay HT (Applied Biosystems, ThermoFisher Scientific) on a GeneTitan MC Instrument (Applied Biosystems, ThermoFisher Scientific), following the manufacturer's instructions was employed. CEL Intensity files were generated by Affymetrix GeneChip Command Console Software (AGCC, ThermoFisher Scientific). Data analyses were performed using Transcriptomic Analysis Console Software (TAC, ThermoFisher Scientific) that provides quality control analysis, performs normalization and summarization, based on the Signal Space Transformation-Robust Multi-Chip Analysis (SST-RMA) analysis algorithm, and provides a list of differentially expressed genes (Limma Bioconductor package). This phase allows us to obtain a list of differentially expressed genes (DEGs), identified based on their expression fold changes with respect to a relevant control experimental condition (i.e. tumour mass without treatments).

11.1.3 IPA Analysis of Transcriptional Profile (Computer Implemented) (Referring to Method A Step 1.4)

The use of IPA allows us to estimate how and to what extent the modulation of gene expression in a biological system influences the biological functions related to the pathology of interest.

The transcriptional modifications profile thus obtained is subjected to a functional pathway enrichment analysis. One of the commercial tools that can be used is Ingenuity Pathway Analysis (IPA version 94302991, Qiagen) [Krämer A, et al. *Causal analysis approaches in Ingenuity Pathway Analysis. Bioinformatics.* 2014]. The list of Differentially expressed genes and corresponding data measurement values (fold change with respect to "Not treated tumour mass) identified in the different experimental conditions were uploaded into the application.

Differentially expressed genes and corresponding fold-changes undergo a filtration process to select only significantly perturbed genes, as indicated by their fold change compared to the "Not treated tumour mass".

The fold change threshold is set to encompass values $\leq-2$ and $\geq+2$, accompanied by a statistical significance denoted by a p-value of $\leq0.05$.

Available identifiers were mapped to their corresponding entity in QIAGEN's Knowledge Base.

By launching "Core Analysis", significantly perturbed DEGs, called Network Eligible molecules, were overlaid onto a global molecular network developed from information contained in the QIAGEN Knowledge Base. Networks of Network Eligible Molecules were then algorithmically generated based on their connectivity.

The core analysis provides a comprehensive list of approximately top 500 biological functions derived from the generated networks. The associations Biological functions-genes are always supported by annotations corresponding to scientific peer review publications that substantiate, through the automatic association of a z-score [Krämer et al. (2014)], the calculated directionality and magnitude of modulation of the biological functions. In essence, this value represents a statistical metric that assesses the similarity between the observed pattern of Differentially Expressed Genes (DEGs) and the expected pattern based on existing literature for a given annotation.

It is the responsibility of the proficient operator to carefully choose the biological functions that are relevant to the specific pathology under investigation. The selection of biological functions will be structured based on the identified hallmarks of the pathology of interest, applying a Z-score threshold set to include values $\leq-2$ and $\geq+2$, accompanied by a statistical significance denoted by a p-value of $\leq0.05$.

The associated Z-score values will then be used to indicate the directionality and magnitude of modulation for each biological function.

11.2 Risk Score Calculation 11.2.1 Definition of Side Effects of Cisplatin (Referring to Method a Step 3.1)

Officially recorded side effects of cisplatin were identified by consulting specific sources:

https://www.torrinomedica.it/schede-farmaci/cisplatino-3/(document made available by AIFA on Jul. 13, 2021)
https://www.drugs.com/sfx/cisplatin-side-effects.html as last updated on Mar. 17, 2024

11.2.2 Identification of IPA Biofunctions Browsing them from the Terms Used to Annotate the Side Effects (Referring to Method A Step 3.2)

The information found in the aforementioned resources is used to identify biological activities (The used IPA source is the Ingenuity Knowledge Base, including curation from journal articles, OMIM, JAX and ClinicalTrials.gov) related to the identified side effects and to interrogate IPA through the following procedure:

Side effects terms are written, one by one, in the "disease and functions" query box and the search is then launched.

The obtained resuming table allows you to filter disease/function that come from many lines of evidence (as shown in FIG. 31 where it is possible to appreciate the correspondences between the IPA biological activities and the annotated side effects). The creation of an in silico model is intended to associate each biological function a defined number of genes whose modulation is able to influence the modulation of the biological function itself (in this specific case, able to represent the side effect).

11.2.3 Overlay Analysis (Referring to Method A Step 3.3)

Overlay analysis focuses on the biological functions identified by the "in silico model of side effects". The selection of biological functions is structured based on the identified side effects of cisplatin.

The "Overlay analysis" is structured by establishing relationship between patterns of differentially expressed genes and selected biological functions (always supported by annotations corresponding to scientific peer review publications that substantiate the directionality and magnitude of modulation of the biological functions) using the following procedure:

Import the set of biological functions selected from the in silico model of the SIDE EFFECT PROFILE of cisplatin into a new sheet called "my pathway."

Utilize the "Build tool" and "Grow tool" to identify Differentially Expressed Genes (DEGs) belonging to the transcriptomic profile under investigation (cisplatin and EpigenAU/11) and are linked to regulation of the biological functions selected in the previous step.

11.2.4 Image Analysis of the Obtained Colour Intensity of Biological Functions (Referring to Method A Step 3.4)

Modulation of the identified DEGs is represented using green colour (indicating down-modulation) and red colour (indicating up-modulation).

To determine the expected calculated impact of such experimentally observed modulations of gene expression on biological functions activity, the "Overlay" and "Molecule Activity Predictor" tool (MAP) are employed. The "Prediction" function is activated within MAP tool to calculate the resulting expected modulation of biological functions. Colour coding is thus established:

orange: increase in activity blue: decrease in activity white: not achievable/not predictable The "Overlay analysis" does not directly calculate the Z-score for each biological function. Therefore, it is necessary to translate the colour intensity of the modulation signal into a numerical value. This is achieved by converting the use of dedicated app: "IPAmap_Parser" (version 2.1-1).

The app is a web port app of Pipeline Pilot designed to assign a score, called a z-score, to genes and biofunctions based on their colouring within a biological pathway generated by QIAGEN's Ingenuity Pathway Analysis software. The key step of the algorithm is the conversion from the RGB colour model to the LAB [https://www.xrite.com/it-it/blog/lab-color-space]model, a colorimetric encoding that allows for the recording of colour intensity, not just the RGB composition. This conversion takes place within a Pipeline Pilot "component" that utilizes a procedure written in R software, relying on specific functionalities of the colorspace package [https://cran.r-project.org/web/packages/colorspace/index.html].

FIG. 33A-B shows final list of biological activities and corresponding values obtained for each treatment under investigation.

11.2.5 Calculation of Global Risk Score (Referring to Method A Step 3.5)

Risk score is therefore calculated by sum of each positive values obtained from overlay analysis (to indicate that the given side effect is induced by the treatment).

Benefit scores calculation of EpigenAU/11 and cisplatin treatments after 6 hours of treatment (FIG. 33C shows the risk scores obtained by summing each annotated biological activity value for each of the treatments under investigation).

11.3 Benefit Score Calculation 11.3.1 CoreE Analysis Biofunctions Selection and Export Using core analysis obtained at 11.1.3, biological activities taking into account those whose trend is consistent with the therapeutic indications of the product under investigation (i.e. antitumoral activities) were selected (FIG. 32A). (Referring to Method A step 2.1)

Hence biological activities Z-score values are transformed in absolute values and the lists thus obtained are exported in a table which reports the specification of the biofunctions and their relative modulation values (FIG. 32B top panel). (Referring to Method A step 2.2)

The sum of each value for each treatment are considered as the benefit score (FIG. 32B bottom panel). (Referring to Method A step 2.3)

Optionally, biological activities can be grouped in activity hallmarks and each hallmark is given a weight coefficient based on its importance in the pathogenesis of interest. (FIG. 32C). In this case biological activity values will be multiplied by the corresponding coefficient, obtaining a final list value that will be used for the final calculation of the benefit score (FIG. 32D)

11.4 Benefit/Risk Score Calculation (Referring to Method A Step 4)

Once the risk scores and the benefit scores have been calculated, they are applied to the following formula:

$$\frac{\text{BENEFIT SCORE}}{\text{RISK SCORE}}$$

The value of the ratio must therefore be interpreted as follows: the higher the value obtained, the greater the safety of the administered treatment, as the benefits are greater than the risks.

Figure 34:
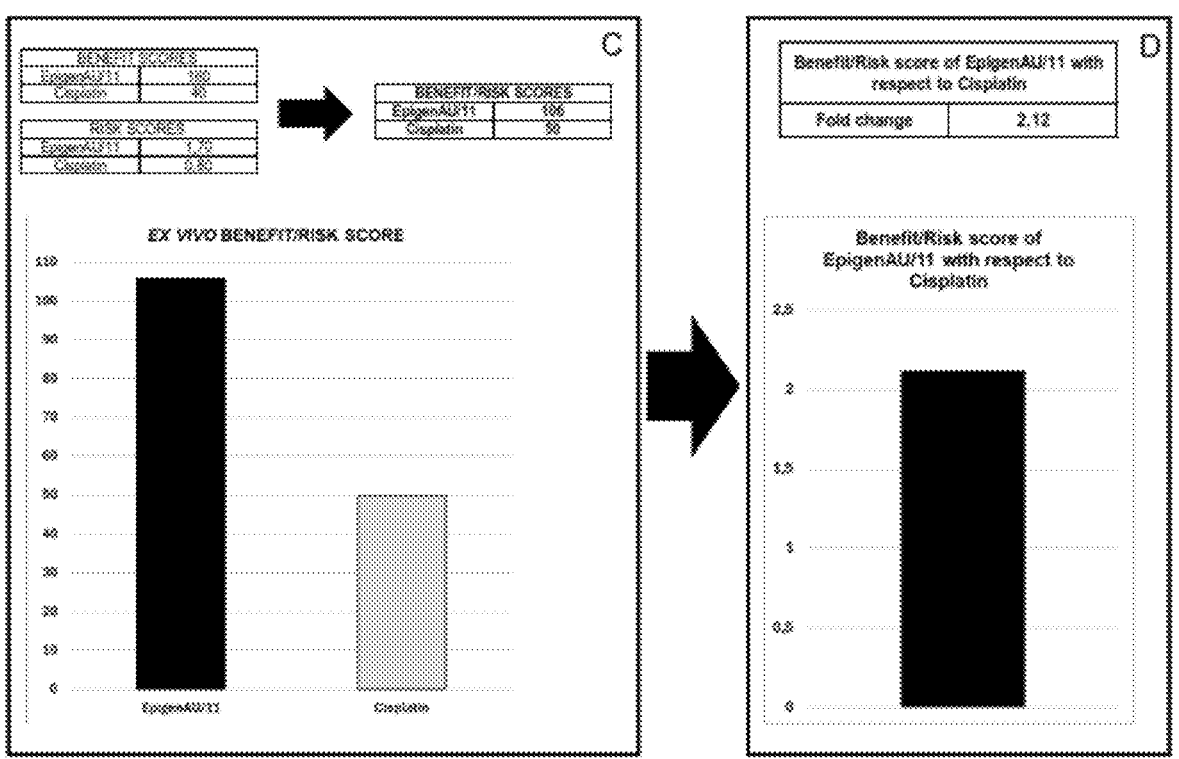

FIG. 34 shows the results of benefit/risk scores obtained with EpigenAU/11 and cisplatin treatments after 6 hours (A). Calculation of the fold change of the score obtained with EpigenAU/11 compared to that obtained with cisplatin: the EpigenAU/11 score is twice that of cisplatin (B).

When the benefit/risk score is calculated while taking into account the optional steps described above, we obtain the results shown in FIG. 34C and calculation of the fold change of the score obtained with EpigenAU/11 compared to that obtained with cisplatin: the EpigenAU/11 score is still twice that of cisplatin (FIG. 34D).

Hence, the benefit/risk scores, calculated with and without optional steps, are consistent with each other.

12. Validation of the Proposed Transcriptomics-Based "Method A" Via the Comparison with "Method B", Intended as Canonical Evaluation of Benefit/Risk Ratio Profile Associated to In Vivo Administration of EpigenAU/11 and Cisplatin 12.1. In Vivo Assay (Referring to Method B Step 1)

EpigenAU/11 (DoE2) and cisplatin were administered in vivo in a mouse model. The risk (intended as side effects) was estimated through the observation of behavioural parameters (impacting the behaviour itself, the locomotor system, muscle strength and nervous reflexes) and through the potential weight loss of the animal.

The table below shows the experimental values, representing the in vivo side effects, that have not yet been reprocessed for the purpose of risk score calculation.

| | | RISK | Vehicle | | EpigonAU/11 | | Cisplatin | | |
|---|---|---|---|---|---|---|---|---|---|
| | HALLMARK | PARAMETERS | Mean | Dev.st | Mean | Dev.st | Mean | Dev.st | Limits |
| BEHAVIOURAL DATA | Behaviour | Spontaneous activity | 4.00 | 0.00 | 3.70 | 0.45 | 2.50 | 1.56 | 4-0 |
| | | Passivity | 0.00 | 0.00 | 0.30 | 0.45 | 1.00 | 1.62 | 0-4 |
| | | Clearing | 4.00 | 0.00 | 3.80 | 0.45 | 2.90 | 1.67 | 4-0 |
| | | Curiosity | 4.00 | 0.00 | 3.80 | 0.27 | 2.60 | 1.67 | 4-0 |
| | | Reactivity | 4.00 | 0.00 | 3.90 | 0.22 | 2.20 | 1.30 | 4-0 |
| | Locomotor system | Stereotipies | 0.00 | 0.00 | 0.00 | 0.00 | 0.00 | 0.00 | 0-4 |
| | | Straightening reflex | 4.00 | 0.00 | 3.80 | 0.45 | 2.60 | 1.47 | 4-0 |
| | Muscle | Physical strength | 4.00 | 0.00 | 3.80 | 0.27 | 2.70 | 1.68 | 4-0 |

-continued

| | RISK | Vehicle | | EpigonAU/11 | | Cisplatin | | |
|---|---|---|---|---|---|---|---|---|
| HALLMARK | PARAMETERS | Mean | Dev.st | Mean | Dev.st | Mean | Dev.st | Limits |
| Nervous system | Palpebral reflex | 4.00 | 0.00 | 3.80 | 0.45 | 2.80 | 1.68 | 4-0 |
| | Pallor | 0.00 | 0.00 | 1.20 | 0.84 | 2.00 | 1.22 | 0-4 |
| | Palpebral opening | 4.00 | 0.00 | 3.50 | 0.71 | 2.00 | 0.94 | 4-0 |
| BODY WEIGHT Nutritional and metabolic | Tremors | 0.00 | 0.00 | 0.10 | 0.22 | 0.80 | 1.10 | 0-4 |
| DATA system | Body weight | 37.48 | 1.89 | 35.26 | 1.60 | 29.12 | 2.93 | / |

The benefit (intended as therapeutic activity) was instead evaluated by taking into consideration the reduction in size of the tumour mass compared to the untreated tumour.

For this purpose, immunocompromised mice bearing xenografted FaDu head and neck squamous carcinoma cells were included in the study once tumours reached a volume of 100 mm³. Mice received daily intratumoral injections of EpigenAU/11 and intraperitoneal cisplatin on alternating days.

The table below shows the experimental values, representing the in vivo benefit effect, that have not yet been reprocessed for the purpose of benefit score calculation.

| | BENEFIT | Vehicle | | EpigenAU/11 | | Cisplatin | |
|---|---|---|---|---|---|---|---|
| HALLMARK | PARAMETERS | Mean | Dev.st | Mean | Dev.st | Mean | Dev.st |
| Tumor viability | Size of tumor masses | 1.38 | 0.11 | 0.15 | 0.12 | 0.50 | 0.36 |

The values obtained show that the canonically evaluated benefit/risk ratio profile associated to EpigenAU/11 is more favourable with respect to that associated to cisplatin. Data generated using a canonical in vivo observation thus confirms the predictability of the hereby reported novel method based on ex vivo transcriptomics and substantiates its validation.

The results obtained on the risk and benefit parameters monitored are reported below:12.2 EpigenAU/11 and Cisplatin Benefit/Risk Ratio Comparison Based on Data Obtained From In Vivo Experimentation Interpretation of the in vivo generated data revealed the need for an additional method that would allow for a reduction in the dimensionality of such datasets and enable a punctual quantitative representation of the benefit/risk ratio observed and usually only qualitatively discussed for the therapeutic solution. Again, such a tool would objectivate the comparison between the profiles associated to two therapeutics solutions.

12.2.1 Risk Score Calculation (Referring to Method B Step 3.1)

Data obtained by animal testing, considered in the context of the risk, are behavioural parameters and body weight loss at the end of experimentation.

The behavioural parameters monitored are listed below:
1. Loss of Spontaneous activity
2. Loss of Cleaning
3. Loss of Curiosity
4. Loss of Reactivity
5. Loss of Straightening reflex
6. Loss of Physical strength
7. Impairment of Palpebral opening
8. Palpebral reflex 9. Tremors
10. Pallor
11. Stereotypies
12. Passivity The values of the parameters 1-8 are normalized as: "Not treated animal value" (always equal to 0)+"Treated animal value".

The values of the parameters 9-12 are normalized as: "Not treated animal value"-"Treated animal value".

The potential weight loss of the treated animals was also assessed." Data were processed using the formula:

$$1-[\text{"Body weight of treated animals (day of observation: 27)/body weight of untreated animals (day of observation: 19)}]$$

The table below summarises the Risk score calculation of EpigenAU/11 and cisplatin treatments with sum of the data derived from in vivo experimentation. (Referring to Method B step 3.2)

| | | RISK | EpigenAU/ | |
|---|---|---|---|---|
| HALLMARK | | PARAMETERS | 11 | Cisplatin |
| BEHAVIOURAL DATA | Behaviour | Loss of Cleaning | 0.20 | 1.50 |
| | | Loss of Curiosity | 0.20 | 1.60 |
| | | Passivity | 0.30 | 1.10 |
| | | Loss of Reactivity | 0.10 | 1.40 |
| | | Loss of Spontaneous activity | 0.30 | 1.80 |
| | Locomotor system | Stereotypies | 0.00 | 0.00 |
| | | Loss of Straightening reflex | 0.20 | 1.40 |
| | Muscle | Loss of Physical strength | 0.20 | 1.30 |

-continued

| | | | EpigenAU/11 | CISPLATIN |
|---|---|---|---|---|
| | Nervous system | Tremors | 0.10 | 0.80 |
| | | Loss of Palpebral reflex | 0.20 | 1.20 |
| | | Pallor | 1.20 | 2.00 |
| | | Impairment of Palpebral opening | 3.50 | 2.00 |
| WEIGHT LOSS VALUE | Nutritional and metabolic system | Weight loss | 0.06 | 0.22 |
| | | IN VIVO RISK SCORE | | |
| | | EpigenAU/11 | 7 | |
| | | CISPLATIN | 16 | |

12.2.2 Benefit Score Calculation (Referring to Method B Step 2)

Data obtained by animal testing, considered in the context of benefit, is the tumour mass size reached at the end of in vivo test for each treatment.

Data were calculated as "Reduction in the size of tumour mass" by the formula:

1–["Tumour mass size collected from treated animals (day of observation: 27)/Tumour mass size collected from untreated animals (day of observation: 19)]

Below is reported the benefit score calculation of EpigenAU/11 and cisplatin treatments with data derived from in vivo experimentation.

| HALLMARK | BENEFIT PARAMETER | EpigenAU/11 | Cisplatin |
|---|---|---|---|
| Tumour viability | Reduction in the size of tumour mass | 0.89 | 0.64 |
| | IN VIVO BENEFIT SCORE | | |
| | EpigenAU/11 | 0.89 | |
| | CISPLATIN | 0.64 | |

12.3 Benefit/Risk Score Calculation (Referring to Method B Step 4)

Once the risk scores and the benefit scores have been calculated, they are applied to the following formula:

$$\frac{\text{BENEFIT SCORE}}{\text{RISK SCORE}}$$

The value of the ratio must therefore be interpreted as: the higher the value obtained, the greater the safety of the administered treatment, as the benefits are greater than the risks.

Figure 35:
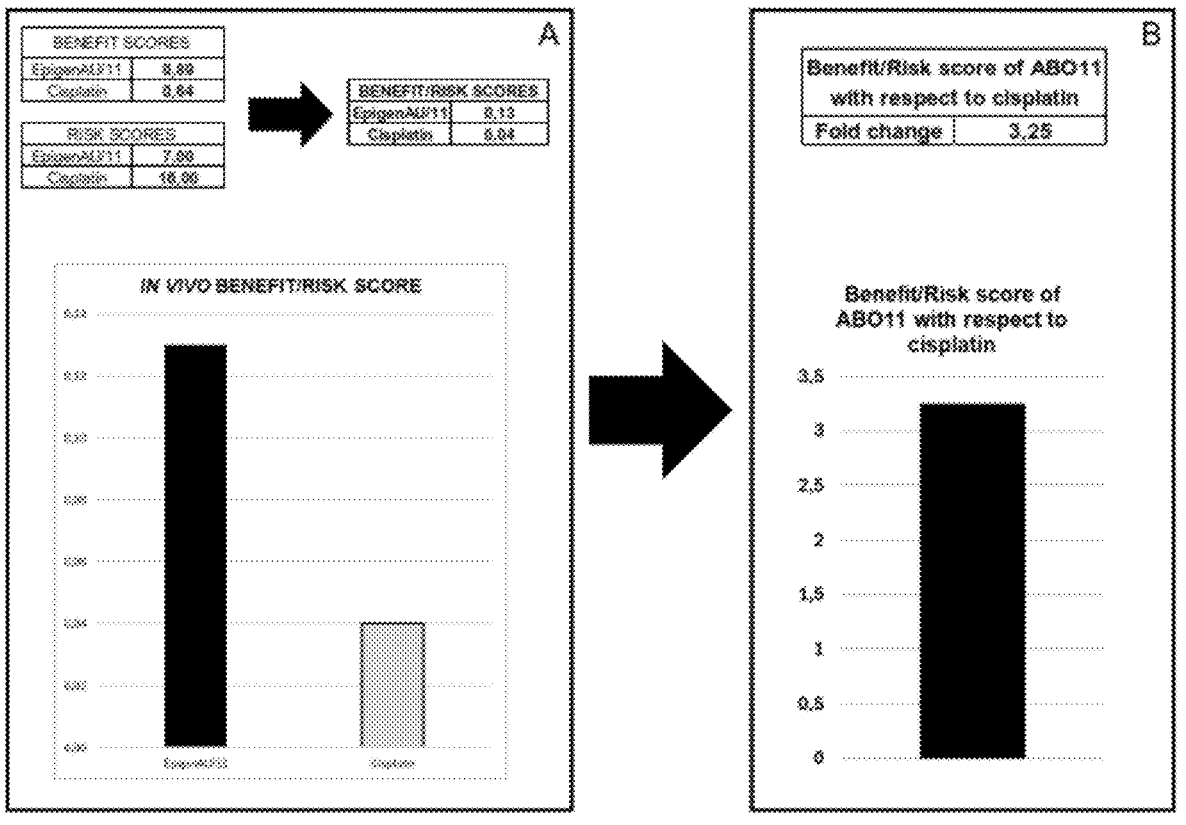
Figure 36:
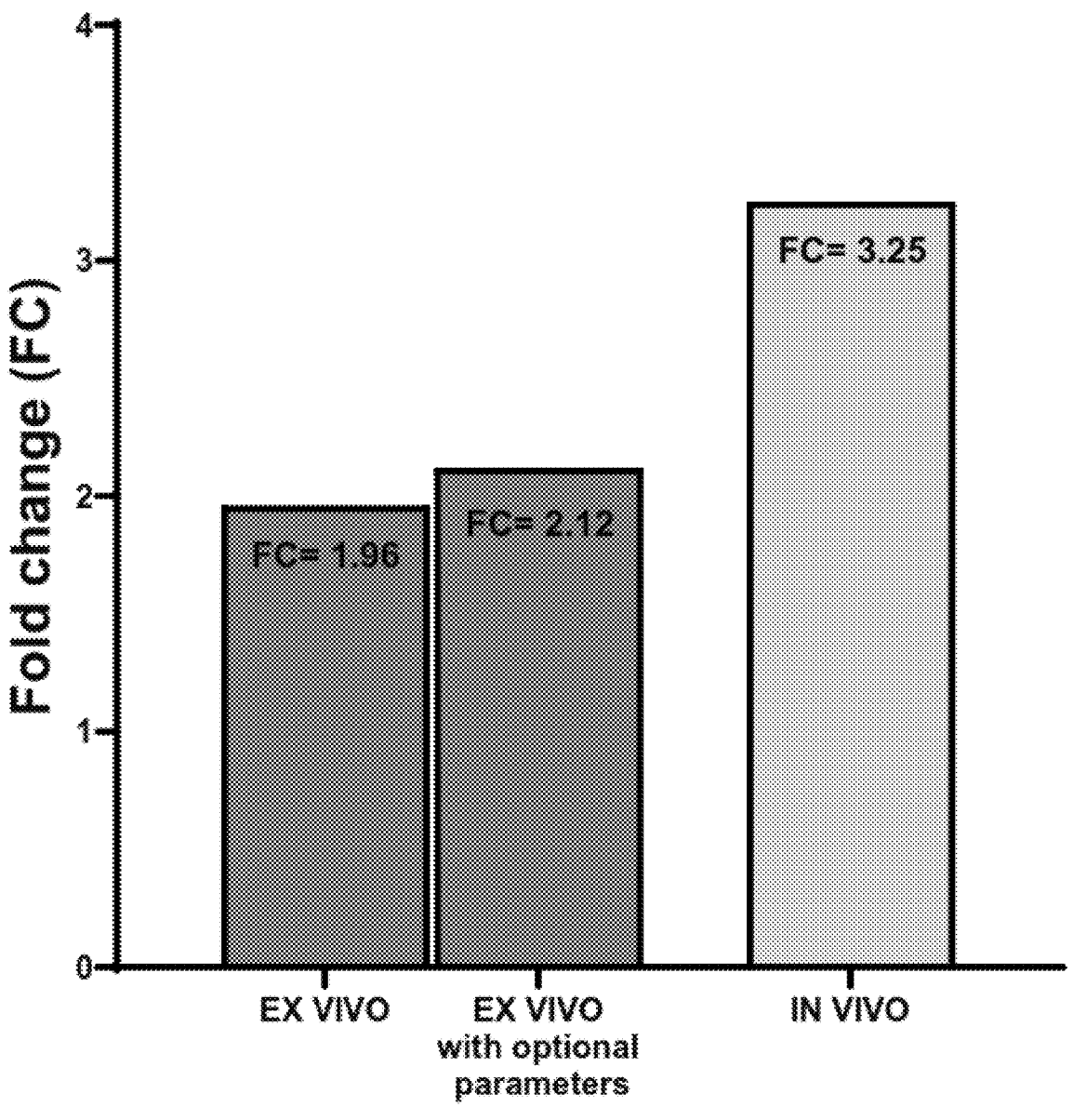

FIG. 35 shows the Benefit/Risk scores obtained with in vivo EpigenAU/11 and cisplatin treatments (A). Calculation of the fold change of the score obtained with EpigenAU/11 compared to that obtained with cisplatin: the EpigenAU/11 score is three times that of cisplatin (B).

The two methods disclosed in examples 11 and 12 (with or without optional steps) proved to be useful in order to objectivate the comparison between benefit/risk profile of two anticancer treatments. The first method is based on ex vivo transcriptomics data and proved to be able to correctly predict the favourability of EpigenAU/11 profile with respect to that of cisplatin, undergoing a validation based on comparison with results generated using a canonical qualitative approach based on in vivo data. The second method enables to summarize such in vivo data in a single parameter that enables that facilitates and renders more easily approachable the comparison between the benefit/risk profiles of therapeutic options. Both methods produce similar results demonstrating the superiority of EpigenAU/11's benefit/risk score over Cisplatin (FIG. 36), thus proving the consistency of the ex vivo method with the one generated using a canonical in vivo approach, thereby representing a favourable profile for EpigenAU/11 with respect to that of Cisplatin, returning a result coherent with that generated using a canonical in vivo approach.

13. Evaluation of the Association of EpigenAU/11 with Conventional Cancer Therapy 13.1 Association with Various Chemotherapeutical Drugs EpigenAU/11 effects were evaluated in various contexts, particularly in conjunction with established chemotherapeutics. Cell viability assays according to the previous experiments were performed on FaDu and A431 cell lines, both of which are of squamous origin and commonly associated with cisplatin treatment. This combination is relevant as cisplatin is a standard therapeutic agent in the management of squamous cell carcinoma.

Figure 37:
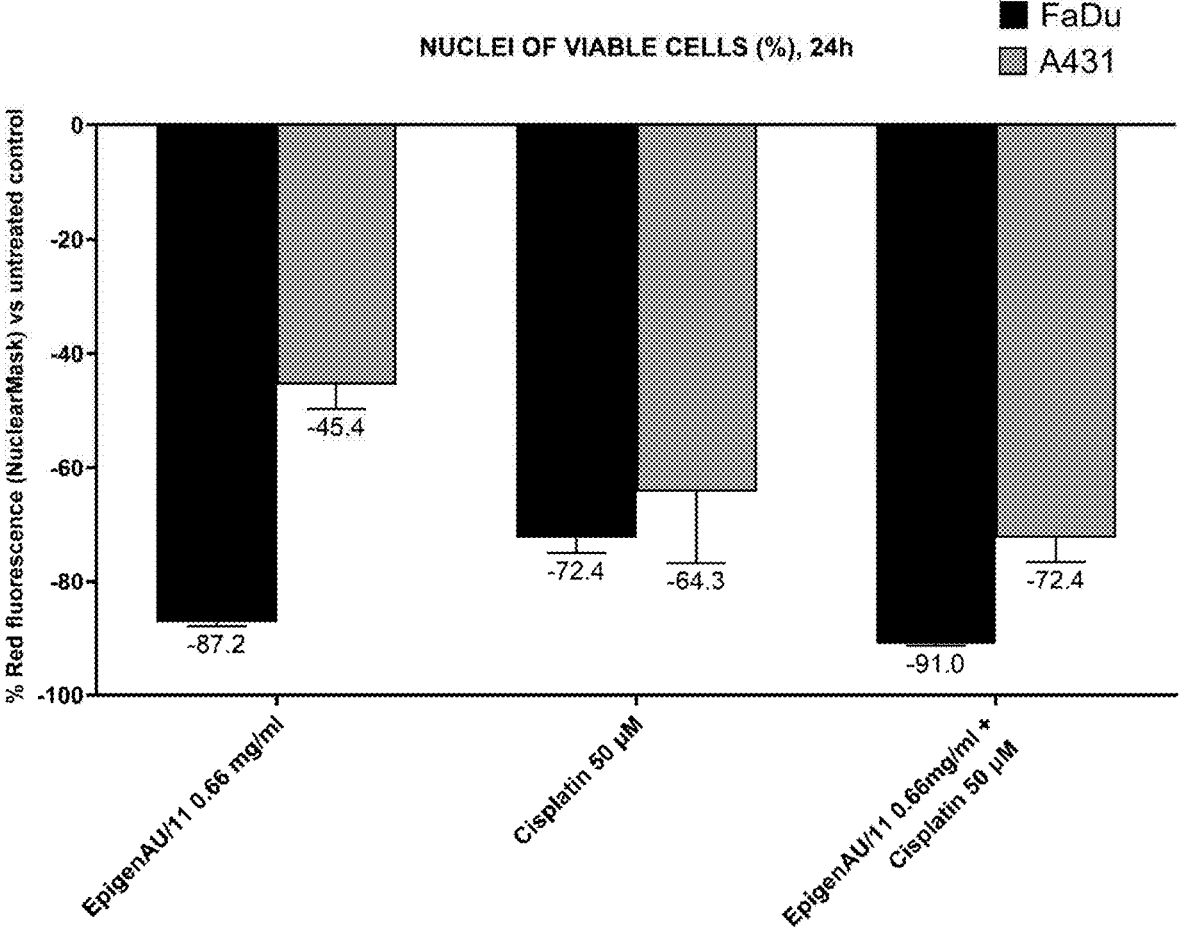

The results of the experiments demonstrated that both EpigenAU/11 and cisplatin exhibit significant efficacy against these cancer cell lines. Notably, when administered in combination, there was an enhancement in the therapeutic effect, suggesting synergistic interaction between EpigenAU/11 and cisplatin. Importantly, no detrimental effects were observed when these agents were used together, indicating that EpigenAU/11 does not interfere negatively with the established action of cisplatin, which is considered as the reference drug in this treatment context (FIG. 37).

On behalf of the applicant and of the inventors, the Department of Pharmaceutical Sciences at the University of Pavia conducted further viability assays on breast cancer, focusing on two triple-negative breast cancer lines, MDA-MB-231 and SUM159PT. These assays involved standard chemotherapy agents for this tumour type: carboplatin, paclitaxel, and gemcitabine. Using the Cell Titer-Glo® 3D Viability Assay, the effects of combinations such as EpigenAU/11+Carboplatin+Paclitaxel or EpigenAU/11+Carboplatin+Gemcitabine were examined. In the combination experiments the amount of EpigenAU/11 used was 0.22 mg/ml, the drugs used in the combination experiments were the same dosages used with the drugs alone. The results indicated that these combinations did not demonstrate a worsening effect compared to the corresponding combinations without EpigenAU/11; rather, an additive effect was observed in both tumour lines (FIG. 38). This further suggested that the chemotherapy agents and EpigenAU/11 acted through different mechanisms without interfering with each other.

Figure 39:
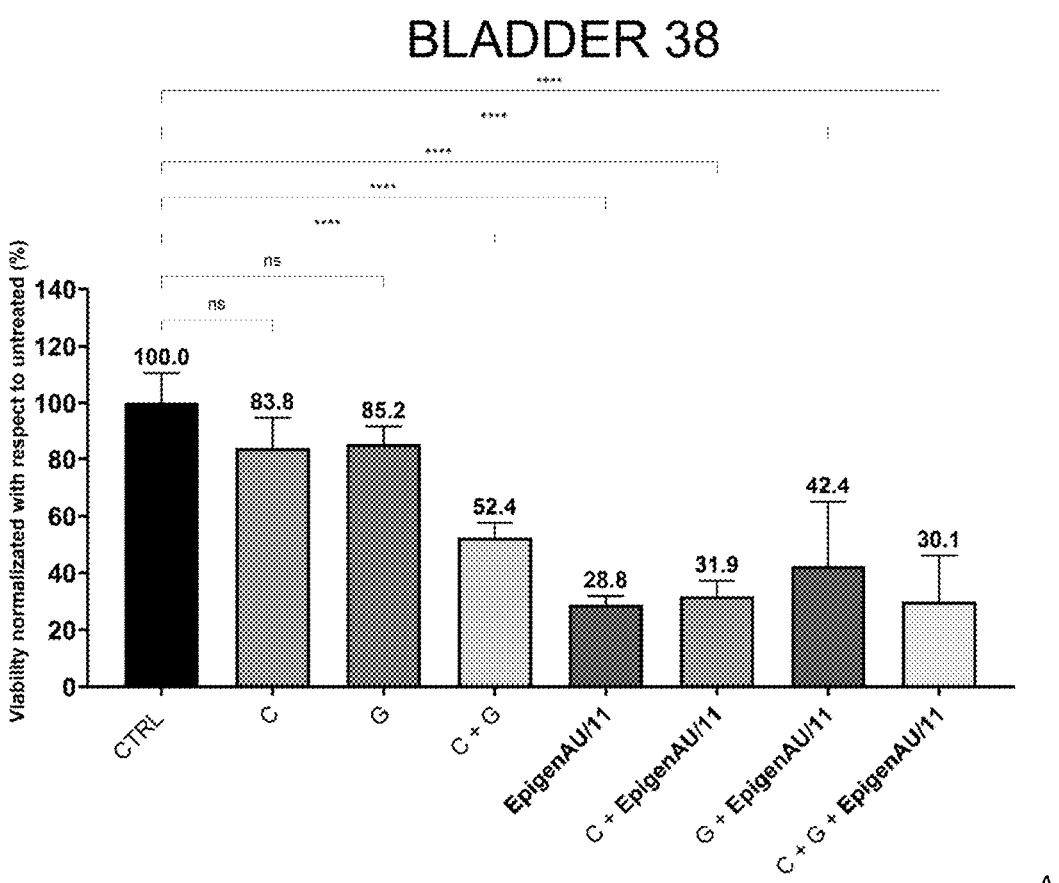
Figure 39:
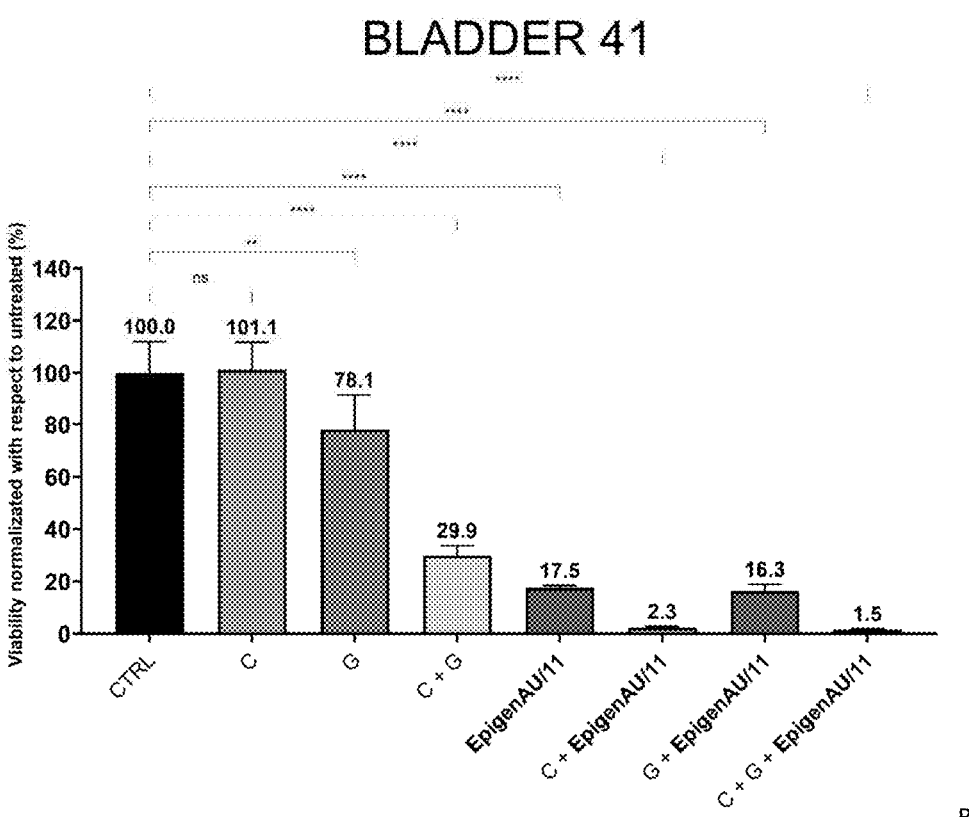
Figure 39:
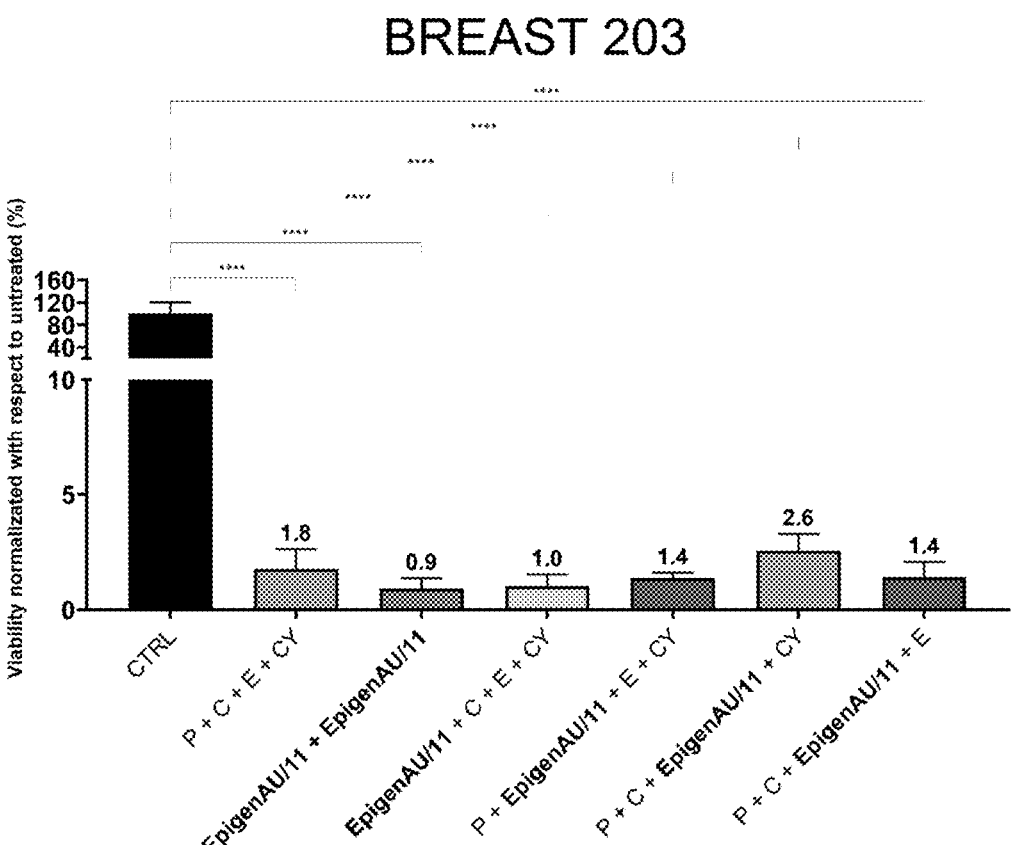
Figure 39:
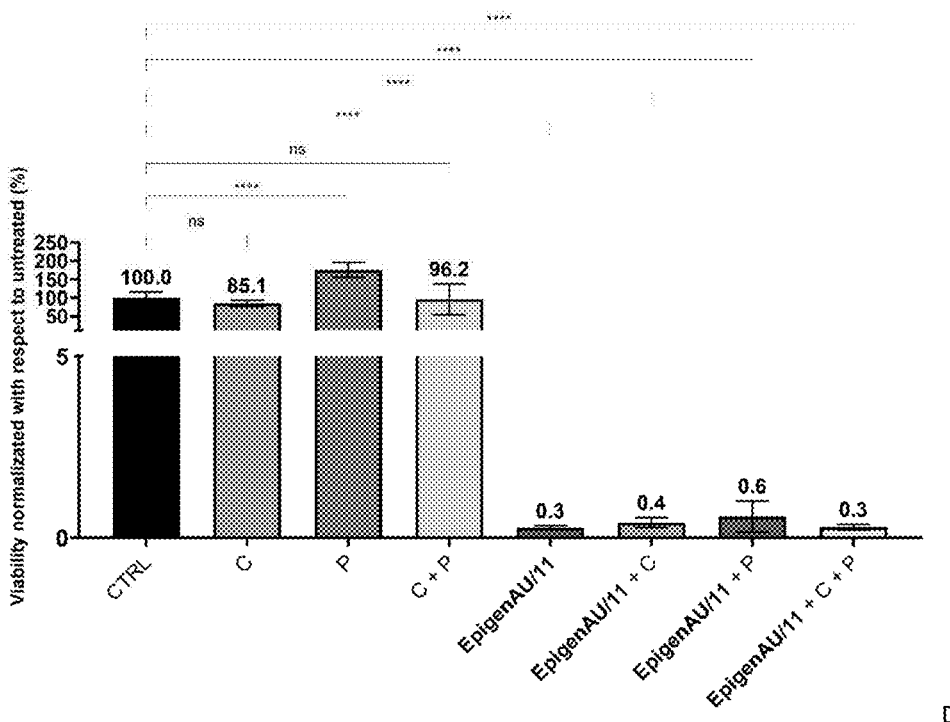

To further explore the potential interactions between traditional chemotherapeutic agents and EpigenAU/11, the team at the Regina Elena National Cancer Institute in Rome conducted viability assays using EpigenAU/11 in combination with chemotherapy drugs on patient-derived tumour organoids (PDOs). Specifically, various organoids were treated with standard-of-care therapies either alone or in combination with EpigenAU/11 for 72 hours (FIG. 39 A-D).

In bladder tumour organoids (Bladder 41-FIG. 39A, and Bladder 38 FIG. 39B), cisplatin, gemcitabine and their combination were tested. EpigenAU/11 was subsequently evaluated both as a standalone treatment and in combination with these drugs. The results demonstrated that EpigenAU/11 significantly reduced tumour viability, with a pronounced additive effect when combined with cisplatin and gemcitabine, achieving near-complete elimination of tumour viability in some cases. These findings highlight not only the absence of interference but also a strongly beneficial impact.

In experiments with breast cancer organoids (Breast 203-FIG. 39C), a sequential regimen was applied: paclitaxel and carboplatin were administered for 72 hours, followed by an additional 72-hour treatment with epirubicin and cyclophosphamide. The addition of EpigenAU/11 to these regimens resulted in no loss of efficacy; instead, the data suggested that EpigenAU/11 maintained or enhanced overall effectiveness, even when combined with multiple chemotherapeutic agents.

In an endometrial tumour organoid (Endometrium 12-FIG. 39D), EpigenAU/11 alone drastically outperformed the standard treatments. While carboplatin alone reduced viability to 85.1%, and the combination of carboplatin and viability to just 0.3%, demonstrating remarkable potency. Furthermore, the inclusion of EpigenAU/11 alongside carboplatin, paclitaxel, or their combination further enhanced its therapeutic effect, underscoring its potential superiority over standard treatments.

These results, collected across four distinct organoid models, demonstrate the strong potential of EpigenAU/11 to not only complement existing chemotherapeutic regimens but also, in some cases, surpass their efficacy. These findings underscore EpigenAU/11's promise as a novel therapeutic agent with the potential to enhance and transform current cancer treatments.

In conclusion, the consistent findings observed across various cancer models underscore the significant potential of EpigenAU/11 to enhance (adjuvate) treatment outcomes when used in combination with standard chemotherapeutic agents. The data indicate that EpigenAU/11 can operate synergistically with established therapies, promoting additive effects without compromising their efficacy. This aspect is particularly important as it suggests that EpigenAU/11 may provide a complementary approach to existing treatment protocols.

Below a summary table of EpigenAU/11 combinations with various chemotherapeutics on patient-derived tumour organoids. The table highlights EpigenAU/11's non-interference with standard treatments and shows additive or synergistic effects in most cases.

| Tumour Type | Chemotherapy Treatment | EpigenAU/11 active | Detrimental Interference with EpigenAU/11 | Cooperative Effect with EpigenAU/11 |
|---|---|---|---|---|
| Bladder Cancer | Cisplatin | YES | NO | YES |
| | Gemcitabine | YES | NO | NO |
| | Cisplatin + Gemcitabine | YES | NO | YES |
| Breast Cancer | Carboplatin + Epirubicin + Cyclophosphamide | YES | NO | NO |
| | Paclitaxel + Epirubicin + Cyclophosphamide | YES | NO | NO |
| | Carboplatin + Paclitaxel + Cyclophosphamide | YES | NO | NO |
| | Paclitaxel + Carboplatin + Epirubicin | YES | NO | NO |
| Endometrial Cancer | Carboplatin | YES | NO | NO |
| | Paclitaxel | YES | NO | NO |
| | Carboplatin + Paclitaxel | YES | NO | NO |
| Head and Neck Cancer | Cisplatin | YES | NO | YES | paclitaxel reduced viability to 96.2%, paclitaxel alone had no significant effect. In contrast, EpigenAU/11 reduced The pharmacological class and mechanism of action of the tested drugs is summarised below:

| Drug | Pharmacological Class | Mechanism of Action |
|---|---|---|
| Cisplatin | Alkylating Agent (Platinum-Based) | Forms DNA cross-links, preventing replication and leading to cell death. |
| Gemcitabine | Antimetabolite | Mimics nucleotides, incorporating into DNA during synthesis and halting cell growth. |
| Carboplatin | Alkylating Agent (Platinum-Based) | Similar to cisplatin, damages DNA through cross-linking, causing apoptosis. |
| Epirubicin | Anthracycline (Cytotoxic Antibiotic) | Interferes with topoisomerase II, blocking DNA synthesis and forming toxic free radicals. |

-continued

| Drug | Pharmacological Class | Mechanism of Action |
|---|---|---|
| Cyclophosphamide | Alkylating Agent | Activated in the liver, forms covalent bonds with DNA, blocking cell division. |
| Paclitaxel | Antimitotic Agent (Microtubule Inhibitor) | Binds to microtubules, stabilizing them and disrupting mitosis. |

Determination of Maximum Tolerated Dose for EpigenAU/11. Local and Systemic Administration Following extensive in vitro studies across a range of models, including 2D, 3D, and organoid systems, EpigenAU/11 demonstrated a notable capacity to selectively reduce cell viability. This effect was more pronounced in cancerous cells compared to healthy ones, reinforcing EpigenAU/11 as a promising candidate for further exploration. These in vitro results underscored the need to evaluate its tolerability and determine the maximum tolerated dose (MTD) in more complex, in vivo systems.

Moving into in vivo studies, the determination of the MTD is crucial, as animal models can reveal different dynamics compared to in vitro settings. The tolerability and behaviour of the compound in a living organism, specifically in wild-type mice, are distinct from the controlled environments of cellular assays. Therefore, a comprehensive assessment of local and systemic toxicity was conducted prior to efficacy testing.

Local toxicity was evaluated through subcutaneous injections of EpigenAU/11 at varying concentrations. Examination revealed that a concentration of 50 mg/ml exhibited no local toxicity, as evidenced by the absence of adverse effects at the injection site.

Simultaneously, a systemic toxicity study was conducted through daily intravenous injections of 100 μl of EpigenAU/11 at 100 mg/ml for one week. Remarkably, no signs of general distress were observed in the animals throughout the treatment period. Notably, assessments of key biochemical markers, including GOT, GPT, gamma GT, and creatinine, showed no significant variations, indicating the absence of systemic toxicity induced by the treatment.

In contrast, similar toxicity assessments were carried out for previous formulations at higher doses, which exhibited high mortality rates, underscoring their adverse effects.

13.2 Evaluation of the Association of EpigenAU/11 with Radiotherapy in Head and Neck Squamous Cell Carcinoma To evaluate the potential synergistic effect of EpigenAU/11 in combination with radiotherapy, two head and neck squamous cell carcinoma (HNSCC) organoid models were utilized: HNSCC 10847 (radiotherapy-sensitive) and HNSCC 10632 (radiotherapy-resistant). Using the Cell Titer-Glo® 3D Viability Assay, the results (FIG. 40) showed that in the radiotherapy-sensitive HNSCC 10847 organoid model, treatment with 0.66 mg/mL EpigenAU/11 in combination with radiotherapy resulted in a significant reduction in cell viability compared to radiotherapy alone. The presence of EpigenAU/11 at 0.66 mg/mL enhanced the cytotoxic effect, producing an additive effect on cell mortality. This suggests that EpigenAU/11 can potentiate the efficacy of radiotherapy in this model, leading to greater tumour cell death. Conversely, the HNSCC 10632 organoid model, which exhibited resistance to radiotherapy even at high doses (8 Gy), demonstrated sensitivity to EpigenAU/11 treatment. When administered alone, EpigenAU/11 at 0.66 mg/mL significantly reduced cell viability. Furthermore, in the presence of both EpigenAU/11 and radiotherapy, cell viability was further reduced at the highest radiation dose (8 Gy), indicating that EpigenAU/11 enhances the response to radiotherapy in this otherwise resistant model.

The findings from these studies demonstrate the significant potential of EpigenAU/11 as an adjuvant in cancer therapy, effectively enhancing the efficacy of conventional treatment approaches such as chemotherapy and radiotherapy. EpigenAU/11 exhibits a synergistic effect when combined with standard chemotherapeutic agents, improving treatment outcomes without interfering with their established mechanisms of action. Notably, its combination with radiotherapy has shown promise in sensitizing resistant tumour models, leading to a greater reduction in tumour viability at higher radiation doses. These results suggest that EpigenAU/11 can act as a powerful complementary agent in multimodal cancer treatment strategies, offering a novel approach to improving therapeutic effectiveness across various tumour types.

14. Farmacokinetics, ADME (Adsorbtion, Distribution, Metabolism, Excretion) Evaluation of EpigenAU/11

Changes in Gene Expression Following EpigenAU/11 (DoE2) Administration: Effects on Different Organs Provide Insights into Metabolic Kinetics Understanding the pharmacokinetics of EpigenAU/11 is essential for evaluating its local persistence and overall behaviour within the organism. Traditional techniques for assessing drug distribution often face limitations, particularly when working with complex systems like EpigenAU/11, which is derived from various plant sources and inherently variable at molecular level. The diverse constituents of such extracts can also interact in unpredictable ways, making it challenging to isolate and quantify individual components and their respective pharmacokinetic profiles.

Due to the heterogeneous nature of EpigenAU/11, conventional pharmacokinetic studies, which typically rely on measuring specific compounds over time, may not provide an accurate picture of how the extract behaves within biological systems. This complexity arises because the interactions within the EpigenAU/11 matrix can affect absorption, distribution, metabolism, and excretion (ADME) in ways that are not observable when assessing isolated compounds. For instance, some components might enhance the absorption of others, while some might inhibit metabolic processes, leading to variances in how long and in what form EpigenAU/11 persists in tissues. Furthermore, reproducibility at molecular level of different batches is factually unachievable and most importantly, as duly discussed, not relevant with respect to the intimate nature of the product.

Consequently and coherently, a more sophisticated approach is needed to comprehensively assess the pharmacokinetic behaviour of EpigenAU/11 following the presence/absence of its biological effect rather than of its molecular components.

Figure 41:
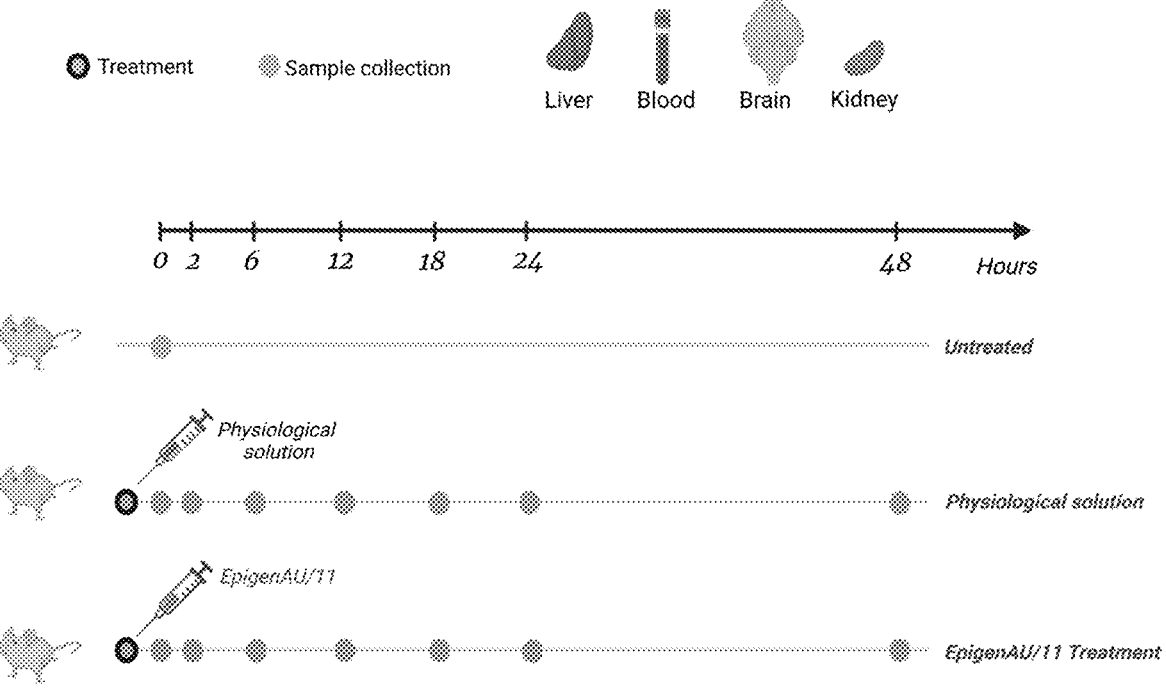
Figure 42:
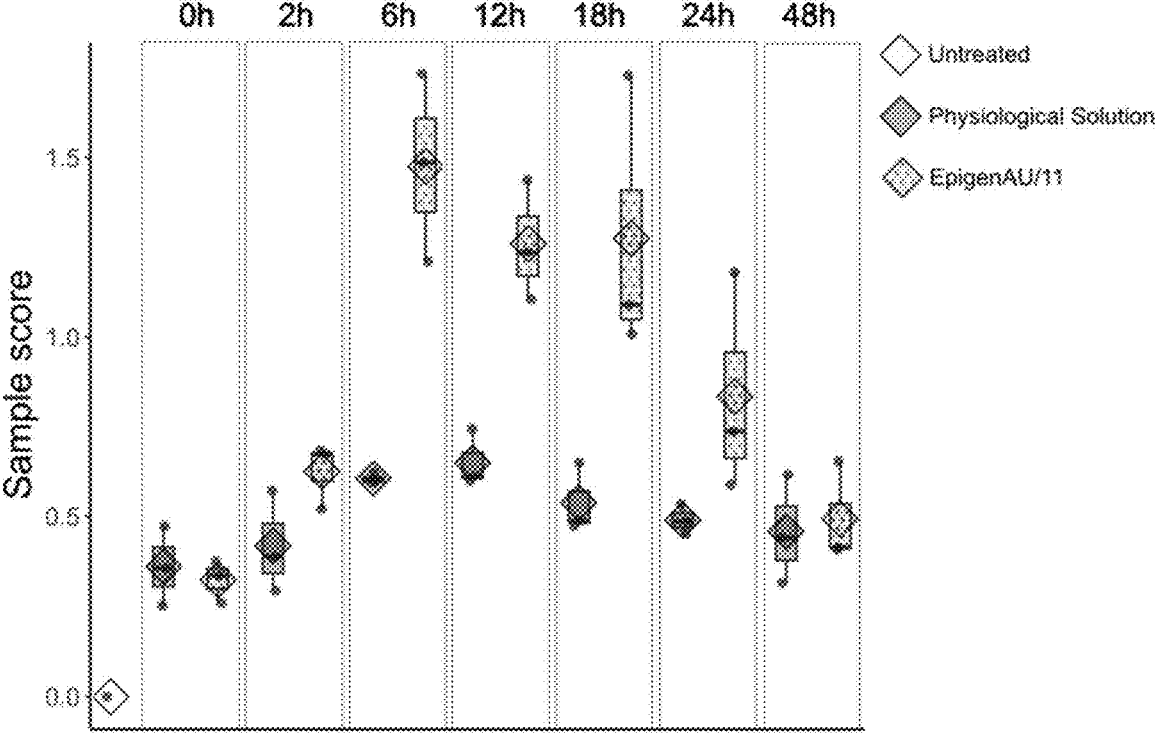

To address this, an experiment involving the treatment of healthy mice with EpigenAU/11 was conducted, characterizing the transcriptomic profiles of various organs at several time points post-injection (0, 2, 6, 12, 18, 24, and 48 hours), as shown in FIG. 41. The primary aim was to explore the overall gene expression profiles across different organs and uncover potential patterns related to EpigenAU/11 metabolism. Control samples consisted of liver, blood, brain, and kidney from mice treated with a physiological solution, collected at the same time points as the EpigenAU/11-treated mice. Additionally, untreated samples from all four organs were collected at time point 0 to serve as baseline controls.

In blood and brain samples, data distribution using Principal Component Analysis (PCA) did not show clear clustering of samples from mice that received EpigenAU/11, as was the case for Liver and Kidney samples.

Figure 40:
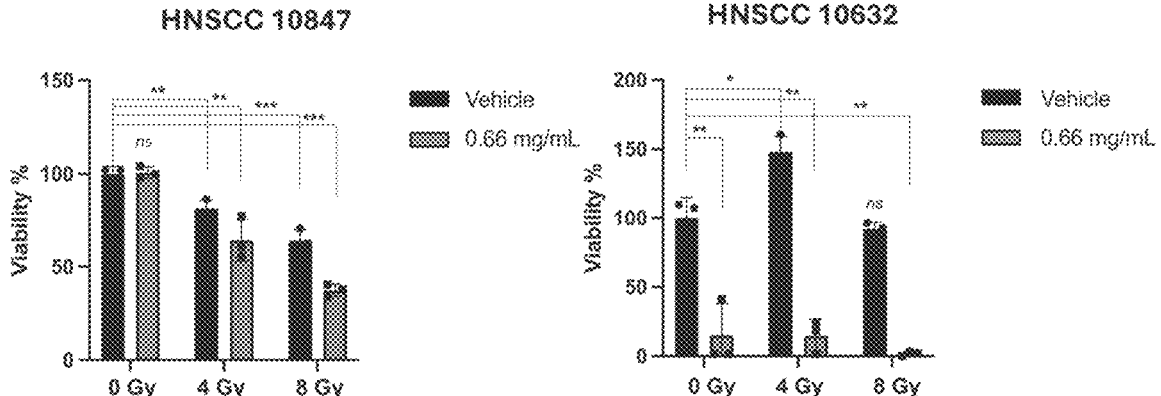

In liver samples, Principal Component Analysis (PCA) and Co-expression Analysis have shown a specific pattern in which the transcriptomic perturbations increase after EpigenAU/11 administration, with a peak at 6 hours, gradually decreasing over-time. To further explore this aspect, Molecular Degree of Perturbation (MDP) tool was used to understand the grade of transcriptomic perturbation of each sample in comparison to untreated samples. This approach was also applied to a subset of the dataset, selecting only the genes related to the ADME (Absorption, Distribution, Metabolism and Excretion) processes, according to a gene set used in a previous work by Dong Gui Hu et al (Dong Gui Hu et al. The Expression Profiles of ADME Genes in Human Cancers and Their Associations with Clinical Outcomes Cancers 2020, 12(11), 3369). The main result that reflects the time-course perturbation of ADME genes in the liver are represented in FIG. 40.

After 48 hours of EpigenAU/11 administration, the perturbation of genes involved in ADME processes in the liver (represented by red boxes) is comparable to that in mice treated with the physiological solution (green boxes). Among the perturbed genes are SOD2 and NR1I3, which encode proteins functioning as Modifiers; TAP1 and NOS1AP, which encode Phase I (functionalization) enzymes; SUL1B and GSTT2, which encode Phase II (conjugation) enzymes; and TAP2 and SLC16A1, which encode Transporters.

Figure 43:
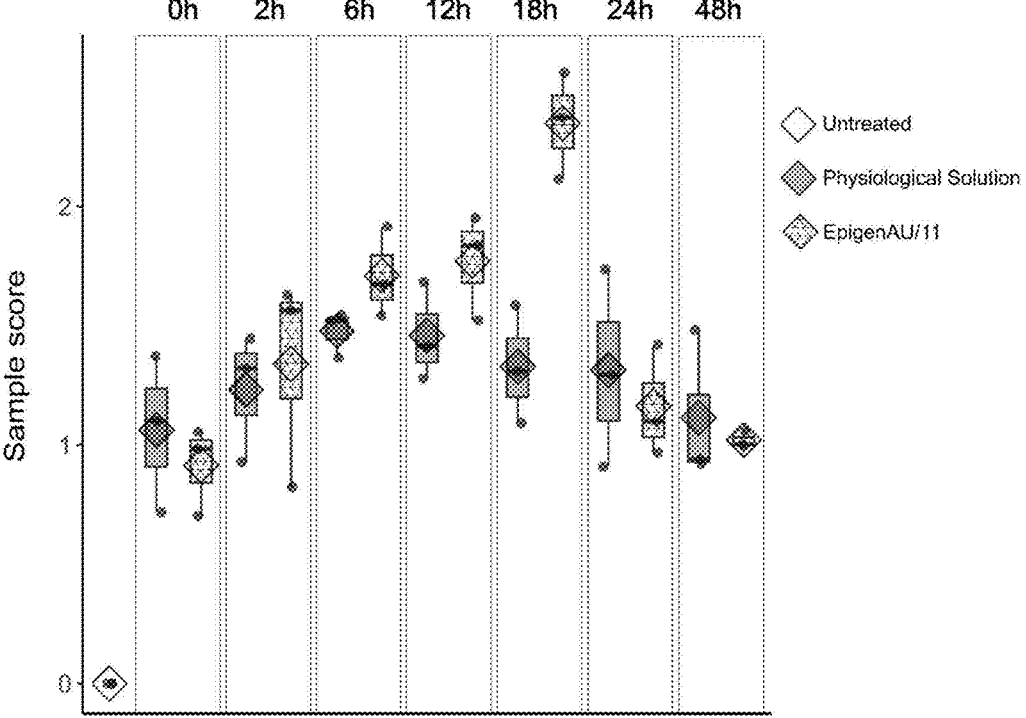

In Kidney samples, PCA has also shown clustering of samples treated with EpigenAU/11, even though the explained variance in PC 1 and 2 are less than in the liver's PCA. Again MDP was used to assess both overall transcriptomic perturbation and specific perturbations linked to ADME process. The gene set chosen for the kidney is described by a Genome-wide association study (GWAS) of metabolite concentrations (Schlosser, P., Li, Y., Sekula, P. et al. Genetic studies of urinary metabolites illuminate mechanisms of detoxification and excretion in humans. Nat Genet 52, 167-176 (2020). https://doi.org/10.1038/s41588-019-0567-8), 63 genes were selected (genes found by the GWAS and that are known to participate on metabolic-related pathways in general). The result of this analysis is presented in FIG. 43.

While the peak of perturbation for the ADME genes in the liver of mice treated with EpigenAU/11 occurred at 6 hours post-treatment, the kidney samples showed a distinct peak of ADME-related gene perturbation at 18 hours. This timing difference aligns well with the established roles of these organs within the pharmacokinetic ADME framework, where the liver primarily handles the metabolism and modification of substances, while the kidney is principally responsible for excretion and clearance from the body.

In the liver, the initial metabolic processing of EpigenAU/11 likely triggers early transcriptional activity as the organ responds to the influx of phytochemicals, leading to an observed peak in gene expression perturbation at 6 hours. This response may reflect the upregulation of detoxifying enzymes and transporters, which assist in metabolizing and modifying EpigenAU/11 before it circulates to other tissues.

In contrast, the kidneys exhibit a delayed but notable response, with gene expression perturbations peaking around 18 hours post-treatment. This timeline may indicate the phase when EpigenAU/11 is being processed for excretion. The kidney's role in filtration and elimination likely involves an accumulation phase as it clears EpigenAU/11 from the bloodstream, explaining the delayed peak relative to the liver.

By 48 hours post-treatment, both the overall and ADME-specific gene expression perturbations in both organs had normalized, becoming comparable to those in mice treated with physiological solution. This return to baseline suggests that EpigenAU/11's, is largely processed and cleared within this timeframe. The normalization of gene expression highlights a transient impact on the metabolic and excretory systems, which may be beneficial in assessing the safety and tolerability profile of EpigenAU/11 in a biological context.

15. Quality Control

The method used for batch-to-batch quality control of EpigenAU/11 allows to evaluate the complexity of the formulation as well as quali-quantitative variations thereof.

15.1 Strategy of Batch Release

Given the impossibility of assigning product biological activity based on the qualitative-quantitative profile of one or more chemical markers and, therefore, of associating biological activity of a product with emergent system properties to specific chemical markers, an approach based on FTIR spectroscopy was developed.

Therefore, the FTIR spectrum, characteristic of each material (in this case a vegetal biological matrix), could be used to check the conformity of a new batch. This allows to confirm that each new production meets production standards.

The aim is to build a predictive model based on the correlation between the FTIR spectrum and the cell-based assay using machine learning, in order to obtain a model used to discriminate good quality samples from poor quality samples.

The batches used to construct the training set were selected according to the claims and represent quantitative formulation variations within a predefined range from the reference standard (EpigenAU/11 DoE2), useful for characterizing a trend in biological performance with respect to quantitative formulation variations. All batches of the training set were tested by cell assay (see example 2).

Once the biological acceptability parameters of the activity were defined and the predictive model validated (internal validation), two good formulation qualities were analysed using the same operational methods. Based on the result obtained after the analysis, the test samples were confirmed to be of good or poor quality, depending on whether they had passed the test performed with the biological analysis to confirm the constructed model.

Next, for the good quality of the formulation rejected by the predictive model and the cell assay, incremental formulation rates were tested with the predictive model.

Each individual formulation permutation was tested by the model, and once a good biological correlation was predicted, all permutations were tested with the cell assay to confirm the results and the good response of the predictive model.

The aim of this study, therefore, was to propose a procedure to build a model of FTIR spectra that can predict the in vitro biological activity of different batches of a product formulation in the right ratio and, in case of negative results, to be able to evaluate adjustments in the formulation ratios to obtain the desired activity.

The prediction of biological activity was thus performed using Partial Least Squares (PLS) regression models based on FTIR spectra.

The DoEs used in these examples are the one disclosed in example 9.1 and related table.

Below are the twelve batches (DoEs) used to create the FTIR library and the list of samples analysed as tests:

Training Set:
two batches of EpigenAU/11 in right percentage of formulation, (DoE 2 and 3.)
ten batches of EpigenAU/11 (2 bad qualities and 8 derived from permutation of right formulation of DoE 2 and 3). CQ1_Lot2, DoE2.1, 2.2, 2.3.; CQ1_Lot3, DoE3.1, 3.2, 3.3, Test Set:
two batches of EpigenAU/11 in right percentage of formulation, (DoE 1 and 4)
four batches of EpigenAU/11 (2 bad qualities and 2 derived from permutation of right formulation of 2 batch of DoE4, DoE4.1 and 4.2.

15.2 FTIR Instruments and Set Up.

Alpha spectrometer from BRUKER Optics. Instrument is equipped with a GLOBAR source emitting in the Far and Mid-Infrared regions, a ROCKSOLID interferometer (Michelson type), a KBr beam splitter, and an RT-DLATGS detector.

Resolution: 2 cm−1
Spectral range: 5000-300 cm−1
Background scans: 50
Scans for sample acquisition: 50

Preparation of the Sample

Each sample was transferred into the appropriate sample holder for ATR-FTIR analysis of solids and liquids. Approximately 10 mg of the sample were deposited and pressed onto the diamond crystal of the ATR support. Before recording the measurement, it was verified that the entire sample holder was properly covered.

Sample Acquisition

For each sample, at least three measurements were repeated to verify the reproducibility of the data. The replicates were then averaged to obtain a representative spectrum of the sample for characterization.

Spectral Data Pre-Processing

The signals appear in two distinct regions of the measured spectral range: the OH and CH stretching bands in the high-frequency range, and the group frequencies along with collective bands in the fingerprint region within the 1800-500 cm$^{-1}$ interval. In the high-frequency range, most of the intensity is related to the presence of humidity rather than the sample itself. Therefore, we focused our attention on the more relevant 1800-500 cm$^{-1}$ range.

For the ATR spectra acquired as described above, in the selected spectral range between 1800 and 500 cm$^{-1}$, the second derivative was calculated using a 25-point Savitzky-Golay smoothing filter. The second-derivative profiles were then normalized to the intensity of the (negative) peak at 1076.4 cm$^{-1}$ for comparison. The 1076.4 cm$^{-1}$ peak was chosen as an internal standard due to its minimal variability in intensity and position across different sample compositions. These manipulations were performed using Opus 8.1 software from Bruker Optics.

15.3 Cell-Based Assay Result

In order to build a predictive model, the batches of training set were tested by cell-based assay.

As discussed in example 10 above, and as shown in FIG. 28, the cell-based assays results show that 0.66 mg/ml of all DoEs (1-4) induce, after 24 hours from administration to each cell culture, A mortality ≤61% of healthy cells HuDe;
A mortality ≥71% of FaDu tumour cells;
A mortality ≥55% of A431 tumour cells;
or even
A mortality ≤61% of healthy cells HuDe;
A mortality ≥71% of FaDu tumour cells;
A ≥65% mortality of A431 tumour cells;

Cell Culture Conditions:
HuDe, FaDu and A431 cell lines were cultured according to their conventional specified protocols, wherein:
HuDe cells were cultured in MEM medium with 10% FBS, 1% penicillin/streptomycin, and 1% sodium pyruvate, seeded at about 7,000 cells per well.
FaDu cells were cultured in EMEM medium with 10% FBS, 1% penicillin/streptomycin, seeded at about 12,500 cells per well.
A431 cells were cultured in DMEM medium with 10% FBS, 1% penicillin/streptomycin, seeded at about 8,500 cells per well.
The amount of medium per well was 200 µl.
The seeded cells were cultured in a humid incubator at 37° C. with 5% CO2 and treated for 24 hrs with 0.66 mg/ml of each DoE.

Although the ranges above can still be considered compliant, the limits of cell-based assay to define a batch as compliant for biological activity was set on the results of reference standard DoE2 as this batch was also tested ex vivo and in vivo

|  | HuDe_Mean | FaDu_Mean | A431_Mean |
|---|---|---|---|
| DoE2 | −47 | −95 | −66 |

Based on these results the vitality (opposite of mortality) limits for the test were set as reported below:
50%≤HuDe≤−40%
FaDu≤−90%
A431≤−65%
The numbers, indicated with the negative value, represent the reduction of the cells vitality. Therefore, by way of example, −68% with reference to the vitality corresponds to a 68% of cell mortality.

In the table below, not compliant indicates values that are.

Given the extensive characterisation of DoE2 also in terms of therapeutic effect, the cytotoxicity values in the cell-based assay on HuDe, FaDu and A431 cells (see example 2), were used as desired target for the EpigenAU/11 performance envisaging a manufacturing quality control of the product.

Hence, performances that did not satisfy the following criteria
i.e.
A 40-50% mortality of healthy cells HuDe;
A ≥90% mortality of FaDu tumour cells;
A mortality ≥55% of A431 tumour cells;
although showing a therapeutic effect valid, were considered as "non-desirable".

Performances that did not satisfy even

A mortality ≤61% of healthy cells HuDe;

A mortality ≥71% of FaDu tumour cells;

A mortality ≥65% of A431 tumour cells;

Were considered as non-compliant.

It is to be born in mind that the definition of "compliant" was based hereinbelow exclusively on the DoE2 performances as this lot was extensively tested and characterised and therefore considered as desirable for a large scale manufacturing setup.

All the samples of the training set were tested by cell-based assay according to example 2 and the results are reported below:

|  | HuDe Mean (%) | FaDu Mean (%) | A431 Mean (%) | Status |
|---|---|---|---|---|
| CQ1_Lot2 | −68 | −90 | −60 | Not compliant |
| DoE2.1 | −44 | −89 | −63 | Not desirable |
| DoE2.2 | −38 | −91 | −55 | Not desirable |
| DoE2.3 | −27 | −91 | −81 | Not desirable |
| DoE3 | −42 | −95 | −81 | Compliant |
| CQ1_LOT3 | −70 | −86 | −70 | Not compliant |
| DoE3.1 | −56 | −86 | −70 | Not desirable |
| DoE3.2 | −38 | −93 | −79 | Not desirable |
| DoE3.3 | −28 | −93 | −73 | Not desirable |
|  |  |  | — |  |

When referred to the cell-based assay, the tables indicate "compliant" when the batch was considered acceptable in terms of quality with the most stringent cut-offs selected on the basis of the DoE2 performance on the tumour cells vitality and on the healthy cells.

Once this acceptability limits ware set for cell-based assay PLS prediction model was built.

15.4 Spectral Acquisition

All spectra of batches of the training set in 15.2 were first acquired.

These spectra and cell-based assay result were used in the creation of PLS regression model.

FTIR Spectroscopy Data Analysis Workflow

The prediction of cell viability was performed using Partial Least Squares (PLS) regression models. The following sections outline the data preparation, model training, and evaluation process.

Data Pre-Processing

Training and Test Set Formation:

The dataset was divided into training and test sets for model development and evaluation:

Training Set: Samples from the DoE2 and DoE3 groups were selected to train the PLS regression model. These samples were deemed suitable for training based on their composition and experimental consistency.

Test Set: Samples from the DoE1 and DoE4 groups were used as test sets. The test set was reserved for model evaluation to understand the model's predictive performance assessed on unseen data.

Feature Selection on Wavelengths

To further reduce the dimensionality of the data and focus on relevant features, a wavelength selection with a first PLS model was carried out. This step involved identifying wavelengths that were highly correlated with cell viability. Wavelengths were selected based on their correlation with cell viability for at least one of the cell types. Only wavelengths with a correlation coefficient greater than 0.7 or less than −0.7 were included in the final model. This ensured that only the most predictive wavelengths were used in the analysis. In this process 247 features remained in the dataset.

15.5 PLS Regression Model Development

After feature selection, the final Partial Least Squares (PLS) regression model was built using the training set, which was previously filtered to present the same 247 features selected in the previous step. Partial Least Squares (PLS) regression is a multivariate statistical method used to predict a set of dependent variables (responses) from a set of independent variables (predictors), it is highly effective for predicting response variables from noisy, collinear, or complex data, being widely used in spectroscopy data analysis.

Training Process:

The model was trained on the selected wavelengths from the DoE2 and DoE3 samples, identifying the relationship between the intensity measurements and cell viabilities for the three cell types.

Model Testing:

The trained PLS model was then applied to the test sets (DoE1 and DoE4) to predict cell viability.

Prediction Evaluation:

The evaluation of the model was performed by comparing the predicted cell viability values against the true values.

Data Comparison and PLS Regression Model Validation.

After PLS model generation, an internal validation of the prediction model was performed:

| PREDICTED | | | | MEASURED | | | |
|---|---|---|---|---|---|---|---|
|  | HuDe_ | FaDu | A431_ |  | HuDe_Mean | FaDu_Mean | A431_Mean |
| DoE2 | −44 | −95 | −68 | DoE2 | −47 | −95 | −66 |
| CQ1_Lot2 | −62 | −90 | −60 | CQ1_Lot2 | −68 | −90 | −60 |
| DoE2.1 | −46 | −89 | −65 | DoE2.1 | −44 | −89 | −63 |
| DoE2.2 | −40 | −92 | −55 | DoE2.2 | −38 | −91 | −55 |
| DoE2.3 | −33 | −91 | −78 | DoE2.3 | −27 | −91 | −81 |
| DoE3 | −47 | −95 | −78 | DoE3 | −42 | −95 | −81 |
| CQ1_Lot3 | −62 | −86 | −70 | CQ1_Lot3 | −70 | −86 | −70 |
| DoE3.1 | −61 | −87 | −73 | DoE3.1 | −56 | −86 | −70 |
| DoE3.2 | −43 | −90 | −73 | DoE3.2 | −38 | −93 | −79 |
| DoE3.3 | −32 | −92 | −76 | DoE3.3 | −28 | −93 | −73 |
|  |  | — |  |  |  |  |  |

Once the model was validated, four samples (DoE1 and DoE4,) were tested and the predicted values were after confirmed by cell-based assay (see FIG. 28).

| PREDICTED | | | | MEASURED | | |
|---|---|---|---|---|---|---|
| | | | | HuDe_ | FaDu_ | A431_ |
| HuDe_ | FaDu_ | A431_ | | Mean | Mean | Mean |
| DoE1 −43 | −92 | −71 | DoE1 | −41 | −96 | −80 |
| DoE4 −57 | −91 | −65 | DoE4 | −61 | −96 | −81 |

According to the data above and in FIG. 28, it emerges that different permutations of the formula as claimed can better satisfy the cytotoxicity standards identified as cut-off for defining the UoA of EpigenAU/11 (e.g. DoE 4 and DoE 4.2 where the 4.2 formulation shows a preferable cytotoxicity profile.

A study on the possible permutation of DoE4 formula was carried out, as the basic formula resulted as "non desirable" with the high-quality cut-offs decided above.

results of this study, it is evident that two permutations of the correct formulation of DoE4 (DoE 4.1 and DoE 4.2) were tested against the prediction model in order to explore possible modifications of the formulation that could achieve the desired biological activity (i.e. similar to DoE2).

| PREDICTED | | | | MEASURED | | |
|---|---|---|---|---|---|---|
| | | | | HuDe_ | FaDu_ | A431_ |
| HuDe_ | FaDu_ | A431_ | | Mean | Mean | Mean |
| DoE4.1 −52 | −90 | −62 | DoE4.1 | −59 | −93 | −72 |
| DoE4.2 −45 | −90 | −65 | DoE4.2 | −50 | −93 | −65 |

Eventually, DoE4.2 in the prediction model showed the desired activity and was then tested with a cell assay to confirm the result.

The results of the cell-based assay confirmed that a change of 6% more in absolute value of SP2 coextract was able to achieve the desired activity. In this way internal and external validation of control chart was carried out. Therefore, according to the FTIR prediction test with the acceptability limits evaluated by the method of the invention, all batches of the training set were found to comply in the internal model validation process. To confirm the validity of the process for the purpose of the study, the samples in the test set were tested on the FTIR prediction model and the results were confirmed by a cell assay for biological activities.

Processes and methods were then identified to define the acceptability criteria for a product comprising or consisting of one or more natural matrices and to assess its biological activity a priori, with the aim of making any quantitative changes in the ratios among the components that might eventually allow the biological activity to be restored to the desired level. According to the method of the invention, therefore, quantitative changes in the formulation can lead to the maintenance of desired biological activity regardless of the notion of composition at the molecular level.

16. Network Analysis

A network analysis of the pathologies treated by EpigenAU/11 was performed, the data obtained show how the natural matrices-based products tested are able to influence the body on a systemic scale.

Specifically, relative to the condition in a pathological state (FIG. 44 Panel A): Systemic inflammation is closely associated with the clinical symptoms of the tumour, indicating its presence and progression. Cytokines, inflammatory proteins and immune cells are present and easily detectable in systemic circulation [Dolan R D, Lim J, McSorley S T, Horgan P G, McMillan D C. The role of the systemic inflammatory response in predicting outcomes in patients with operable cancer: Systematic review and meta-analysis. Sci Rep. 2017; Dolan R D, McMillan D C. The prevalence of cancer associated systemic inflammation: Implications of prognostic studies using the Glasgow Prognostic Score. Crit Rev Oncol Hematol. 2020; Roxburgh C S, McMillan D C. Cancer and systemic inflammation: treat the tumour and treat the host. Br J Cancer. 2014].

the condition when treated with drug reference (FIG. 44 Panel B): drug reference is not able to counteract the systemic inflammation.

the state when treated with EpigenAU/11 (FIG. 44 Panel C): EpigenAU/11 is able to modulate specific biological activities capable of beneficially influencing systemic inflammation.

Graphs were designed using Gephi, an open-source network visualization platform (Bastian M., Heymann S., Jacomy M. (2009). Gephi: an open source software for exploring and manipulating networks. International AAAI Conference on Weblogs and Social Media). The layout Yifan Hu was chosen for the "Pathology" network, the conformation of the graph was saved and applied in the construction of the "Natural Product" and the "Reference Drug" graphs.

The direction of the modulation is represented by the black filling of the nodes for up-regulation and empty nodes for down-regulation. Nodes in grey do not present a modulation in a specific direction. The size of the nodes represents the Z-scores, which were previously scaled based on all the values used in the specific panel. In Gephi, size of the nodes was controlled by using the "Ranking" parameter with a size range from 15 to 60.

The "HUBs" of the networks represent central biological processes of interest for the specific Pathology. They are represented in grey colour, labelled in capital letters and their expected modulation is illustrated by arrows going up or down, according to literature (for Pathology networks) or based on the modulation of the diseases and Biofunctions/biological parameters (for "Natural Product" and "Reference Drug" networks).

The invention claimed is:

1. A product consisting of:
20-50 weight percent of component a;
49-80 weight percent of component b; and
0.6-1.2 weight percent of component c; wherein
component a is a coextract of *Filipendula* leaves and flowers, *Laurus* leaves, *Brassica* seeds and *Withania* roots, and the weight percent of the raw materials prior to coextraction consists of 17.5-32.5% *Filipendula* leaves and flowers, 17.5-32.5% *Laurus* leaves, 17.5-32.5% *Brassica* seeds and 17.5-32.5% *Withania* roots;
component b is a coextract of *Cynara* leaves, *Curcuma* roots and *Tanacetum* flowers, and the weight percent of the raw materials prior to coextraction consists of 10-19% *Cynara* leaves, 29-55% *Curcuma* roots, 29-55% *Tanacetum* flowers;
and
component c is an extract of *Agave* leaves.

2. The product according to claim 1 consisting of 30-40% by weight of component a;

60-70% by weight of a component b;

and 0.6-1.2% by weight of component c.

3. The product according to claim 1 consisting of:

36.05% by weight of component a;

63.06% by weight of a component b; and 0.89% by weight of component c.

4. The product according to claim 1 wherein component a is a freeze-dried coextract in water of *Filipendula* leaves and flowers, *Laurus* leaves, *Brassica* seeds and *Withania* roots, wherein the weight percent of the raw materials prior to coextraction consists of 17.5-32.5% *Filipendula* leaves and flowers, 17.5-32.5% *Laurus* leaves, 17.5-32.5% of *Brassica* seeds and 17.5-32.5% *Withania* roots;

component b is a freeze-dried coextract in water of *Cynara* leaves, *Curcuma* roots and *Tanacetum* flowers, wherein the weight percent of the raw materials prior to coextraction consists of 10-19% *Cynara* leaves, 29-55% *Curcuma* roots, 29-55% *Tanacetum* flowers; and component c is a freeze-dried extract in water of *Agave* leaves.

5. The product according to claim 1 wherein:

component a is a freeze-dried coextract in water of *Filipendula* leaves and flowers, *Laurus* leaves, *Brassica* seeds and *Withania* roots, wherein the weight percent of the raw materials prior to coextraction consists of 25% *Filipendula* leaves and flowers, 25% *Laurus* leaves, 25% *Brassica* seeds and 25% *Withania* roots, and component b is a freeze-dried coextract in water of *Cynara* leaves, *Curcuma* roots and *Tanacetum* flowers, wherein the weight percent of the raw materials prior to coextraction consists of 14.30% *Cynara* leaves, 42.85% *Curcuma* roots, 42.85% *Tanacetum* flowers; and component c is a freeze-dried extract in water of *Agave* leaves.

6. The product according to claim 1 wherein *Filipendula* is selected between *Filipendula* ulmaria and *Filipendula* vulgaris or a mixture thereof, *Laurus* is selected from *Laurus* azorica and *Laurus* nobilis or a mixture thereof, *Brassica* is selected from *Brassica* rapa, *Brassica* nigra, *Brassica* oleracea botrytis cymosa or a mixture thereof, *Withania* is selected from *Withania* siniensis and *Withania* somnifera or a mixture thereof, *Cynara* is selected from *Cynara* cardunculus scolymus and *Cynara* flavescens or a mixture thereof, *Curcuma* is selected from *Curcuma* zedoaria and *Curcuma* longa or a mixture thereof, *Tanacetum* is selected from *Tanacetum* cinerariifolium, *Tanacetum* parthenium and *Tanacetum* vulgare or a mixture thereof, *Agave* is selected from *Agave* americana and *Agave* sisalana or a mixture thereof.

7. The product according to claim 1 wherein *Filipendula* is *Filipendula vulgaris*, *Laurus* is *Laurus nobilis*, *Brassica* is *Brassica oleracea botrytis cymosa*, *Withania* is *Withania somnifera*, *Cynara* is *Cynara cardunculus scolymus*, *Curcuma* is *Curcuma longa*, *Tanacetum* is *Tanacetum parthenium*, *Agave* is *Agave sisilana*.

8. The product according to claim 1 wherein when 0.66 mg/ml of said product is administered to HuDe, FaDu or A431 cells in culture, said product induces:

(a) a mortality ≤61% of HuDe healthy cells, said HuDe cells seeded at about 7,000 cells per well in 200 µl of the appropriate medium;

(b) a mortality ≥71% of FaDu tumour cells, said FaDu cells seeded at about 12,500 cells per well in 200 µl of the appropriate medium; or (c) a mortality ≥55% of A431 tumour cells; A431 cells seeded at about 8,500 cells per well in 200 µl of the appropriate culture medium.

9. A unit of activity of the product according to claim 1, said unit being defined as the amount of said product that, when administered separately to HuDe, FaDu and A431 cells in culture, induces the following cell mortality:

(a) a 40-50% mortality of healthy cells HuDe;

(b) a ≥90% mortality of FaDu tumour cells; or (c) a ≥65% mortality of A431 tumour cells; after 24 hour incubation in cell culture; and wherein the HuDe cells are seeded at about 7,000 cells per well in 200 µl of the appropriate medium;

the FaDu cells are seeded at about 12,500 cells per well in 200 µl of the appropriate medium, and the A431 cells are seeded at about 8,500 cells per well in 200 µl of the appropriate culture medium.

10. A composition comprising the product according to claim 1; at least one of an anticancer agent and a pharmaceutically acceptable carrier.

11. The composition according to claim 10 wherein said anticancer agent is a chemotherapeutic, an antibody or a therapeutically active fragment thereof, or a therapeutically active small molecule.

12. The composition according to claim 11 wherein said chemotherapeutic is Cisplatin, Paclitaxel, Gemcitabine, Epirubicin, Cyclophosphamide, Carboplatin, Oxaliplatin, Mitomycin C, Bleomycin, Doxorubicin, Busulfan, Dacarbazine, Temozolomide, Ifosfamide, Melphalan, Clofosfamide, Lomustine, or Bendamustine.

13. The composition according to claim 11, wherein said antibody is a monoclonal antibody is Rituximab, Trastuzumab, Bevacizumab, Pembrolizumab, Ipilimumab, Nivolumab, Atezolizumab, or Cetuximab.

14. A therapeutic adjuvant or a vehicle for anticancer therapy comprising the product according to claim 1 and a pharmaceutically acceptable carrier.

15. The composition according to claim 10 which is formulated for oral, nasopharyngeal, oropharyngeal, aerosol, systemic injection, microneedle injection, intratissutal injection, endovenous, topical, rectal, vaginal, ocular, or intratissutal administration.

16. The composition according to claim 15 which is in the form of a suspension, a solution, a freeze-dried material, a cream, an ointment, a spray, a tablet, a soft gelatine capsule, a hard gelatine, a gel, an emulsion, an eye drop, an enema, a suppository, a vaginal ovule, a powder, a granule, loaded vesicles, or loaded liposomes.

17. A kit of parts comprising separate vials of the therapeutic adjuvant or vehicle according to claim 14 and of at least one anticancer agent.

18. The kit of parts according to claim 17 wherein said anticancer agent is a chemotherapeutic, an antibody or a therapeutically active fragment thereof, or a therapeutically active small molecule.

19. The kit of parts according to claim 18 wherein said chemotherapeutic is Cisplatin, Paclitaxel, Gemcitabine, Epirubicin, Cyclophosphamide, Carboplatin, Oxaliplatin, Mitomycin C, Bleomycin, Doxorubicin, Busulfan, Dacarbazine, Temozolomide, Ifosfamide, Melphalan, Clofosfamide, Lomustine, or Bendamustine.

20. The kit of parts according to claim 18 wherein said antibody is Rituximab, Trastuzumab, Bevacizumab, Pembrolizumab, Ipilimumab, Nivolumab, Atezolizumab, or Cetuximab.

21. The product according to claim 1 consisting of:
30.00% by weight of component a;
69.11% by weight of component b; and
0.89% by weight of component c.

22. The product according to claim 1, wherein said product exerts its therapeutic or adjuvant effect on cancer through a physiological mechanism of action.

\* \* \* \* \*